(12) United States Patent
Stumpf et al.

(10) Patent No.: US 10,906,918 B2
(45) Date of Patent: Feb. 2, 2021

(54) PROCESS FOR THE PREPARATION OF TRICYCLIC PI3K INHIBITOR COMPOUNDS AND METHODS FOR USING THE SAME FOR THE TREATMENT OF CANCER

(71) Applicant: GENENTECH, INC., South San Francisco, CA (US)

(72) Inventors: Andreas Stumpf, South San Francisco, CA (US); Remy Angelaud, South San Francisco, CA (US); Andrew McClory, South San Francisco, CA (US); Herbert Yajima, South San Francisco, CA (US); Chudi Ndubaku, South San Francisco, CA (US); Alan Olivero, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/780,328

(22) PCT Filed: Dec. 16, 2016

(86) PCT No.: PCT/US2016/067174
§ 371 (c)(1),
(2) Date: May 31, 2018

(87) PCT Pub. No.: WO2017/106647
PCT Pub. Date: Jun. 22, 2017

(65) Prior Publication Data
US 2018/0354970 A1    Dec. 13, 2018

Related U.S. Application Data

(60) Provisional application No. 62/268,149, filed on Dec. 16, 2015, provisional application No. 62/288,832, filed on Jan. 29, 2016, provisional application No. 62/291,248, filed on Feb. 4, 2016.

(51) Int. Cl.
| | |
|---|---|
| *C07D 498/14* | (2006.01) |
| *C07D 487/04* | (2006.01) |
| *C07D 498/22* | (2006.01) |
| *A61P 35/00* | (2006.01) |
| *A61K 9/00* | (2006.01) |
| *A61K 31/495* | (2006.01) |
| *A61K 31/5383* | (2006.01) |
| *A61K 39/395* | (2006.01) |
| *A61K 45/06* | (2006.01) |

(52) U.S. Cl.
CPC .......... *C07D 498/14* (2013.01); *A61K 9/0053* (2013.01); *A61K 31/495* (2013.01); *A61K 31/5383* (2013.01); *A61K 39/3955* (2013.01); *A61K 45/06* (2013.01); *A61P 35/00* (2018.01); *C07D 487/04* (2013.01); *C07D 498/22* (2013.01)

(58) Field of Classification Search
CPC ... C07D 487/04; C07D 498/14; C07D 498/22
See application file for complete search history.

(56) References Cited

U.S. PATENT DOCUMENTS

| | | | |
|---|---|---|---|
| 6,262,268 B1 * | 7/2001 | Palucki | C07D 213/38 546/122 |
| 2012/0171199 A1 * | 7/2012 | Dotson | C07D 487/14 424/133.1 |
| 2015/0079081 A1 | 3/2015 | Dotson et al. | |

FOREIGN PATENT DOCUMENTS

| | | |
|---|---|---|
| WO | 2009/116069 A2 | 9/2009 |
| WO | 2010/052569 A2 | 5/2010 |
| WO | 2011/021038 A1 | 2/2011 |
| WO | 2015/049369 A1 | 4/2015 |
| WO | 2017/106647 A1 | 6/2017 |

OTHER PUBLICATIONS

International Search Report and Written Opinion for International Patent Application Serial No. PCT/US2016/067174 dated Mar. 23, 2017.
Suzuki et al., Cross-coupling reactions of organoboranes: An easy way to construct C—C bonds (Nobe Lecture). Agnew. Chem. Int. Ed., vol. 50, pp. 6722-6737 (2011).
Syzmanska et al., Methods for the synthesis of xanthine-derived polycyclic fused systems. Heterocycl. Commun., vol. 19, pp. 297-310 (2013).

* cited by examiner

*Primary Examiner* — Barbara P Badio
(74) *Attorney, Agent, or Firm* — K&L Gates LLP; Louis C. Cullman; Benjamin D. Heuberger

(57) ABSTRACT

The present disclosure provides for methods for preparing tricyclic PI3K inhibitor compounds in high yield and purity in aqueous solvent systems.

25 Claims, 29 Drawing Sheets

Vehicle　　　　　　　GDC-0084

Vehicle control (4-week)    GDC-0084 (4-week)

PROCESS FOR THE PREPARATION OF TRICYCLIC PI3K INHIBITOR COMPOUNDS AND METHODS FOR USING THE SAME FOR THE TREATMENT OF CANCER

This application is a national phase entry of PCT/US2016/067174, filed Dec. 16, 2016, which claims the benefit of U.S. provisional patent application No. 62/268,149, filed Dec. 16, 2015, U.S. provisional patent application No. 62/288,832, filed Jan. 29, 2016, and U.S. provisional patent application No. 62/291,248, filed Feb. 4, 2016, the entire disclosures each of which is incorporated herein by reference.

FIELD OF THE DISCLOSURE

The disclosure relates generally to methods for preparing compounds which inhibit PI3 kinase activity. The disclosure also relates to methods of using the compounds for in vitro, in situ, and in vivo diagnosis or treatment of mammalian cells, or associated pathological conditions. The disclosure also relates to methods of treating cancer characterized by the overexpression of PI3 kinase.

BACKGROUND

Any discussion of the prior art throughout the specification should in no way be considered as an admission that such prior art is widely known or forms part of the common general knowledge in the field. Phosphatidylinositol is one of a number of phospholipids found in cell membranes which play an important role in intracellular signal transduction. Cell signaling via 3'-phosphorylated phosphoinositides has been implicated in a variety of cellular processes, e.g., malignant transformation, growth factor signaling, inflammation, and immunity (Rameh et al. (1999) J. Biol Chem, 274:8347-8350). The enzyme responsible for generating these phosphorylated signaling products, phosphatidylinositol 3-kinase (also referred to as PI 3-kinase or PBK), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al. (1992) Trends Cell Biol 2:358-60).

Phosphoinositide 3-kinases (PI3K) are lipid kinases that phosphorylate lipids at the 3-hydroxyl residue of an inositol ring (Whitman et al. (1988) Nature, 332:664). The 3-phosphorylated phospholipids (PIP3s) generated by PI3-kinases act as second messengers recruiting kinases with lipid binding domains (including plekstrin homology (PH) regions), such as AKT and phosphoinositide-dependent kinase-1 (PDK1). Binding of AKT to membrane PIP3s causes the translocation of AKT to the plasma membrane, bringing AKT into contact with PDK1, which is responsible for activating AKT. The tumor-suppressor phosphatase, PTEN, dephosphorylates PIP3 and therefore acts as a negative regulator of AKT activation. The PI3-kinases AKT and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al. (2002) Nature Rev. Cancer 2:489; Phillips et al. (1998) Cancer 83:41).

The main PI3-kinase isoform in cancer is the Class I PI3-kinase, p110α (alpha) (see, e.g., U.S. Pat. Nos. 5,824,492; 5,846,824; 6,274,327). Other isoforms are implicated in cardiovascular and immune-inflammatory disease (Workman P (2004) Biochem Soc Trans 32:393-396; Patel et al. (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al. (2008) J. Med. Chem. 51:5522-5532; Yaguchi et al. (2006) Jour. of the Nat. Cancer Inst. 98(8):545-556).

Malignant gliomas are the most common primary brain tumors in adults. In glioblastoma (GBM), the most aggressive glioma subtype, tumor formation and growth appear to be driven by amplification or overexpression of gene products involved in growth factor-initiated signal transduction acting in cooperation with genetic alterations disrupting cell-cycle control (Holland E C (2001) Nat Rev Genet 2:120-129). Of the genomic alterations described in GBM, PTEN mutation and/or deletion is the most common, with an estimated frequency of 70-90% (Nutt C, Louis D N (2005) Cancer of the Nervous System (McGraw-Hill, New York), 2nd Ed, pp 837-847.). These findings, along with the prognostic value of PTEN status in GBM cases (Phillips H S, et al. (2006) Cancer Cell 9:157-163), suggest the importance of the phosphoinositide 3-kinase (PI3K)/Akt pathway in promoting highly aggressive glial malignancies, as well as the opportunities for treatment with PI3K inhibitors possessing blood-brain barrier penetrant properties.

Certain tricyclic PI3K inhibitor compounds of Formula III (below) disclosed in U.S. Pat. No. 8,883,799 have been discovered to possess PI3 kinase modulating or inhibitory activity, anti-cancer properties, anti-inflammatory properties and/or immunoregulatory properties.

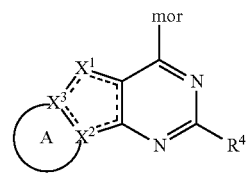

Formula III

The Formula III compounds of the U.S. Pat. No. 8,883,799 patent may be useful in the treatment of hyperproliferative disorders such as cancer that are characterized by the modulation of PI3 kinase function, for example by mutations or overexpression of the proteins. Useful methods for preparing Formula III are known. However, a need exists for improved methods for preparing compounds of Formula III in high yield and purity.

SUMMARY

In some embodiments, the disclosure relates to a process for preparing compound a Formula III from compound a Formula II in a reaction mixture according to the following reaction scheme:

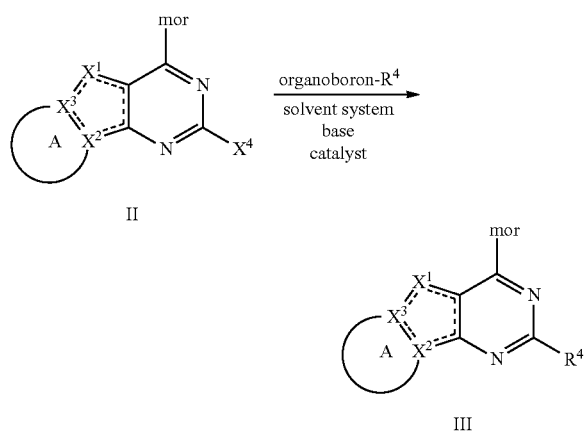

The process comprises: (i) forming a reaction mixture comprising the compound Formula II, organoboron-$R^4$, the solvent system comprising at least 5 v/v % water, the base and the catalyst; (ii) reacting the reaction mixture at a temperature of less than 100° C. to form a reaction product mixture comprising compound Formula III; and (iii) isolating the compound Formula III, a stereoisomer, geometric isomer, tautomer, or a pharmaceutically acceptable salt thereof, from the reaction product mixture. The catalyst comprises palladium and the reaction mixture comprises less than 0.05 equivalents of catalyst per equivalent of compound Formula II.

Further, $X^1$ is S, O, N, $NR^6$, $CR^1$, $C(R^1)_2$, or —C$(R^1)_2$O—. $X^2$ is C, $CR^2$ or N. $X^3$ is C, $CR^3$ or N. $X^4$ is halogen. A is a 5, 6, or 7-membered carbocyclyl or heterocyclyl ring fused to $X^2$ and $X^3$, optionally substituted with one or more $R^5$, $R^{10}$ and/or $R^{15}$ groups. $R^1$, $R^2$, and $R^3$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —CF3, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2$, —$CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl.

Yet further, $R^6$ is H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)(—$C_2$-$C_{20}$ heterocyclyl), —($C_1$-$C_{12}$ alkylene)-C(=O)—($C_2$-$C_{20}$ heterocyclyl), ($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_3$, —$CH_2CH_3$, —$C(CH_3)_3$, —$CH_2OH$, —$CH_2CH_2OH$, —$(CH_3)_2OH$, —$CH_2OCH_3$, —CN, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl.

Still further, $R^4$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —CN, —$CF_3$, —$CH_2OH$, —$CO_2H$, —$CONH_2$, $CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —$NHC(O)NHCH_3$, —$NHC(O)NHCH_2CH_3$, —$NHS(O)_2CH3$, —$N(CH_3)C(O)OC(CH_3)_3$, —$S(O)_2CH_3$, benzyl, benzyloxy, morpholinyl, morpholinomethyl, and 4-methylpiperazin-1-yl.

Each $R^5$, $R^{10}$ and $R^{15}$ is independently selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl); or two geminal $R^5$, $R^{10}$ and/or $R^{15}$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —NH—$COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl.

Further, mor is selected from:

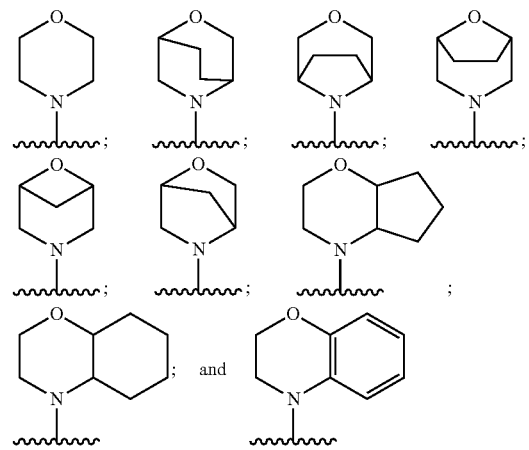

wherein mor is optionally substituted with one or more $R^7$ groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2OH$, —$CH(CH_3)OH$, —$CH(CH_2CH_3)OH$, —$CH_2CH(OH)CH_3$, —$C(CH_3)_2OH$, —$C(CH_3)_2OCH_3$, —$CH(CH_3)F$, —$C(CH_3)F_2$, —$CH(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —$NHCH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, =O, —OH, —$OCH_3$, —$OCH_2CH_3$, —$OCH(CH_3)_2$, —SH, —$NHC(O)NHCH_3$, —$NHC(O)NHCH_2CH_3$, —$S(O)CH_3$, —$S(O)$ $CH_2CH_3$, $-S(O)_2CH_3$, $-S(O)_2NH_2$, $-S(O)_2NHCH_3$, $-S(O)_2N(CH_3)_2$, and $-CH_2S(O)_2CH_3$.

In some other embodiments, the disclosure relates to a process for preparing a compound of Formula IIa from a compound of Formula I according to the following reaction scheme:

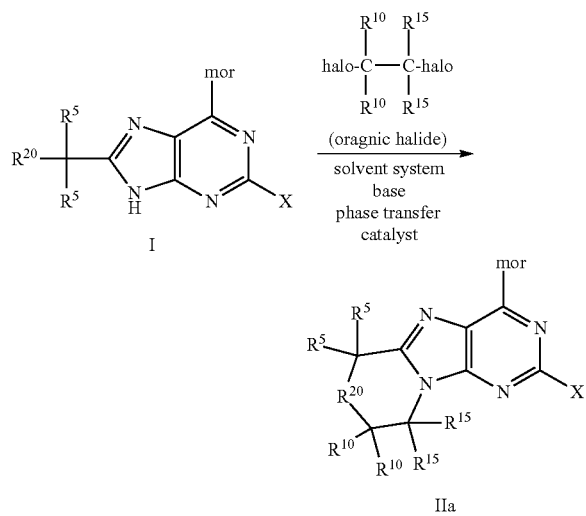

The process comprises: (i) forming a reaction mixture comprising compound Formula I, an organic halide, a solvent system, a phase transfer catalyst, and a base; (ii) reacting the reaction mixture to form a reaction product mixture comprising compound Formula IIa, a stereoisomer, geometric isomer, tautomer, or a pharmaceutically acceptable salt thereof, and (iii) isolating compound Formula IIa from the reaction product mixture.

Further, the solvent system comprises at least 5 v/v % water. X is a halide. Each $R^5$, $R^{10}$ and $R^{15}$ is independently selected from H, $C_1$-$C_{10}$ hydrocarbyl or from $C_1$-$C_5$ hydrocarbyl, wherein each hydrocarbyl is optionally substituted, two geminal $R^5$, $R^{10}$ and/or $R^{15}$ groups are oxo, or two geminal $R^5$, $R^{10}$ and/or $R^{15}$ groups form a 3, 4, 5, 6, or 7-membered carbocyclyl or heterocyclyl, wherein the carbocyclyl or heterocyclyl is optionally substituted. Mor is selected from:

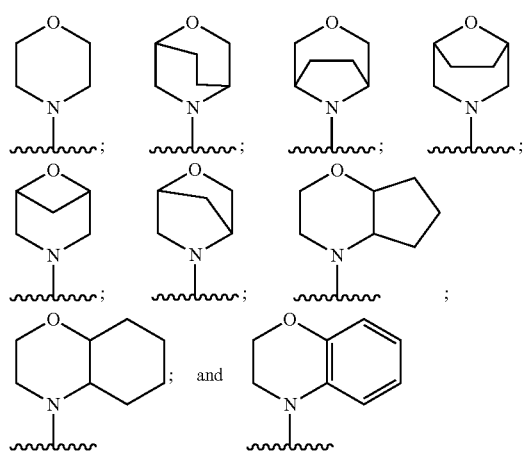

wherein mor is optionally substituted with one or more $R^7$ groups independently selected from F, Cl, Br, I, $-CH_3$, $-CH_2CH_3$, $-CH_2CH_2CH_3$, $-CH(CH_3)_2$, $-C(CH_3)_3$, $-CH_2OCH_3$, $-CHF_2$, $-CN$, $-CF_3$, $-CH_2OH$, $-CH_2OCH_3$, $-CH_2CH_2OH$, $-CH_2C(CH_3)_2OH$, $-CH(CH_3)OH$, $-CH(CH_2CH_3)OH$, $-CH_2CH(OH)CH_3$, $-C(CH_3)_2OH$, $-C(CH_3)_2OCH_3$, $-CH(CH_3)F$, $-C(CH_3)F_2$, $-CH(CH_2CH_3)F$, $-C(CH_2CH_3)_2F$, $-CO_2H$, $-CONH_2$, $-CON(CH_2CH_3)_2$, $-COCH_3$, $-CON(CH_3)_2$, $-NO_2$, $-NH_2$, $-NHCH_3$, $-N(CH_3)_2$, $-NHCH_2CH_3$, $-NHCH(CH_3)_2$, $-NHCH_2CH_2OH$, $-NHCH_2CH_2OCH_3$, $-NHCOCH_3$, $-NHCOCH_2CH_3$, $-NHCOCH_2OH$, $-NHS(O)_2CH_3$, $-N(CH_3)S(O)_2CH_3$, $=O$, $-OH$, $-OCH_3$, $-OCH_2CH_3$, $-OCH(CH_3)_2$, $-SH$, $-NHC(O)NHCH_3$, $-NHC(O)NHCH_2CH_3$, $-S(O)CH_3$, $-S(O)CH_2CH_3$, $-S(O)_2CH_3$, $-S(O)_2NH_2$, $-S(O)_2NHCH_3$, $-S(O)_2N(CH_3)_2$, and $-CH_2S(O)_2CH_3$. In formula I $R^{20}$ is $-OH$ or $-NHR^{21}$, $R^{21}$ is as defined for $R^5$, and in formula IIa $R^{20}$ is $-O-$ or $-NR^{21}-$.

In some other embodiments, the disclosure relates to a process for preparing a compound of Formula IIIa from a compound of Formula IIa according to the following reaction scheme, wherein compound Formula IIa is prepared according to the process described immediately above:

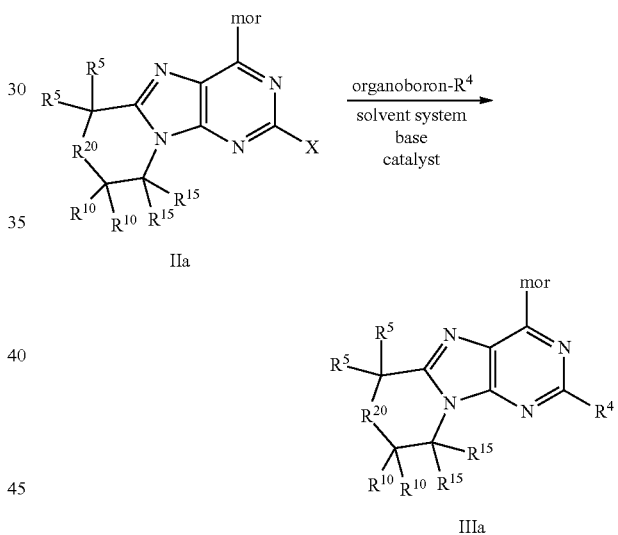

The process comprises: (i) forming a reaction mixture comprising compound Formula IIa, organoboron-$R^4$, the solvent system comprising at least 5 v/v % water, the base and the catalyst; (ii) reacting the reaction mixture to form a reaction product mixture comprising compound Formula IIIa; and (iii) isolating compound Formula IIIa, a stereoisomer, geometric isomer, tautomer, or a pharmaceutically acceptable salt thereof, from the reaction product mixture by solid liquid separation wherein the yield of compound Formula IIIa is at least 75%.

The catalyst comprises palladium and the reaction mixture comprises less than 0.05 equivalents of catalyst per equivalent of compound Formula IIa.

$R^4$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, $-CH_3$, $-CH_2CH_3$, $-CH(CH_3)_2$, $-CH_2CH(CH_3)_2$, $-CH_2CH_3$, $-CH_2CN$, $-CN$, $-CF_3$, $-CH_2OH$, $-CO_2H$, $-CONH_2$, $CONH(CH_3)$, $-CON(CH_3)_2$, $-NO_2$, $-NH_2$, —NHCH$_3$, —NHCOCH$_3$, —OH, —OCH$_3$, —OCH$_2$CH$_3$, —OCH(CH$_3$)$_2$, —SH, —NHC(O)NHCH$_3$, —NHC(O)NHCH$_2$CH$_3$, —NHS(O)$_2$CH$_3$, —N(CH$_3$)C(O)OC(CH$_3$)$_3$, —S(O)$_2$CH$_3$, benzyl, benzyloxy, morpholinyl, morpholinomethyl, and 4-methylpiperazin-yl. Each R$^5$, R$^{10}$ and R$^{15}$ is independently selected from H, C$_1$-C$_{10}$ hydrocarbyl or from C$_1$-C$_5$ hydrocarbyl, wherein each hydrocarbyl is optionally substituted, two geminal R$^5$, R$^{10}$ and/or R$^{15}$ groups are oxo, or two geminal R$^5$, R$^{10}$ and/or R$^{15}$ groups form a 3, 4, 5, 6, or 7-membered carbocyclyl or heterocyclyl, wherein the carbocyclyl or heterocyclyl is optionally substituted.

In some other embodiments, the disclosure relates to a method for treating cancer in a patient wherein the cancer is characterized by the overexpression of PI3 kinase, the method comprising administering a therapeutically effective amount of a PI3 kinase inhibitor compound of Formula III as previously defined to a person in need of such treatment.

DETAILED DESCRIPTION

Figure 1:
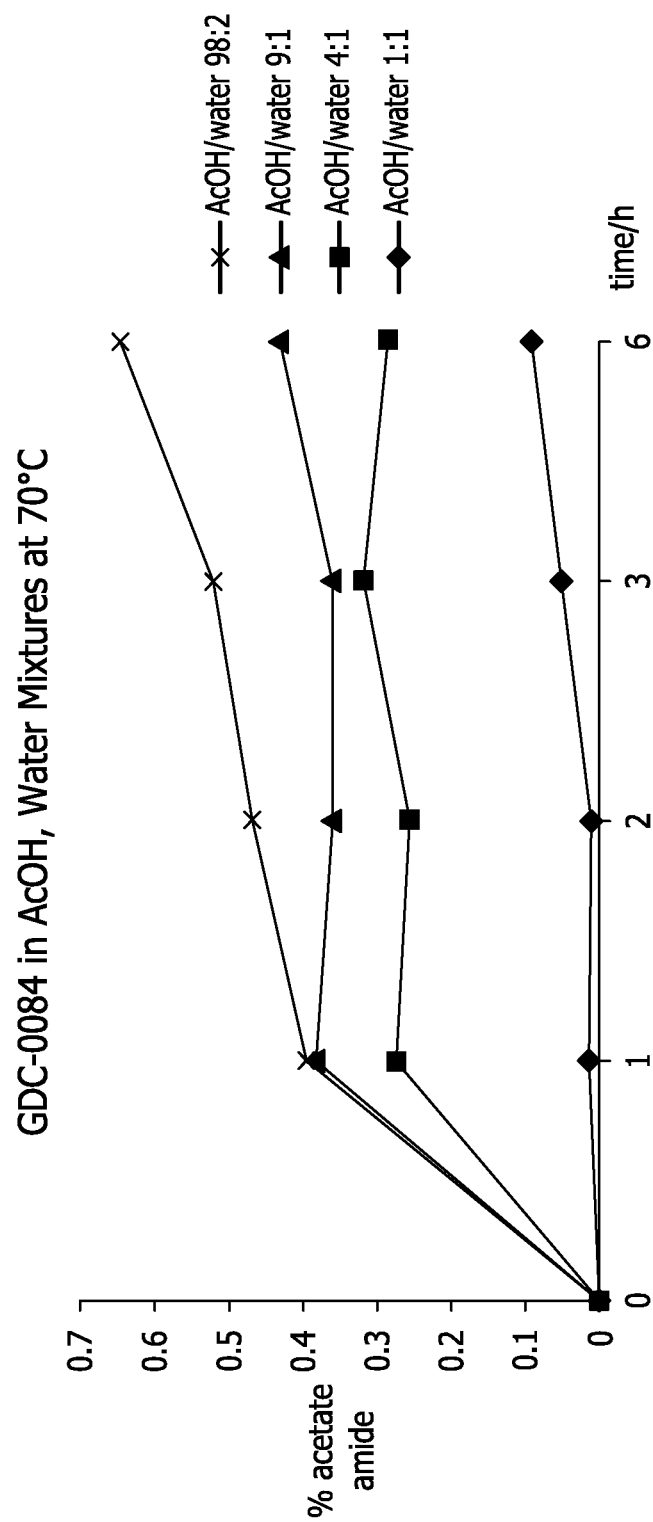
FIG. 1 shows a plot of the amide impurity of 5-(6,6-dimethyl-4-morpholino-8,9-dihydro-6h-[1,4]oxazino[3,4-e]purin-2-yl)pyrimidin-2-amine during crystallization from an acetic acid-water solvent system at ratios of acetic acid to water of 1:1 v/v %, 4:1 v/v %, 9:1 v/v % and 98:2 v/v %.

Reference will now be made in detail to certain embodiments of the disclosure, examples of which are illustrated in the accompanying structures and formulas. While the disclosure will be described in conjunction with the enumerated embodiments, it will be understood that they are not intended to limit the disclosure to those embodiments. On the contrary, the disclosure is intended to cover all alternatives, modifications, and equivalents which may be included within the scope of the present disclosure as defined by the claims. One skilled in the art will recognize many methods and materials similar or equivalent to those described herein, which could be used in the practice of the present disclosure. The present disclosure is in no way limited to the described methods and materials. In the event that one or more of the incorporated literature, patents, and similar materials differs from or contradicts this application, including but not limited to defined terms, term usage, described techniques, or the like, this application prevails.

The present disclosure provides improved processes for preparing tricyclic PI3K inhibitor compounds of Formula III from compounds of Formula II by Suzuki coupling according to reaction scheme (1):

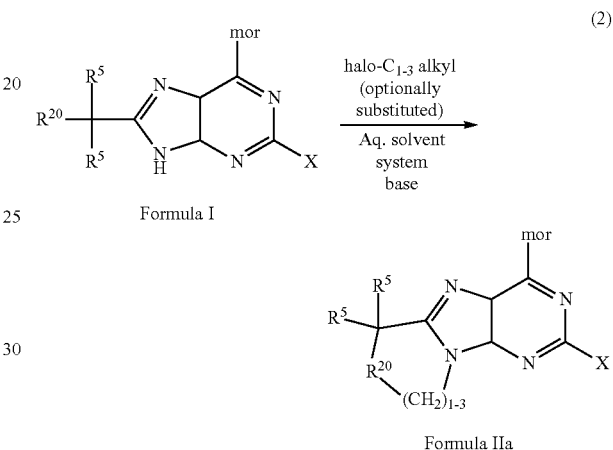

wherein $X^1$, $X^2$, $X^3$, A, mor, $X^4$, organoboron, $R^4$, the solvent system, the base and the catalyst are defined elsewhere herein. The A ring may be optionally substituted with one or more $R^5$, $R^{10}$ and/or $R^{15}$ groups as defined elsewhere herein. As compared to known processes, the appropriate selection of at least one process variable from among the catalyst comprising Pd, the base species, the solvent system, and the/or reaction temperature range, or alternatively the appropriate selection of 2, 3 or all 4 of these process variables, provides for the improved yield and/or purity of Formula III, thus enabling the elimination of one or more process steps and/or purification steps.

The present disclosure further provides processes for forming tricyclic compounds of Formula IIa from bicyclic compounds precursor compounds of Formula I by annulation through condensation with an alkyl halide according to reaction scheme (2):

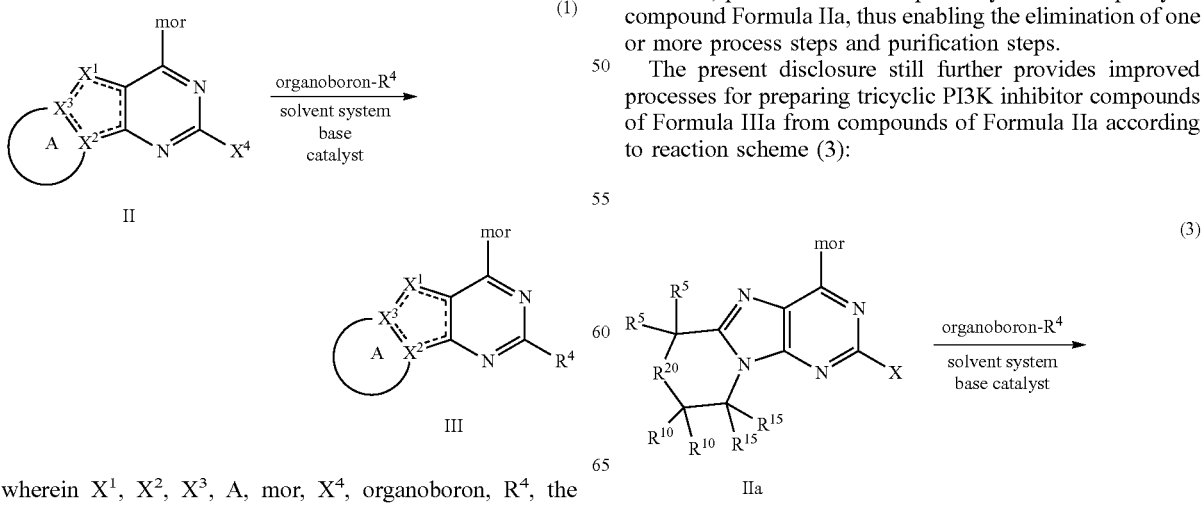

wherein $R^5$, $R^{20}$, mor, X, the aqueous solvent system, and the base are defined elsewhere herein. The halo-$C_{1-3}$ may be optionally substituted with one or more $R^{10}$ or $R^{15}$ groups as defined elsewhere herein. The formed ring may be optionally substituted with one or more $R^5$, $R^{10}$ and/or $R^{15}$ groups as defined elsewhere herein. As compared to known processes, the appropriate selection of at least one process variable from among the solvent system, a phase transfer catalyst, the equivalent ratio of two or more of the reactants, and/or the reaction temperature range, or alternatively the appropriate selection of 2, 3 or all 4 of these process variables, provides for the improved yield and/or purity of compound Formula IIa, thus enabling the elimination of one or more process steps and purification steps.

The present disclosure still further provides improved processes for preparing tricyclic PI3K inhibitor compounds of Formula IIIa from compounds of Formula IIa according to reaction scheme (3):

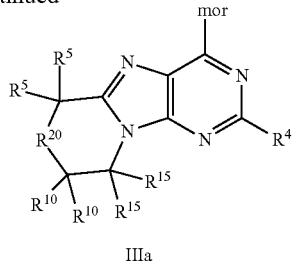

IIIa wherein $R^5$, $R^{10}$, $R^{15}$, $R^{20}$, mor, X and $R^4$ are as defined elsewhere herein. Reaction scheme (3) proceeds generally in accordance with reaction scheme (1).

As further detailed below, the present disclosure still further provides method of treatment using the above-noted tricyclic PI3K inhibitor compounds.

A. SUZUKI COUPLING

In the Suzuki coupling reaction of reaction scheme (1) and reaction scheme (3), a reaction product mixture comprising compound Formula III or IIIa, a stereoisomer, a geometric isomer, a tautomer, or a pharmaceutically acceptable salt thereof, is formed from a reaction mixture comprising a compound Formula II or IIa, a solvent system comprising water, an organoboron-$R^4$, a base and less than 0.05 equivalents of a catalyst comprising palladium per equivalent of the compound Formula II or IIa.

In reaction scheme (1): $X^1$ is S, O, $NR^a$, $CR^1$, $C(R^1)_2$ or $C(R^1)_2O$, wherein $R^1$ is as further defined below; $X^2$ is C, $CR^2$ or N, wherein $R^2$ is as further defined below; $X^3$ is C, $CR^3$ or N, wherein $R^3$ is as further defined below; $X^4$ is a halogen; the dashed lines represent an optional double bond; $R^4$ is an optionally substituted $C_6$-$C_{20}$ aryl, $C_2$-$C_{20}$ heterocyclyl or $C_1$-$C_{20}$ heteroaryl; A is a 5, 6, or 7-membered carbocyclyl or heterocyclyl ring fused to $X^2$ and $X^3$, optionally substituted with one or more $R^5$, $R^{10}$ and/or $R^{15}$ groups, wherein each $R^5$, $R^{10}$ and $R^{15}$ is independently H, halogen, oxo, hydroxyl, nitro, amino, hydrocarbyl, or substituted hydrocarbyl, two geminal $R^5$, $R^{10}$ and/or $R^{15}$ groups are oxo, or two geminal $R^5$, $R^{10}$ and/or $R^{15}$ groups form a 3, 4, 5, 6, or 7-membered carbocyclyl or heterocyclyl, wherein the carbocyclyl or heterocyclyl is optionally substituted; and mor is an morpholine ring optionally substituted with one or more $R^7$ groups as defined elsewhere herein.

In some aspects of the disclosure, $X^1$ is N, $NR^a$, $CR^1$, $C(R^1)_2$ or $C(R^1)_2O$ and $X^3$ is C or $CR^3$. In some other aspects, $X^1$ and $X^2$ are N, and $X^3$ is C.

In some aspects of the disclosure, A is an optionally substituted 6-membered heterocycle comprising at least one heteroatom selected from N and O. In some other aspects, A is optionally substituted morpholine.

In some aspects of the disclosure, $R^6$ is H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)(—$C_2$-$C_{20}$ heterocyclyl), —($C_1$-$C_{12}$ alkylene)-C(=O)—($C_2$-$C_{20}$ heterocyclyl), ($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CO_2H$, —$COCH_3$, —$COC(CH_3)_3$, —$CO_2CH_3$, —$CONH_2$, —$CONHCH_3$, —$CON(CH_3)_2$, —C($CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxothiopyran-4-yl. In some aspects $R^6$ is H or $C_{1-4}$ alkyl. In still other aspects, $R^6$ is H or methyl.

In some aspects, $R^1$, $R^2$, and $R^3$ are independently selected H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2$, —$CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxothiopyran-4-yl.

In reaction scheme (3), each $R^5$, $R^{10}$ and $R^{15}$ is independently selected from H, $C_{1-10}$ hydrocarbyl or from $C_{1-5}$ hydrocarbyl, wherein each hydrocarbyl is optionally substituted, two geminal $R^5$, $R^{10}$ and/or $R^{15}$ groups together are oxo, two geminal $R^5$, $R^{10}$ and/or $R^{15}$ groups together form a 3, 4, 5, 6, or 7-membered carbocyclyl or heterocyclyl, wherein the carbocyclyl or heterocyclyl is optionally substituted. $R^{20}$ in ring A is —O— or —$NR^{21}$—, and $R^{21}$ is as defined for $R^5$.

In reaction schemes (1) and (3) the organoboron is generally any species suitable to achieve the desired yield and/or purity disclosed herein. Examples of organoborons are included in A. Lennox and G Lloyd-Jones, *Selection of boron reagents for Suzuki-Miyaura coupling, Chem. Soc. Rev.*, 2014, 412-443. Non-limiting examples of organoborons include 5-(4,4,5,5-tetramethyl-1,3,2-dioxaborolan-2 yl), boronic acid pinacol ester, pinacol boronic ester, boronic acids, and organotrifluoroborates. In some particular aspects, the organoboron is 5-(4,4,5,5-tetramethyl-1,3,2-dioxaborolan-2 yl).

In some aspects of the disclosure, in reaction schemes (1) and (3), $R^4$ is independently selected from $C_{6-20}$ aryl, $C_{2-20}$ heterocyclyl and $C_{1-20}$ heteroaryl, each of which are optionally substituted with one or more groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —CN, —$CF_3$, —$CH_2OH$, —$CO_2H$, —$CONH_2$, —$CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —NHC(O)$NHCH_3$, —NHC(O)$NHCH_2CH_3$, —$NHS(O)_2CH_3$, —$N(CH_3)C(O)OC(CH_3)_3$, —$S(O)_2CH_3$, benzyl, benzyloxy, morpholinyl, morpholinomethyl, and 4-methylpiperazin-1-yl. In other aspects, $R^4$ is optionally substituted $C_6$ heteroaryl comprising one or two N heteroatoms, or is optionally substituted pyrimidine. In other aspects, $R^4$ is phenyl substituted with one or more groups selected from F, Cl, Br, I, —$CH_3$, —$CH_2CH_3$, —CH(CH3)2, —CN, —$CF_3$, —$CH_2OH$, —$CO_2H$, —$CONH_2$, —$CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —NHC(=O)$NHCH_3$, —NHC(=O)$NHCH_2CH_3$, —$NHS(O)_2CH_3$, —$N(CH_3)C(=O)OC(CH_3)_3$, and —$S(O)_2CH_3$. In still other aspects, $R^4$ is an optionally substituted bicyclic heteroaryl group selected from 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]

pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1 (2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine. In yet other aspects, $R^4$ is an optionally substituted monocyclic heteroaryl group selected from 2-furanyl, 3-furanyl, 2-imidazolyl, 4-imidazolyl, 3-isoxazolyl, 4-isoxazolyl, 5-isoxazolyl, 2-oxazolyl, 4-oxazolyl, 5-oxazolyl, 3-pyrazolyl, 4-pyrazolyl, 2-pyrazinyl, 3-pyridazinyl, 4-pyridazinyl, 5-pyridazinyl, 2-pyrimidinyl, 5-pyrimidinyl, 6-pyrimidinyl, 2-pyridyl, 3-pyridyl, 4-pyridyl, 2-pyrrolyl, 3-pyrrolyl, 2-thienyl, 3-thienyl, 5-tetrazolyl, 1-tetrazolyl, 2-tetrazolyl, 2-thiazolyl, 4-thiazolyl, 5-thiazolyl, 3-triazolyl, and 1-triazolyl. In some aspects, $R^4$ is an optionally substituted monocyclic heteroaryl group selected from pyridyl, pyrimidinyl and pyrazolyl. In some other aspects, $R^4$ is an optionally substituted monocyclic pyrimidinyl. In some aspects $R^4$ is 1H-imidazol-4-yl or 2-aminopyrimidin-yl. In some particular aspects, $R^4$ is the optionally substituted moiety $R^4cb$ depicted below.

Non-limiting examples of the $R^4$ moiety include the following wherein each may optionally be substituted and wherein the wavy line indicates the site of attachment:

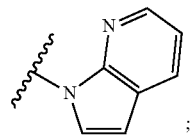
$R^4a$

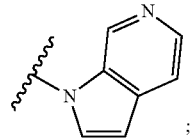
$R^4b$

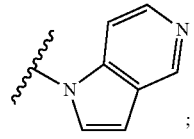
$R^4c$

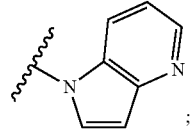
$R^4d$

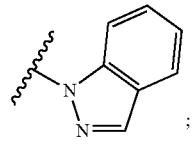
$R^4e$

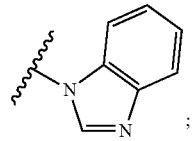
$R^4f$

-continued

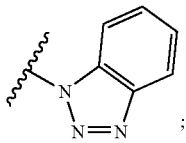
$R^4g$

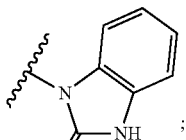
$R^4h$

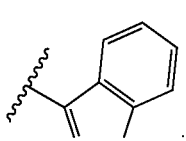
$R^4i$

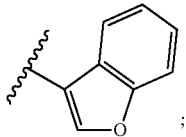
$R^4j$

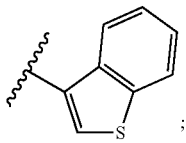
$R^4k$

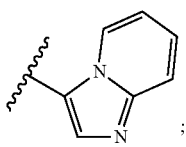
$R^4l$

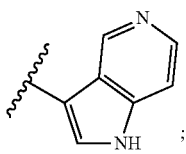
$R^4m$

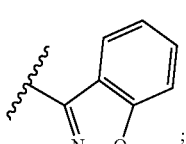
$R^4n$

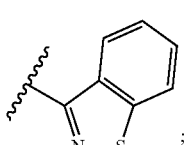
$R^4o$

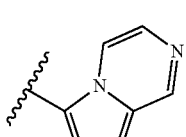
$R^4p$

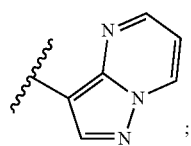 R⁴q
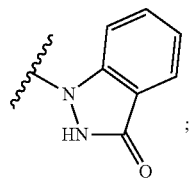 R⁴r
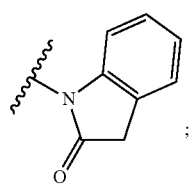 R⁴s
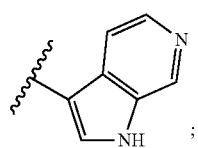 R⁴t
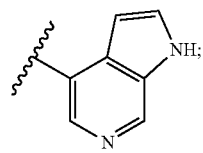 R⁴u
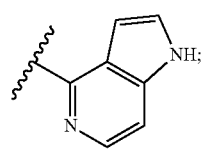 R⁴v
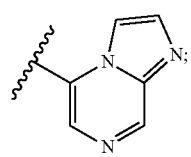 R⁴w
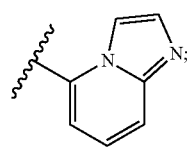 R⁴x
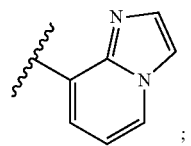 R⁴y
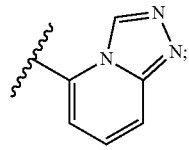 R⁴z
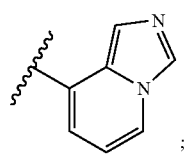 R⁴aa
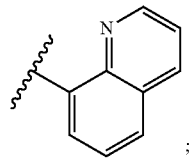 R⁴ab
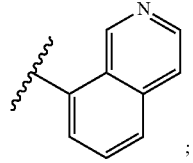 R⁴ac
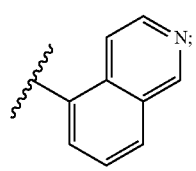 R⁴ad
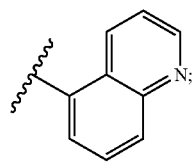 R⁴ae
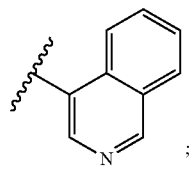 R⁴af
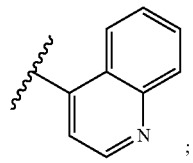 R⁴ag
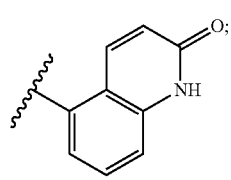 R⁴ah -continued
R⁴ai 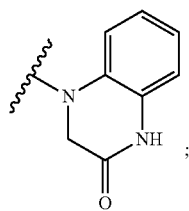;
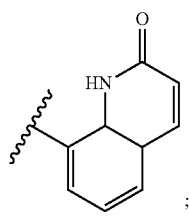;
R⁴aj 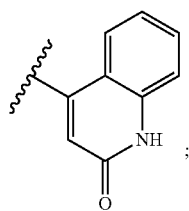;
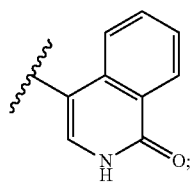;
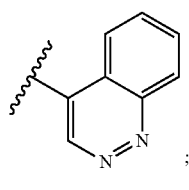;
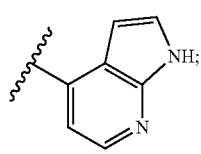;
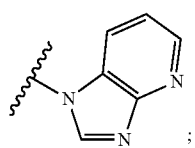;
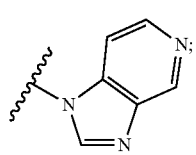;
-continued
R⁴aq 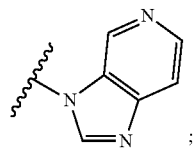;
R⁴ar 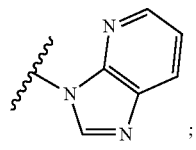;
R⁴as 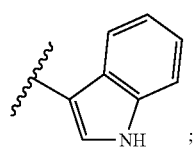;
R⁴at 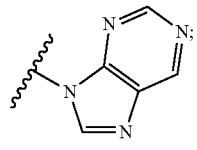;
R⁴au 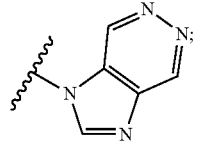;
R⁴av 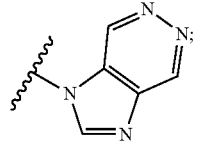;
R⁴aw 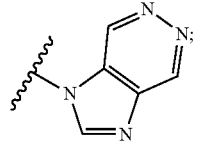;
R⁴ax 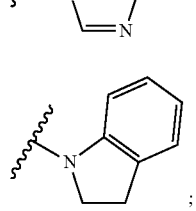;
R⁴ay 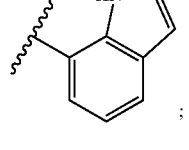;
R⁴az 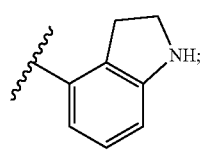;
R⁴ak
R⁴al
R⁴am
R⁴an
R⁴ao
R⁴ap -continued
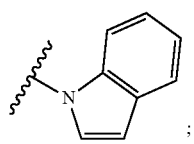 ;
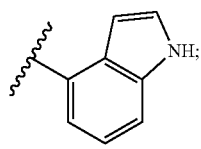 ;
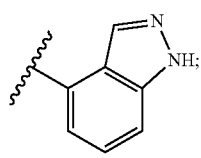 ;
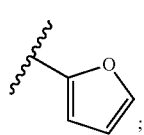 ;
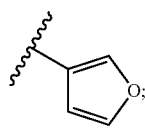 ;
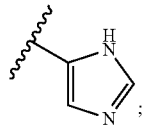 ;
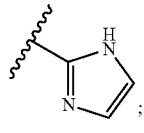 ;
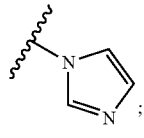 ;
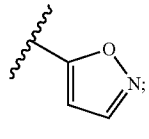 ;
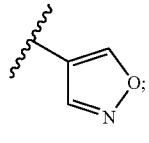 ;
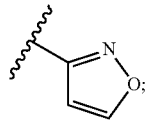 ;
-continued
R⁴ba
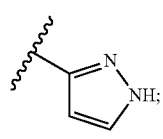 ;
R⁴bb
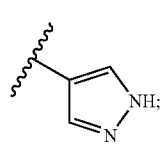 ;
R⁴bc
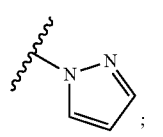 ;
R⁴bd
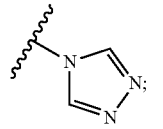 ;
R⁴be
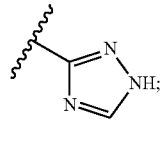 ;
R⁴bf
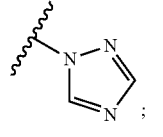 ;
R⁴bg
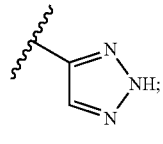 ;
R⁴bh
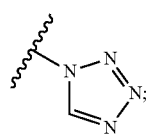 ;
R⁴bi
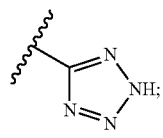 ;
R⁴bj
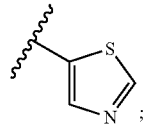 ;
R⁴bk
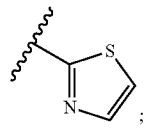 ;
R⁴bl
R⁴bm
R⁴bn
R⁴bo
R⁴bp
R⁴bq
R⁴br
R⁴bs
R⁴bt
R⁴bu
R⁴bv -continued R⁴bw 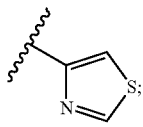

R⁴bx 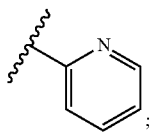

R⁴by 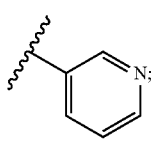

R⁴bz 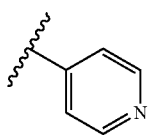

R⁴ca 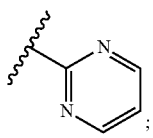

R⁴cb 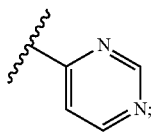

R⁴cc 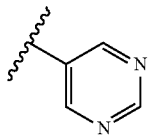

R⁴cd 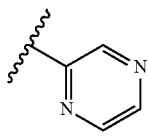

R⁴ce 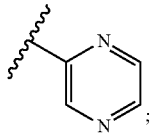

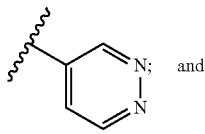 and

-continued

R⁴cf 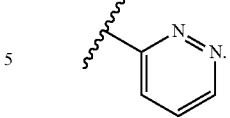

R⁴bw

In some aspects, $R^5$, $R^{10}$ and $R^{15}$ are independently selected from $C_{1-12}$ alkyl, $C_{2-8}$ alkenyl, $C_{2-8}$ alkynyl, —($C_{1-12}$ alkylene)-($C_{3-12}$ carbocyclyl), —($C_{1-12}$ alkylene)-($C_{2-20}$ heterocyclyl), —($C_{1-12}$ alkylene)-C(O)—($C_{2-20}$ heterocyclyl), —($C_{1-12}$ alkylene)-($C_{6-20}$ aryl), and —($C_{1-12}$ alkylene)-($C_{1-20}$ heteroaryl); or two geminal $R^5$, $R^{10}$ and/or $R^{15}$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —CH₃, —CH₂CH₃, —C(CH₃)₃, —CH₂OH, —CH₂CH₂OH, —C(CH₃)₂OH, —CH₂OCH₃, —CN, —CH₂F, —CHF₂, —CF₃, —CO₂H, —COCH₃, —COC(CH₃)₃, —CO₂CH₃, —CONH₂, —CONHCH₃, —CON(CH₃)₂, —C(CH₃)₂CONH₂, —NO₂, —NH₂, —NHCH₃, —N(CH₃)₂, —NH—COCH₃, —NHS(O)₂CH₃, —N(CH₃)C(CH₃)₂CONH₂, —N(CH₃)CH₂CH₂S(O)₂CH₃, =O, —OH, —OCH₃, —S(O)₂N(CH₃)₂, —SCH₃, —S(O)₂CH₃, cyclopropyl, cyclobutyl, oxetanyl, morpholino, and 1,1-dioxo-thiopyran-4-yl.

In some aspects, $R^5$, $R^{10}$ and $R^{15}$ are independently $C_{1-12}$ alkyl optionally substituted with one or more groups selected from F, Cl, Br, I, —CH₃, —CH₂CH₃, —C(CH₃)₃, —CH₂OH, —CH₂CH₂OH, —C(CH₃)₂OH, —CH₂OCH₃, —CN, —CH₂F, —CHF₂, —CF₃, —CO₂H, —COCH₃, —COC(CH₃)₃, —CO₂CH₃, —CONH₂, —CONHCH₃, —CON(CH₃)₂, —C(CH₃)₂CONH₂, —NO₂, —NH₂, —NHCH₃, —N(CH₃)₂, —NHCOCH₃, —NHS(O)₂CH₃, —N(CH₃)C(CH₃)₂CONH₂, —N(CH₃)CH₂CH₂S(O)₂CH₃, =O, —OH, —OCH₃, —S(O)₂N(CH₃)₂, —SCH₃, —S(O)₂CH₃, cyclopropyl, cyclobutyl, oxetanyl, morpholino, and 1,1-dioxo-thiopyran-4-yl. In some aspects, $R^{10}$ and $R^{15}$ are hydrogen and $R^5$ is methyl optionally substituted with one or more groups as defined herein, and in particular may be substituted with one or more substituents selected from F, OH and =O.

In some other aspects, one or more $R^5$, $R^{10}$ and/or $R^{15}$ groups are independently selected from H, F, Cl, Br, I, —CH₃, —CH₂CH₃, —C(CH₃)₃, —CH₂OH, —CH₂CH₂OH, —C(CH₃)₂OH, —CH₂OCH₃, —CN, —CH₂F, —CHF₂, —CF₃, —CO₂H, —COCH₃, —COC(CH₃)₃, —CO₂CH₃, —CONH₂, —CONHCH₃, —CON(CH₃)₂, —C(CH₃)₂CONH₂, —NO₂, —NH₂, —NHCH₃, —N(CH₃)₂, —NHCOCH₃, —NHS(O)₂CH₃, —N(CH₃)C(CH₃)₂CONH₂, —N(CH₃)CH₂CH₂S(O)₂CH₃, =O, —OH, —OCH₃, —S(O)₂N(CH₃)₂, —SCH₃, —S(O)₂CH3, cyclopropyl, cyclobutyl, oxetanyl, morpholino, and 1,1-dioxo-thiopyran-4-yl.

Non-limiting examples of mor include the following where the wavy line indicates the site of attachment:

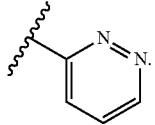 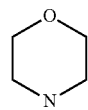 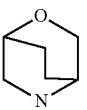 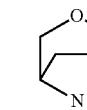

mor-a   mor-b   mor-c   mor-d

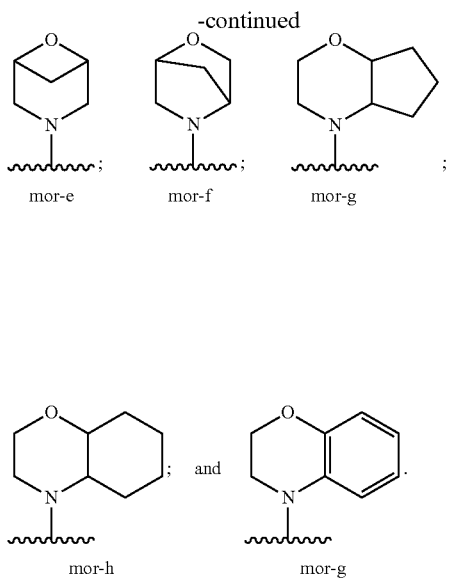

mor-e; mor-f; mor-g;

mor-h   and   mor-g.

In this regard it is to be noted that one or more of the carbon atoms in the above illustrated rings for mor may be optionally substituted with one or more $R^7$ groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH2OH$, —$CH_2C(CH_3)_2OH$, —$CH(CH_3)OH$, —CH$(CH_2CH_3)OH$, —$CH_2CH(OH)CH_3$, —$C(CH_3)_2OH$, —$C(CH_3)_2OCH_3$, —$CH(CH_3)F$, —$C(CH_3)F_2$, —CH$(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —NHCH$(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, =O, —OH, —$OCH_3$, —$OCH_2CH_3$, —$OCH(CH_3)_2$, —SH, —NHC(O)NHCH_3$, —$NHC(O)NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, and —$CH_2S(O)_2CH_3$. In some aspects, mor is mor-a depicted above.

It is to be understood that every embodiment relating to a specific residue, $X^1$, $X^2$, $X^3$, A, $R^1$, $R^2$, $R^3$, $R^4$, $R^5$, $R^6$, $R^7$, $R^{10}$, $R^{15}$ and mor as disclosed herein may be combined with any other embodiment relating to another residue $X^1$, $X^2$, $X^3$, A, $R^1$, $R^2$, $R^3$, $R^4$, $R^5$, $R^6$, $R^7$, $R^1$, $R^{15}$ and mor as disclosed herein.

The catalyst comprising palladium is generally any such catalyst suitable to achieve the yield and purity disclosed herein. In some aspects, the catalyst comprising palladium is selected from chloro(2-dicyclohexylphosphino-2',4',6'-triisopropyl-1,1'-biphenyl)[2-(2-aminoethyl) phenyl)]palladium(II) (e.g., "Xphos PdG1", "Xphos PdG2" and "Xphos PdG3"); 1,1'-bis(diphenylphosphino)ferrocene] dichloropalladium(II) complex with dichloromethane ("PdCl$_2$(dppf) .CH$_2$Cl$_2$"); Bis(di-tert-butyl(4-dimethylaminophenyl)phosphine)dichloropalladium(II) ("Pd(amphos)Cl$_2$"); dichlorobis(di-tert-butylphenylphosphine)palladium(II); Dichlorobis(di-tert-butylphenylphosphine)palladium(II) ("PdCl$_2$[($^t$Bu$_2$Ph)P]$_2$"); PdCl$_2$(PPh$_3$)$_2$; Chloro(2-dicyclohexylphosphino-2',4',6'-triisopropyl-1,1'-biphenyl)[2-(2'-amino-1,1'-biphenyl)]palladium(II) (Xphos pD G2) of the structure:

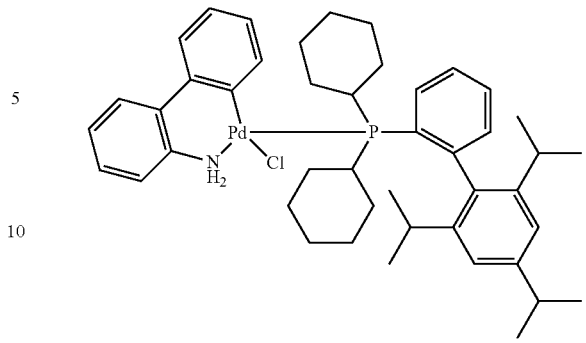

Pd(t-Bu)$_3$; Pd(PPh$_3$)$_4$; Pd(OAc)/PPh$_3$; Cl$_2$Pd[(Pet$_3$)]$_2$; Pd(DIPHOS)$_2$; Cl$_2$Pd(Bipy); [PdCl(Ph$_2$PCH$_2$PPh$_2$)]$_2$; Cl$_2$Pd[P(o-tol)$_3$]$_2$, Pd$_2$(dba)$_3$/P(o-tol)$_3$; Pd$_2$(dba)/P(furyl)$_3$; Cl$_2$Pd[P(furyl)$_3$]$_2$; Cl$_2$Pd(PmePh$_2$)$_2$; Cl$_2$Pd[P(4-F-Ph)$_3$]$_2$; Cl$_2$Pd[P(C$_6$F$_6$)$_3$]$_2$; Cl$_2$Pd[P(2-COOH-Ph)(Ph)$_2$]$_2$; Cl$_2$Pd[P(4-COOH-Ph)(Ph)$_2$]$_2$; and encapsulated catalysts Pd EnCat™ 30 (palladium acetate, microencapsulated in a polyuria matrix, comprising 0.4 mmol/g Pd), Pd EnCat™ TPP30 (palladium acetate and triphenylphosphine, microencapsulated in a polyuria matrix, comprising 0.4 mmol/g Pd and 0.3 mmol/g phosphorous), and Pd(II)EnCat™ BINAP30 (palladium acetate and BINAP, microencapsulated in a polyuria matrix, comprising 0.4 mmol/g Pd—see e.g., U.S. Pat. Application Pub. No. 2004/0254066, which is incorporated by reference herein). In some other aspects, the catalyst comprising palladium is selected from chloro(2-dicyclohexylphosphino-2',4',6'-triisopropyl-1,1'-biphenyl)[2-(2-aminoethyl) phenyl)]palladium(II) and 1,1'-bis(diphenylphosphino)ferrocene]dichloropalladium(II) complex with dichloromethane, or is chloro(2-dicyclohexylphosphino-2',4',6'-triisopropyl-1,1'-biphenyl)[2-(2-aminoethyl) phenyl)]palladium(II). In some aspects, the catalyst is chloro(2-dicyclohexylphosphino-2',4',6'-triisopropyl-1,1'-biphenyl)[2-(2-aminoethyl) phenyl)]palladium(II) or 1,1'-bis(diphenylphosphino)ferrocene]dichloropalladium(II) complex with dichloromethane. In other aspects, the catalyst comprising palladium is chloro(2-dicyclohexylphosphino-2',4',6'-triisopropyl-1,1'-biphenyl)[2-(2-aminoethyl) phenyl)]palladium(II).

The equivalent ratio of the catalyst comprising palladium to compound Formulae II or IIa is typically between about 0.003:1 and about 0.05:1, about 0.003:1 to about 0.03:1 or about 0.004:1 to about 0.02:1. In some particular aspects, the catalyst is chloro(2-dicyclohexylphosphino-2',4',6'-triisopropyl-1,1'-biphenyl)[2-(2-aminoethyl) phenyl)]palladium (II) or 1,1'-bis(diphenylphosphino)ferrocene]dichloropalladium(II) complex with dichloromethane and the equivalent ratio of the catalyst comprising palladium to compound Formulae II or IIa is from about 0.005:1 to about 0.04:1, from about 0.005:1 to about 0.03:1, from about 0.01:1 to about 0.03:1, or about 0.02:1. In some other particular aspects, the catalyst is chloro(2-dicyclohexylphosphino-2',4',6'-triisopropyl-1,1'-biphenyl)[2-(2-aminoethyl) phenyl)] palladium(II) and the equivalent ratio of the catalyst comprising palladium to compound Formulae II or IIa is from about 0.004:1 to about 0.015:1, from about 0.004:1 to about 0.01:1, from about 0.004:1 to about 0.007:1, or about 0.005:1.

The base may in general be selected from any base that is soluble in the solvent system and that is suitable to achieve the desired yield and purity disclosed herein. In some aspects, the base is selected from K₃PO₄, Cs₂CO₃, K₂CO₃, KOAc, NaOAc, Na₂CO₃ and KOH. In some other aspects, the base is K₃PO₄. The equivalent ratio of base to compound Formulae II or IIa is typically at least 1:1, and may be in the range of from about 1:1 to about 3:1 or about 1.5:1 to about 2.5:1. In a particular aspect, the ratio may be about 2:1.

In any of the various aspects of the disclosure, the Suzuki coupling solvent system typically comprises about 5 v/v % water, about 10 v/v % water, about 15 v/v % water, about 20 v/v % water, about 25 v/v % water, or more, and in some aspects may fall within the range of from about 5 v/v % to about 25 v/v %, or about 10 v/v % to about 20 v/v %.

The solvent system further comprises at least one co-solvent typically selected from non-polar solvents, polar protic solvents and polar aprotic solvents. Suitable polar aprotic solvents include, but are not limited to, N-methylpyrrolidone, methyl isobutyl ketone, methyl ethyl ketone, tetrahydrofuran ("THF"), dichloromethane, ethyl acetate, acetone, N,N-dimethylformamide, acetonitrile and dimethyl sulfoxide. Suitable polar protic solvents include, but are not limited to, methanol, ethanol, n-propanol, i-propanol, n-butanol, i-butanol, t-butanol, and acetic acid. Suitable non-polar solvents include dioxane, toluene, hexane, cyclohexane, and diethyl ether.

In some aspects, the solvent system comprises water and at least one polar aprotic solvent. In some other aspects, the solvent system consists essentially of water and a least one polar aprotic solvent. In some further aspects, the ratio of water to the at least one polar aprotic solvent is from about 1:10 v/v to about 5:1 v/v, from about 1:1 v/v to about 1:10 v/v, or from about 1:3 v/v to about 1:7 v/v. In some other aspects, the solvent system consists essentially of water and at least one polar aprotic solvent.

In some aspects, the solvent system comprises water and THF.

The reaction temperature is typically less than 100° C., and in some aspects may be between about 40° C. and 100° C., from about 40° C. to about 90° C., from about 40° C. to about 80° C., from about 50° C. to about 80° C. or from about 55° C. to about 75° C. The reaction time to completion is typically from about 4 hours to about 48 hours, from about 4 hours to about 36 hours, or from about 4 hours to about 24 hours.

Non-limiting examples of compounds of compound Formulae III and/or IIIa include the following wherein R¹, R², R³ and R⁴ are as defined elsewhere herein:

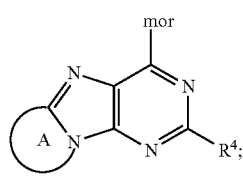

IIIa

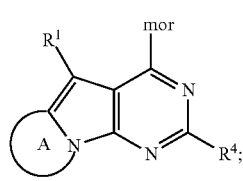

IIIb

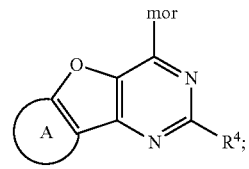

IIIc

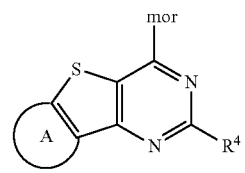

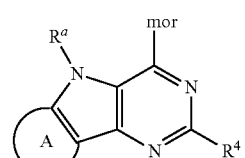

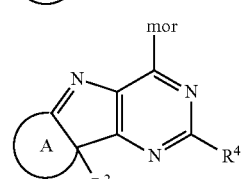

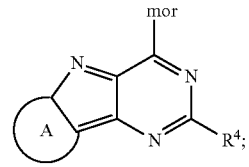

IIIg

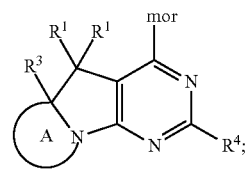

IIIh

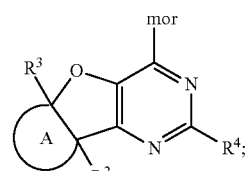

IIIi

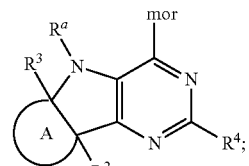

IIIj

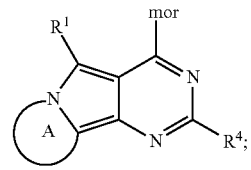

IIIk

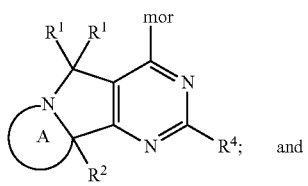    IIIl

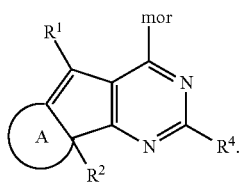    IIIm

In any of the above Formula III compounds, the A ring may be optionally substituted with one or more R⁵, R¹⁰ and/or R¹⁵ groups (not shown), which may be independently selected from those options detailed elsewhere herein.

Further non-limiting examples of compounds of Formulae III and IIIa include wherein R⁴ and R⁵ are as defined elsewhere herein:

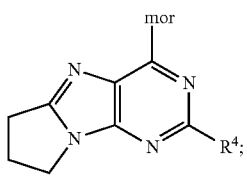    IIIn

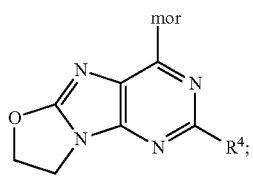    IIIo

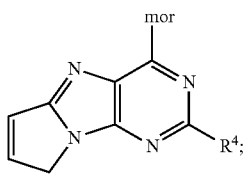    IIIp

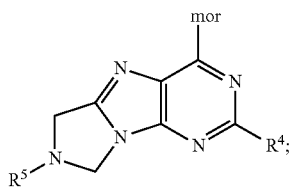    IIIq

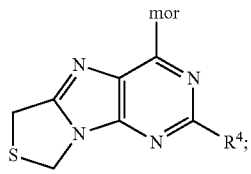    IIIr

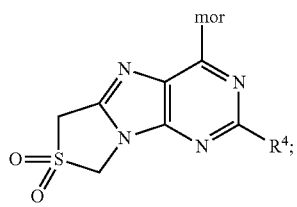    IIIs

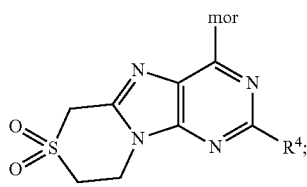    IIIt

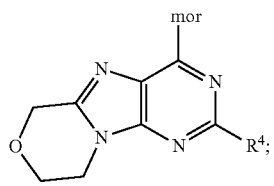    IIIu

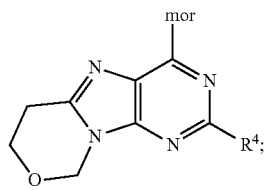    IIIv

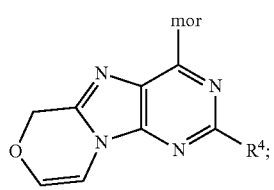    IIIw

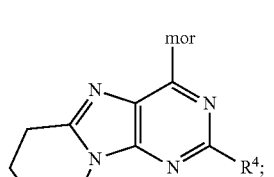    IIIx

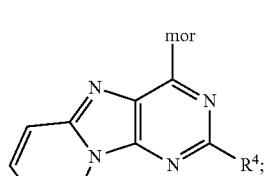    IIIy

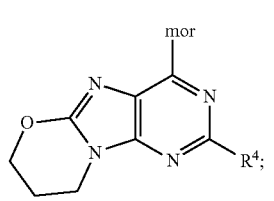    IIIz

-continued
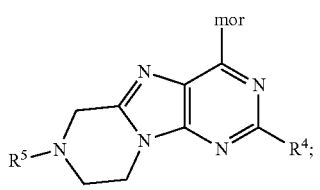
IIIaa
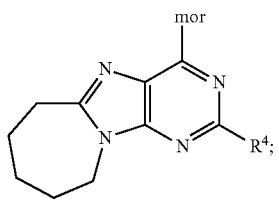
IIIab
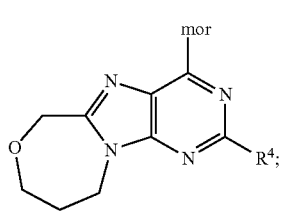
IIIac
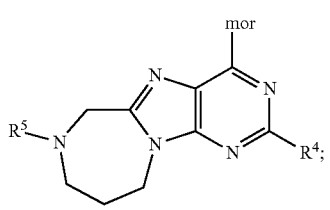
IIIad
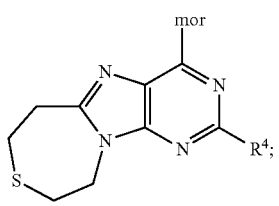
IIIae
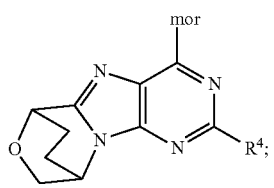
IIIaf
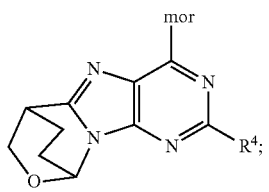
IIIag
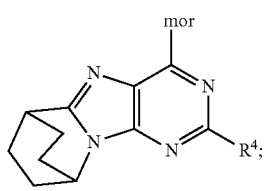
IIIah
-continued
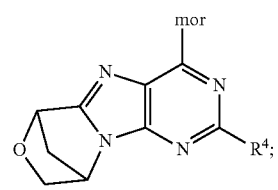
IIIai
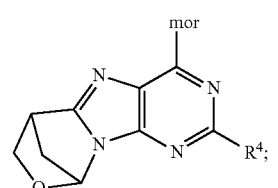
IIIaj
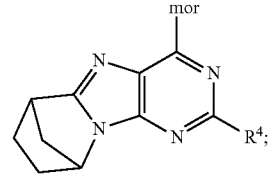
IIIak
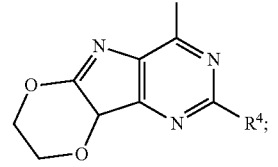
IIIal
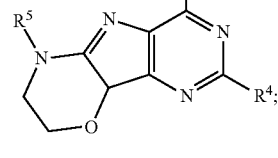
IIIam
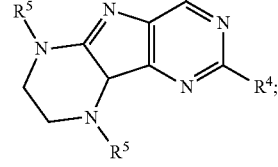
IIIan
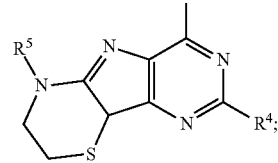
IIIao
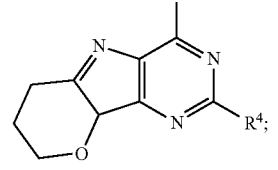
IIIap
and

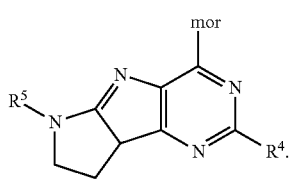
IIIaq
Further non-limiting examples of compounds of Formulae III and/or IIIa include:
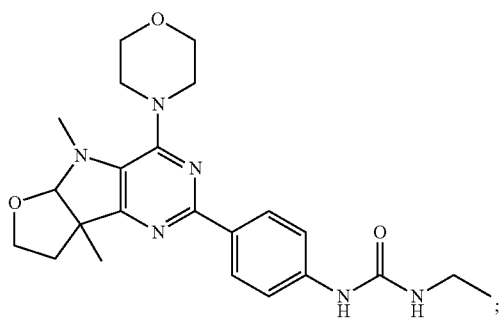
IIIar
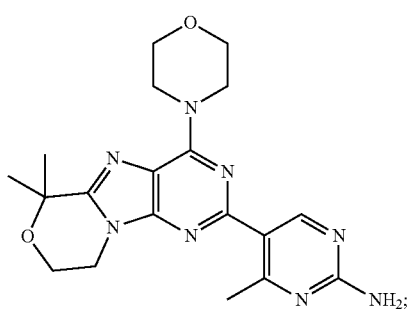
IIIas
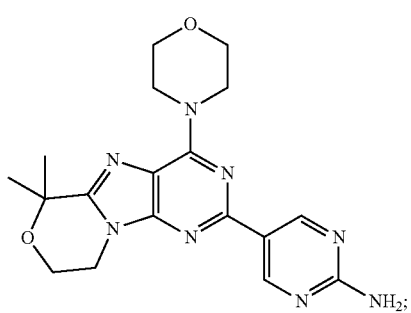
IIIat
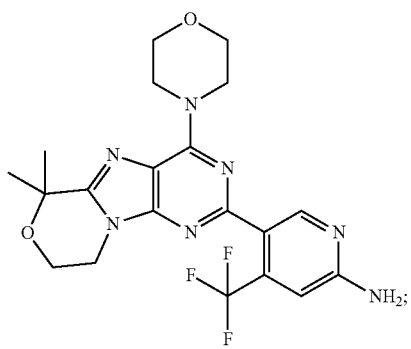
IIIau
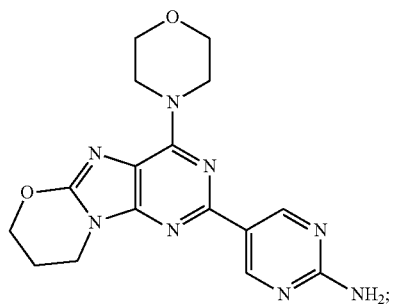
IIIav
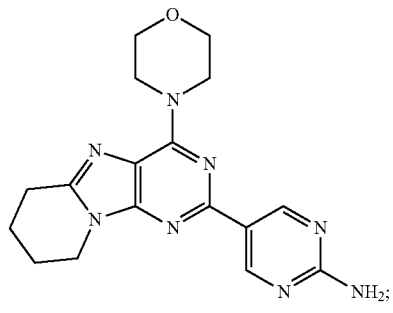
IIIaw
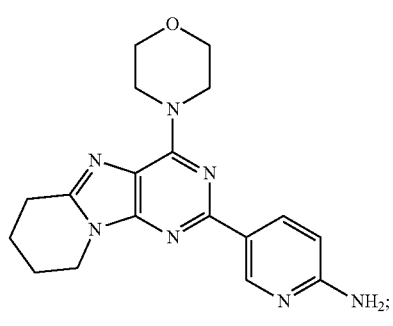
IIIax
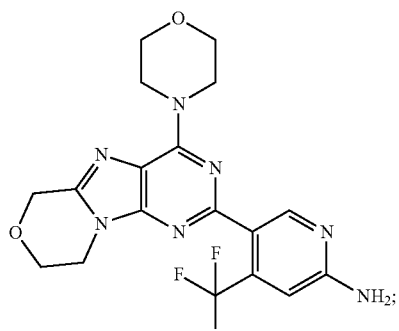
IIIay
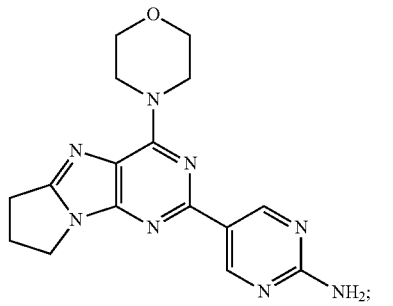
IIIaz

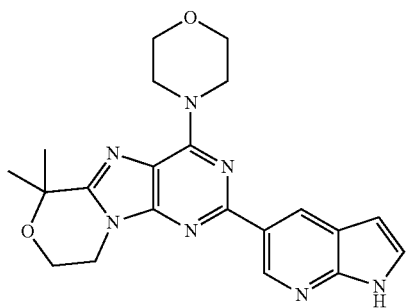
IIIba
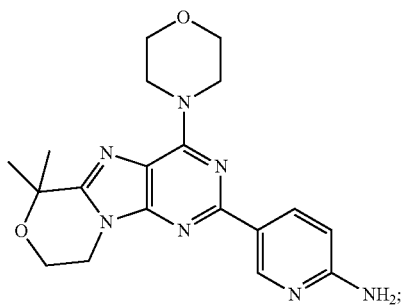
IIIbb
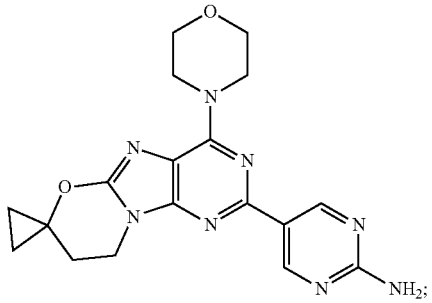
IIIbc
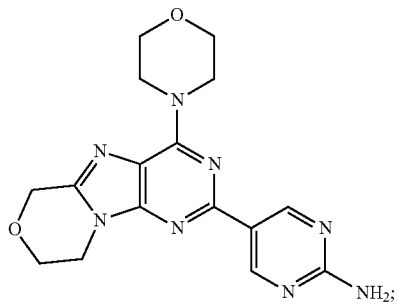
IIIbd
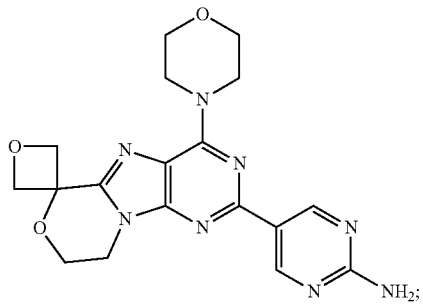
IIIbe
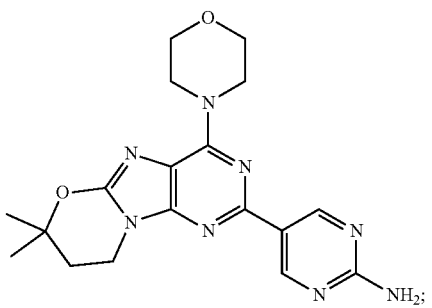
IIIbf
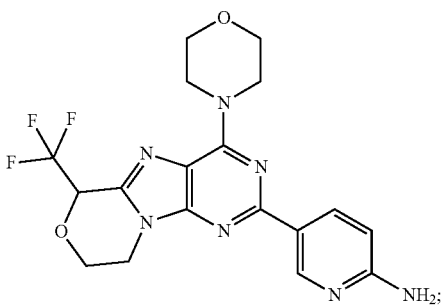
IIIbg
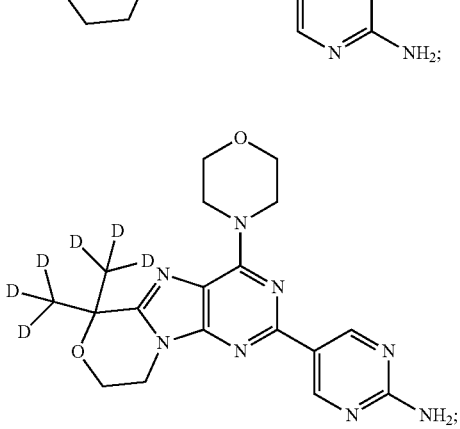
IIIbh
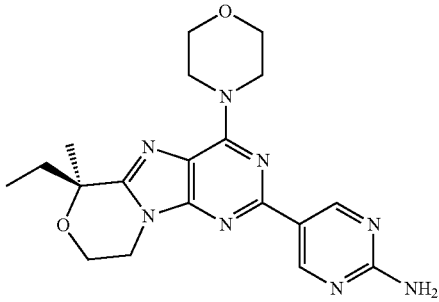
IIIbi
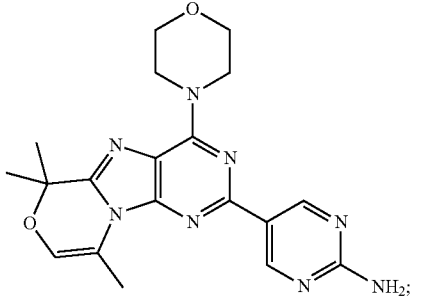
IIIbj -continued
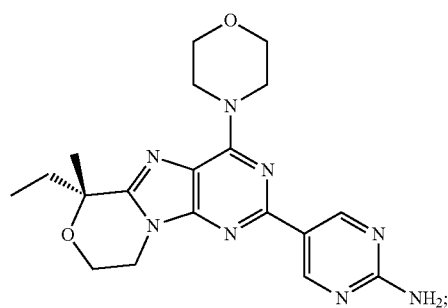
IIIbk
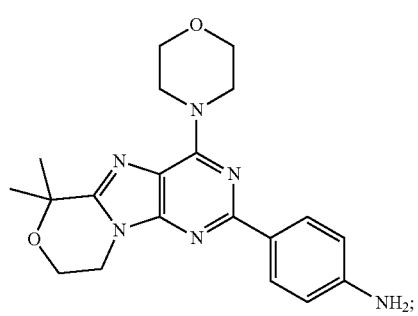
IIIbl
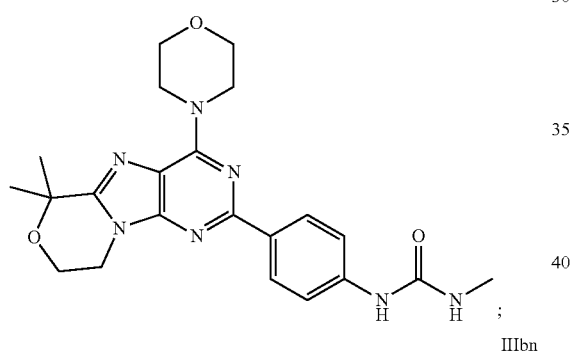
IIIbm
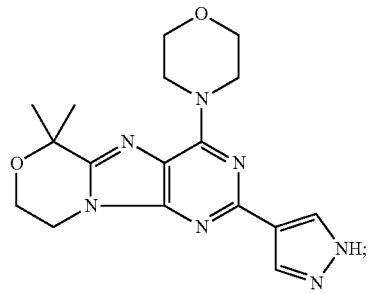
IIIbn
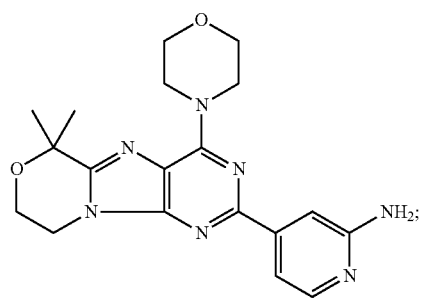
IIIbo
-continued
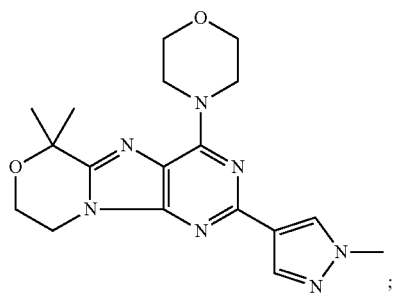
IIIbp
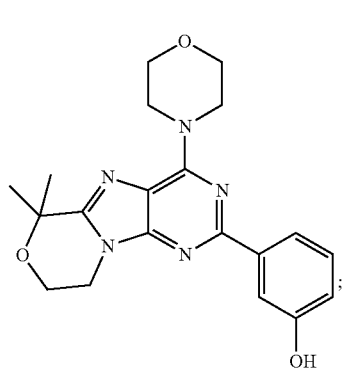
IIIbq
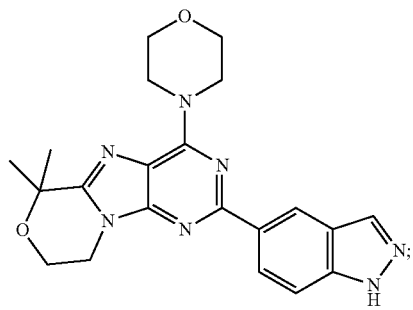
IIIbr
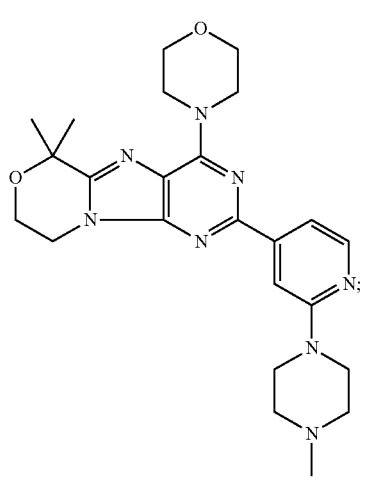
IIIbs

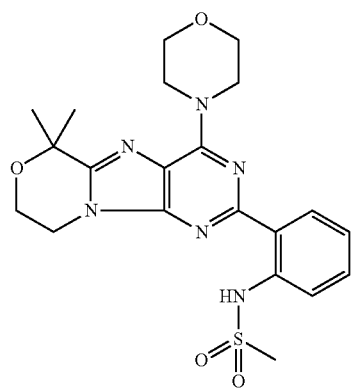
IIIbt
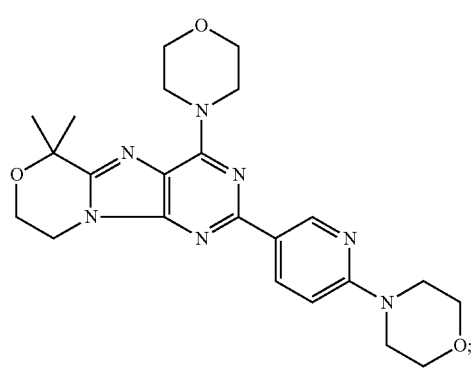
IIIbu
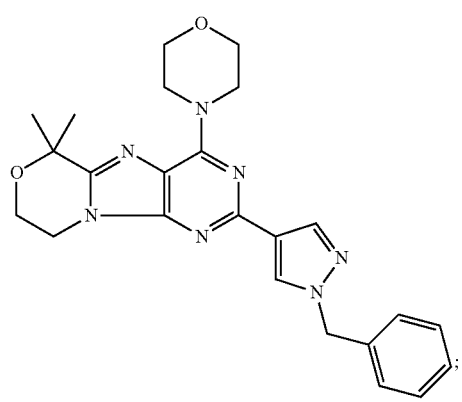
IIIbv
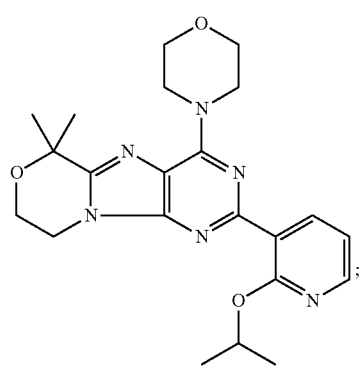
IIIbw
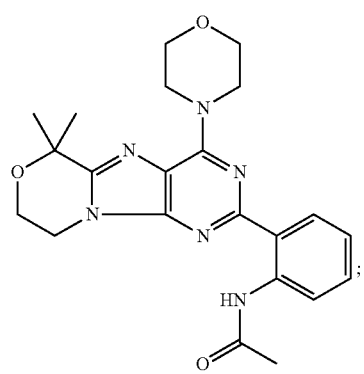
IIIbx
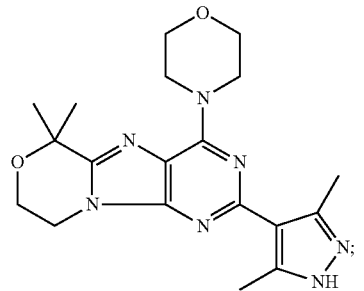
IIIby
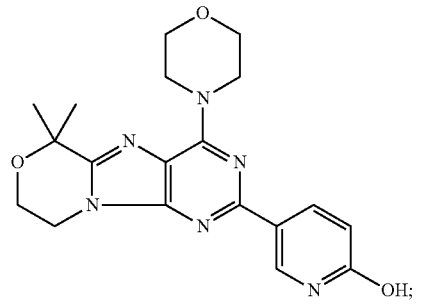
IIIbz
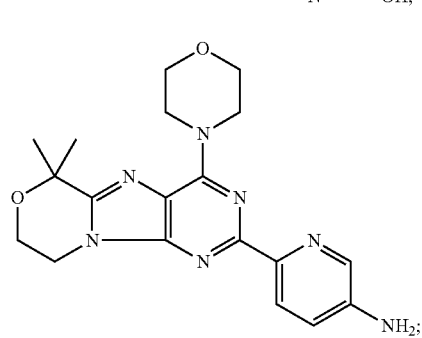
IIIca
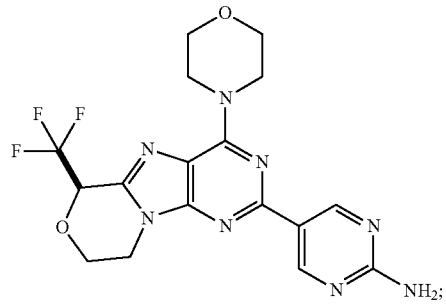
IIIcb

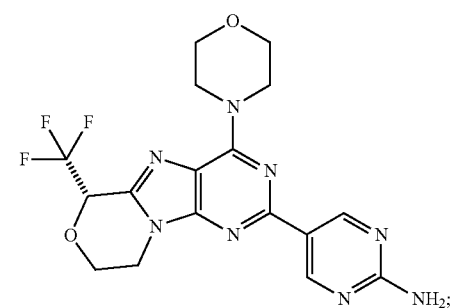
IIIcc
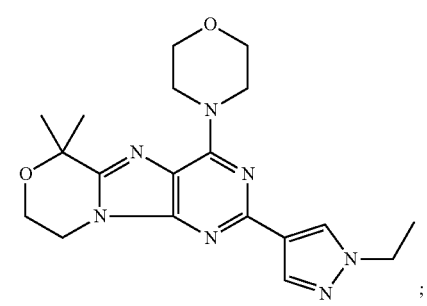
IIIcd
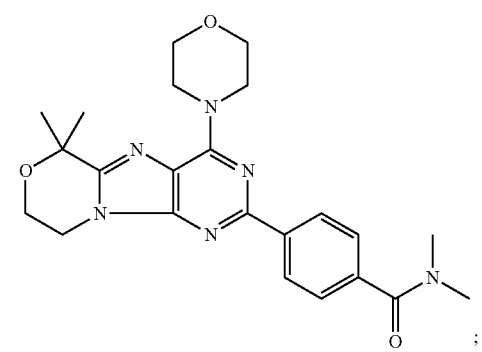
IIIce
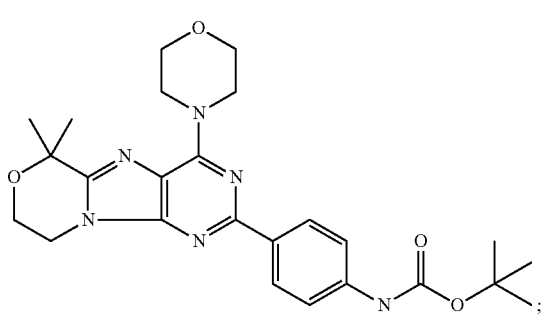
IIIcf
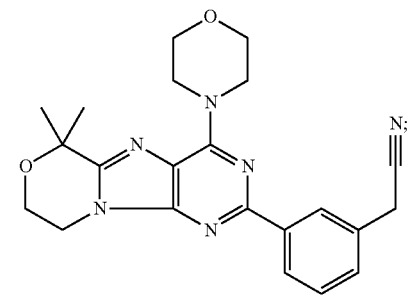
IIIcg
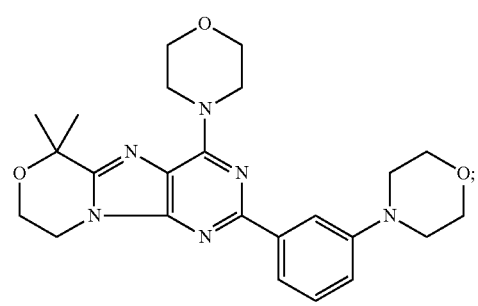
IIIch
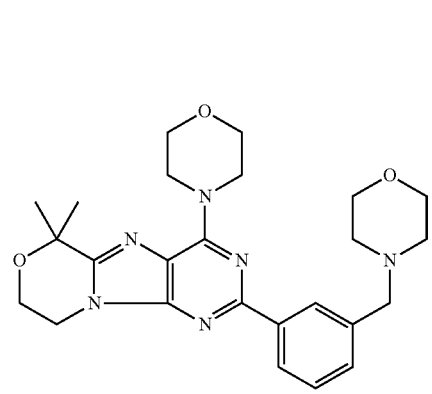
IIIci
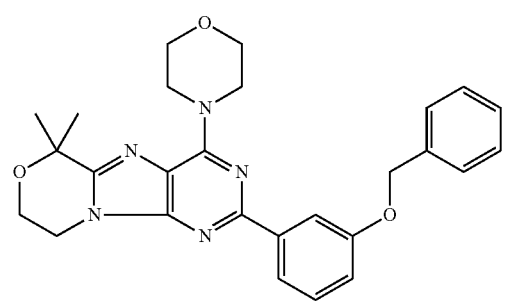
IIIcj
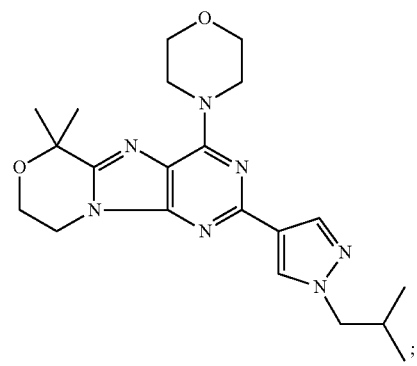
IIIck 41
-continued
IIIcl
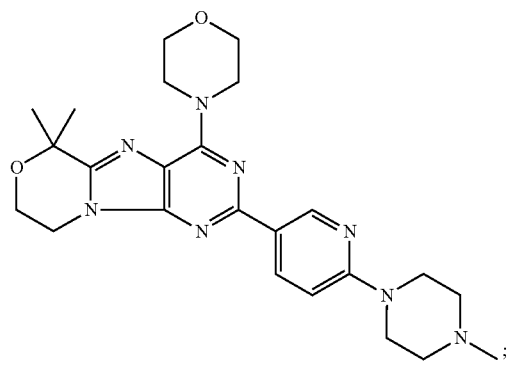
IIIcm
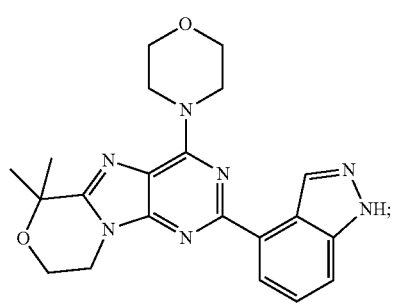
IIIcn
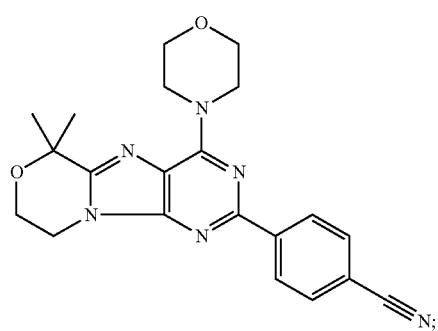
IIIco
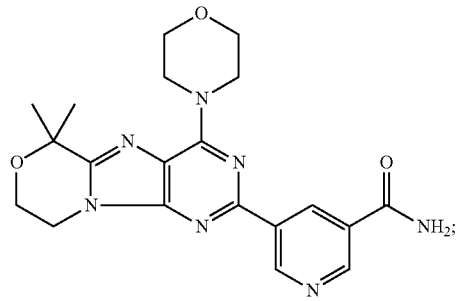
42
-continued
IIIcp
IIIcq
IIIcr
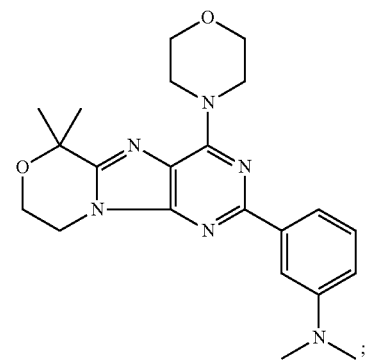
IIIcs
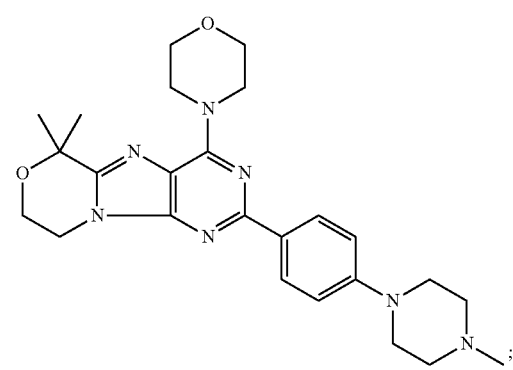

IIIct
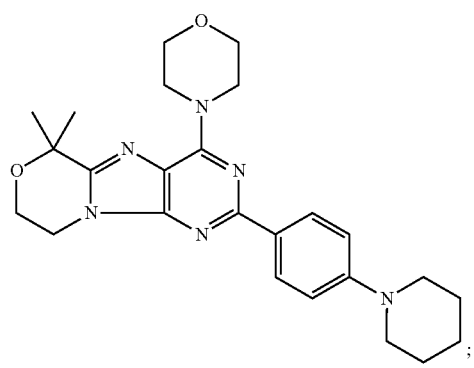
IIIcu
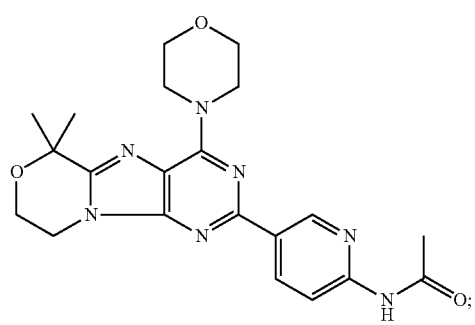
IIIcv
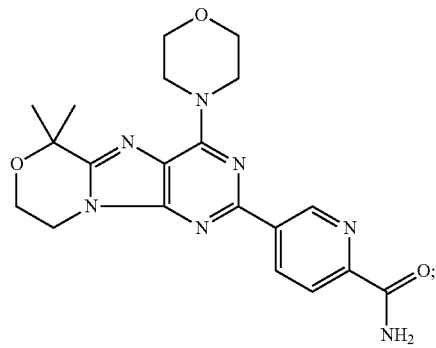
IIIcw
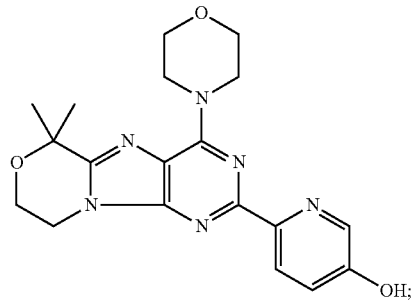
IIIcx
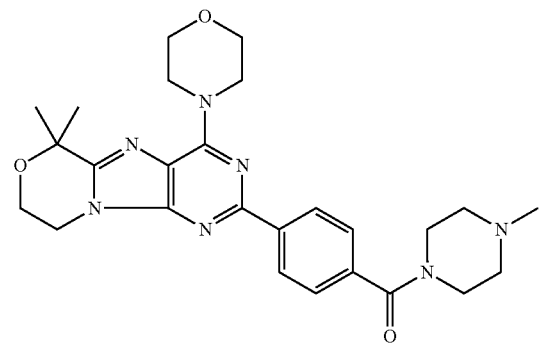
IIIcy
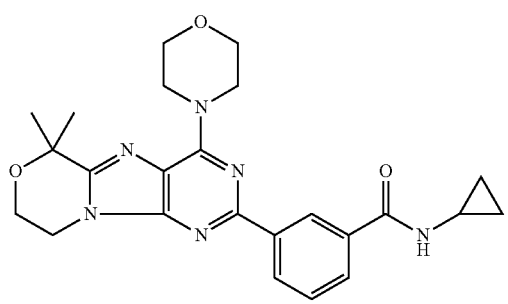
IIIcz
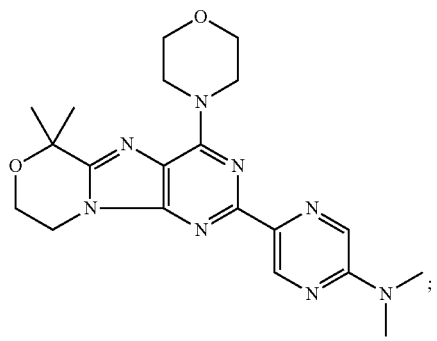
IIIda
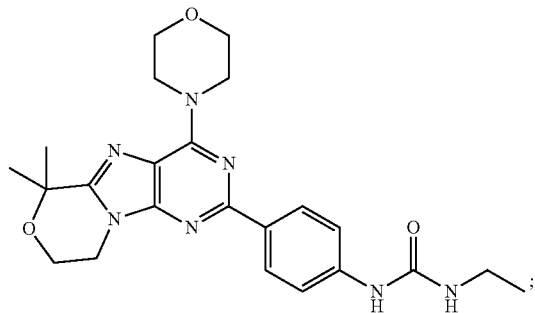

-continued
IIIdb
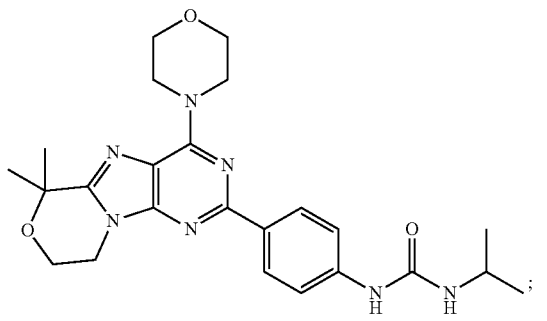
IIIdc
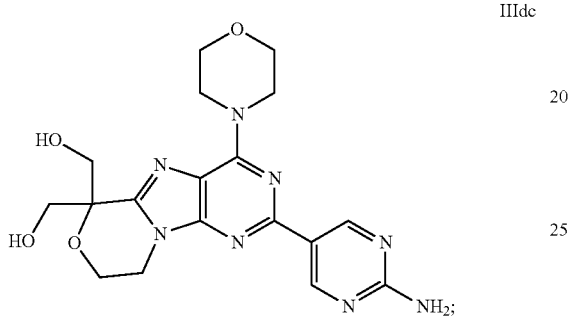
IIIdd
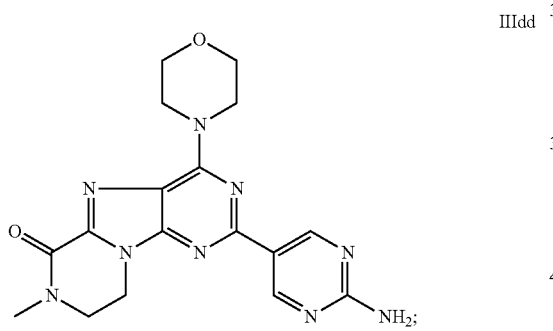
IIIde
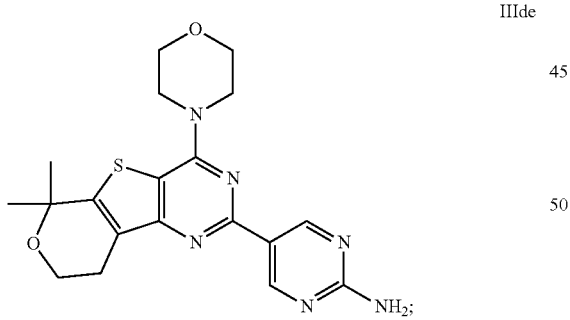
IIIdf
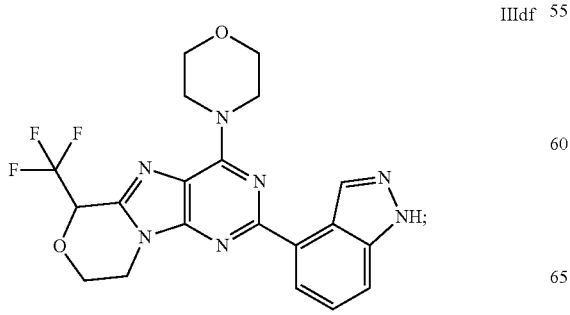
-continued
IIIdg
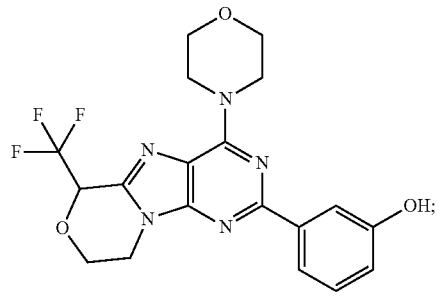
IIIdh
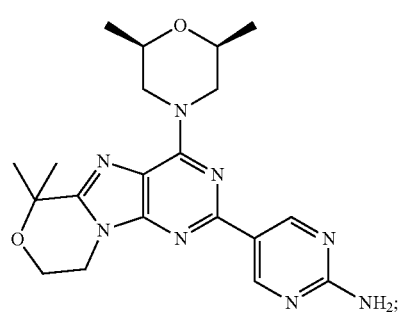
IIIdi
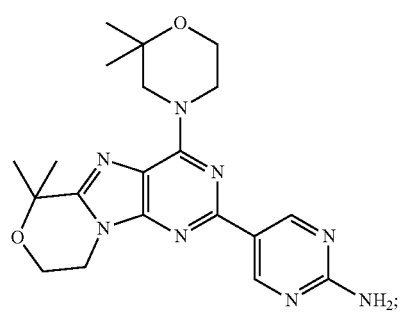
IIIdj
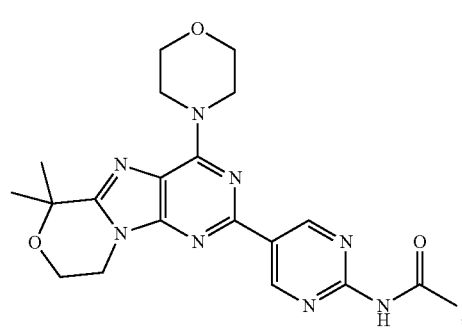
IIIdk
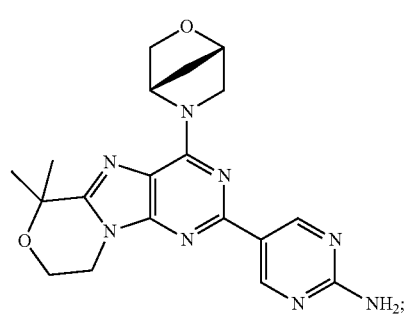

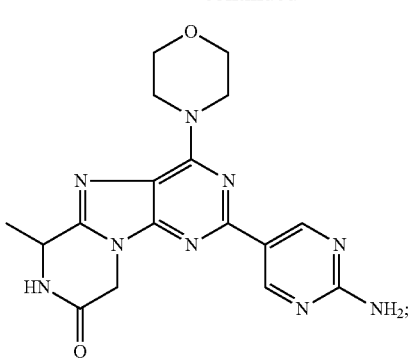
IIIdl

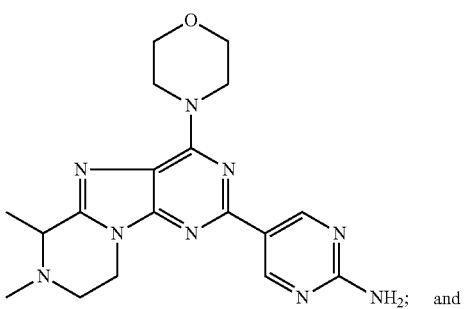
IIIdm; and

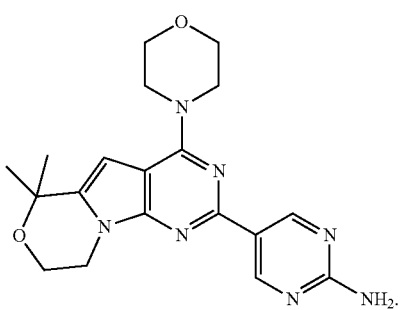
IIIdn

In some particular aspects, compound Formulae III and IIIa is:

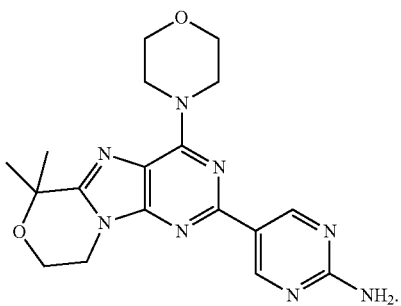
IIIat

In some aspects, it has been discovered that precipitation or crystallization of Formula III and IIIa (collectively referred to as Formula III) from the reaction mixture may be induced by addition of water, methanol, ethanol, n-propanol or i-propanol to the reaction mixture to form Formula III crystals or precipitate that may be cleanly separated using, for example, solid-liquid separation techniques known in the art. In some particular aspects the polar protic solvent is water. In such aspects, the polar protic solvent is added to the reaction mixture to a final concentration of at least 25 v/v %, at least 40 v/v %, at least 50 v/v %, at least 60 v/v %, or at least 70 v/v %. In such aspects, the volume ratio of the solvent system in the reaction mixture to polar protic solvent added to the reaction product mixture is from about 1:5 v/v to about 5:1 v/v, from about 1:3 v/v to about 3:1 v/v, from about 1:2 v/v to about 2:1 v/v, from about 1:1.5 v/v to about 1.5:1 v/v, or about 1:1 v/v. In any of the various aspects, the polar protic solvent (e.g., water) may be added to the reaction mixture at the reaction temperature, or at a lower temperature. After addition, the reaction mixture-polar protic solvent admixture may optionally be held at reaction temperature or from about 10° C. to about 20° C. lower than the reaction temperature for from about 0.5 hours to about 8 hours or from about 1 hour to about 4 hours. The admixture may then be further cooled to from about 0° C. to about 10° C. and held for from about 0.5 hours to about 8 hours, or from about 1 hour to about 4 hours, to complete crystallization of Formula III. In some aspects, in a first step, the temperature may be reduced to from about 10° C. to about 30° C. and held from about 0.5 hours to about 8 hours or from about 1 hour to about 4 hours and then cooled to 0° C. to about 10° C. in a second step held from about 0.5 hours to about 8 hours or from about 1 hour to about 4 hours. In some other aspects, Formula III seed crystals may be added to induce crystallization. Formula III solids may be isolated by solid-liquid separation techniques generally known in the art such as filtration and centrifugation. Optionally, the collected Formula III solids may be washed with additional polar aprotic solvent.

Formulae II, IIa, III and IIIa may be isolated from the reaction mixture and purified by various methods generally known in the art. Formula III reaction mixtures may comprise some amount of side product (such as Impurities 1 to 5 disclosed, in the examples), unreacted Formula II and palladium. In some aspects of the disclosure, Formulae II, IIa, III and IIIa reaction mixtures and/or isolated compounds may be purified by one or more purification methods. The desired product(s) of each step or series of steps is separated and/or purified (hereinafter separated) to the desired degree of purity by the techniques common in the art. Formulae II, IIa and III may be isolated from the reaction mixture and/or purified by various methods including: (i) precipitation or crystallization such as by evaporation, cooling and/or addition of an anti-solvent in optional further combination with seed crystal addition; (ii) extraction, such as multiphase extraction; (iii) evaporation or distillation to form a solid residue comprising the Formulae II, IIa or III; (iv) ultrafiltration; (v) chromatography; (vi) reverse phase HPLC; (vii) sublimation; (viii) chelation; and/or (ix) combinations thereof. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

In chelation methods, Formula III is admixed with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. In one chelation purification method, Formula III is processed to remove residual palladium in a method whereby Formulae III is admixed with a metal scavenger in a solvent system in which Formula III is soluble. The temperature of the admixture is increased to dissolve the compound of Formula III, the solution is held for a period of time, and the solution is filtered to remove chelated palladium. Formula III may then be crystallized from the filtered solution as described elsewhere herein. In some aspects: (i) the solvent system comprises water and acetic acid, or consists essentially of water and acetic acid, wherein the volume ratio of acetic acid to water is from about 1:1 to about 10:1, from about 1:1 to about 5:1 or from about 1:1 to about 3:1, or about 3:1; (ii) the metal scavenger is silica-thiol; and (iii) the dissolution temperature is from about 80° C. to about 100° C., the seed crystals are combined with the filtrate at a temperature of from about 70° C. to about 80° C., and the crystallization temperature is from about 0° C. to about 10° C.

In any of the various aspects of the disclosure, the yield of compound Formula III is at least 75%, at least 80% at least 85% or at least 90%. The purity of compound Formula III is at least 97%, at least 97.5%, or at least 98% (area %, as determined by HPLC).

In one or more of the above-noted reactions, the solvent may suitably be water and THF at a ratio of water to THF of about 1:5 w/w, the organoboron-$R^4$ may suitably be 5-(4,4,5,5-tetramethyl-1,3,2-dioxaborolan-2-yl)pyrimidin-2-amine, the catalyst may suitably be Xphos (e.g., Xphos PdG1, Xphos PdG2 and Xphos PdG3) the base may suitably be $K_3PO_4$, and the reaction temperature may suitably be about 55° C. to about 75° C. From about 0.8 to about 1.2 volumes of water based on the volume of the reaction mixture may suitably be admixed with the reaction product mixture, and the admixture may suitably be cooled to from about 10° C. to about 30° C. to form crystallized or precipitated reaction product.

The Formula III compounds of the disclosure may contain asymmetric or chiral centers, and therefore exist in different stereoisomeric forms. It is intended that all stereoisomeric forms of the compounds of the disclosure, including but not limited to, diastereomers, enantiomers and atropisomers, as well as mixtures thereof such as racemic mixtures, form part of the present disclosure.

In addition, the present disclosure embraces all geometric and positional isomers. For example, if a Formula III compound incorporates a double bond or a fused ring, the cis- and trans-forms, as well as mixtures thereof, are embraced within the scope of the disclosure. Both the single positional isomers and mixture of positional isomers are also within the scope of the present disclosure.

In the structures shown herein, where the stereochemistry of any particular chiral atom is not specified, then all stereoisomers are contemplated and included as the compounds of the disclosure. Where stereochemistry is specified by a solid wedge or dashed line representing a particular configuration, then that stereoisomer is so specified and defined.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present disclosure may be atropisomers (e.g., substituted biaryls) and are considered as part of this disclosure. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1) above, diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2) above, the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as methyl derivatives, followed by separation of the diastereomers and hydrolysis to yield the pure or enriched enantiomer. A method of determining optical purity involves making chiral esters of the racemic mixture, such as a methyl ester, for example with (−) methyl chloroformate, in the presence of base, or Mosher ester, α-methoxy-α-(trifluoromethyl)phenyl acetate (Jacob III. J. Org. Chem. (1982) 47:4165), and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 1996/015111). By method (3) above, a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

The compounds of the present disclosure may exist in unsolvated as well as solvated forms with pharmaceutically acceptable solvents such as water, ethanol, and the like, and it is intended that the disclosure embrace both solvated and unsolvated forms.

The compounds of the present disclosure may also exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the disclosure, and their uses. Exemplary isotopes that can be incorporated into compounds of the disclosure include isotopes of hydrogen, carbon, nitrogen, oxygen, phosphorus, sulfur, fluorine, chlorine and iodine, such as $^2$H (D), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present disclosure (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present disclosure can generally be prepared by following procedures analogous to those disclosed in the Schemes and/or in the Examples herein by substituting an isotopically labeled reagent for a non-isotopically labeled reagent.

B. ANNULATION

In the annulation (ring forming) reaction of reaction scheme (2): each $R^5$, each $R^{10}$ and each $R^{15}$ is independently selected from H, $C_1$-$C_{10}$ hydrocarbyl or from $C_1$-$C_5$ hydrocarbyl, wherein each hydrocarbyl is optionally substituted; two geminal $R^5$ groups, $R^{10}$ groups and/or $R^{15}$ groups together are oxo or together form a 3, 4, 5, 6, or 7-membered carbocyclyl or heterocyclyl, wherein the carbocyclyl or heterocyclyl is optionally substituted. $R^{20}$ is —OH or —NHR$^{21}$; $R^{21}$ is as defined for $R^5$; and $R^{20}$ in the ring formed in Formula IIa is —O— or —NR$^{21}$—. Mor is an optionally substituted morpholine ring. X is halogen (e.g., Br, I or Cl). In some aspects of the present disclosure, compounds of Formula IIa are formed from bicyclic compounds precursor compounds of Formula I by annulation through condensation with a nucleophile derived from 1,2 ethane diol and epoxide, such as an organic halide. In any of the various such reactions, a reaction mixture is formed comprising a compound Formula I, halo-alkyl, a solvent system, a phase transfer catalyst, and a base. The reaction mixture is reacted at elevated temperature to form a reaction product mixture comprising compound Formula IIa, a stereoisomer, geometric isomer, tautomer, or a pharmaceutically acceptable salt thereof, and compound Formula IIa is then isolated from the reaction product mixture. In some aspects of the present disclosure, compound Formula IIa may be purified in one or more purification steps.

In some aspects of the disclosure, the solvent system comprises at least one polar protic solvent. Examples of such solvents include, without limitation, water, methanol, ethanol, n-propanol, i-propanol, n-butanol, i-butanol, t-butanol, and acetic acid ("HOAc"). In such aspects, the solvent system comprises at least 5 v/v % water, at least 25 v/v % water, at least 50 v/v % water, at least 75 v/v % water, at least 90 v/v % water, or consists essentially of water.

In some aspects of the disclosure, the solvent system comprises at least one polar aprotic solvent. Examples of such solvents include, without limitation, dichloromethane, tetrahydrofuran ("THF"), ethyl acetate, acetone, N—N-dimethylformamide ("DMF"), acetonitrile ("MeCN"), dimethylsulfoxide, N-methylpyrrolidone ("NMP"), methyl isobutyl ketone and methyl ethyl ketone. In such aspects, the solvent comprises DMF or predominantly comprises DMF.

In yet other aspects of the disclosure, the solvent system comprises at least one polar protic solvent and at least one polar aprotic solvent at a ratio of total polar protic solvent to total polar aprotic solvent of from about 1:10 to about 10:1, from about 1:5 to about 5:1, from about 1:10 to about 1:1, from about 1:5 to about 1:1, from about 10:0 to about 1:1, or from about 5:1 to about 1:1. In some such aspects, the solvent system comprises water and THF or water and DMF.

Total solvent loading, in terms of volumes based on Formula I, is about 2, about 3, about 4, about 5, about 6, about 7, about 8, about 9, about 10, about 15 or about 20, and ranges thereof, such as from about 2 to about 20, from about 2 to about 15, from about 2 to about 10, from about 5 to about 15, from about 2 to about 7, from about 3 to about 7, or from about 3 to about 5.

The nucleophile for annulation by condensation reaction may be a nucleophile derived from (i) 1,2-ethanediol or a mesylate, tosylate or triflate derivative thereof or (ii) an epoxide. In some aspects, the nucleophile is a halide or pseudohalide, such as an organic halide. In some aspects, the organic halide is a halogenated alkyl. In some particular aspects, the halide is a Cl, Br or I halogenated $C_1$ to $C_3$ alkyl. In some aspects, the organic halide is optionally substituted. In some aspects the alkyl is di-substituted with halogen at the terminal ends. An example of one such organic halide is 1,2-dibromoethane. The equivalent ratio of organic halide to compound Formula I is greater than 2:1, about 2.5:1, about 3:1, about 3.5:1, about 4:1, about 4.5:1 or about 5:1, and ranges thereof, such as between 2:1 and about 5:1, between 2:1 and about 4:1, from about 2.5:1 to about 4:1, from about 2.5:1 to about 3.5:1, or about 3:1. The organic halide may be combined with the reaction mixture in one or more addition steps.

In some aspects of the present disclosure, the reaction mixture comprises a phase transfer catalyst. In some such aspects, the phase transfer catalyst may be selected from a quaternary ammonium salt and a phosphonium salt. Examples of such phase transfer catalysts include, without limitation, tetra-n-butylammonium bromide ("TBAB"), benzyltrimethylammonium chloride, benzyltriethylammonium chloride, methyltricaprylammonium chloride, methyltributylammonium chloride, and methyltrioctylammonium chloride. In particular aspects, the phase transfer catalyst is TBAB. The equivalent ratio of phase transfer catalyst to compound Formula I is about 0.1:1, about 0.2:1, about 0.3:1, about 0.4:1, about 0.5:1 or about 0.6:1 and ranges thereof, such from about 0.1:1 to about 0.6:1, from about 0.2:1 to about 0.5:1, from about 0.2:1 to about 0.4:1, or about 0.3:1.

In any of the various annulation aspects of the present disclosure, the reaction mixture comprises a base. Examples of suitable bases include, without limitation, KOH, NaOH, $K_3PO_4$, $K_2CO_3$, $NaHCO_3$ and $Cs_2CO_3$. In some aspects, the base is KOH, NaOH or $K_3PO_4$, and in other aspects the base is KOH. The equivalent ratio of the base to compound Formula I is greater than 2:1, about 2.5:1, about 3:1, about 3.5:1, about 4:1, about 4.5:1 or about 5:1, and ranges thereof, such as between 2:1 and about 5:1, between 2:1 and about 4:1, from about 2.5:1 to about 4:1, from about 2.5:1 to about 3.5:1, or about 3:1. In some aspects, the base and the organic halide are present in about equimolar amounts. The base may be combined with the reaction mixture in one or more addition steps.

The reaction temperature is suitably from about 40° C. to about 90° C., from about 40° C. to about 70° C., from about 40° C. to about 60° C., or about 50° C. Based on experimental evidence to date, it has been discovered that the purity profile of Formula IIa varies inversely with reaction temperature, such that lower reaction temperatures provide for improved purity profiles as measured by HPLC as compared with higher reaction temperatures. The reaction time required to achieve sufficient conversion varies with the quantitative and qualitative characteristics of the reaction mixture and the reaction temperature, and is typically about 4 hours, about 8 hours, about 12 hours, about 16 hours, about 20 hours, about 24 hours or about 28 hours, and ranges thereof, such as about 4 hours to about 28 hours, about 4 hours to about 20 hours or about 4 hours to about 12 hours.

Compound Formula IIa may be isolated from the reaction mixture by various methods including precipitation, crystallization and extraction. In an example of a first extraction method, the reaction mixture may be cooled, such as to room temperature, diluted with water (e.g., 5 to 15 volumes of water) and held with agitation (e.g., 5 to 15 hours). Formula IIa may then be extracted from the diluted reaction mixture into an organic solvent (e.g., 1 to 3 volumes of a suitable solvent such as polar aprotic solvent such as ethyl acetate) followed by isolation of the organic solvent from the reaction mixture by phase separation. Multiple such extractions are within the scope of the first method. The organic phase may suitably be washed with NaCl and concentrated (e.g., by distillation) to yield crude solid Formula IIa. Crude Formula IIa may optionally be crystallized such as by dissolution in a suitable solvent at elevated temperature (e.g., 65° C. in isopropanol) followed by crystallization by cooling. In an example of a second extraction method, water (e.g., 5 to 10 volumes) and an organic solvent (e.g., 2 to 6 volumes ethyl acetate) may be added to a cooled reaction mixture followed by phase separation to remove the organic layer. In some aspects, additional water (e.g. 2 to 6 volumes) and organic solvent (e.g., 2 to 6 volumes ethyl acetate) may be added to the aqueous phase followed by phase separation to remove the organic layer. The combined organic layers may be concentrated (e.g., by distillation) to yield solid crude Formula IIa. Formula IIa may optionally be combined with a solvent (e.g., isopropanol) followed by a second concentration step. Crude Formula IIa may optionally be crystallized such as by dissolution in a suitable solvent at elevated temperature (e.g., 65° C. in isopropanol) followed by crystallization by cooling. In aspects of the disclosure where the reaction mixture solvent system comprises water, an alcohol (e.g., ethanol) may be added to the reaction product mixture and the temperature of the admixture may be reduced to induce crystallization of compound Formula IIa. In some optional aspects, seed crystals of compound Formula IIa may be added to the admixture. In such aspects, the volume ratio of the reaction mixture solvent system to alcohol is from about 1:5 v/v to about 5:1 v/v, from about 1:3 v/v to about 3:1 v/v, from about 1:2 v/v to about 2:1 v/v, from about 1:1 v/v to about 1:2 v/v, or about 1:1.3 v/v. Crystallized compound Formula IIa may be isolated by solid liquid separation techniques known in the art.

In any of the various aspects, the yield of compound Formula IIa is at least 65% at least 70% or at least 75%. The purity of compound Formula IIa is at least 97%, at least 97.5%, at least 98%, at least 98.5% or at least 99% (area % as determined by HPLC).

Non-limiting examples of reactions within the scope of the present disclosure include:

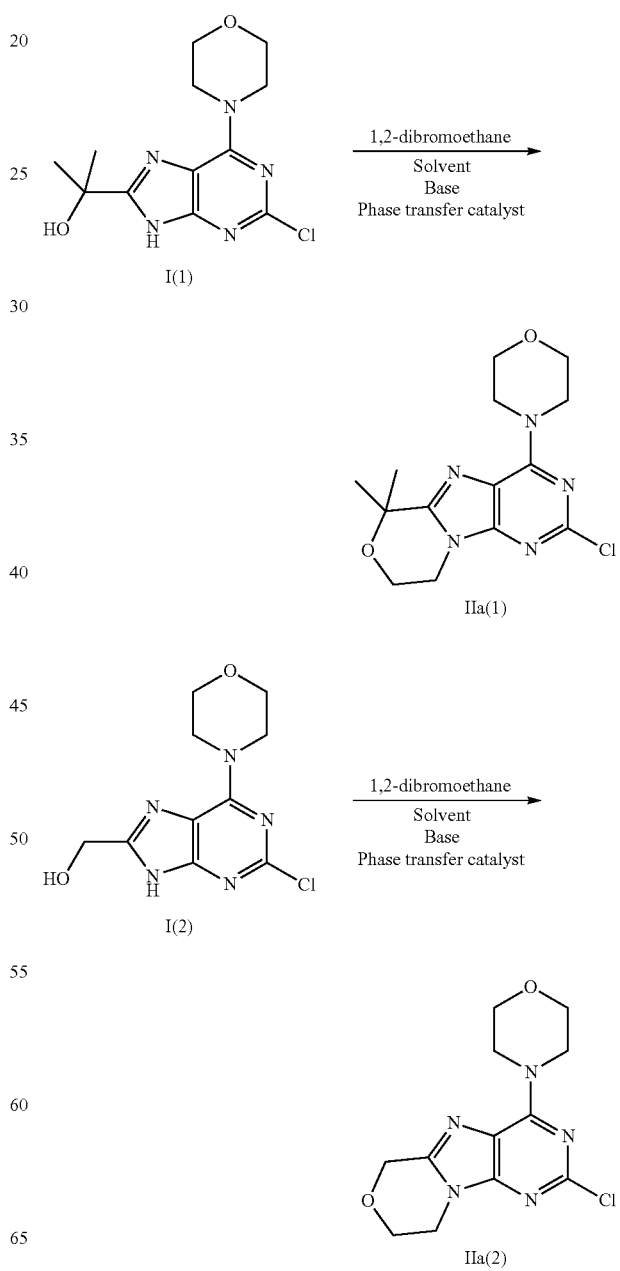

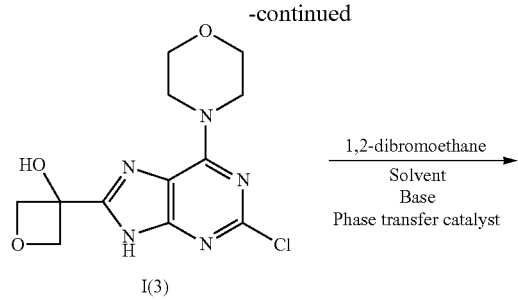
I(3)
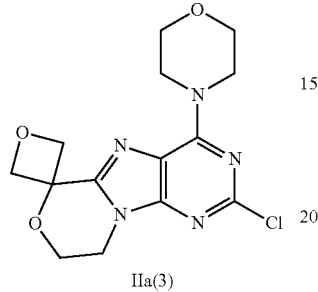
IIa(3)
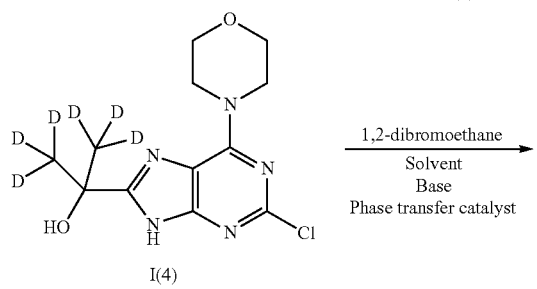
I(4)
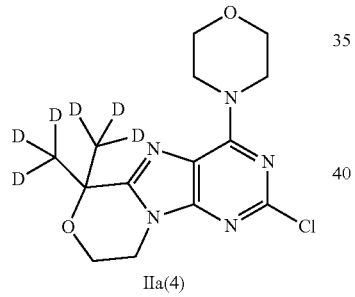
IIa(4)
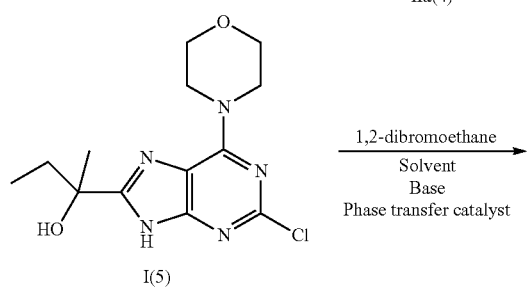
I(5)
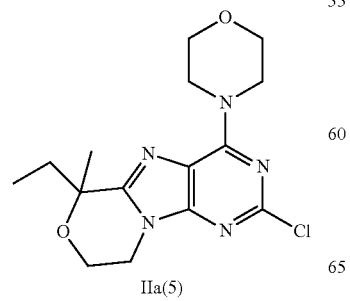
IIa(5)
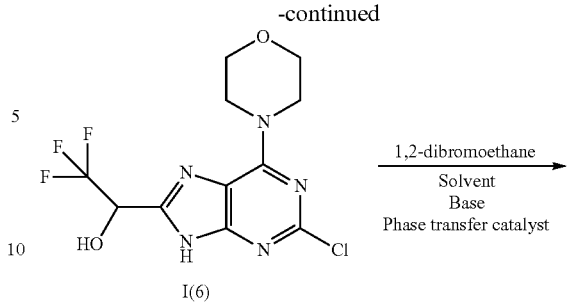
I(6)
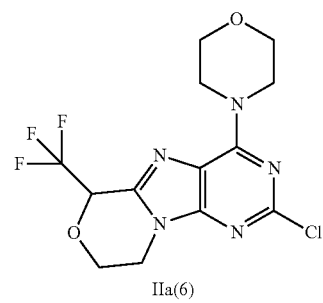
IIa(6)
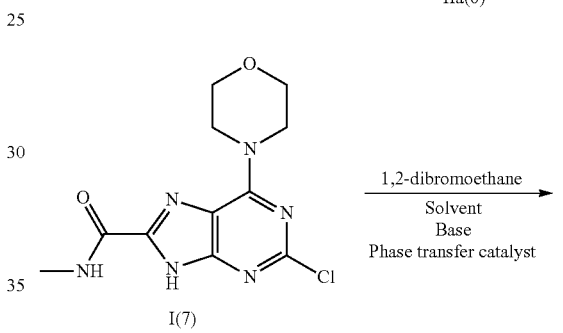
I(7)
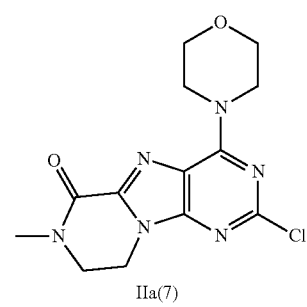
IIa(7)
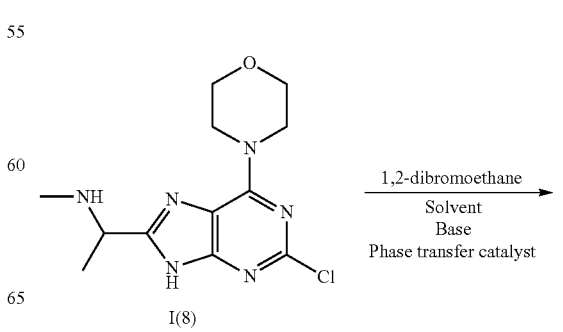
I(8)

-continued

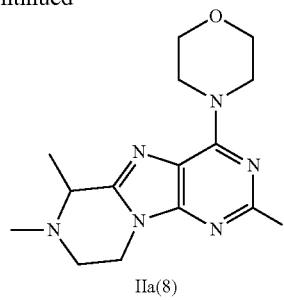

IIa(8)

In one or more of the above-noted reactions, the solvent may suitably be water, the base may suitably be KOH, the phase transfer catalyst may suitably be tetra-n-butylammonium bromide, and the reaction temperature may suitably be about 50° C. Ethanol may suitably be admixed with the reaction product mixture and the admixture may suitably be cooled to from about 0° C. to about 10° C. in the presence of reaction product seed crystals to form crystallized reaction product.

C. EXEMPLARY EMBODIMENTS

In a first exemplary embodiment of the present disclosure, the compound of Formula IIIat (GDC-0084):

IIIat

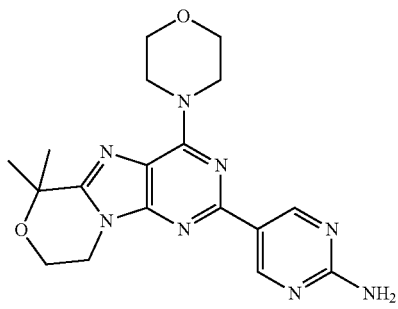

or a salt thereof, is prepared by a process comprising contacting a compound of Formula IIa:

IIa

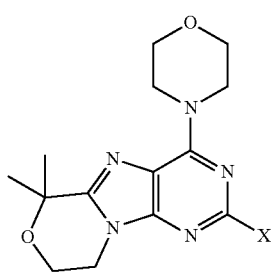

or a salt thereof, wherein X is chloro or bromo, in a solvent system comprising a least 5% v/v % water and at a reaction temperature of less than 100° C. with an organoboron-pyrimidin-2-amine in the presence of a base and less than 0.05 equivalents of a Suzuki coupling palladium catalyst per equivalent of compound Formula IIa.

In one aspect of the first exemplary embodiment, the solvent system comprises water and tetrahydrofuran, wherein the ratio of water to tetrahydrofuran is from about 1:3 v/v to about 1:7 v/v, or about 1:5 v/v. In some other aspects of the first exemplary embodiment, the organoboron-pyrimidin-2-amine is 5-(4,4,5,5-tetramethyl-1,3,2-dioxaborolan-2-yl)pyrimidin-2-amine. In yet other aspects of the first exemplary embodiment, the base is $K_3PO_4$ and the equivalent ratio of the base to compound Formula IIa is from about 1:1 to about 3:1, or about 2:1. In still other aspects of the first embodiment, the catalyst is chloro(2-dicyclohexylphosphino-2',4',6'-triisopropyl-1,1'-biphenyl)[2-(2-aminoethyl) phenyl)]palladium(II) and the equivalent ratio of the catalyst comprising palladium to compound Formula IIa is from about 0.004:1 to about 0.007:1, or about 0.005:1. In still other aspects of the first embodiment, the catalyst is 1,1'-bis(diphenylphosphino)ferrocene]dichloropalladium (II) complex with dichloromethane and the equivalent ratio of the catalyst comprising palladium to compound Formula IIa is from about 0.01:1 to about 0.03:1, or about 0.02:1. In yet other aspects of the first embodiment, the reaction temperature is from about 55° C. to about 75° C. In any of the various aspects of the first embodiment, water is added to the reaction product mixture to form an admixture comprising greater than 25 v/v % water to form a precipitate or crystalline compound Formula IIIa, which may be isolated from the reaction product mixture. In some such aspects, the volume ratio of the solvent system to added water is from about 1:1.5 v/v to about 1.5:1 v/v, or about 1:1 v/v.

In a second exemplary embodiment of the present disclosure, the compound of Formula IIa:

IIa

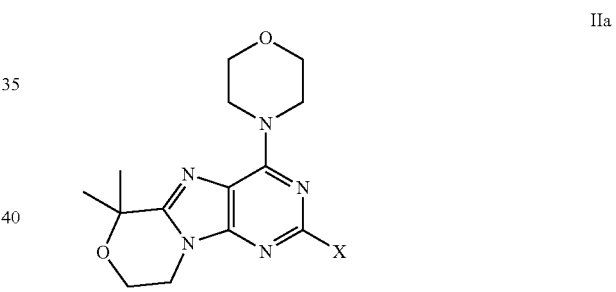

or a salt thereof, is prepared by a process comprising: (a) forming a reaction mixture comprising a solvent system comprising at least 5 v/v % water, 1,2-dibromoethane, a phase transfer catalyst, a base, and compound Formula I:

I

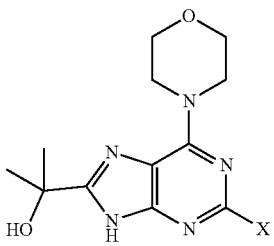

or a salt thereof, wherein X is bromo, chloro or iodo; and, (b) reacting the reaction mixture to form a reaction product mixture comprising compound Formula IIa.

In one aspect of the second exemplary embodiment, the solvent system comprises at least 90 v/v % water or consists essentially of water. In some other aspects of the second exemplary embodiment, the base is KOH and the phase transfer catalyst is tetra-n-butylammonium bromide. In yet other aspects, the mole ratio of 1,2-dibromoethane to compound Formula I is between about 2:1 and about 4:1, or about 3:1, and the mole ratio of 1,2-dibromoethane to the base is about 1:1. In other aspects, the reaction temperature is from about 40° C. to about 60° C., such as about 50° C. In other aspects, ethanol is admixed with the reaction product mixture followed by cooling of the admixture to form crystallized compound Formula IIa, wherein the volume ratio of the solvent system to ethanol is from about 1:1 v/v to about 1:2 v/v, or about 1:1.3 v/v %. In yet other aspects, compound Formula IIa seed crystals are combined with the ethanol-reaction product mixture.

D. METHODS OF TREATMENT

The Formula III compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with e.g. the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

In one embodiment, the composition comprising a compound of Formula III or salt thereof is formulated as a solid dosage form for oral administration. Solid dosage forms for oral administration include capsules, tablets, pills, powders, and granules. In certain embodiments, the solid oral dosage form comprising a compound of Formula III or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of Formula III or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of Formula III or salt thereof, and optionally, further comprises one or more excipients.

In another embodiment, compositions comprise liquid dosage formulations comprising a compound of Formula III or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of Formula III, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of Formula III or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of Formula III.

Example dosage forms for topical or transdermal administration of a compound of Formula III include ointments, pastes, creams, lotions, gels, powders, solutions, sprays, inhalants or patches. The compound of Formula III or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of Formula III or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of Formula III or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of Formula III or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being about 0.1 to 15 mg/kg/day, about 0.1 to 10 mg/kg/day, about 0.1 to 5 mg/kg/day, about 0.1 to 3 mg/kg/day, about 0.3 to 1.5 mg/kg/day, or about 0.4 to 1 mg/kg/day. In another embodiment, oral unit dosage forms, such as tablets and capsules, contain from about 5 to about 100 mg, about 10 to 75 mg, about 25 to 75 mg, or about 25 to 50 mg of the compound of the invention.

An example tablet oral dosage form comprises about 2 mg, about 5 mg, about 25 mg, about 50 mg, about 100 mg, about 250 mg or about 500 mg of a compound of Formula III or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of Formula III or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

A dose to treat human patients may range from about 10 mg to about 1000 mg, from about 10 mg to about 500 mg, from about 10 mg to about 100 mg, from about 25 mg to about 100 mg, or from about 25 mg to about 75 mg of Formula III compound. A typical dose may be about 100 mg to about 300 mg of the compound. A dose may be administered once a day (QID or QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

In some embodiments, a total of from about 0.2 mg/kg/day to about 1.5 mg/kg/day, from about 0.3 mg/kg/day to about 1 mg/kg/day, or from about 0.4 mg/kg/day to about 0.75 mg/kg/day of compound Formula III is administered once daily or in a twice daily dosage regimen. In some such embodiments, under such a dosage regimen the following pharmacokinetic results are achieved for a single dose on the first day of a dosage cycle. A $T_{1/2}$ (hr) of from about 10 to about 24 hours, from about 12 to about 22 hours, or from about 15 to about 20 hours. A $T_{max}$ (hr) of from about 1 to about 8 hours, from about 2 to about 6 hours, from about 2 to about 4 hours, or from about 2 to about 3 hours. A $C_{max}$ (μM) of from about 0.01 to about 0.5 μM, from about 0.05 to about 0.4 M, or from about 0.1 to about 0.3 μM. An $AUC_{inf}$ (μM*hr) of from about 0.2 to about 10 μM*hr, from about 0.5 to about 10 μM*hr, from about 1 to about 8 μM*hr, or from about 2 to about 6 μM*hr. An $AUC_{0-24}$ (μM*hr) of from about 0.1 to about 10 μM*hr, from about 0.5 to about 5 μM*hr, from about 1 to about 5 μM*hr, or from about 2 to about 4 μM*hr. In some other such embodiments, the following pharmacokinetic results are achieved for a single dose after the 15$^{th}$ day of a 2 mg to 30 mg per day dosage regimen or for a single does after the 8$^{th}$ day of a 45 mg to 65 mg per day dosage regimen. A $T_{max}$ (hr) of from about 1 to about 5 hours, from about 1 to about 3 hours, or from about 2 to about 4 hours. A $C_{max}$ (μM) of from about 0.03 to about 1 μM, from about 0.1 to about 1 μM, from about 0.3 to about 0.8 μM, or from about 0.3 to about 0.6 μM. A $C_{min}$ (μM) of from about 0.005 to about 0.5 μM, from about 0.01 to about 0.4 μM, from about 0.05 to about 0.3 μM, or from about 0.1 to about 0.3 μM. An $AUC_{0-24}$ (μM*hr) of from about 0.1 to about 15 μM*hr, from about 0.5 to about 15 μM*hr, from about 3 to about 15 μM*hr, or from about 5 to about 10 μM*hr. An accumulation ratio of from about 1 to about 4 or from about 1.5 to about 3. As used herein, $T_{1/2}$ refers to terminal half-life; $T_m$ax refers to time to maximum plasma concentration; $C_{max}$ refers to maximum observed plasma concentration; $AUC_{inf}$ refers to area under the concentration-time curve from Time 0 to infinity; $AUC_{0-24}$ refers to refers to area under the concentration-time curve from Time 0 to 24 hours; $C_{min}$ refers to minimum concentration; and Accumulation Ratio refers to $AUC_{0-24 \text{ hr multiple dose}}/AUC_{0-24 \text{ hr single dose}}$. In some particular embodiments, compound Formula III is GDC-0084 (Formula IIIat).

Formula III compounds may be useful for treating conditions of the brain and central nervous system which require transport across the blood-brain barrier. Certain Formula III compounds, such as compound Formula IIIat (GDC-0084) disclosed elsewhere herein, have favorable penetrant properties across the blood-brain barrier for delivery to the brain. Disorders of the brain which may be effectively treated with Formula III compounds include metastatic and primary brain tumors, such as glioma (glioblastoma multiforme) and melanoma.

The compounds of Formula III or salts thereof may be employed alone or in combination with other agents for treatment. For example, the second agent of the pharmaceutical combination formulation or dosing regimen may have complementary activities to the compound of Formula III such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of Formula III or a salt thereof, and a further active pharmaceutical ingredient or ingredients, including cytotoxic agents. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of Formula III, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of Formula III or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{25}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

In some embodiments, the PI3 kinase inhibitors of the present disclosure are administered to a patient with an additional therapeutic agent selected from a chemotherapeutic agent, an anti-angiogenesis therapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some such embodiments, the additional therapeutic agent is bevacizumab. In some other such embodiments, the additional therapeutic agent is temozolomide.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5 [[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{88}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R) vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium (GENASENSE®); pixantrone; farnesyltransferase inhibitors such as lonafamib (SCH 6636, SARASAR®); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

E. DEFINITIONS

The term "hydrocarbyl" as used herein describes organic compounds or radicals consisting exclusively of the elements carbon and hydrogen. These moieties include, without limitation, alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include, but are not limited to, halogen, heterocyclo, alkoxy, alkenoxy, alkynoxy, aryloxy, hydroxy, keto, acyl, acyloxy, nitro, tertiary amino, amido, nitro, cyano, thio, sulfinate, sulfonamide, ketals, acetals, esters and ethers.

The term "alkyl" as used herein refers to a saturated linear or branched-chain monovalent hydrocarbon radical of one to twelve carbon atoms ($C_{1-12}$), wherein the alkyl radical may be optionally substituted independently with one or more substituents described below. In another embodiment, an alkyl radical is one to eight carbon atoms ($C_{1-8}$), or one to six carbon atoms ($C_{1-6}$). Examples of alkyl groups include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

The term "alkylene" as used herein refers to a saturated linear or branched-chain divalent hydrocarbon radical of one to twelve carbon atoms ($C_{1-12}$), wherein the alkylene radical may be optionally substituted independently with one or more substituents described below. In another embodiment, an alkylene radical is one to eight carbon atoms ($C_{1-8}$), or one to six carbon atoms ($C_{1-6}$). Examples of alkylene groups include, but are not limited to, methylene, ethylene, propylene, and the like.

The term "alkenyl" refers to linear or branched-chain monovalent hydrocarbon radical of two to eight carbon atoms ($C_{2-8}$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl, allyl, and the like.

The term "alkenylene" refers to linear or branched-chain divalent hydrocarbon radical of two to twelve carbon atoms ($C_{2-12}$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene, allyl, and the like.

The term "alkynyl" refers to a linear or branched monovalent hydrocarbon radical of two to eight carbon atoms ($C_{2-8}$) with at least one site of unsaturation, i.e., a carbon-carbon, sp triple bond, wherein the alkynyl radical may be optionally substituted independently with one or more substituents described herein. Examples include, but are not limited to, ethynyl, propynyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_{3-12}$) as a monocyclic ring or 7 to 12 carbon atoms as a bicyclic ring. Bicyclic carbocycles having 7 to 12 atoms can be arranged, e.g., as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_{6-20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g.: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "organoboron" refers to organic derivatives of boron. Examples of organoboron compounds include esters of the following structure:

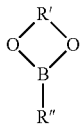

where R' is suitably is suitably hydrocarbyl, substituted hydrocarbyl, alkyl, alkylene, carbocycle, heterocycle, aryl, heteroaryl and aryl-alkyl. Examples of R' include ethylene (—CH$_2$CH$_2$—), neopentyl (—CH$_2$C(CH$_3$)(CH$_3$)CH$_2$—), and pinacol (—C(CH$_3$)(CH$_3$)C(CH$_3$)(CH$_3$)C—). R" is suitably optionally substituted hydrocarbyl, substituted hydrocarbyl, alkyl, alkylene, carbocycle, heterocycle, aryl, heteroaryl and aryl-alkyl. Examples of R" include substituted heteroaryl compounds including 2-hydroxypyridine and 2-aminopyrimidine. In some particular aspects, R' is pinacol and R" is 2-aminopyrimidine. Other examples of organoboron compounds include triorganoboranes and hydrides, borinic and boronic acids and esters, carboranes, and boryl compounds.

The term "volumes" refers to the amount of a first liquid compound in reference to the volume of a second compound or second mixture of compounds to which it is combined. For instance, four volumes of a first liquid added to a second compound (1 volume) correlates to a volume percent of the first liquid of 80% calculated by: (4 volumes first liquid)/(4 volumes first liquid+1 volume second compound)*100=80 v/v %.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this disclosure," and "compounds of the present disclosure" and "compounds of Formulae II, IIa, III and IIIa" include compounds of Formulae II, IIa, III and IIIa and stereoisomers, geometric isomers, tautomers, solvates, metabolites, and pharmaceutically acceptable salts and prodrugs thereof.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

EXAMPLES

Methods

The chemical reactions described in the Examples may be readily adapted to prepare a number of other PI3K inhibitors of the disclosure, and alternative methods for preparing the compounds of this disclosure are deemed to be within the scope of this disclosure. For example, the synthesis of non-exemplified compounds according to the disclosure may be successfully performed by modifications apparent to those skilled in the art, e.g., by utilizing other suitable reagents known in the art other than those described, and/or by making routine modifications of reaction conditions. Alternatively, other reactions disclosed herein or known in the art will be recognized as having applicability for preparing other compounds of the disclosure.

In the Examples described below, unless otherwise indicated all temperatures are set forth in degrees Celsius. Reagents were purchased from commercial suppliers, such as Sigma Aldrich Chemical Company, J. T. Baker, Boron Molecular, Mallinckrodt, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl3, $d_6$-DMSO, CH3OD or $d_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in hertz (Hz).

HPLC may be conducted by the following exemplary methods:

| LCMS short method - 10 min run HPLC - Agilent 1200 | |
| --- | --- |
| Mobile phase A | Water with 0.05% TFA |
| Mobile phase B | Acetonitrile with 0.05% TFA |
| Column | Agilent ZORBAX SD-C18, 1.8 µm, 2.1 × 30 mm |
| Column temperature | 40° C. |
| LC gradient | 3-95% B in 8.5 min, 95% in 2.5 min |
| LC flowrate | 400 µL/min |
| UV wavelength | 220 nm and 254 nm |
| Mass Spec - Agilent quadrupole 6140 | |
| Ionization | ESI positive |
| Scan range | 110-800 amu |

| Waters Acquity/LCT long method - 20 min run Waters Acquity UPLC | |
| --- | --- |
| Mobile phase A | Water with 0.05% TFA |
| Mobile phase B | Acetonitrile with 0.05% TFA |
| Column | Acquity UPLC BEH C18, 1.7 µm, 2.1 × 50 mm |
| Column temperature | 40° C. |
| LC gradient | 3-98% B in 17.0 min, 98% in 1.5 min |
| LC flowrate | 600 µL/min |
| UV wavelength | 254 nm |
| Mass Spec - Waters LCT Premier XE | |
| Ionization | ESI positive |
| Scan range | 110-800 amu |

| Phenomenex Onyx | |
| --- | --- |
| Mobile phase A | 0.05% Formic Acid/Water |
| Mobile phase B | 0.05% Formic Acid/Acetonitrile |
| Column | Phenomenex Onyx Monolithic C18 column, 2 × 50 mm (CV = 0.157 mL) |
| Column temperature | 35° C. |
| Flow Rate | 0.785 mL/minute (5 CV/min) |
| Injection Volume | 2 µL |
| Sample Concentration | 0.5-1.0 mg/mL in 50% Acetonitrile/water |
| Signal | 220 nm Bandwidth 4 nm, Reference off |
| Store spectrum | 190-400 nm |
| Range Step | 2.0 nm |
| Threshold | 1.0 mAU |
| Peakwidth | >0.01 min |
| Slit | 4 nm |

HPLC analysis of 2-(2-chloro-6-morpholino-9H-purin-8-yl)propan-2-ol (Compound 5), 2-chloro-6,6-dimethyl-4-morpholino-8,9-dihydro-6H-[1,4]oxazino[3,4-e]purine (Compound 7), and 5-(6,6-dimethyl-4-morpholino-8,9-dihydro-6h-[1,4]oxazino[3,4-e]purin-2-yl)pyrimidin-2-amine (GDC-0084) may be done as follows. Diluent: acetonitrile. Mobile phase A: 0.05% TFA/water. Mobile phase B: 0.05% TFA/acetonitrile. Column: Ace 3 C18 HL column, 3×50 mm 3.0 μm. Column temperature: 35° C. Detector wavelength: 220 nm. Injection volume: 2 μL. Flow rate: 1 mL/min. Sample Concentration: 0.5-1.0 mg/mL in 50% acetonitrile/water. Program: 0.0 min 5.0% B, 0.3 min 5.0% B, 2.0 min 60.0% B, 4.0 min 90% B, 5.0 min 90% B, 5.1 min 5.0% B, 6.5 min 5.0%. Typical retention times: 5 (RT 2.61 min), 7 (RT 2.20 min), GDC-0084 (RT 2.67 min).

Figure 5:
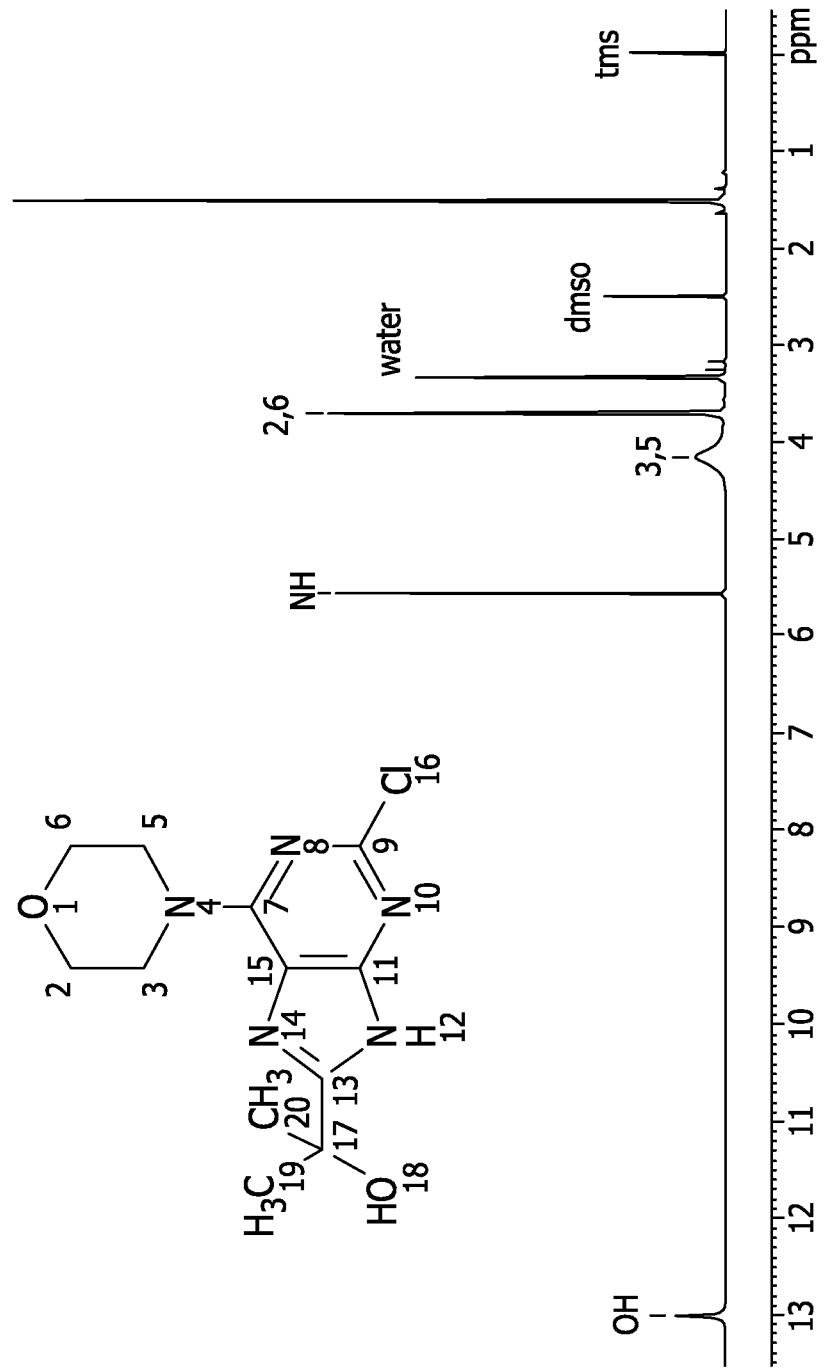
FIG. 5 is a $^1$H NMR (500 MHz, CDCl$_3$) spectrum of 2-(2-chloro-6-morpholino-9H-purin-8-yl)propan-2-ol (compound 5).
Figure 6:
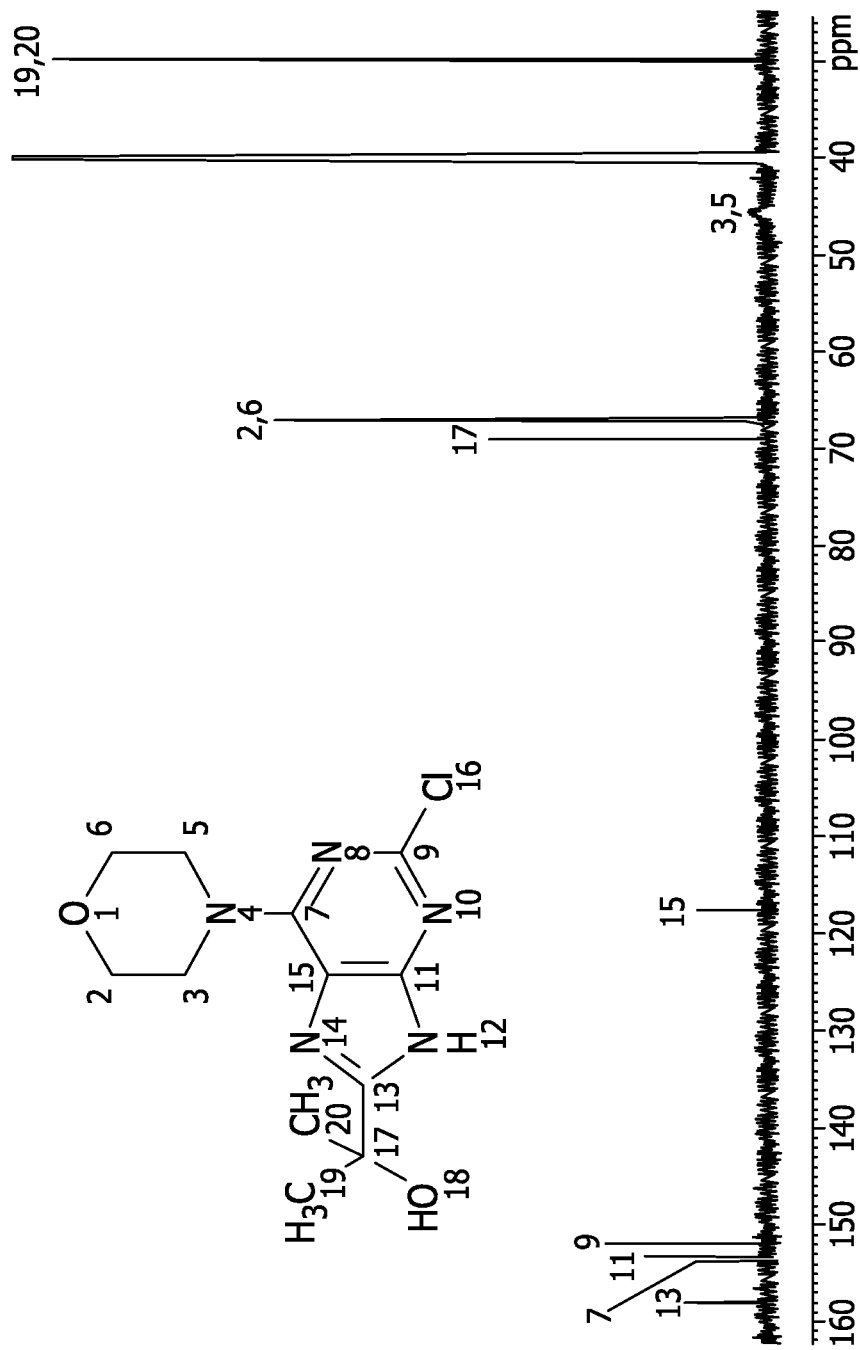
FIG. 6 is a $^{13}$C NMR (125 MHz, CDCl$_3$) spectrum of 2-(2-chloro-6-morpholino-9H-purin-8-yl)propan-2-ol (compound 5).
Figure 7:
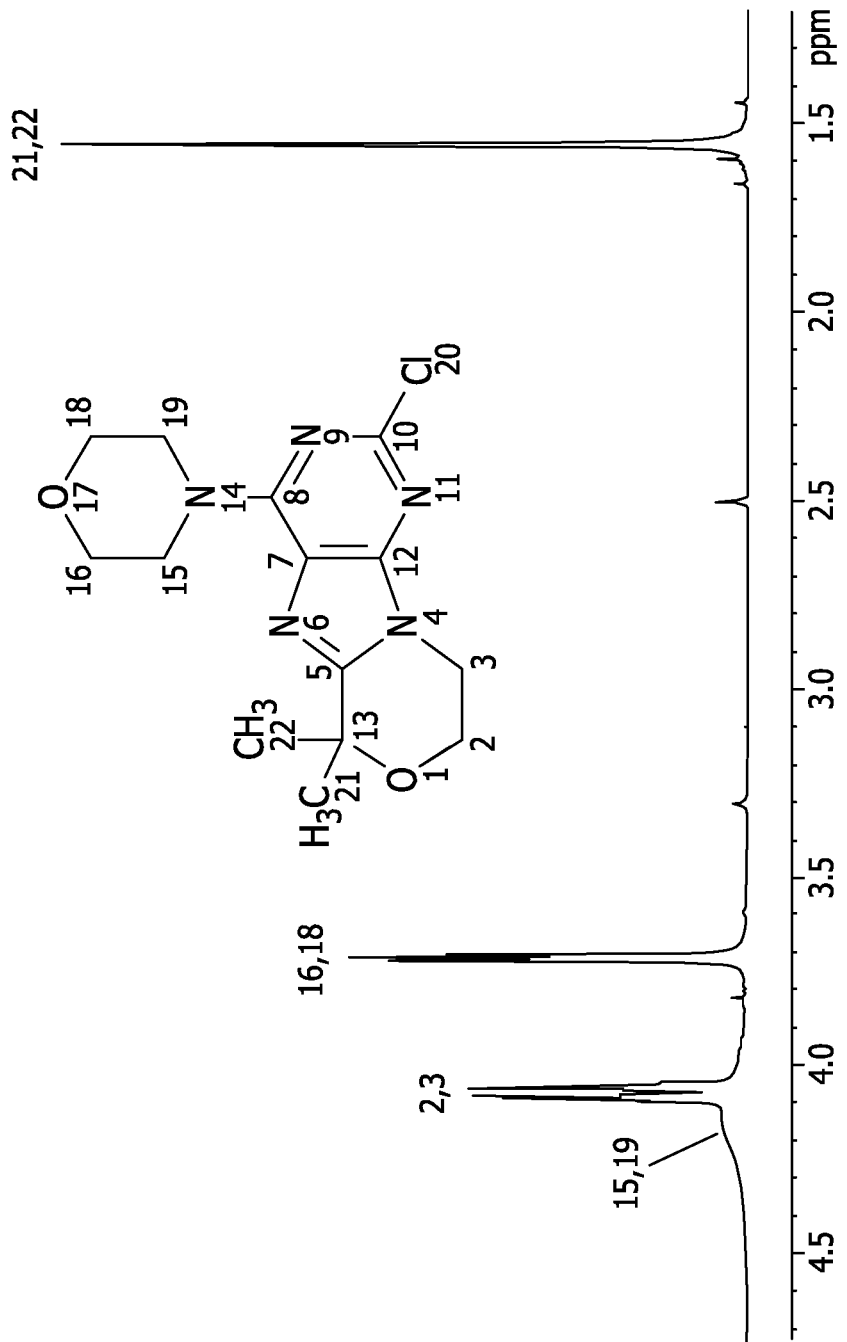
FIG. 7 is a $^1$H NMR (500 MHz, CDCl$_3$) spectrum of 2-chloro-6,6-dimethyl-4-morpholino-8,9-dihydro-6H-[1,4]oxazino[4,3-e]purine (compound 7).
Figure 8:
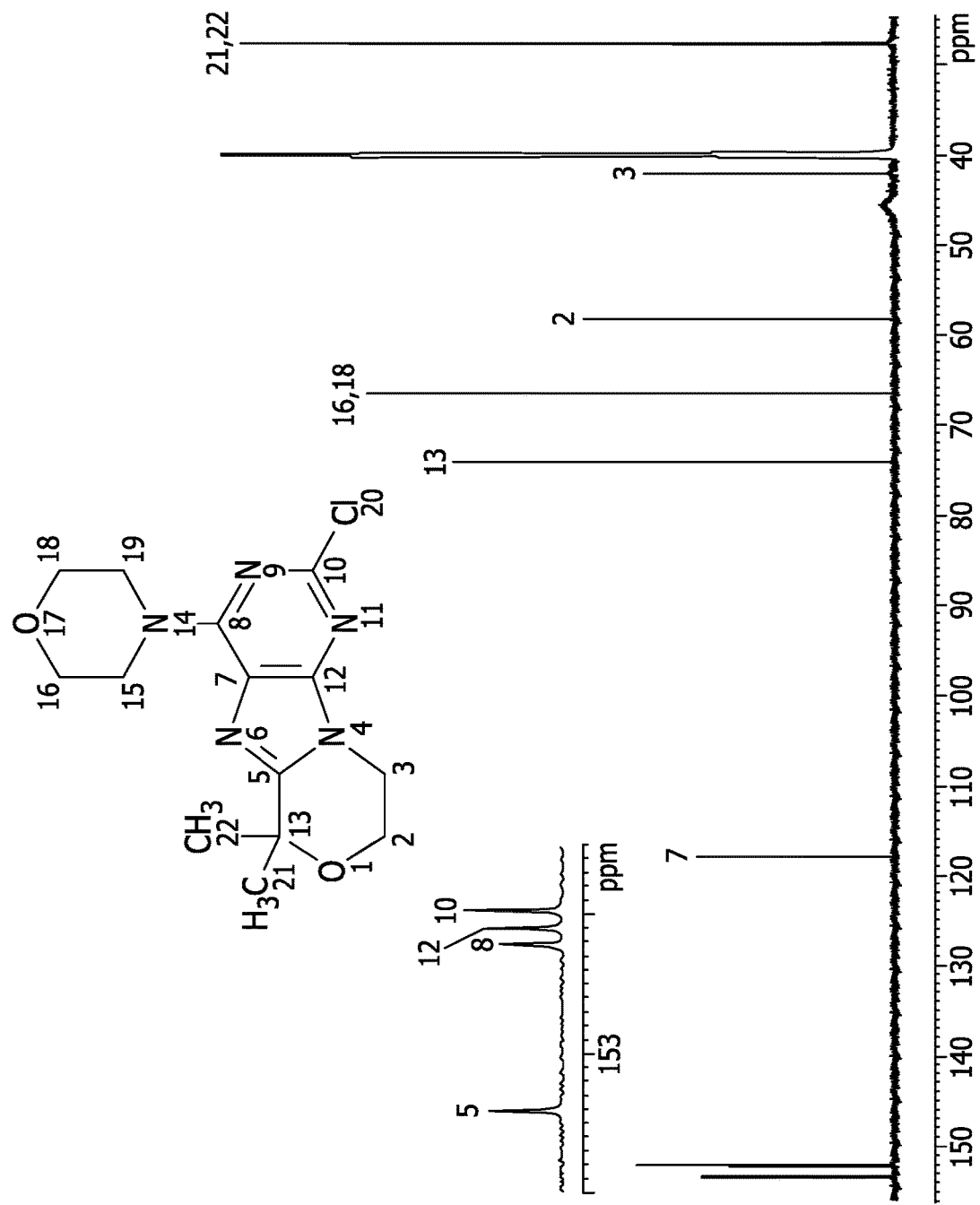
FIG. 8 is a $^{13}$C NMR (125 MHz, CDCl$_3$) spectrum of 2-chloro-6,6-dimethyl-4-morpholino-8,9-dihydro-6H-[1,4]oxazino[4,3-e]purine (compound 7).
Figure 11:
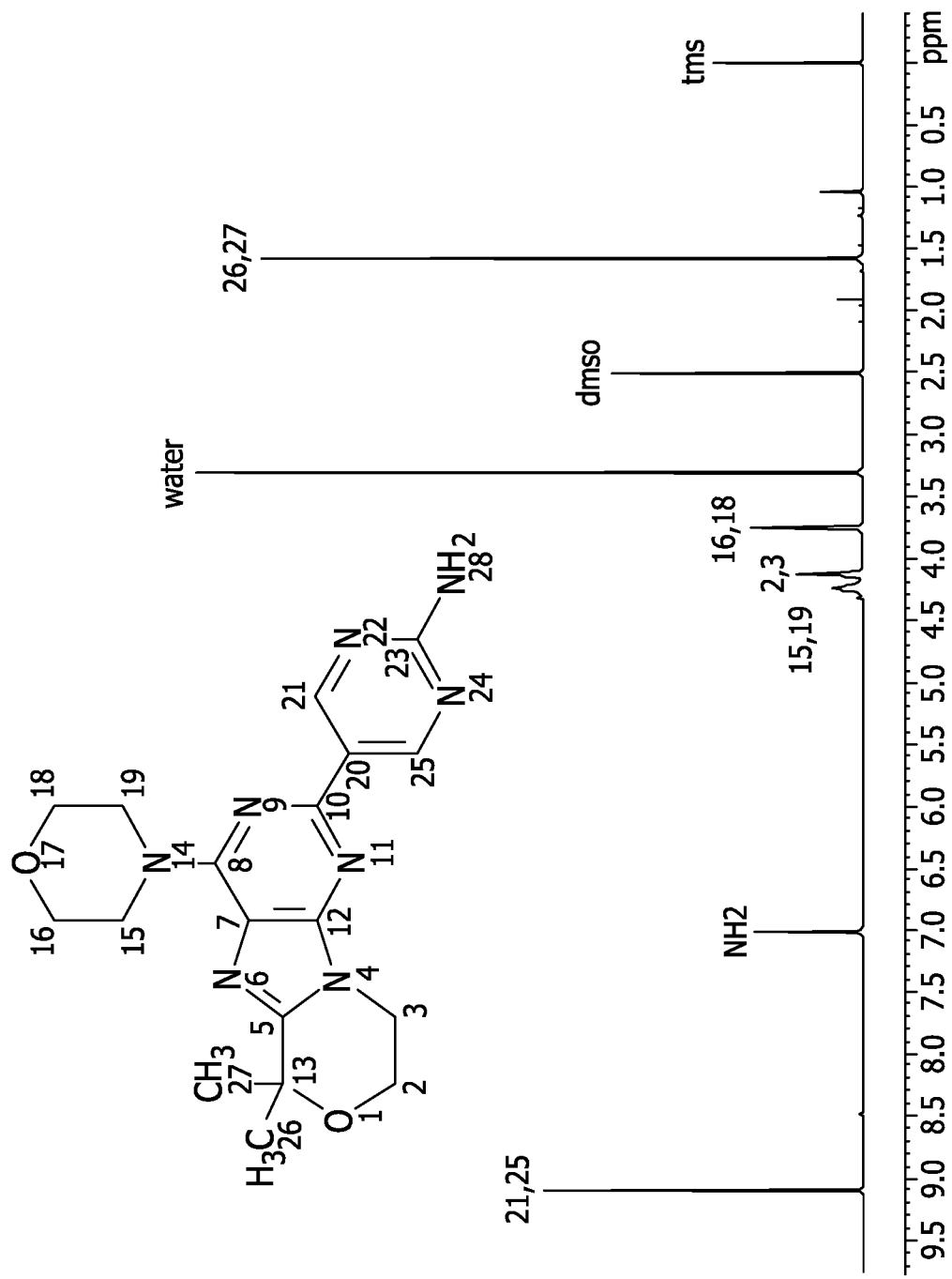
FIG. 11 is a $^1$H NMR (500 MHz, CDCl$_3$) spectrum of 5-(6,6-dimethyl-4-morpholino-8,9-dihydro-6H-[1,4]oxazino[4,3-e]purin-2-yl)pyrimidin-2-amine (GDC-0084).
Figure 12:
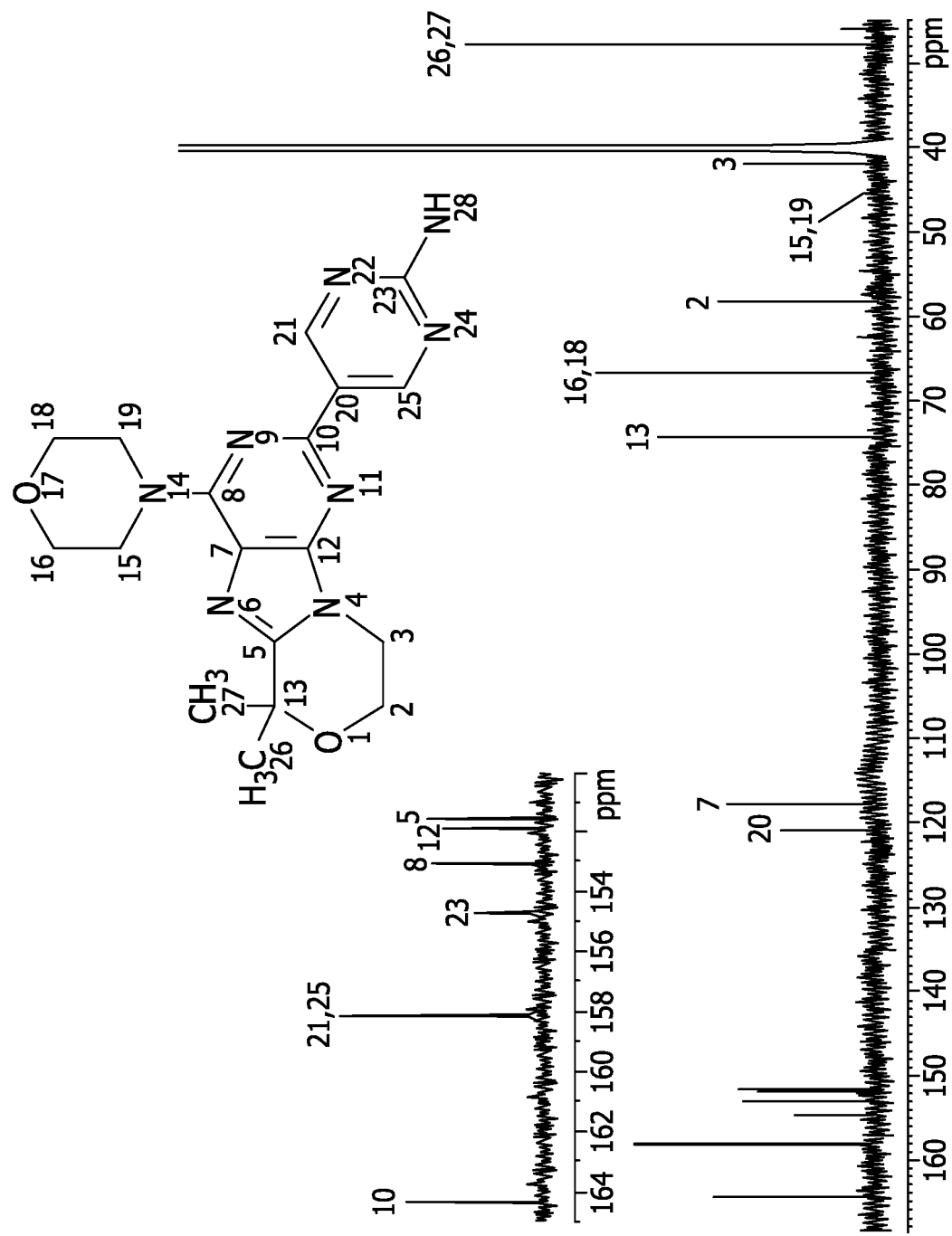
FIG. 12 is a $^{13}$C NMR (125 MHz, CDCl$_3$) spectrum of 5-(6,6-dimethyl-4-morpholino-8,9-dihydro-6H-[1,4]oxazino[4,3-e]purin-2-yl)pyrimidin-2-amine (GDC-0084).

The structure of compound 5 was verified by NMR (see FIGS. 5 and 6). The structure of compound 7 was verified by NMR (see FIGS. 7 and 8). The structure of GDC-0084 was verified by NMR (see FIGS. 11 and 12).

Example 1: Preparation of 2,6-dichloro-9-(tetrahydro-2H-pyran-2-yl)-9H-purine (Compound 2) as Indicated Below

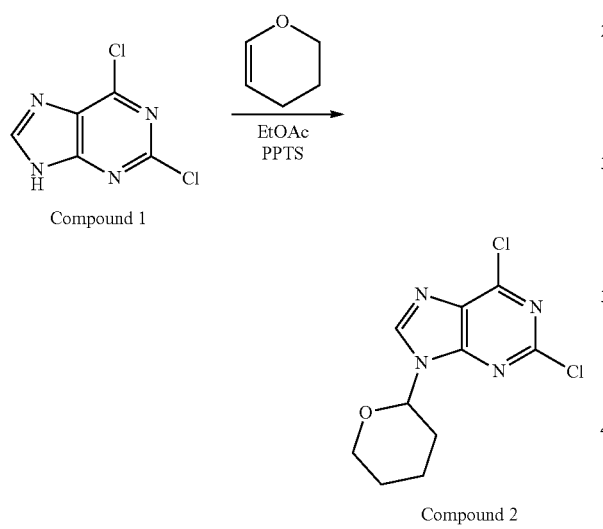

To a reactor was charged 2,6-dichloro-9H-purine (compound 1) (28.50 kg, 150.79 mol, 100 mol %), EtOAc (285.00 L, 10 vol), and pyridinium p-toluenesulfonate (PPTS) (568.5 g, 2.26 mol, 1.5 mol %), followed by a slow addition of 3,4 dihydro-2H-pyran (34.25 kg, 407.16 mol, 270 mol %) at 20 to 25° C. The mixture was slowly heated to 50 to 55° C. and maintained until HPLC analysis showed compound 1 to be no more than 1.0 A % (3 h). The reaction mixture was then cooled to 20° C., washed with saturated aqueous NaHCO$_3$ (81 L, 2.8 vol) and brine (81.00 L, 2.8 vol), dried over Na$_2$SO$_4$ (14.30 kg), filtered, and distilled under vacuum to remove EtOAc (230 L). The crude product was filtered and charged back to the reactor. Hexanes (142 L) was added and the mixture was agitated for 15 min. The mixture was filtered, then dried under vacuum at 55° C. for 8 h to afford 39.90 kg of compound 2 (97% yield, 99A % HPLC) as a green solid: mp 116° C.; $^1$H NMR (500 MHz, DMSO-d$_6$) δ 8.92 (s, 1H), 5.72 (dd, 1H), 4.01 (m, 1H), 3.72 (m, 1H), 2.25 (m, 1H), 1.98 (m, 2H), 1.74 (m, 1H), 1.58 (m, 2H); $^{13}$C NMR (125 MHz, DMSO-d$_6$) δ 153.2, 151.7, 150.4, 146.9, 131.1, 82.2, 68.2, 30.2, 24.8, 22.5. HRMS [M+H]$^+$ calcd for C$_{10}$H$_{10}$Cl$_2$N$_4$O 273.0304. found 273.0300.

Example 2: Preparation of 4-(2-chloro-9-(tetrahydro-2H-pyran-2-yl)-9H-purin-6-yl)morpholine (Compound 3) as Indicated Below

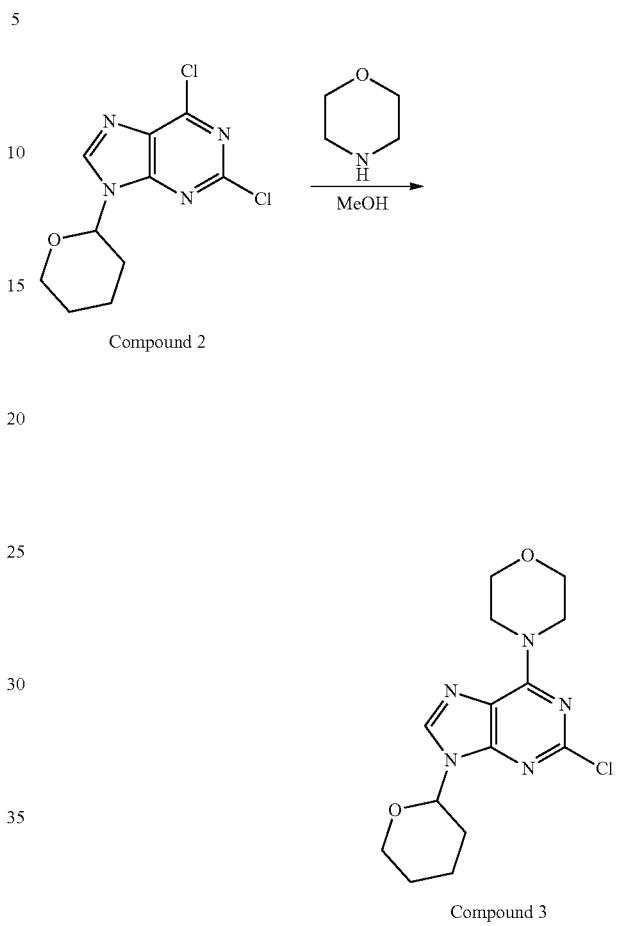

A reactor was charged with compound 2 (39.90 kg, 146.09 mol, 100 mol %) and MeOH (399 L), then cooled to 0° C. Morpholine (38.20 kg, 438.48 mol, 300 mol %) was added at 0-5° C. The reaction mixture was warmed to 20 to 25° C. until HPLC analysis showed 2 to be no more than 1.0 A % (24 h). The mixture was cooled to 0 to 5° C., held for 1 h, and then filtered. The cake was washed with hexanes (200 L, 5 vol) and dried under vacuum at 55° C. for 14 h to afford 44.40 kg of compound 3 (94% yield, 99A % HPLC) as a green solid: mp 139° C.; $^1$H NMR (500 MHz, DMSO-d$_6$) δ 8.39 (s, 1H), 5.60 (dd, 1H), 4.20 (bs, 4H), 4.01 (m, 1H), 3.71 (m, 4H), 2.17 (m, 1H), 1.94 (m, 2H), 1.74 (m, 1H), 1.58 (m, 2H); $^{13}$C NMR (125 MHz, DMSO-d$_6$) δ 153.9, 153.2, 151.6, 139.0, 118.4, 83.3, 68.2, 66.5, 45.8, 30.6, 24.9, 22.7. HRMS [M+H]$^+$ calcd for C$_{14}$H$_{18}$ClN$_5$O$_2$ 324.1222. found 324.1222.

Example 3: Preparation of 2-(2-chloro-6-morpholino-9-(tetrahydro-2H-pyran-2-yl)-9H-purin-8-yl)propan-2-ol 2-(2-chloro-6-morpholino-9-(tetrahydro-2H-pyran-2-yl)-9H-purin-8-yl)propan-2-ol (compound 4) was prepared from 4-(2-chloro-9-(tetrahydro-2H-pyran-2-yl)-9H-purin-6-yl) morpholine (compound 3) as indicated below.

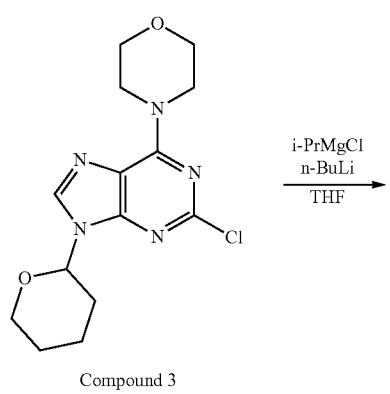

Compound 3

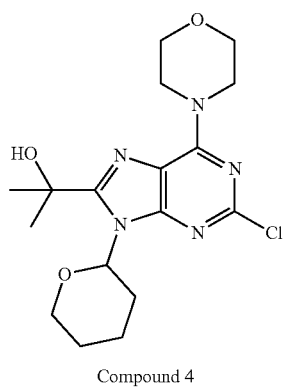

Compound 4

Compound 3 (310 g, 100 mol %) and tetrahydrofuran (4.0 L, 13 vol.) were added to a 12 L round bottom flask and a reaction solution was formed. The solution was cooled to −10° C. and i-PrMgCl (287 mL, 2.0 M in THF) was added while maintaining the temperature at less than or equal to −5° C. A reaction mixture was formed by combining n-BuLi (421 mL, 2.5 M in hexane) with the reaction solution while maintaining the temperature at less than or equal to −5° C. The reaction mixture was maintained at less than or equal to −5° C. until analysis by HPLC indicated that compound 3 was no more than 5 area percent by HPLC ("A %"). Acid was added to the reaction mixture that was then quenched by adding H$_2$O (8.0 L, 0° C.). The layers were separated, and the aqueous phase was extracted with MTBE (1.5 L). The combined organic extracts were washed with saturated aqueous NaCl (1.5 L), then concentrated to near dryness. i-PrOH (1.5 L) was combined with the organic extracts and the admixture was concentrated to near dryness. The concentrate was transferred to a 2 L round bottom flask, combined with 2-propanol (1 L), and heated at 50° C. for 3 h. The mixture was cooled to 25° C. to form a slurry by crystallization and held at that temperature for 12 h. The slurry was then cooled to 0° C., held at that temperature for 3 h, filtered to isolate a filter cake, and washed with cold 2-propanol (200 mL). The filter cake was dried in vacuo at 50° C. for 12 h. The process yielded 329 g of compound 4 (90% yield) as an off-white solid. About a 3% loss of compound 4 was noted during crystallization.

In a scale up evaluation, to compound 3 (40.80 kg, 126.01 mol, 100 mol %) in anhydrous THF (408 L, 10 vol) was added a solution of i-PrMgCl (1.0 M in THF, 82 L, 82.00 mol, 65 mol %) at −15° C. under N$_2$, followed by the addition of n-BuLi (2.5 M in hexane, 55 L, 137.50 mol, 109 mol %) between −10° C. and −5° C. After 30 min at this temperature acetone (16.20 kg, 278.92 mol, 221 mol %) was added slowly to the solution. The reaction mixture was stirred 2 h at −10±5° C. until HPLC analysis showed compound 3 to be no more than 1.0 A % (2 h). The mixture was then transferred to a reactor containing water (40.80 kg, 1 vol) at 0 to 5° C., the mixture was agitated for 5 min, and the layers were separated. The aqueous phase was extracted with MTBE (136 L, 3.3 vol). The combined organic extracts were washed with brine (119 L, 2.9 vol), dried over Na$_2$SO$_4$ (34 kg), filtered, and evaporated to provide the crude product. The yellow residue was suspended in 2-propanol (204 L, 5 vol) and the resulting slurry was heated to 50° C. for 60 min. The slurry was cooled to 25° C. over 2 h and then cooled to 0 to 5° C. over 1 h. The product was collected by filtration, washed with cold 2-propanol (40.8 L, 1 vol), and dried under vacuum at 55° C. for 12 h to afford 42.50 kg of compound 4 (91% yield) as an off-white powder: mp 181° C.; $^1$H NMR (500 MHz, DMSO-d$_6$) δ 6.27 (dd, 1H), 5.81 (s, 1H), 4.15 (vbs, 4H), 4.05 (m, 1H), 3.69 (m, 4H), 3.55 (m, 1H), 1.97 (m, 1H), 1.70 (m, 1H), 1.60 (s, 3H), 1.56 (m, 3H), 1.53 (s, 3H); $^{13}$C NMR (125 MHz, DMSO-d$_6$) δ 155.2, 154.0, 153.7, 152.3, 117.1, 84.3, 70.0, 68.5, 66.5, 45.8, 30.5, 29.7, 28.0, 25.0, 23.5. HRMS [M+H]$^+$ calcd for C$_{17}$H$_{24}$ClN$_5$O$_3$ 382.1640. found 382.1644.

Example 4: Preparation of 2-(2-chloro-6-morpholino-9H-purin-8-yl)propan-2-ol 2-(2-chloro-6-morpholino-9H-purin-8-yl)propan-2-ol (compound 5) was prepared from 2-(2-chloro-6-morpholino-9-(tetrahydro-2H-pyran-2-yl)-9H-purin-8-yl)propan-2-ol (compound 4) as indicated below.

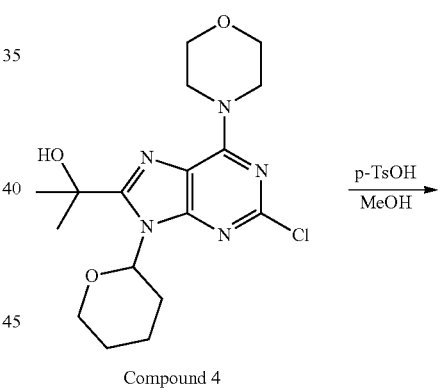

Compound 4

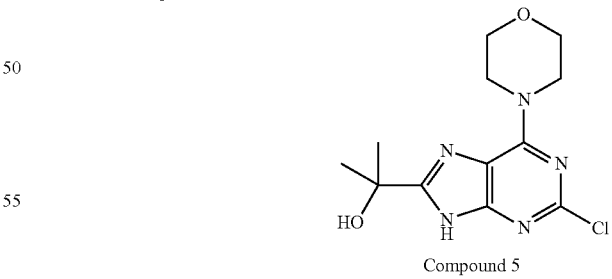

Compound 5

Compound 4 (327 g, 100 mol %), p-toluenesulfonic acid monohydrate (4.88 g, 3 mol %), and methanol (2.6 L, 8 vol) were combined in a 5 L round bottom flask to form a solution. The solution was heated to 50° C., and then held at that temperature for 3 h whereupon the compound 4 content was no more than 1 A % as measured by HPLC. The solution was cooled to ambient temperature, concentrated to dryness and combined with water (1.0 L). A solid product was isolated by filtration and washed with water (2×500 mL) and then with heptane (2×500 mL), and then dried in vacuo at 50° C. for 12 h. The process yielded 246 g compound 5 as a pale yellow fluffy solid.

Example 5: Preparation of 2-chloro-6,6-dimethyl-4-morpholino-8,9-dihydro-6H-[1,4]oxazino[3,4-e]purine 2-chloro-6,6-dimethyl-4-morpholino-8,9-dihydro-6H-[1,4]oxazino[3,4-e]purine (Compound 7) was prepared from 2-(2-chloro-6-morpholino-9H-purin-8-yl)propan-2-ol (Compound 5) as indicated below.

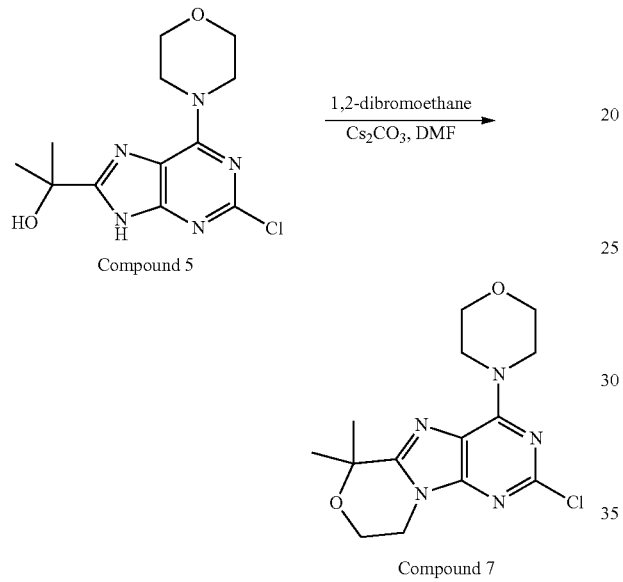

Example 6: Preparation of 5-(6,6-dimethyl-4-morpholino-8,9-dihydro-6H-[1,4]oxazino[3,4-e]purin-2-yl)pyrimidin-2-amine (GDC-0084)

5-(6,6-dimethyl-4-morpholino-8,9-dihydro-6H-[1,4]oxazino[3,4-e]purin-2-yl)pyrimidin-2-amine (GDC-0084) was prepared from 2-chloro-6,6-dimethyl-4-morpholino-8,9-dihydro-6H-[1,4]oxazino[3,4-e]purine (Compound 7) as indicated below.

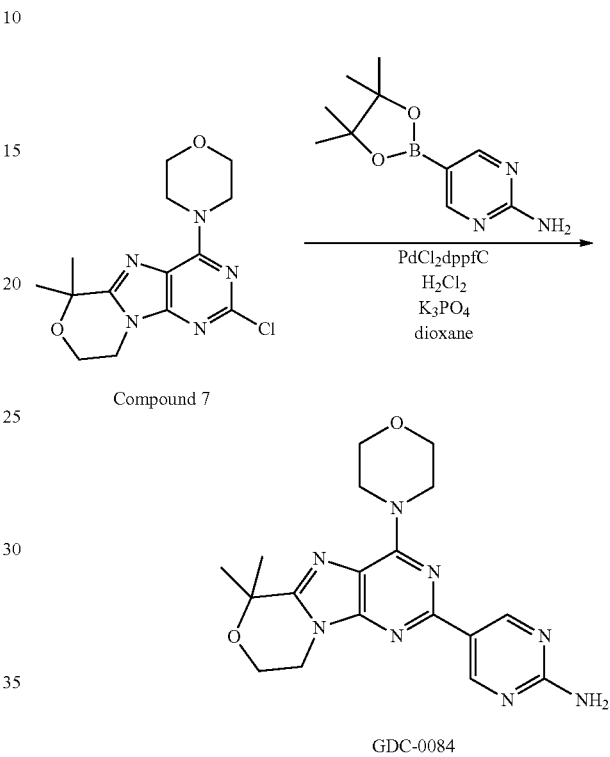

Compound 5 (240 g, 100 mol %), DMF (806 mL, 3.6 vol), cesium carbonate (303 g, 115 mol %), and 1,2-dibromoethane (139 mL, 200 mol %) were combined in a 5 L round bottom flask. The resulting heterogeneous mixture was heated to 90° C. for 3 hours whereupon HPLC analysis indicated that compound 5 was 30 A % and compound 7 was 49 A %. Additional 1,2-Dibromoethane (69.4 mL, 100 mol %) was charged and reacted for 3 hours whereupon HPLC analysis indicated that compound 5 was 28 A % and compound 7 was 54 A %. Additional cesium carbonate (355 g, 135 mol %) and 1,2-dibromoethane (34.7 mL, 50 mol %) were then charged and reacted for 3 hours whereupon HPLC analysis indicated that compound 5 was 2 A % and compound 7 was 87 A %. The mixture was cooled to ambient temperature, water (2.2 L) was added, and the admixture was stirred for 12 h. Attempts to crystallize product after addition of water to quench the reaction was not successful as a gummy solid was produced. EtOAc (1.3 L) was added, the layers were separated, and the organic phase was washed with saturated aqueous NaCl (3×1.2 L). The organic phase was concentrated to minimum stir volume to produce a sticky solid. Isopropanol (300 mL) was added to the solid, the admixture was heated to 65° C. and held for 2 hours at temperature, and then admixture was cooled to ambient temperature. The resulting solids were filtered and dried in vacuo at 50° C. for 12 h. The process yielded 147 g compound 7 as a yellow crystalline solid.

Figure 9:
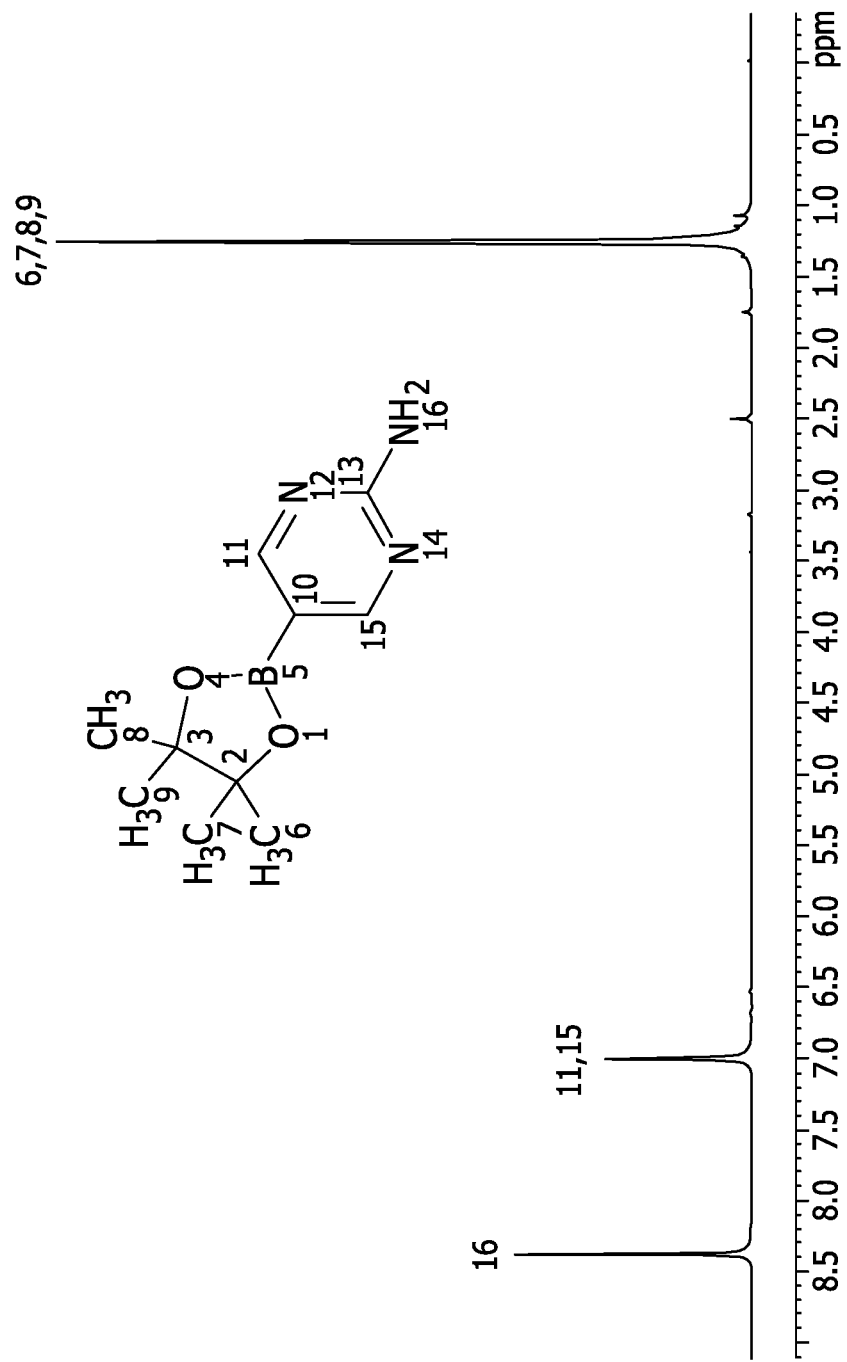
FIG. 9 is a $^1$H NMR (500 MHz, CDCl$_3$) spectrum of 5-(4,4,5,5-tetramethyl-1,3,2-dioxaborolan-2-yl)pyrimidin-2-amine (pinacolboronate).
Figure 10:
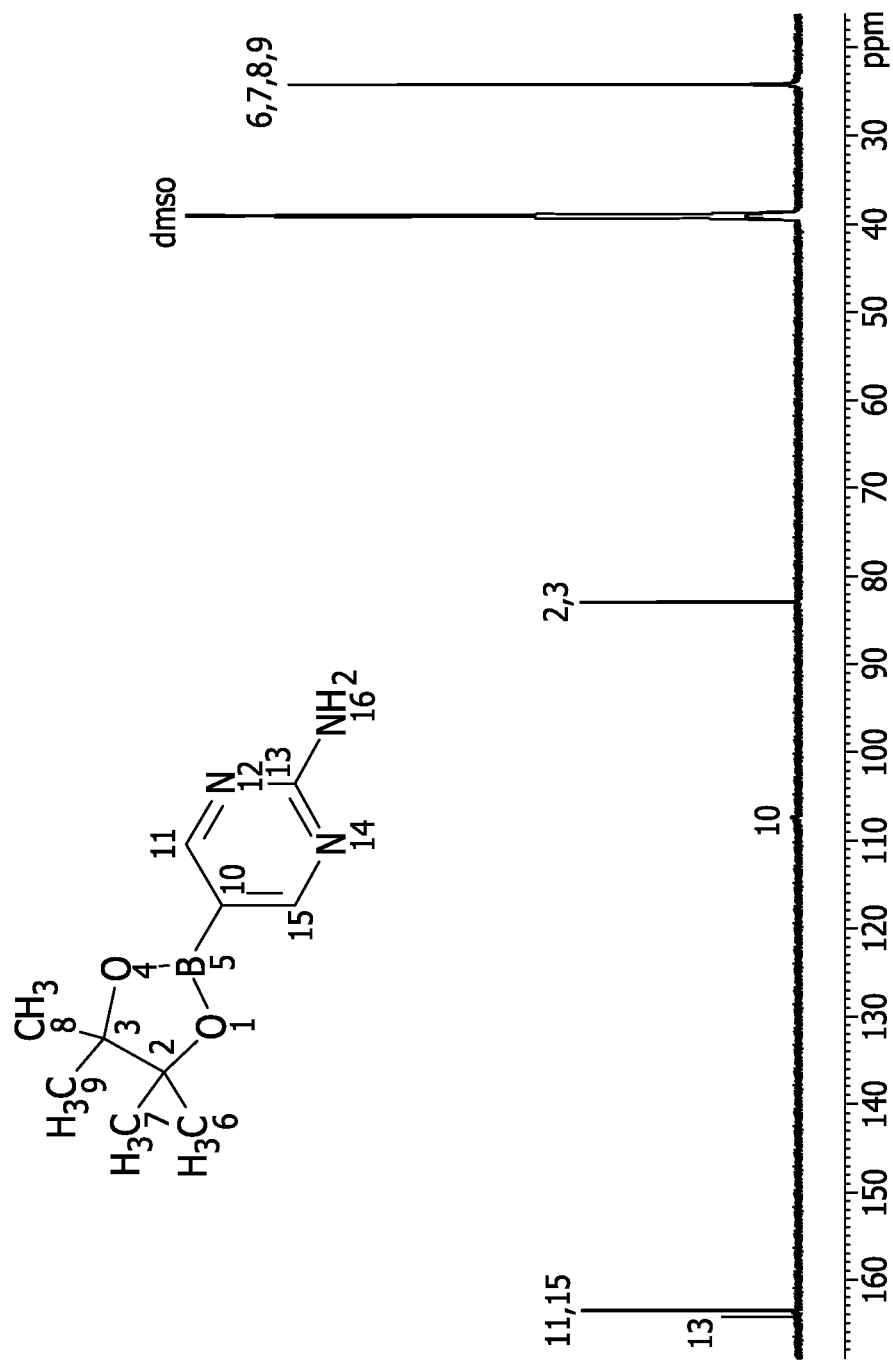
FIG. 10 is a $^{13}$C NMR (125 MHz, CDCl$_3$) spectrum of 5-(4,4,5,5-tetramethyl-1,3,2-dioxaborolan-2-yl)pyrimidin-2-amine (pinacolboronate).

In a Suzuki cross-coupling reaction, compound 7 (138 g, 100 mol %), 5-(4,4,5,5-tetramethyl-1,3,2-dioxaborolan-2-yl)pyrimidin-2-amine ("pinocolboronate") (113 g, 120 mol %), dioxane (1.7 L), and potassium phosphate (aq. 3.0 M, 284 mL, 200 mol %) were combined in a 3 L round bottom flask. The structure of pinocolboronate was verified by NMR (see FIGS. 9 and 10). The contents were sparged with N₂ for 30 min, PdCl₂dppf.CH₂Cl₂ (6.96 g, 2 mol %) was then charged, and the admixture was sparged with N₂ for 10 min. The mixture was heated to 80° C. and then held at that temperature for 2 h, after which analysis by HPLC showed complete consumption of compound 7. The admixture was transferred to a 12 L round bottom flask, water was added (6.8 L), the mixture was cooled to 5° C., filtered, and the filter cake was washed with water (2×500 mL). The filter cake was dried in vacuo at 50° C. for 12 h. The resulting crude GDC-0084 was transferred to a 5 L round bottom flask and combined with THF (3.2 L), HOAc (1.6 L), and water (480 mL). The admixture was heated to 50° C. and Si—(CH₂)₃SH ("Si-Thiol") (80 g) was added to the resulting solution. The admixture was held 3 h at 50° C., cooled to ambient temperature and held for 12 h. The mixture was filtered through a pad of Celite/silica gel and the filtrate was concentrated to dryness. The resulting pale brown solid was transferred to a 5 L round bottom flask and combined with THF (3.2 L), HOAc (1.6 L), and water (480 mL). The admixture was heated to 50° C. and THF (100 mL) was added to obtain a clear solution. In order to improve the color of the solution, Si-Thiourea (80 g) was added, the mixture was held 2 h at 50° C. and then filtered while hot through a 2 mm Teflon filter. The resulting pale yellow solution was distilled to dryness, slurried with n-butanol (3 L), filtered, and washed with heptane (2×1 L). The washed filtrate was dried in vacuo at 70° C. for 24 h. The process gave 149 g GDC-0084 (91% yield over 2 steps) as a yellow crystalline solid. Purity by HPLC was 98.9 A % with the major impurities identified as Impurity-1 and Impurity-2 illustrated below, and a residual Pd level of 12 ppm.

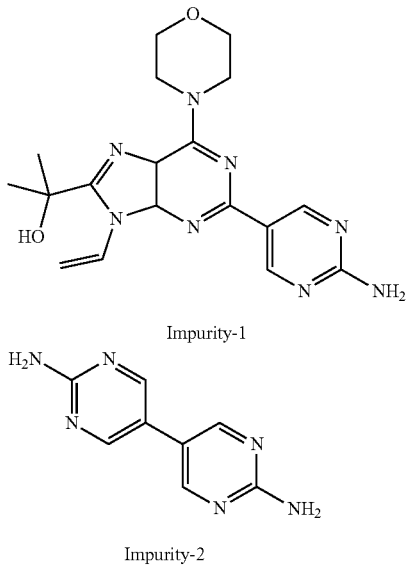

Impurity-1

Impurity-2

The overall yield of GDC-0084 by the series of reaction steps of Examples 1 to 4 was 44% with Impurity-1 present at 0.52 A % (HPLC) and Impurity-2 present at 0.18 A % (HPLC).

Example 7: Annulation of aminoalcohol Compound 5 to Form Fused Morpholine Compound 7

The effect of solvent, base and reaction temperature for the alkylation of compounds 5 with 1,2-dibromoethane to form compound 7 was evaluated. Table 1 below lists the combination of process parameters and reagents and associated reaction conversion for Experiments 1 to 10 where Experiments 1 to 8 were performed on a 0.3 g scale, Experiment 9 was done on a 60 g scale, and Experiment 10 was done on a 100 g scale. Experiments 1 to 8 were conducted by combining the reagents (1.0 mmol of compound 5) with 1.5 mL solvent in vials with stir bar mixing at ambient temperature followed by elevation to reaction temperature. The reactions for experiments 9 and 10 were done by mixing the reagents with mechanical mixing at ambient temperature followed by elevation to reaction temperature. For Experiment 9, 1,2-dibromoethane was added drop-wise over 1 hour to the heated reaction mixture and an exotherm was observed. For Experiment 10, compound 5 was added in two portions to the heated reaction mixture with 1 hour between additions. The total reaction time for each experiment was 12 hours. The results are reported in Table 5 below wherein "Exp" refers to experiment number, "DBU" refers to diazabicycloundecene, "Temp" refers to the reaction temperature, "A % sub" refers to the area percent (HPLC) of substrate 2-(2-chloro-6-morpholino-9H-purin-8-yl)propan-2-ol, "A % prod" refers to the area percent (HPLC) of 2-chloro-6,6-dimethyl-4-morpholino-8,9-dihydro-6H-[1,4]oxazino[3,4-e]purine, "A % Imp.3" refers to the area percent (HPLC) of Impurity 3 (depicted below—area percent by HPLC after 12 hour reaction time) and "A % Imp. 4" refers to the area percent (HPLC) of Impurity 4 (depicted below—area percent by HPLC).

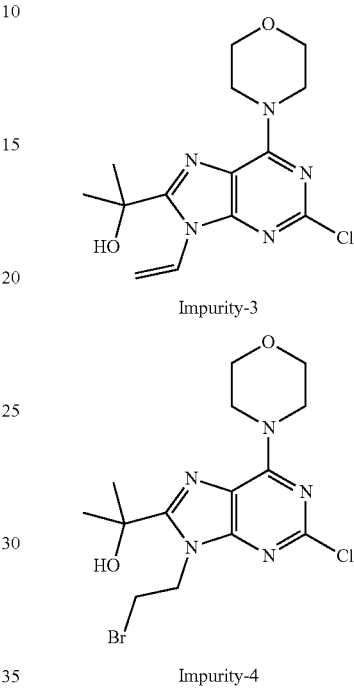

Impurity-3

Impurity-4

TABLE 1

| Exp | Base | Solvent | Temp | A % Sub | A % prod | A % Imp. 3 | A % Imp. 4 |
|---|---|---|---|---|---|---|---|
| 1 | Cs$_2$CO$_3$ | DMF | 90° C. | 1 | 86 | 13 | 0 |
| 2 | K$_2$CO$_3$ | DMF | 90° C. | 1 | 87 | 12 | 0 |
| 3 | Cs$_2$CO$_3$ | MIBK | 90° C. | 4 | 82 | 13 | 1 |
| 4 | K$_2$CO$_3$ | MIBK | 90° C. | 33 | 56 | 7 | 4 |
| 5 | Cs$_2$CO$_3$ | THF | 90° C. | 5 | 79 | 15 | 1 |
| 6 | K$_2$CO$_3$ | THF | 90° C. | 46 | 36 | 7 | 11 |
| 7 | Cs$_2$CO$_3$ | CH$_3$CN | 90° C. | 3 | 84 | 14 | 0 |
| 8 | K$_2$CO$_3$ | CH$_3$CN | 90° C. | 4 | 81 | 11 | 4 |
| 9 | K$_2$CO$_3$ | DMF | 100° C. | 0 | 85 | 11 | 0 |
| 10 | K$_2$CO$_3$ | DMF | 110° C. | 0 | 85 | 11 | 0 |

Cesium carbonate and potassium carbonate were found to function similarly in terms of conversion, which the latter afforded a slightly lower amount of Impurity 3. The ratio of the product to Impurity 3 was relatively insensitive to base, solvent and temperature. The reaction was found to be exothermic at larger scale, and dose-control additions were investigated to mitigate possible safety risk. Slow addition of 1,2-dibromoethane to a mixture of compound 5 and K$_2$CO$_3$ (experiment 9) did not adversely affect the conversion, but did lead to the formation of impurity 5 (below). Portion-wise addition of compound 5 to a mixture of 1,2-dibromoethane and K$_2$CO$_3$ (experiment 10) suppressed the formation of impurity 5 to less than 1 area % (by HPLC) without negatively impacting conversion.

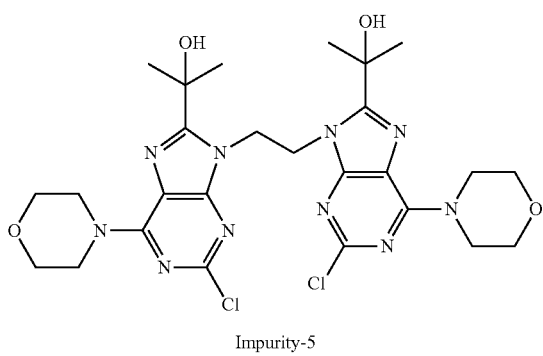 [SMILES: CC(C)(O)c1nc2c(N3CCOCC3)nc(Cl)nc2n1CCn1c(C(C)(C)O)nc2c(N3CCOCC3)nc(Cl)nc21]

Impurity-5

The exothermic annulation reaction was further examined by reaction calorimetry. In a first experiment, an Advanced Reactive System Screening Tool (ARSST™) found a reaction exotherm at 45° C. and an exothermic decomposition temperature ($T_{D24}$—the temperature at which time-to-maximum-rate is 24 hours) of 185° C. ARSTT methodology is known in the art and is available from Fauske & Associates, Inc. See, for instance, James P. Burlebach, "Advanced Reactive System Screening Tool (ARSST)", North American Thermal Analysis Society, 28$^{th}$ Annual Conference, Orlando, Oct. 4-6, 2000. In a second calorimetry experiment, integration of the reaction heat flow curve in an isothermal reaction calorimeter at 90° C. showed an adiabatic temperature rise of 76.5° C., an exotherm that was dose-controlled by portion-wise addition of compound 5. Taken together, the calorimetry data indicates that the exotherm may be effectively controlled by employing dose-controlled addition.

Example 8: Study of Suzuki Coupling Process Parameters

Various process parameters were investigated for the Suzuki cross coupling reaction of compound 7 with pinocolboronate to yield GDC-0084. The reactions for each experiment were done by mixing the reagents indicated in Table 2 at ambient temperature and then heating with mixing. The reactions were done in vials by mixing the reagents (0.9 mmol of compound 7) in the solvent (3.9 mL) at a solvent ratio of 10:1 at ambient temperature, evacuating and backfilling with nitrogen, sealing the vials, and then heating the sealed vials. Each of experiments 1, 2 and 4 to 7 were reacted for 2 hours at 80° C. The experiment 3 reaction was run for 10 hours. The results are reported in Table 2 below wherein "Exp" refers to experiment number, "Cat %" refers to mole percent catalyst, and "Ratio" refers to the molar ratio of product to substrate.

TABLE 2

| | Cat | | | Ratio | |
|---|---|---|---|---|---|
| Exp | % | Catalyst | Solvent | Product | Substrate |
| 1 | 5 | PdCl$_2$dppf•CH$_2$Cl$_2$ | Dioxane, H$_2$O | 99 | 1 |
| 2 | 2 | PdCl$_2$dppf•CH$_2$Cl$_2$ | Dioxane, H$_2$O | 99 | 1 |
| 3 | 1 | PdCl$_2$dppf•CH$_2$Cl$_2$ | Dioxane, H$_2$O | 88[1] | 12 |
| 4 | 2 | PdCl$_2$dppf•CH$_2$Cl$_2$ | THF, H$_2$O | 98 | 2 |
| 5 | 2 | PdCl$_2$dppf•CH$_2$Cl$_2$ | MeTHF, H$_2$O | 91 | 9 |
| 6 | 2 | PdCl$_2$dppf•CH$_2$Cl$_2$ | CH$_3$CN, H$_2$O | 94 | 6 |
| 7 | 2 | PdCl$_2$dppf•CH$_2$Cl$_2$ | IPA, H$_2$O | 93 | 7 |

[1]After 10 hours the ratio of product to substrate for Experiment 9 was 99:1.

In terms of catalyst loading, conversion was found to be slow at 1 mol %. The conversion was found to be high in most solvents.

Example 9: Solubility Tests

The solubility of GDC-0084 in various mono- and ternary-solvent systems was measured at 50° C., wherein each ternary solvent mixture had a solvent ratio of 67:24:9 on a volume basis. The solubility results are indicated in Table 3 below in wt % (mg/g).

TABLE 3

| Solvent | Solubility | Solvent | Solubility |
|---|---|---|---|
| DMF | 0.9 wt. % | DMF/HOAc/H$_2$O | 0.3 wt. % |
| THF | 0.7 wt. % | THF/HOAc/H$_2$O | 3.7 wt. % |
| MeTHF | 0.3 wt. % | MeTHF/HOAc/H$_2$O | 2.7 wt. % |
| MeOH | 0.2 wt. % | MeOH/HOAc/H$_2$O | 0.4 wt. % |
| EtOH | 0.1 wt. % | EtOH/HOAc/H$_2$O | 1 wt. % |
| n-PrOH | 0.1 wt. % | n-PrOH/HOAc/H$_2$O | 1.8 wt. % |
| i-BuOH | 0.1 wt. % | i-BuOH/HOAc/H$_2$O | 2.1 wt. % |
| n-BuOH | 0.1 wt. % | n-BuOH/HOAc/H$_2$O | 2.4 wt. % |
| PhMe | 0.1 wt. % | Toluene/HOAc/H$_2$O | 3.8 wt. % |
| HOAc | 2.8 wt. % | HOAc/HOAc/H$_2$O | 2.1 wt. % |

The results indicate that toluene/HOAc/water (67:24:9) was the best solvent system for GDC-0084 solubility. A ratio of 69:30:1 was selected for scale-up evaluations.

Example 10: Study of Pd Removal

The crude GDC-0084 prepared according to example 8 was found to contain elevated levels of residual palladium. In this example, removal of palladium from crude GDC-0084 was examined. In a series of experiments, 5 g solutions of GDC-0084 in THF/HOAc (2:1 ratio) comprising 2400 ppm Pd were exposed to a variety of metal scavengers (at 20 wt % loading) at 55° C. for 14 h, followed by filtration and concentration of the filtrate, and analysis of the resulting purified GDC-0084 for palladium content. The scavengers included: 0.3-0.8 mm porous carbon beads having a 1200 m$^2$/g surface area ("Quadrapure C"); 100 mesh activated carbon (Darco G-60); greater than 45 m activated carbon ("Darco KB-G"); ("SiTAACoNa"); Si—(CH$_2$)$_3$NHC(=S)NHCH$_3$ ("Si-Thiourea"); Si-Thiol; and powdered synthetic magnesium-silica gel ("Si-Thiol/Florisil"). Si-Thiol and Si-Thiourea are proprietary solid-supported resins available from Silicycle. The results are presented in Table 4 below where Si-Thiourea and Si-Thiol were the most efficient scavengers.

TABLE 4

| Scavenger | ppm Pd | Scavenger | Ppm Pd |
|---|---|---|---|
| None (control) | 2400 | SiTAAcONa | 900 |
| Quadrapure C | 2200 | Si-Thiourea | 16 |
| Darco G-60 | 1600 | Si-Thiol | 6 |
| Darco KGB | 900 | Si-Thiol/Florisil | 7 |

Example 11: Preparation of Purified GDC-0084

Purified GDC-0084 was prepared from compound 5 in a three step process as depicted below:

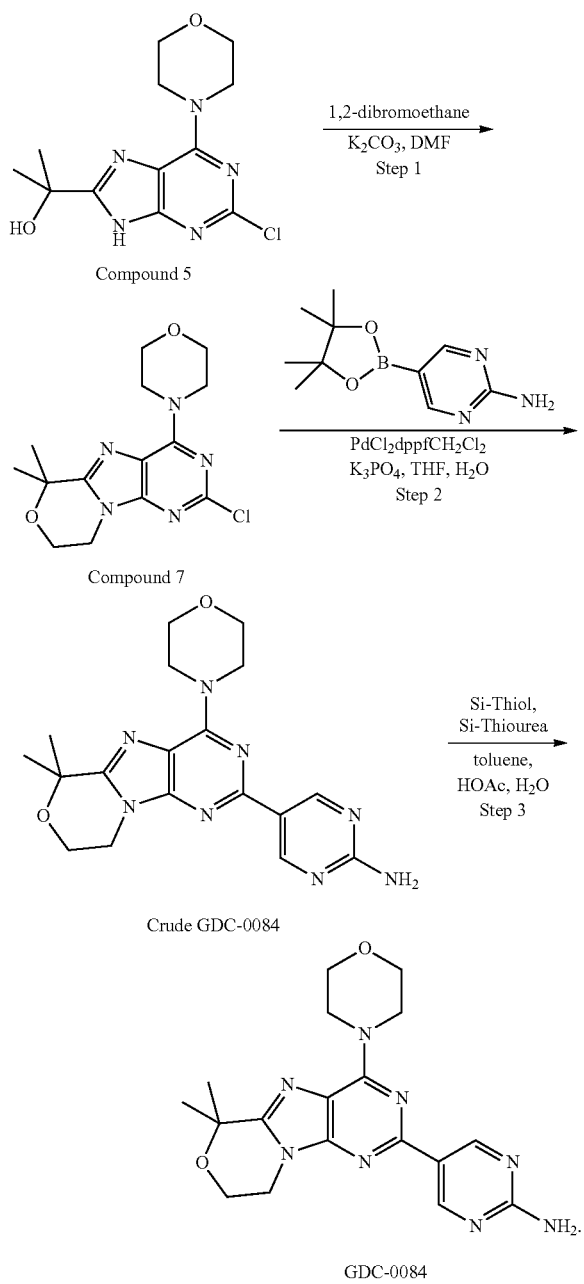

Compound 5

Compound 7

Crude GDC-0084

GDC-0084

In the first step, compound 7 was prepared from compound 5. A 100 L reactor was charged with DMF (20.0 L, 3.43 vol), 1,2-dibromoethane (7.36 kg, 39.2 mol, 200 mol %), potassium carbonate (6.76 kg, 48.9 mol, 250 mol %), and a first portion of compound 5 (3.01 kg, 10.1 mol, 52 mol %) ($^1$H NMR (500 MHz, DMSO-d6): δ 13.02 (s, 1H), 5.55 (s, 1H), 4.44-3.91 (m, 4H), 3.83-3.57 (m, 4H), 1.52 (s, 6H). $^{13}$C NMR (125 MHz, DMSO-d6): δ 157.7, 153.4, 153.0, 151.7, 117.2, 68.4, 66.0, 45.3, 29.3). The admixture was heated to 103° C., held at that temperature for 2 h, and then cooled to 50° C. HPLC IPC showed compound 5 to be 0.05 A %, and Impurity 4 to be 3.9 A %. The second portion of compound 5 (2.82 kg, 9.47 mol, 48 mol %) was charged to the reactor. The admixture was heated to 85° C., held at that temperature for 16 h, then cooled to 53° C. HPLC IPC showed compound 5 to be 0.05 A % and Impurity 4 to be 0.05 A %. The reaction was cooled to 21° C. and ethyl acetate (19.5 L) and purified water (40.0 L) were added. The aqueous layer was removed and additional ethyl acetate (19.5 L) and purified water (20.0 L) were added to the reactor. The second aqueous phase was removed. GC IPC showed DMF to be 0.7 wt % in the organic solution. This solution was transferred, along with ethyl acetate rinse (1.0 L), from the 100 L reactor to a 50 L reactor. Distillation was carried out to minimum stir volume (9 L) and isopropanol (12 L) was charged to the reactor. Distillation was again carried out to minimum stir volume (9 L) and 2-propanol (30 L) was added. GC IPC showed ethyl acetate to be 0.06 wt %. The 2-propanol suspension (39 L) was then heated to 65° C., held at that temperature for 2 h, cooled to 5° C. over 1 h, and the mixture was held for 2 h at reduced temperature. HPLC IPC indicated the product concentration in supernatant to be 14 mg/g. The mixture was filtered on an Aurora filter and the cake was washed with isopropanol (16 L). After no more filtrate could be collected from the filter, the cake was dried on the filter at 50±5° C. (jacket temperature) under house vacuum with a nitrogen purge. HPLC IPC showed Impurity 3 to be <1.0 A %. Drying was continued until GC IPC showed 2-propanol to be 0.91 wt %. The process gave 4.27 kg compound 7 product (67% yield; 97.8 A % by HPLC) as a light yellow solid. $^1$H NMR (500 MHz, DMSO-d6): δ 4.75-4.00 (m, 8H), 3.73-3.71 (m, 4H), 1.56 (s, 6H). $^{13}$C NMR (125 MHz, DMSO-d6): δ 152.9, 151.7, 151.6, 151.5, 117.3, 73.6, 66.0, 57.6, 45.3, 41.6, 27.2.

In the second step, crude GDC-0084 was prepared from compound 7. A glass carboy was charged with K$_3$PO$_4$.H$_2$O (5.84 kg, 24.8 mol, 200 mol %) in purified water (8.45 L). The contents were stirred until homogeneous, and then sparged with N$_2$ for ≥1 h. A 100 L reactor was charged with the aqueous K$_3$PO$_4$ solution, compound 7 from the first step (4.10 kg, 12.7 mol, 100 mol %), pinocolboronate (3.36 kg, 15.2 mol, 120 mol %) ($^1$H NMR (500 MHz, DMSO-d6): δ 8.38 (s, 2H), 7.02 (s, 2H), 1.27 (s, 12H). 13C NMR (125 MHz, DMSO-d6): δ 164.6, 163.9, 107.8, 83.4, 24.6), and THF (55.8 L). The contents were sparged with N$_2$ for 45 min, and then PdCl$_2$dppf.CH$_2$Cl$_2$ catalyst (0.207 kg, 0.25 mol, 2 mol %) was charged. The admixture was sparged with N$_2$ for 10 min, heated to ≥61° C., and held at that temperature for 4 h. HPLC IPC showed compound 7 to be 0.027 mg/mL. Purified water (45.8 L) was added and the reaction mixture was cooled to 7° C. and held at that temperature for 1 h. The reaction mixture was filtered on an Aurora filter and the filter cake was washed with purified water (4×30.0 L). After no more filtrate could be collected from the filter, the filter cake was dried on the filter at 70° C. (jacket temperature) under house vacuum with a N$_2$ purge. Drying was continued for 8 h. HPLC IPC impurity 2 to be 0.4 A %. The contents of the Aurora filter (crude GDC-0084) were transferred to a 100 L reactor and combined with Si-Thiol (2.22 kg), Si-Thiourea (2.22 kg), acetic acid (17.5 L), toluene (7.5 L), and purified water (0.25 L) to form an admixture. The admixture was heated to 90° C. and held at that temperature for 3 h. The admixture was transferred, along with acetic acid (7.5 L)/toluene (3.5 L) rinses (2×), to a Nutsche filter, and the hot filtrate (about 70° C.) was passed through an in-line filter (polish filtration) directly into a 50 L reactor. Metal analysis IPC showed residual Pd to be ≤3 ppm. Distillation was carried out to minimum stir volume (10 L), and then the contents were heated to 70° C. 2-Propanol (40.0 L) was charged to the reactor through an in-line filter (polish filtration) and the resulting suspension was heated to 70° C., held at that temperature for 1 h, cooled to 18° C. over 4 h, and held for 9 h at reduced temperature. HPLC IPC indicated the GDC-0084 concentration in supernatant to be 1.5 mg/g. The mixture was filtered through a filter dryer and the filter cake was washed with isopropanol (48 L). After no more filtrate could be collected from the filter, the filter cake was dried in the filter dryer at 70° C. (jacket temperature) under house vacuum with a $N_2$ purge. GC IPC showed isopropanol to be 0.52 wt % and acetic acid to be 0.44 wt %. The process gave 3.87 kg GDC-0084 (80% yield in step 2; 99.4 A % by HPLC) as a light yellow solid. $^1$H NMR (500 MHz, DMSO-d6): δ 9.09 (s, 2H), 7.03 (s, 2H), 4.32-4.17 (m, 4H), 4.17-4.04 (m, 4H), 3.84-3.65 (m, 4H), 1.58 (s, 6H). 13C NMR (125 MHz, DMSO-d6): δ 163.8, 157.6, 154.2, 152.5, 151.3, 151.0, 120.3, 117.3, 73.7, 66.2, 57.8, 45.2, 41.5, 27.3.

The overall synthesis for the combination of steps 1 and 2 gave 3.87 kg (99.6% purity) of GDC-0084 at a yield of 55%. Measured impurities included Impurity 2 (0.08 A %) and Impurity 6 (0.24 A %) (depicted below); and the total unspecified impurities were <0.05 A %. The final solvent content was 1 wt. % including 0.57 wt % (i-PrOH) and 0.43 wt % HOAc, the final water content was 0.09 wt %, and the final residual Pd level was <3 ppm.

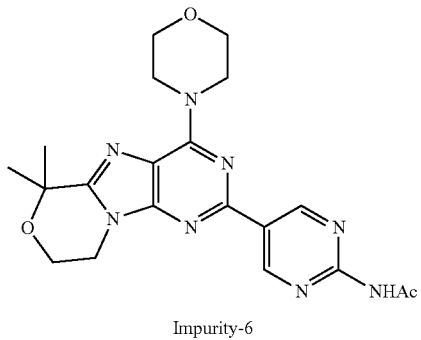 [SMILES: CC(=O)Nc1ncc(-c2nc(N3CCOCC3)c3nc4n(c3n2)CCOC4(C)C)cn1]

Impurity-6

Example 12: Preparation of 2-chloro-6,6-dimethyl-4-morpholino-8,9-dihydro-6H-[1,4]oxazino[3,4-e]purine A process for the conversion of compound 5 to compound 7 was evaluated using a phase transfer catalyst. More particularly, preparation of compound 7 by condensation of compound 5 with 1,2-dibromoethane in toluene/alkaline water solvent systems in the presence of the phase transfer catalyst Aliquat 336 (a quaternary ammonium salt comprising a mixture of $C_8$ and lesser amounts of $C_{10}$ chains; 1-octanaminium, N-methyl-N,N-dioctyl chloride) was evaluated and about a 50% conversion to compound 7 was achieved.

Solvent screens were then done for the preparation of compound 7 by condensation of compound 5 with 1,2-dibromoethane in each of chlorobenzene, THF, Me-THF, DCM and DCE. No conversion was achieved in DCE, partial conversion was achieved in chlorobenzene, and the conversion was less than in toluene/alkaline water for the remainder of the solvents.

Preparation of compound 7 by condensation of compound 5 with 1,2-dibromoethane in an alkaline water solvent in the absence of an organic solvent and in the presence of the phase transfer catalyst tetrabutylammonium bromide (TBAB) was evaluated. It was discovered that the condensation reaction went to completion in the aqueous solvent in the absence of an organic co-solvent. Base screening experiments were done with the bases KOH, NaOH, $K_2CO_3$ and NaHCO$_3$ and it was found that each base showed similar reactivity and provided for complete conversion with a similar purity profile. KOH was selected for further evaluation due to the highest aqueous solubility.

Reagent stoichiometry evaluations were done as summarized in Table 5 below for the conversion of one equivalent of compound 5 to compound 7 by condensation with 1,2-dibromoethane in an alkaline water solvent in the presence of TBAB phase transfer catalyst. In the reactions, 0.34 mmol of compound 5, KOH, TBAB and 1,2-dibromoethane were combined with 10 mL solvent at ambient temperature in vials and the reaction mixture was heated with vigorous stirring to 90° C. and held for 17 hours. Conversion was measured by HPLC. In Table 5, "Exp" refers to experiment, "1,2-DBE" refers to 1,2-dibromoethane, "equiv" refers to equivalents, and "Conv. %" refers to % conversion of 2-(2-chloro-6-morpholino-9H-purin-8-yl)propan-2-ol.

TABLE 5

| Exp | 1,2-DBE mol % | KOH mol % | TBAB mol % | Conv. % |
|---|---|---|---|---|
| 1 | 200 | 200 | 15 | 52 |
| 2 | 200 | 400 | 30 | 45 |
| 3 | 400 | 200 | 30 | 68 |
| 4 | 400 | 400 | 15 | 87 |
| 5 | 400 | 400 | 30 | 100 |
| 6 | 300 | 300 | 30 | 100 |

The data show that complete conversion was achieved with equimolar amounts of 1,2-dibromoethane and KOH in combination with a catalytic amount of TBAB (0.3 equiv.). Optimization of the reagent stoichiometry helped to drive the reaction to completion. One set of optimized conditions was determined to be equivalent amounts of 1,2-dibromoethane and KOH (300 mol % each) and a catalytic amount of TBAB (30 mol %) in water at 90° C. for 17 hours. It is believed that the use of excess base and 1,2-dibromoethane minimizes the competitive generation of vinyl bromide.

Example 13: Reaction Temperature Studies

Reaction temperature evaluations were done as summarized in Table 6 below for the conversion of compound 5 (100 mol %) to compound 7 by condensation with 1,2-dibromoethane (400 mol %) in an alkaline water solvent (400 mol % KOH) in the presence of TBAB phase transfer catalyst (30 mol %) and at a 22 hour reaction time. The results are also reported in Table 6 below, where "Exp" refers to experiment, and "A %" refers to area percent 2-chloro-6,6-dimethyl-4-morpholino-8,9-dihydro-6H-[1,4]oxazino[3,4-e]purine as analyzed by HPLC.

TABLE 6

| Exp. | Temperature | A % |
|---|---|---|
| 1 | 90.0 | 80.9 |
| 2 | 80.0 | 89.9 |
| 3 | 70.0 | 91.2 |
| 4 | 60.0 | 92.9 |
| 5 | 50.0 | 96.0 |
| — | — | — |

The results indicate that a reduction of the reaction temperature of from 90° C. to 50° C. resulted in an improved impurity profile.

Example 14: Crystallization Solvent Study

The phase transfer catalyst reactions of Examples 12 and 13 resulted in the compound 7 product separating from the aqueous layer as an oil containing significant concentrations of 1,2-dibromoethane. In those reactions, 2-propanol was added to facilitate product precipitation (crystallization). Seeding with 1% product seed crystals slightly improved crystallization but some oiling out of product was observed. It was discovered that replacement of i-propanol with ethanol allowed for an essentially clean isolation of the product as a solid from the product mixture, wherein a water to ethanol ratio of 1.3:1 provided the cleanest separation.

Example 15: Reaction Conditions Study

Reaction conditions found in Examples 12 to 14 that provided for the high relative conversions were evaluated for the preparation of compound 7 by the reaction of compound 5 (480 g), 1,2-dibromoethane (300 mol %), KOH (300 mol %), TBAB (30 mol %) and $H_2O$ (5 vol), where the equivalent amounts of reactant are based on the equivalents of starting material. The reaction was run at 50° C. for 12 hours, after which time EtOH (5.5 vol) was added to crystallize the product. Compound 7 was formed in 64% yield at 99.4 A % purity by HPLC.

Example 16: Pd Catalyst Study

Various catalysts comprising palladium were evaluated for the preparation of GDC-0084 from compound 7. For each experimental reaction, 3 mmol of compound 7 was admixed with THF (8 mL), water (1.2 mL), $K_3PO_4$ (6 mmol-200 mol %) and pinocolboronate (4.0 mmol-130 mol %). The reaction was run at 65° C. for 5 hours. For product crystallization, water (7.1 mL) was added to the reaction product mixture at 50° C., cured for 1 hour at temperature, and cooled to 20° C. The reaction product was isolated by filtration and washed 3× with 1 vol. water per wash. The results are reported in Table 7 where "Exp" refers to experiment number; "Cat. Eq." refers to equivalents of catalyst; "Add Lig." Refers to additional ligand in mol %; "Lig. Eq." refers to equivalents of ligand; "Base Eq." refers to equivalents of base; and "Conv. %" refers to percent conversion of compound 7 as determined by HPLC.

TABLE 7

| Exp | Catalyst | Cat. Mol % | Add Lig. Mol % | Lig. Mol % | Base mol % | Conv. % |
|---|---|---|---|---|---|---|
| 1 | $PdCl_2dppl \cdot CH_2Cl_2$ | 1 | — | — | 200 | 84% |
| 2 | $Pd(amphos)Cl_2$ | 0.5 | — | — | 200 | 0% |
| 3 | $PdCl_2(t-Bu_2PhP)_2$ | 0.5 | — | — | 200 | 0% |
| 4 | PdXPhos | 0.5 | XPhos/1 | 1 | 200 | 100% |
| 5 | PdXPhos | 0.5 | XPhos/0.5 | 0.5 | 200 | 100% |
| 6 | PdXPhos | 0.5 | — | — | 200 | 100% |
| 7 | PdXPhos | 0.5 | XPhos/0.6 | 0.6 | 200 | 32% |

PdXPhos was the most active catalyst, providing for complete conversion, and the catalytic activity was preserved at a concentration of 0.5 mol % (0.5 mol %) even in the absence of added ligand (experiment 6). Reduction of PdXPhos catalyst loading to 0.3 mol % (0.3 mol %) reduced conversion. The $Pd(amphos)C_2$ (Experiment 2) and $PdCl_2$ $(t-Bu_2PhP)_2$ catalysts were inactive at the evaluated concentrations.

Example 17: Catalyst Optimization Study

The reaction conditions found in Example 16 to provide for the highest conversion were evaluated for the preparation of GDC-0084 from a reaction mixture comprising compound 7 (78 g) starting material, pinocolboronate (120 mol %), THF (8 vol), $H_2O$ (1.2 vol), PdXphos (0.5 mol %), and $K_3PO_4$ (200 mol %). The reaction was run at 65° C. for 4 hours. The reaction mixture was purified by the Si-thiol purification method of Example 6, but using only 10 g Si-thiol. The Si-Thiourea purification step of Example 6 was not done in this Example. GDC-0084 was formed in 94% yield at 99.3 A % purity by HPLC, wherein the residual Pd was 815 ppm.

As compared to Example 6, this example replaced the $PdCl_2dppf.CH_2Cl_2$ catalyst with the more reactive PdXPhos catalyst, reduced palladium loading from 2 mol % (2 mol %) to 0.5 mol % (0.5 mol %), eliminated the Si-Thiourea scavenger, and reduced overall scavenger loading by about 90%, and reduced total solvent by 71%, while providing for comparable yield and purity.

Example 18: Purification by Crystallization

Purification of crude GDC-0084 by crystallization may suitably be done by crystallization from an acetic acid-water solvent. However, GDC-0084 may react with acetic acid to form acetamide impurity 6.

In a first evaluation, the formation of impurity 6 in solution with of GDC-0084 (2.6 mmol), acetic acid (3.6 mL), toluene (1.6 mL) and a trace amount of water (0.01 mL) at 90° C. over time was evaluated. The results are reported in Table 8 below where "% Acet." refers to percent acetamide.

TABLE 8

| Time (h) | % Acet. | Time (h) | % Acet. |
|---|---|---|---|
| 0 | 0 | 9 | 0.9 |
| 1 | 0.25 | 23 | 1.25 |
| 2 | 0.4 | 26 | 1.25 |
| 3 | 0.5 | 29 | 1.3 |
| 6 | 0.8 | — | — |

In a second evaluation, toluene was removed and the formation of impurity 6 of GDC-0084 in solution with 11 volumes of acetic acid and water at 70° C. over time was evaluated. Four ratios of acetic acid to water were evaluated including 98:2, 9:1, 4:1 and 1:1. The results are depicted in FIG. 1 and indicate that as the amount of water increases, the amount of acetamide (impurity 6) formed after 6 hours was reduced 6-fold from 0.6 area % (by HPLC) to 0.1 area %. The results further indicate that the acetamide impurity was less than 0.15 A % for ratios of acetic acid to water of less than 4:1 at 70° C.

Further development indicated that GDC-0084 fully dissolved in 10 vol of acetic acid:water (3:1) at 90° C. and crystallized out at 60° C. The 30° C. temperature width of the metastable zone was deemed to be sufficient to perform polish filtration at 90° C. Based on a Pd loading reduction of from 2 to 0.5 mol %, it was found that treatment with only 10 wt % of Si-Thiol was sufficient to reduce residual Pd to below 10 ppm.

Under conditions derived in Examples 12 to 18 for preparing GDC-0084 from compound 5 including (i) annulation of compound 5 with 1,2-dibromoethane using a phase transfer catalyst in water to generate compound 7, (ii) Suzuki cross-coupling with pinocolboronate using 0.5 mol % of XPhos Pd G2 catalyst, to provide crude GDC-0084; and (iii) a final scavenging/recrystallization from acetic acid/water provided GDC-0084 in 52% yield with 99.7 area % purity and in polymorphic form. The acetamide impurity 6 was reduced from 0.25 area % to less than 0.05 area % (HPLC) by adjusting the crystallization solvent composition.

Under conditions derived in Examples 12 to 18 for preparing GDC-0084 from compound 5, as compared to the preparation of GDC-0084 from compound 5 according to Examples 5 and 6: (i) in stage 1 (preparation of compound 7 from compound 5), both DMF and EtOAc were eliminated from the process, the total solvent volume was reduced by 54%, and all extractions and solvent exchanges were eliminated; (ii) in stage 2 (preparation of crude GDC-0084 from compound 7), the total solvent volume was reduced from 58 to 17 vol (71% reduction); and (iii) in stage 3 (crude GDC-0084 purification process), toluene was eliminated and the total solvent volume for recrystallization was lowered from 33 to 21 vol (37% reduction). Overall, the total unit operations were reduced from 21 to 7, the total solvent volume for the three stages was reduced by 64%, toluene and DMF were eliminated. As a result, the process mass intensity (PMI—see Concepcion, J., et al., "Using the Right Green Yardstick: Why Process Mass Intensity is Used in the Pharmaceutical Industry to Drive More Sustainable Processes", Org. Process Res. Dev., 2011, 912-917) was reduced from 140 to 70, which is in the practical range for a commercial process (see Henderson, R. K., et al., "Lessons Learned through Measuring Green Chemistry Performance: The Pharmaceutical Experience", American Chemical Society, Green Chemistry Institute, Pharmaceutical Roundtable: 2008).

Example 19: Preparation of 5-(6,6-dimethyl-4-morpholino-8,9-dihydro-6h-[1,4]oxazino[3,4-e]purin-2-yl)pyrimidin-2-amine Purified GDC-0084 was prepared from compound 5 in a three step process as depicted below:

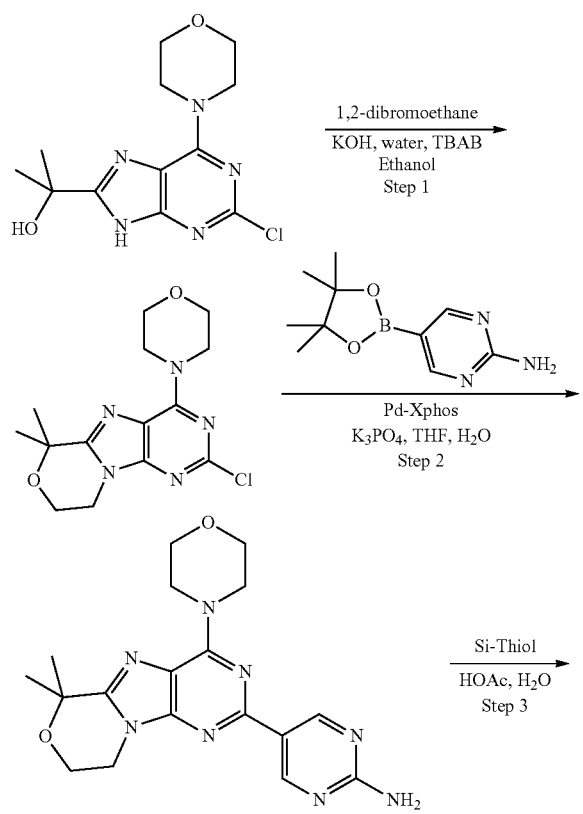

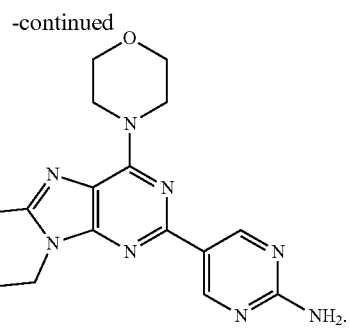

In the first step, a 100 L reactor was charged with water (45.1 kg, 4.8 volumes), potassium hydroxide (5.4 kg, 96.2 mol, 304 mol %), compound 5 (9.40 kg, 31.6 mol, 100 mol %), tetrabutylammonium bromide (2.92 kg, 9.06 mol, 28.7 mol %) and 1,2-dibromoethane (17.7 kg, 94.2 mol, 298 mol %). The mixture was heated to 47° C. and held at that temperature for 20 h. HPLC IPC showed compound 5 to be 3.1 A %. Ethanol (46.2 kg, 6.2 vol) and compound 7 seed crystals (96.6 g, 1 wt %) in ethanol (0.60 kg, 0.06 volumes) were added. The contents of the reactor were held for 2 h, then cooled to 5° C. over 2 h and held for 1 h. The mixture was filtered through a filter dryer and washed with water (27.4 kg, 2.9 volumes). After no more filtrate could be collected from the filter, the filter cake was dried on the filter at 60° C. (jacket temperature) under house vacuum with a nitrogen purge. The process gave 6.85 kg compound 7 (6.85 kg, 67% yield; 98.5 A % by HPLC) as a light yellow solid. Impurities were detected at low levels as follows: Compound 5 (0.43 A %); Impurity-3 (0.22 A %); Impurity-4 (0.1 A %); and Impurity-3 (0.22 A %). Melting point 147° C.; $^1$H NMR (500 MHz, DMSO-$d_6$) δ 4.75-4.00 (m, 8H), 3.73-3.71 (m, 4H), 1.56 (s, 6H); $^{13}$C NMR (125 MHz, DMSO-$d_6$) δ 152.9, 151.7, 151.6, 151.5, 117.3, 73.6, 66.0, 57.6, 45.3, 41.6, 27.2. HRMS [M+H]$^+$ calcd for $C_{14}H_{18}ClN_5O_2$ 324.1222. found 324.1225.

In the second step, a 100 L reactor was charged with water (8.00 kg, 1.2 volumes), THF (39.2 kg, 6.5 volumes), potassium phosphate tribasic monohydrate (9.51 kg, 40.4 mol, 194 mol %), compound 7 (6.75 kg, 20.85 mol, 100 mol %) and pinacolboronate (5.50 kg, 24.88 mol, 119 mol %) to form an admixture. The admixture was cycled from vacuum to nitrogen three times, and then Xphos Pd G2 (82.0 g, 0.104 mol, 0.5 mol %) was charged. The admixture was cycled from vacuum to nitrogen three times, heated to ≥67° C., and held at that temperature for 5 h. HPLC IPC analysis indicated complete conversion. Purified water (48.1 kg, 7.1 volumes) was charged and held for 1 h at 50° C. The reaction was cooled to 20° C. over 2 h, held for more than 2 h at 20, cooled to 5° C., and held at that temperature for 2 h. The admixture was filtered on a filter dryer and the filter cake was washed with water (37.1 kg, 5.5 volumes). After no more filtrate could be collected from the filter, the cake was dried on the filter at 60° C. (jacket temperature) under house vacuum with a nitrogen purge. Crude GDC-0084 was obtained as an off-white solid (7.49 kg, 94% yield; 99.4 A % by HPLC).

In the third step, a 100 L reactor was charged with water (7.75 kg, 1 volume), acetic acid (60.8 kg, 7.5 volumes), crude GDC-0084 (7.70 kg, 20.13 mol, 100 mol %) and silica-thiol (770 g, 10 wt %) to form and admixture. The admixture was heated to 90° C. and then held at that temperature for 3 h. The contents were filtered through an Aurora filter and then through a 1 μm polish filter, and the filter was rinsed with hot acetic acid (7.10 kg, 0.9 volumes). The resulting solution was then cooled to 77° C. and GDC-0084 seed crystals (82 g, 1.1 wt %) were added as a slurry in acetic acid (69 g) and water (87 g). The contents were held for 1 h at 68° C. Purified water (12.0 kg, 1.6 volumes) was charged to the slurry and the slurry was cooled to 45° C., held at 45° C. for 1 h, cooled to 20° C. over 2 h, held at 20° C. for 6 h, cooled to 5° C. over 2 h and held at 5° C. for 2 h. The slurry was filtered on a filter dryer and the filter cake was washed with water (69.9 kg, 9.1 volumes). After no more filtrate could be collected from the filter, the filter cake was dried on the filter at 60° C. (jacket temperature) under house vacuum with a nitrogen purge. GDE-0084 was obtained as an off-white solid (6.41 kg, 83% yield, 99.7 A %). Melting point 211° C.; $^1$H NMR (500 MHz, DMSO-$d_6$) δ 9.09 (s, 2H), 7.03 (s, 2H), 4.32-4.17 (m, 4H), 4.17-4.04 (m, 4H), 3.84-3.65 (m, 4H), 1.58 (s, 6H); $^{13}$C NMR (125 MHz, DMSO-$d_6$) δ 163.8, 157.6, 154.2, 152.5, 151.3, 151.0, 120.3, 117.3, 73.7, 66.2, 57.8, 45.2, 41.5, 27.3. HRMS [M+H]$^+$ calcd for $C_{18}H_{22}N_8O_2$ 383.1938. found 383.1945. The residual Pd level was below 10 ppm.

As compared to the scavenging method of Example 6, the THF was eliminated from the solvent system, the Si-Thiourea scavenging step was eliminated and the Si-thiol scavenger loading was reduced by 90%.

Example 20: 5-(6,6-dimethyl-4-morpholino-8,9-dihydro-6h-[1,4]oxazino[3,4-e]purin-2-yl)pyrimidin-2-amine Blood-Brain Barrier Penetration Determination The capability of GDC-0084 (compound IIIat) to penetrate the blood-brain barrier (BBB) in mice was determined by evaluating the unbound brain-to-unbound plasma concentration (Bu/Pu) ratio in female CD-1 mice. The capability of compound IIIat to penetrate the blood-brain barrier (BBB) in rats was determined by evaluating the concentration of compound IIIat in the cerebrospinal fluid of male Sprague-Dawley rats. The results are presented below in Table 9.

For the mouse study, [Brain]/[Plasma] ratios were determined after an oral dose of 25 mg/kg of compound IIIat as a MCT suspension to female CD-1 mice. MCT refers to the indicated drug dose in 0.5% methylcellulose and 0.2% Tween 80. [Brain]$_u$ and [Plasma]$_u$ refer to the unbound concentration measured in the brain and plasma respectively. The [Brain]/[Plasma] ratios are the mean values from 3 animals per time point determined at both 1 hour and 6 hours after administration. The data show that the Bu/Pu ratio was 0.41 at both 1 and 6 h thereby demonstrating that compound IIIat is capable of substantial free brain penetration. For the male Sprague-Dawley rat study, the concentration of compound IIIat in the cerebrospinal fluid (CSF) was determined and the [Brain]/[Plasma] ratio was evaluated after administration of an oral dose of 15 mg/kg of compound IIIat as a MCT suspension. [Brain]/[Plasma] and determined for 1 animal at each of 0.25 and 2 h and 3 at 8 hours and the data was reported are the range across the three timepoints (average of the 3 animals at 8 h).

The extent of protein binding was determined in vitro, in mouse plasma (Bioreclamation, Inc., Hicksville, N.Y.) by equilibrium dialysis using a HTDialysis 96-well block (HTDialysis® LLC; Gales Ferry, Conn.). The compound was added to pooled plasma from multiple animals (n≥3) at a total concentration of 10 μM. Plasma samples were equilibrated with phosphate-buffered saline (pH 7.4) at 37° C. in 90% humidity and 5% $CO_2$ for 4 hours. Following dialysis, concentration of compounds in plasma and buffer were measured by LC-MS/MS. The percent unbound in plasma was determined by dividing the concentration measured in the post-dialysis buffer by that measured in the post-dialysis plasma and multiplying by 100. Incubations were performed in triplicate and coefficient of variation is not greater than 30%.

The free fraction in mouse brain was determined as described by Kalvass. Briefly, brain tissue was homogenized in 3 volumes of phosphate-buffered saline and compound was added at a final concentration of 10 μM. Aliquots of 300 μl were dialyzed in a RED device (Thermo Scientific, Rockford, Ill.) against a volume of 500 μl buffer for 4 h at 37° C. in an incubator at 90% humidity and 5% $CO_2$. Following dialysis, tissues and buffer samples were analyzed as described for the plasma protein binding studies.

Twelve female CD-1 mice (Charles River Laboratories, Hollister, Calif.) were given an oral (PO) dose of the indicated compound in 0.5% methylcellulose/0.2% Tween 80 (MCT). Two blood samples of approximately 0.15 mL were collected from each mouse (n=3 mice per timepoint) by retro-orbital bleed or terminal cardiac puncture while the animals were anesthetized with isoflurane. Blood samples were collected in tubes containing K2EDTA as the anticoagulant, predose and at 0.083, 0.25, 0.5, 1, 3, 6, 9, and 24 h post-dose. Samples were centrifuged within 1 h of collection and plasma was collected and stored at −80° C. until analysis. Total concentrations of the compound were determined by liquid chromatography-tandem mass spectrometry (LC-MS/MS), following plasma protein precipitation with acetonitrile, and injection of the supernatant onto the column, a Varian MetaSil AQ C18 column (50×2 mm, 5 m particle size). A CTC HTS PAL autosampler (LEAP Technologies, Chapel Hill, N.C.) linked to a Shimadzu SCL-10A controller with LC-10AD pumps (Shimadzu, Columbia Md.), coupled with an AB Sciex API 4000 triple quadrupole mass spectrometer (AB Sciex, Foster City, Calif.) were used for the LC-MS/MS assay. The aqueous mobile phase was water with 0.1% formic acid and the organic mobile phase was acetonitrile with 0.1% formic acid. The lower and upper limits of quantitation of the assay were 0.005 μM and 10 μM, respectively. The total run time was 1.5 min and the ionization was conducted in the positive ion mode. Where brain concentration was determined, brains were collected at 1 and 6 h post-dose from 3 different animals at each time point, rinsed with ice-cold saline, weighed and stored at −80° C. until analysis. For compound quantitation, mouse brains were homogenized in 3 volumes of water. The homogenates were extracted by protein precipitation with acetonitrile. LC-MS/MS analysis was conducted as described for the plasma. Brain homogenate concentrations were converted to brain concentrations for the calculations of brain-to-plasma ratios.

The results are shown in Table 9 and the total brain-to-plasma ratio was 1.4 for mice and 1.9-3.3 for rats. The [Brain]$_u$/[Plasma]$_u$ for mice was 0.41 and the [CSF]/[Plasma]$_u$ for rats was 0.73-1.0. Although brain protein binding was not measured for rats, the CSF concentration has been established as a surrogate for unbound brain concentration. See Liu, X., et al., *Unbound Drug Concentration in Brain Homogenate and Cerebral Spinal Fluid at Steady State as a Surrogate for Unbound Concentration in Brain Interstitial Fluid*, Drug Metab. Dispos. 2009, 37, 787-793. The [CSF]/[plasma]$_u$ concentration ratio was 0.73-1.0, indicating that compound IIIat effectively crosses the BBB in rats.

TABLE 9

| Species | [Brain]/[Plasma] | [Brain]$_u$/[Plasma]$_u$ | [CSF]/[Plasma]$_u$ |
|---|---|---|---|
| Mouse | 1.4 | 0.41 | — |
| Rat | 1.9-3.3 | — | 0.73-1.0 |

The effect of compound IIIat on pAKT in normal brain tissue, expressed as the ratio of phosphorylated AKT (pAKT) to total AKT (tAKT) was evaluated. AKT is critical for proliferation and antiapoptotic signaling pathways, and increased activation of AKT by phosphorylation has been found to be involved in a variety of neoplasia. In the evaluation, female CD-1 mice were administered a single PO dose of the indicated compound. Brains and plasma were collected at the indicated time post-dose, from 3 animals at each time point. Individual brains were split in half for PD analysis and compound concentration measurement. The samples were stored at −70° C. and analyzed for total concentration. For PD analysis, cell extraction buffer (Invitrogen, Camarillo, Calif.) containing 10 mM Tris pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, and 0.5% deoxycholate was supplemented with phosphatase, protease inhibitors (Sigma, St. Louis, Mo.) and 1 mM PMSF and added to frozen brain biopsies. Brains were homogenized with a small pestle (Konte Glass Company, Vineland, N.J.), sonicated briefly on ice, and centrifuged at 20,000 g for 20 min at 4° C. Protein concentration was determined using BCA protein assay (Pierce, Rockford, Ill.). Proteins were separated by electrophoresis and transferred to NuPage nitrocellulose membranes (Invitrogen, Camarillo, Calif.). Licor Odyssey Infrared detection system (Licor, Lincoln, Nebr.) was used to assess and quantify protein expression. PI3K pathway markers were evaluated by immunoblotting using antibodies against $pAkt^{ser473}$ and total Akt (Invitrogen, Camarillo, Calif. and Cell Signaling, Danvers, Mass.). Inhibition of pAkt (%) was calculated by comparing pAkt signal with that measured in untreated mice.

Figure 2:
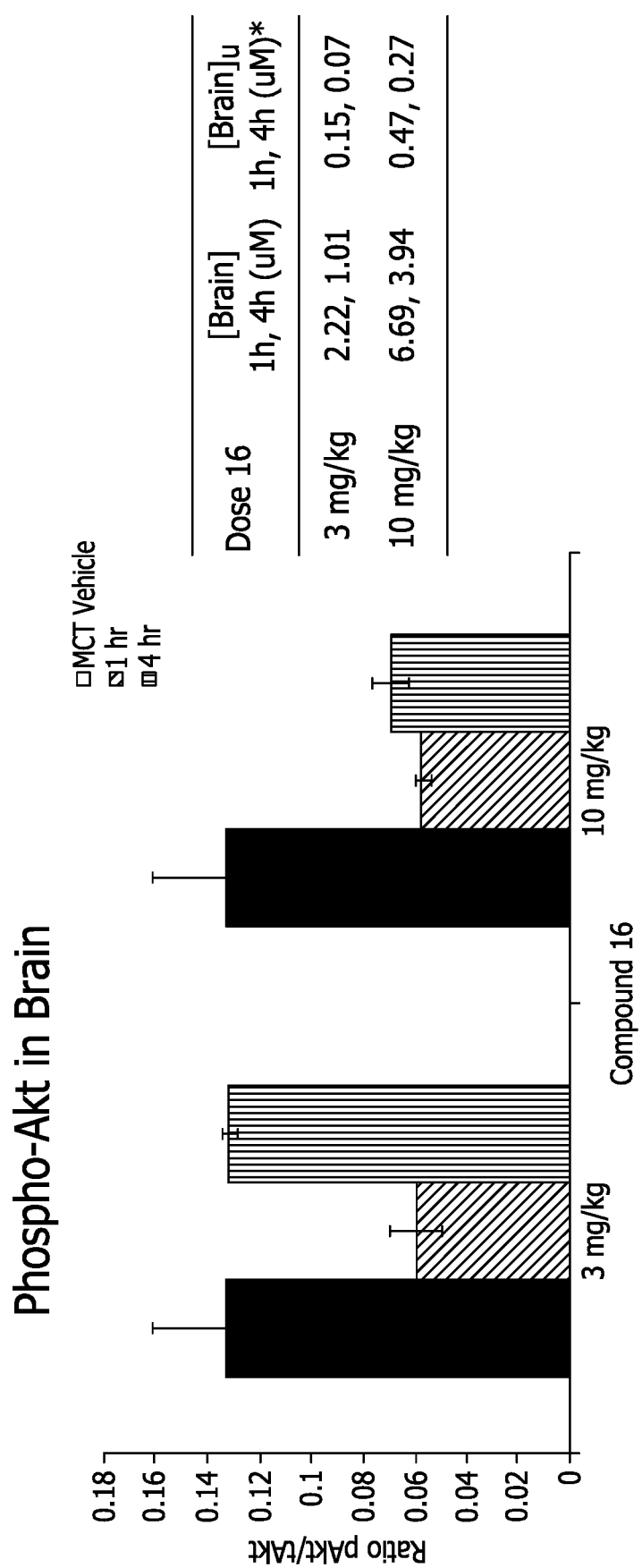
FIG. 2 shows a plot of the effect of the dose of 5-(6,6-dimethyl-4-morpholino-8,9-dihydro-6h-[1,4]oxazino[3,4-e]purin-2-yl)pyrimidin-2-amine versus time after dosage on pAKT in normal brain tissue, expressed as the ratio of phosphorylated AKT (pAKT) to total AKT (tAKT).

The results are shown in FIG. 2 for a 3 mg/kg or 10 mg/kg dose of compound IIIat administered orally where pAKT in normal mouse brain tissue was measured and determined to be inhibited at 1 h post-dose. At 4 hours post-dose, the 3 mg/kg dose no longer resulted in inhibition of pAKT, in contrast to the 10 mg/kg dose. The results demonstrate that compound IIIat engages its target behind a fully intact BBB, therefore freely penetrating mouse brain.

Example 21: Efficacy Evaluation of 5-(6,6-dimethyl-4-morpholino-8,9-dihydro-6H-[1,4]oxazino[3,4-e]purin-2-yl)pyrimidin-2-amine (GDC-0084) Against Glioblastoma The in vivo efficacy of compound GDC-0084 (compound IIIat) versus U87 MG Merchant (MG/M) human glioblastoma xenografts was evaluated in dose escalation studies in subcutaneous tumor-bearing Taconic female NCR nude mice.

All in vivo studies were conducted in compliance with Genentech's Institutional Animal Care and Use Committee. PTEN-null U-87 MG/M human glioblastoma cancer cells (an in-house derivative of U-87 MG cells from American Type Culture Collection (Manassas, Va.)) were cultured in RPMI 1640 media plus 1% L-glutamine with 10% fetal bovine serum (HyClone; Waltham, Mass.). Cells in log-phase growth were harvested and resuspended in HBSS: Matrigel (BD Biosciences; Franklin Lakes, N.J.) (1:1, v:v) for injection into female NCr nude mice (Taconic Farms, Cambridge City, Ind.) aged 20 weeks. Animals received five million cells subcutaneously in the right lateral thorax in 0.1 mL. Mice bearing established tumors in the range of 200-500 $mm^3$ were separated into groups of equally sized tumors (n=6-7/group) to receive escalating doses of 16. The inhibitor was formulated once weekly in 0.5% methylcellulose and 0.2% Tween-80 at concentrations needed for target doses in a volume of 0.2 mL. All formulations were stored in a refrigerator and brought to room temperature and mixed well by vortex before oral administration by gavage once daily for 23 days. Tumor volumes were calculated from perpendicular length and width caliper measurements using the formula: Tumor Volume $(mm^3)$=0.5×(Length×Width$^2$). Changes in body weights are reported as a percentage change from the starting weight.

A mixed modeling approach was used to analyze the repeated measurement of tumor volumes from the same animals over time since this approach addresses both repeated measurements as well as modest dropouts before study end (Pinheiro et al. 2008). Log 2(tumor volume) growth traces were fitted to each dose group with restricted cubic splines for the dose and fixed time effects. Fitting was done via a linear mixed-effects model, using the R package nlme (version 3.1-97) in R version 2.13.0 (R Development Core Team 2008; R Foundation for Statistical Computing; Vienna, Austria). Fitted tumor volumes were plotted in the natural scale in Prism (version 5.0b for Mac) (GraphPad Software; La Jolla, Calif.). Linear mixed-effects analysis was also employed using R to analyze the repeated measurement of body weight changes from the same animals over time.

Figure 3:
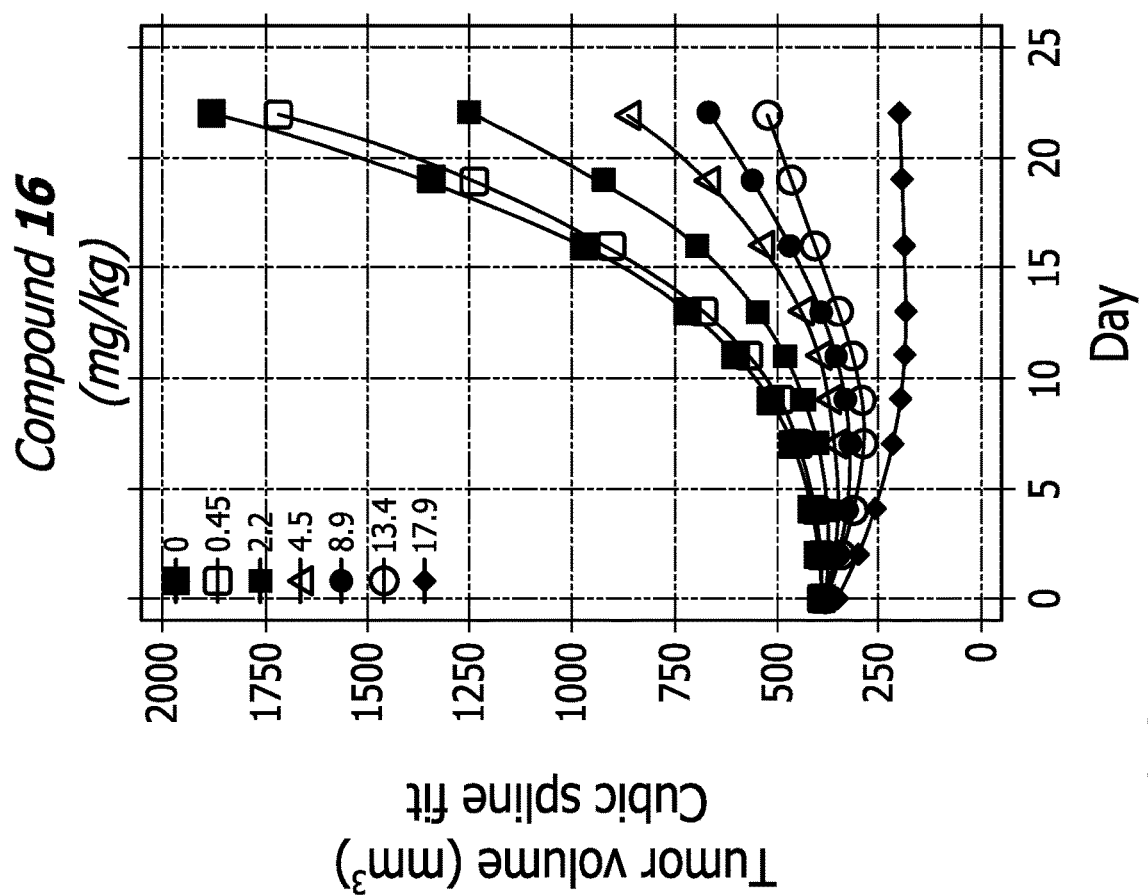
FIG. 3 shows the in vivo efficacy of 5-(6,6-dimethyl-4-morpholino-8,9-dihydro-6H-[1,4]oxazino[3,4-e]purin-2-yl)pyrimidin-2-amine versus U87 MG Merchant (MG/M) human glioblastoma xenografts in dose escalation studies in subcutaneous tumor-bearing Taconic female NCR nude mice and depicts tumor volume versus dosage regimen (dosage rate and time of administration).

Mice bearing the tumor xenographs were dosed at 0 time, 2 days, 4 days, 7 days, 9 days, 11 days 13 days, 16 days, 19 days and 22 days at a compound IIIat dosage rate of 0.45 mg/kg, 2.2 mg/kg, 4.5 mg/kg, 8.9 mg/kg, 13.4 mg/kg or 17.9 mg/kg where compound IIIat was a suspension in vehicle (0.5% methylcellulose/0.2% Tween-80). The mice control group was administered the vehicle in the absence of the drug once at the same dosage schedule. Changes in tumor volumes over time by dose for each compound are depicted in FIG. 3 as cubic spline fits generated via Linear Mixed Effects analysis of log-transformed volumes.

Compound IIIat achieved significant and dose-dependent tumor growth inhibition. Tumor growth inhibition was first observed at a 2.2 mg/kg dose level. Higher doses led to greater tumor growth inhibition, including tumor regressions at the 17.9 mg/kg dose level. Each of these doses was well tolerated for the duration of the study. Compound IIIat was found to have an anti-proliferation $EC_{50}$ of 740 nM in U87 cells.

Figure 4:
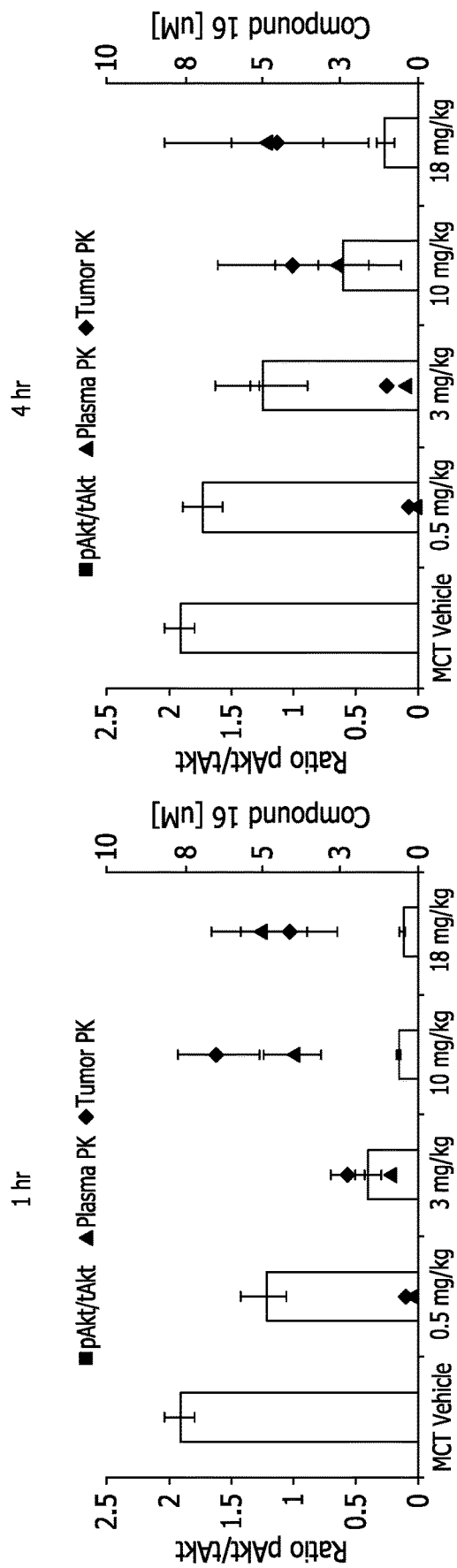
FIG. 4 shows the effect of 5-(6,6-dimethyl-4-morpholino-8,9-dihydro-6h-[1,4]oxazino[3,4-e]purin-2-yl)pyrimidin-2-amine on the ratio of phosphorylated AKT (pAKT) to total AKT (tAKT) in a U87 MG/M human glioblastoma xenograft model after 24 days of continuous dosing at dosage rates of 0.5 mg/kg, 3 mg/kg, 10 mg/kg and 18 mg/kg wherein tumors were excised from animals 1 hour and 4 hours after the last administered dose on day 24.

Example 22: Efficacy Evaluation of 5-(6,6-dimethyl-4-morpholino-8,9-dihydro-6H-[1,4]oxazino[3,4-e]purin-2-yl)pyrimidin-2-amine on pAKT The effect of compound IIIat on the pharmacodynamics (PD) marker pAKT in the U87 MG/M human glioblastoma xenograft model after 24 days of continuous dosing at dosage rates of 0.5 mg/kg, 3 mg/kg, 10 mg/kg and 18 mg/kg was evaluated. Tumors were excised from animals 1 hour and 4 hours after the last administered dose on day 24 and processed for analysis of pAKT and total AKT. The results are reported in FIG. 4 as a ratio of pAKT to total AKT wherein indicated values are the means for groups of 3 animals and error bars indicate ±standard error of the mean.

Levels of pAKT$^{Ser473}$ and total AKT were measured by electrochemiluminescence using Meso Scale Discovery according to manufacturer's instructions (Gaithersburg, Md.).

Compound IIIat was found to have a significant PD effect in the U87 tumors. Dose and concentration dependent inhibition of pAKT was observed at both 1 hour and 4 hours post dose, indicating that tumor growth inhibition is the result of on-target inhibition.

Example 23: Assessment of Kinase Inhibition by GDC-0084

Inhibition of 229 kinases by GDC-0084 (i.e., compound IIIat) Class I PI3K Kiapp's for GDC-0084 was evaluated. The percent inhibition at 1 μM of GDC-0084 against 229 kinases is reported in Table 10 below:

TABLE 10

| Kinase | % inhib |
| --- | --- |
| ACVR1B | 1.1 |
| AKT1 | 0.7 |
| AKT2 | 6.1 |
| AKT3 | 5.9 |
| ALK | 2.3 |
| Abl | 2.0 |
| Arg | 14.1 |
| Aurora_A | 3.2 |
| Aurora_B | −9.1 |
| Aurora_C | −2.5 |
| Axl | 6.0 |
| B-Raf | 7.6 |
| Blk | 28.8 |
| Bmx | 20.8 |
| BrSK1 | 1.6 |
| Brk | 5.9 |
| CDK1/cyclinB | 3.3 |
| CDK2/cyclinA | −2.4 |
| CDK5/p25 | 0.3 |
| CDK5/p35 | 7.5 |
| CDK7/cyclinH | 2.4 |
| CDK9/cyclinT1 | −0.9 |
| CHK1 | 0.6 |
| CHK2 | 11.3 |
| CK1_alpha1 | 1.9 |
| CK1_epsilon1 | 4.8 |
| CK1_gamma1 | 6.8 |
| CK1_gamma2 | 1.4 |
| CK1_gamma3 | −0.2 |
| CK2_alpha1 | 3.2 |
| CK2_alpha2 | 2.3 |
| CLK1 | 4.0 |
| CLK2 | 5.3 |
| CLK3 | 7.0 |
| CSF1R | 21.9 |
| CSK | 10.0 |
| CaMKI | −1.4 |
| CaMKII_beta | 0.2 |
| CaMKI_delta | 11.6 |
| CamKII_alpha | 2.1 |
| CamKII_delta | −1.4 |
| CamKIV | 0.2 |
| Cot | 28.7 |
| DAPK1 | −1.2 |
| DCAMKL2 | 3.3 |
| DNA-PK | 17.7 |
| DYRK1A | 2.8 |
| DYRK1B | −2.7 |
| DYRK3 | −10.8 |
| DYRK4 | 4.6 |
| EGFR | 2.5 |
| ERK1 | 8.6 |
| ERK2 | 5.2 |
| EphA1 | 7.8 |
| EphA2 | −0.7 |

TABLE 10-continued

| Kinase | % inhib |
| --- | --- |
| EphA4 | 3.0 |
| EphA5 | 5.9 |
| EphA8 | 6.9 |
| EphB1 | 1.9 |
| EphB2 | 6.6 |
| EphB3 | −0.1 |
| EphB4 | 4.8 |
| ErbB2 | 8.5 |
| ErbB4 | 7.0 |
| FAK | −1.9 |
| FAK2 | 4.6 |
| FGFR1 | −6.8 |
| FGFR2 | 2.3 |
| FGFR3 | 11.5 |
| FGFR4 | 5.8 |
| Fer | 8.9 |
| Fes | −10.1 |
| Fgr | 37.2 |
| Flt1 | 0.6 |
| Flt3 | 21.9 |
| Flt4 | 4.8 |
| Frk | 8.0 |
| Fyn | 9.0 |
| GCK | 0.9 |
| GRK2 | −3.6 |
| GRK3 | 4.6 |
| GRK4 | −4.2 |
| GRK5 | −10.0 |
| GRK6 | 2.9 |
| GRK7 | −9.5 |
| GSK3_alpha | 2.5 |
| GSK3_beta | 1.0 |
| HIPK1 | 3.3 |
| HIPK2 | 1.6 |
| HIPK4 | 2.6 |
| Haspin | 3.8 |
| Hck | 34.0 |
| Hyl | 3.3 |
| IGF1R | 4.9 |
| IKK_alpha | −3.8 |
| IKK_beta | 2.3 |
| IKK_epsilon | 2.9 |
| IRAK4 | 10.2 |
| IRR | 11.5 |
| InsR | 6.0 |
| Itk | 9.6 |
| JAK1 | −1.6 |
| JAK2 | 15.2 |
| JAK3 | 8.9 |
| JNK1_alpha1 | −4.2 |
| JNK2 | 9.8 |
| JNK3 | −2.7 |
| KDR | −3.6 |
| KHS1 | 1.5 |
| Kit | 14.1 |
| LRRK2 | 10.1 |
| LTK | 7.8 |
| Lck | 38.0 |
| Lyn | 23.3 |
| LynB | 24.9 |
| MAPKAPK2 | 1.1 |
| MAPKAPK3 | 4.4 |
| MARK1 | 4.4 |
| MARK2 | 5.5 |
| MARK3 | 4.3 |
| MARK4 | 1.5 |
| MEK1 | −0.1 |
| MEK2 | 8.1 |
| MELK | −10.4 |
| MLK1 | 28.9 |
| MRCK_alpha | −4.5 |
| MSK1 | 10.9 |
| MSK2 | 0.6 |
| MSSK1 | 11.1 |
| MST1 | 5.0 |
| MST2 | −2.0 |
| MST3 | −1.3 |
| MST4 | −1.5 |

TABLE 10-continued

| Kinase | % inhib |
|---|---|
| MYLK2 (skMLCK) | 3.0 |
| Mer | 8.1 |
| Met | 6.5 |
| Mink1 | 14.3 |
| MuSK | 12.7 |
| NEK1 | -6.4 |
| NEK2 | 20.0 |
| NEK4 | 7.8 |
| NEK6 | 13.1 |
| NEK7 | -0.3 |
| NEK9 | -2.6 |
| PAK1 | 7.0 |
| PAK2 | 3.0 |
| PAK3 | -4.5 |
| PAK4 | 15.2 |
| PAK6 | 15.3 |
| PAK7 | 18.6 |
| PASK | -5.3 |
| PDGFR_alpha | 9.7 |
| PDGFR_beta | 4.8 |
| PDK1 | 13.4 |
| PDK1(direct) | -8.8 |
| PI3KC2a | 13.2 |
| PI3KC2b | 42.6 |
| PI3KC3_hVPS34 | 23.6 |
| PI4Ka | 7.0 |
| PI4Kb | 2.8 |
| PIM1 | 9.7 |
| PIM2 | -4.4 |
| PKA | 8.2 |
| PKC_alpha | 7.5 |
| PKC_beta1 | 12.5 |
| PKC_beta2 | 11.9 |
| PKC_delta | 1.7 |
| PKC_epsilon | 10.7 |
| PKC_eta | -9.0 |
| PKC_gamma | 23.8 |
| PKC_iota | 6.8 |
| PKC_theta | 5.8 |
| PKC_zeta | 1.6 |
| PKD1 | 1.6 |
| PKD2 | 4.5 |
| PKD3 | 19.9 |
| PKG1_alpha | -3.4 |
| PKG2 | 12.1 |
| PLK1 | 3.3 |
| PLK2 | 7.2 |
| PLK3 | -4.8 |
| PRK1 | -12.7 |
| PRKAA1 | 9.3 |
| PRKAA2 | 5.8 |
| PhK_gamma1 | 2.0 |
| PhK_gamma2 | 0.0 |
| PrKX | 8.3 |
| RAF1 (Y340D, Y341D) | 42.3 |
| ROCK1 | 1.3 |
| ROCK2 | -16.1 |
| Ret | 13.4 |
| Ron | 8.0 |
| Ros | -6.7 |
| Rse | 3.6 |
| Rsk1 | -4.6 |
| Rsk2 | 1.4 |
| Rsk3 | 4.4 |
| Rsk4 | 27.4 |
| SGK1 | 13.9 |
| SGK2 | 2.8 |
| SGK3 | -3.5 |
| SIK2 | 6.8 |
| SPHK1 | -2.8 |
| SPHK2 | -2.3 |
| SRPK1 | 5.5 |
| SRPK2 | -7.7 |
| Src | 29.9 |
| Src_N1 | 43.6 |
| Srm | -1.1 |
| Syk | 42.8 |
| TAO1 | -1.3 |
| TBK1 | 4.0 |
| TSSK1 | 5.5 |
| TSSK2 | -6.8 |
| TYK2 | 8.4 |
| Tie2 | 7.4 |
| TrkA | 7.3 |
| TrkB | 4.2 |
| TrkC | 11.7 |
| YSK1 | -8.8 |
| Yes | 31.3 |
| ZAP-70 | -0.9 |
| eEF-2K | 5.2 |
| p38_alpha | -9.4 |
| p38_alpha(direct) | 4.3 |
| p38_beta | 6.5 |
| p38_delta | 12.1 |
| p38_gamma | 11.9 |
| p70S6K | 6.0 |

The selectivity of GDC-0084 for Class I PI3K kinases was evaluated and the results are reported in Table 11 below:

TABLE 11

| Class I PI3K Kinase | Selectivity ($Ki_{app}$) |
|---|---|
| PI3Kα | 2 nM |
| PI3Kβ | 46 nM |
| PI3Kδ | 3 nM |
| PI3Kγ | 10 nM |
| mTOR | 70 nM |

Example 24: Stability Evaluation of 5-(6,6-dimethyl-4-morpholino-8,9-dihydro-6h-[1,4]oxazino[3,4-e]purin-2-yl)pyrimidin-2-amine The hepatocyte stability of compound IIIat was evaluated across preclinical species. Certain in vivo pharmacokinetic parameters were also evaluated. In the example, hepatic clearance was predicted from hepatocyte incubations using the in vitro $t_{1/2}$ method disclosed by Obach, R. S., et al., *The prediction of human pharmacokinetic parameters from preclinical and in vitro metabolism data*, J. Pharmacol. Exp. Ther. 1997, 283, 46-58. Male Sprague-Dawley rats, female CD-1 mice, male cynomolgus monkeys and beagle dogs were dosed intravenously with 1 mg/kg of compound IIIat prepared in 60% PEG400/10% Ethanol. Compound IIIat was administered orally (PO) at the indicated dose in 0.5% methylcellulose with 0.2% Tween 80 (MCT). The results are reported in Table 12 below where "Cyno" refers to cynomolgus monkeys; "$Cl_{hep}$" refers to hepatocyte clearance in mL/min/kg; "in vivo Cl" refers to in vivo clearance after IV administration in mL/min/kg; IV dosage was 1 mg/kg; "Vss" refers to the apparent volume of distribution at steady state in L/kg; oral dose is reported in mg/kg; "Cmax" refers to the peak serum concentration reported in μm; "AUC" refers to the area under the curve in a plot of concentration of compound IIIat in blood plasma versus time and is reported in μm·h; "F %" refers to percentage drug bioavailability; and "PPB %" refers to the percentage of the drug that binds with blood plasma protein.

TABLE 12

| | | IV | | | PO | | | |
|---|---|---|---|---|---|---|---|---|
| Species | Cl$_{hep}$ | In vivo Cl | Vss | Dose | Cmax | AUC | F % | PPB % |
| Mouse | 30 | 17 | 1.7 | 25 | 4.6 | 47 | 75 | 78 |
| Rat | 3 | 28 | 3.2 | 5 | 1.1 | 8.3 | 77 | 71 |
| Cyno | 26 | 46 | 2.9 | 2 | 0.03 | 0.11 | 6 | 75 |
| Dog | 13 | 26 | 3.0 | 2 | 0.2 | 1.6 | 40 | 66 |

With the exception of rat, there was a good correlation between predicted clearance based on hepatocyte stability and in vivo clearance.

Example 25: Human Phase I Trial

An open-label, multicenter, Phase I, dose-escalation study was done using a standard "3+3" design to assess the safety, tolerability, and pharmacokinetics of GDC-0084 (compound Formula IIIat). GDC-0084 is a potent, oral, selective small molecule inhibitor of class I PI3K and mTOR kinase with a mean apparent inhibition constant (Ki) for p110α/p85α, p110β/p85α, p110δ/p85α, and p110γ of 2.2, 41, 2.7, and 9.7 nM, respectively.

GDC-0084 was administered orally once daily in continuous dosing cycles of 28 days to a set of forty-seven patients with progressive or recurrent high-grade gliomas (WHO Grade III-IV) who had progressed during or after treatment with at least one prior radiotherapy-containing regimen for gliomas and/or were not candidates for regimens known to provide clinical benefit. GDC-0084 was provided in capsule formulations in three strengths: 1 mg, 5 mg, and 25 mg. GDC-0084 capsules were stored at room temperature (59° F.-86° F. [15° C. and 30° C.]). Plasma samples for pharmacokinetic ("PK") analysis were collected on day 1 and day 8 or day 15 of cycle 1. Fluorodeoxyglucose positron emission tomography ("FDG-PET") was performed at baseline and on-treatment.

The median time from primary diagnosis was 40.5 months (range: 11-190 months). At study enrollment, 33 patients (70.2%) were classified with WHO Grade IV glioma and 14 patients (29.8%) were classified with WHO Grade III glioma. Of the patients, 55.3% of patients had progressive disease, 40.4% had stable disease, one patient was not evaluable, and the data for one patient was missing. Overall, all patients had received prior cancer surgery, radiotherapy, and systemic therapies. The median number of prior cancer surgeries was 2.0 (range: 1 to 6), the median number of prior radiotherapies was 1.0 (range: 1 to 2), and the median number of prior systemic therapies was 3.0 (range: 1 to 5).

Patients received GDC-0084 daily in cycles of 28 days in length (4 weeks of daily dosing). On Day 1 of Cycle 1, GDC-0084 was administered in a clinical setting that accommodated frequent blood draws over a period of up to 24 hours after the morning dose was administered. Patients took GDC-0084 at the same time of day (±2 hours) when the study drug was taken at home. Dosing times may have been adjusted to accommodate for time shifts from the home administration schedule (e.g., for clinic visits with PK sampling or traveling), but times were to be adjusted by no more than 4 hours at a time.

GDC-0084 was taken on an empty stomach (i.e., approximately 1 hour before or 2 hours after a meal) unless the patient was otherwise instructed, except on days when administration was under fasted conditions (e.g., with extensive PK sampling during Cycle 1, as described elsewhere herein). For administration under fasted conditions, patients fasted overnight for at least 8 hours before dosing and 2 hours after dosing. GDC-0084 capsules were swallowed whole (not chewed) with 240 mL (8 oz) of water.

Dose escalation continued in accordance with the dose-escalation rules until the maximum tolerable dose ("MTD") was exceeded, excessive pill burden (defined as 2 or more patients in a cohort who were unable to take ≥90% of doses consisting of a minimum of eight capsules) was declared, or analysis of available PK data indicated that exposure was unlikely to increase with further increases in the dose of GDC-0084.

In PK evaluations, the patients were treated with GDC-0084 in eight dose groups on a 28-day (once daily) cycle at the following dose levels: Cohort 1 (2 mg); Cohort 2 (4 mg); Cohort 3 (8 mg); Cohort 4 (15 mg); Cohort 5 (20 mg); Cohort 6 (30 mg); Cohort 7 (45 mg); and Cohort 8 (65 mg). PK evaluations were conducted following GDC-0084 administration in a fasted state on Study Days 1 and 8 (for Cohorts 7-8) or 15 (for Cohorts 1-6). A single dose of GDC-0084 was administered orally on Day 1 of Cycle 1, followed by frequent blood sampling, up to 72 hours for Cohorts 1-6 and 24 hours for Cohorts 7-8, to determine the single-dose PK properties of GDC-0084. For Cohorts 1-6 (2-30 mg), the single dose on Cycle 1, Day 1 was followed by a 7 day washout-period, after which continuous once daily dosing, for 28 consecutive days, was started on Day 8. Blood samples for Cohorts 1-6 were collected on Day 15 for PK analysis. For Cohorts 7 and 8 (45-65 mg), subjects were dosed continuously once daily for 28 days starting on Cycle 1, Day 1 and blood samples were collected on Day 8 for multiple dose PK analysis. A validated LC-MS/MS assay with a lower level of quantification (LLOQ) of 0.00052 µM was used to quantify the concentration of GDC-0084 in plasma samples.

Plasma concentration-time data for GDC-0084 were tabulated, and descriptive statistics were computed and compared between cohorts. Mean plasma GDC-0084 concentration data were plotted by cohort relative to nominal time. All plasma concentration-time data collected in Cycle 1 were analyzed using WinNonlin® (Version 6.4, Pharsight Corp, Mountain View, Calif.) to estimate PK parameters, which included but were not limited to $AUC_{0-last}$ (where AUC refers to the area under the concentration-time curve) and/or $AUC_{inf}$, $C_{max}$, $C_{min}$, $t_{max}$, half-life, CL/F, and accumulation ratio. Estimates for each PK parameter and summary statistics (mean, standard deviation, coefficient of variation, median, minimum, and maximum) were tabulated by dose level and schedule. Nominal time data were used in the analysis, and the linear up/log down trapezoidal method was used for calculating AUC.

The pharmacokinetic parameters of GDC-0084 following single and multiple doses are tabulated in Table 13 and Table 14, respectively, where SD refers to standard deviation; % CV refers to the coefficient of variation; ND refers to not determined; $T_{1/2}$ refers to terminal half-life; $T_{max}$ refers to time to maximum plasma concentration; $C_{max}$ refers to maximum observed plasma concentration; $AUC_{inf}$ refers to area under the concentration-time curve from Time 0 to infinity; CL/F refers to apparent oral clearance; $AUC_{0-24}$ refers to refers to area under the concentration-time curve from Time 0 to 24 hours; $C_{min}$ refers to minimum concentration; and Accumulation Ratio refers to $AUC_{0-24\ hr\ multiple\ dose}/AUC_{0-24\ hr\ single\ dose}$.

TABLE 13

PK Parameter Results after Single Dose (Cycle 1, Day 1)

| Parameter | 2 mg n = 7 | 4 mg n = 4 | 8 mg n = 5 | 15 mg n = 6 | 20 mg n = 4 | 30 mg n = 7 | 45 mg n = 8 | 65 mg n = 6 |
|---|---|---|---|---|---|---|---|---|
| $T_{1/2}$ (hr) | | | | | | | | |
| Mean | 16.9 | 21.8 | 18.2 | 18.1 | 14.8 | 22.0 | ND | ND |
| SD | 7.38 | 4.41 | 8.94 | 14.4 | 2.96 | 8.66 | ND | ND |
| % CV | 43.6 | 20.2 | 49.2 | 79.6 | 20.0 | 39.4 | ND | ND |
| $T_{max}$ (hr) | | | | | | | | |
| Median | 2.0 | 3.0 | 3.0 | 2.0 | 2.0 | 2.0 | 3.0 | 2.5 |
| Range | 2.0-4.0 | 2.0-3.0 | 2.0-3.0 | 2.0-4.0 | 2.0-3.0 | 1.0-8.0 | 2.0-4.0 | 2.0-4.0 |
| $C_{max}$ (μM) | | | | | | | | |
| Mean | 0.0177 | 0.0359 | 0.0452 | 0.0912 | 0.159 | 0.174 | 0.234 | 0.255 |
| SD | 0.0055 | 0.00468 | 0.00838 | 0.0278 | 0.0655 | 0.0483 | 0.0905 | 0.113 |
| % CV | 31.1 | 13.0 | 18.5 | 30.5 | 41.2 | 27.8 | 38.7 | 44.3 |
| $AUC_{inf}$ (μM*hr) | | | | | | | | |
| Mean | 0.365 | 0.833 | 0.974 | 1.97 | 2.75 | 5.33 | ND | ND |
| SD | 0.190 | 0.122 | 0.568 | 1.60 | 0.932 | 3.59 | ND | ND |
| % CV | 52.1 | 14.6 | 58.4 | 81.2 | 33.9 | 67.4 | ND | ND |
| CL/F (L/hr) | | | | | | | | |
| Mean | 13.1 | 4.87 | 12.4 | 11.1 | 7.92 | 8.22 | ND | ND |
| SD | 21.1 | 0.634 | 10.4 | 5.79 | 2.63 | 5.26 | ND | ND |
| % CV | 161 | 13.0 | 84.0 | 52.2 | 33.2 | 64.0 | ND | ND |
| $AUC_{0-24}$ (μM*hr) | | | | | | | | |
| Mean | 0.210 | 0.435 | 0.509 | 1.09 | 1.90 | 2.42 | 3.12 | 4.06 |
| SD | 0.0881 | 0.0221 | 0.176 | 0.459 | 0.654 | 0.945 | 1.10 | 1.75 |
| % CV | 41.9 | 5.08 | 34.6 | 42.2 | 34.5 | 39.1 | 35.3 | 43.1 |

TABLE 14

PK Parameter Results after Multiple Doses (Cycle 1, Day 15 for Cohorts 1-6, Cycle 1, Day 8 for Cohorts 7 & 8)

| Parameter | 2 mg n = 6 | 4 mg n = 4 | 8 mg n = 4 | 15 mg n = 6 | 20 mg n = 4 | 30 mg n = 6 | 45 mg n = 8 | 65 mg n = 5 |
|---|---|---|---|---|---|---|---|---|
| $T_{max}$ (hr) | | | | | | | | |
| Median | 2.0 | 2.0 | 2.5 | 3.0 | 2.0 | 2.0 | 3.5 | 3.0 |
| Range | 1.0-3.0 | 2.0-3.0 | 2.0-3.0 | 2.0-4.0 | 2.0-3.0 | 2.0-3.0 | 3.0-4.0 | 1.0-3.0 |
| $C_{max}$ (μM) | | | | | | | | |
| Mean | 0.0331 | 0.593 | 0.0883 | 0.156 | 0.230 | 0.332 | 0.544 | 0.580 |
| SD | 0.0114 | 0.00215 | 0.0256 | 0.0857 | 0.0735 | 0.266 | 0.252 | 0.351 |
| % CV | 34.3 | 3.63 | 29.0 | 55.0 | 31.9 | 80.1 | 46.3 | 60.5 |
| $C_{min}$ (μM) | | | | | | | | |
| Mean | 0.00877 | 0.0207 | 0.0301 | 0.0581 | 0.0635 | 0.155 | 0.206 | 0.271 |
| SD | 0.00495 | 0.00631 | 0.0148 | 0.0651 | 0.0195 | 0.158 | 0.0988 | 0.145 |
| % CV | 56.4 | 30.4 | 49.2 | 112 | 30.7 | 102 | 48.0 | 53.6 |
| $AUC_{0-24}$ (μM*hr)$^a$ | | | | | | | | |
| Mean | 0.346 | 0.833 | 1.16 | 2.34 | 2.87 | 5.67 | 8.06 | 9.01 |
| SD | 0.178 | 0.166 | 0.380 | 1.84 | 0.499 | 5.79 | 2.76 | 4.62 |
| % CV | 51.4 | 19.9 | 32.8 | 78.6 | 17.4 | 102 | 34.2 | 51.3 |
| Accumulation Ratio$^a$ | | | | | | | | |
| Mean | 1.68 | 1.91 | 1.97 | 2.03 | 1.66 | 1.96 | 2.83 | 2.44 |
| SD | 0.328 | 0.327 | 0.342 | 0.781 | 0.650 | 1.41 | 1.19 | 0.775 |
| % CV | 19.5 | 17.1 | 17.3 | 38.4 | 39.2 | 71.9 | 42.0 | 31.7 |

$^a$For Cohort 6 (30 mg), n = 5.

Figure 13:
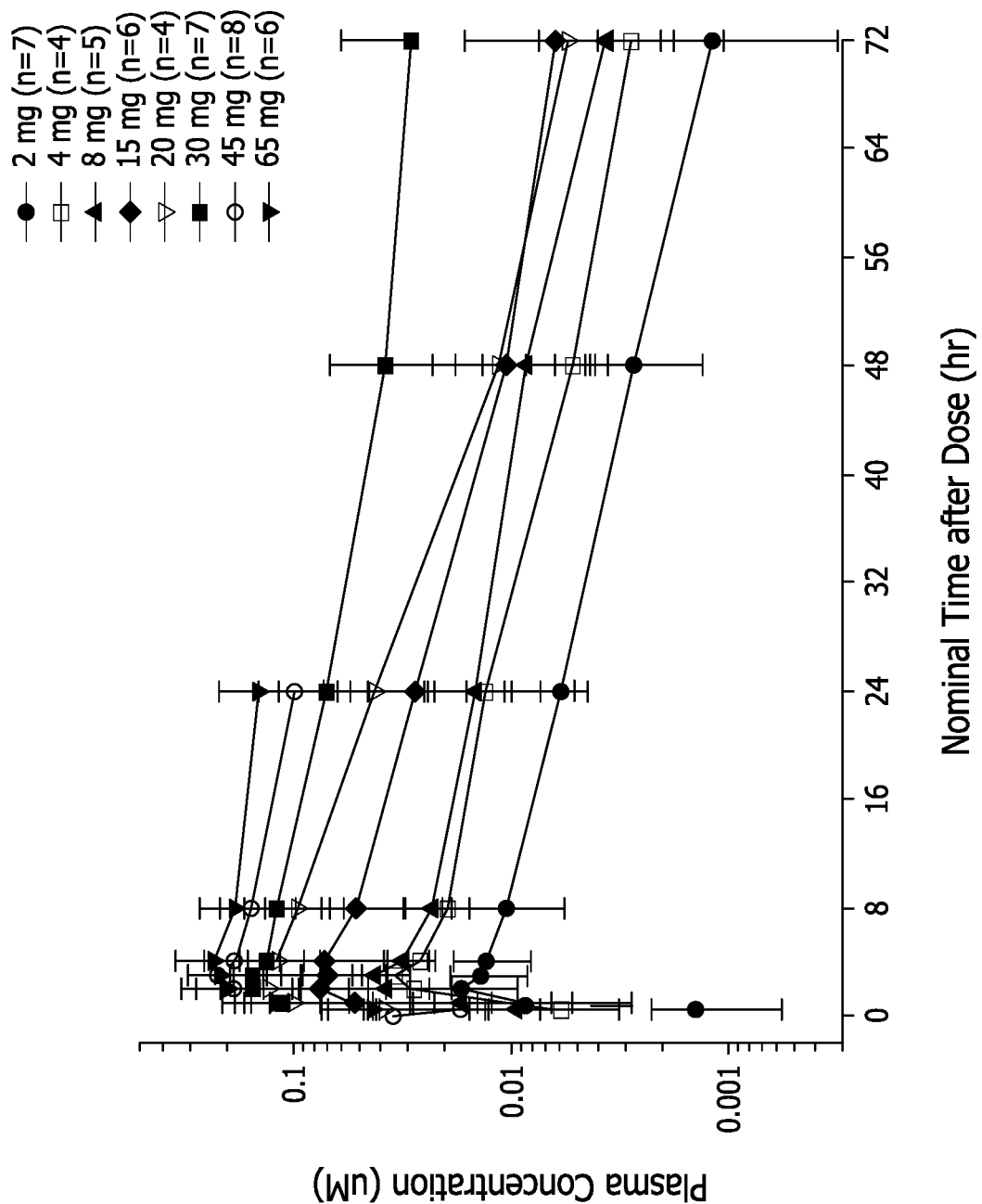
FIG. 13 is a plot of mean±single day plasma concentration vs. time profiles of GDC-0084 following a single dose.
Figure 14:
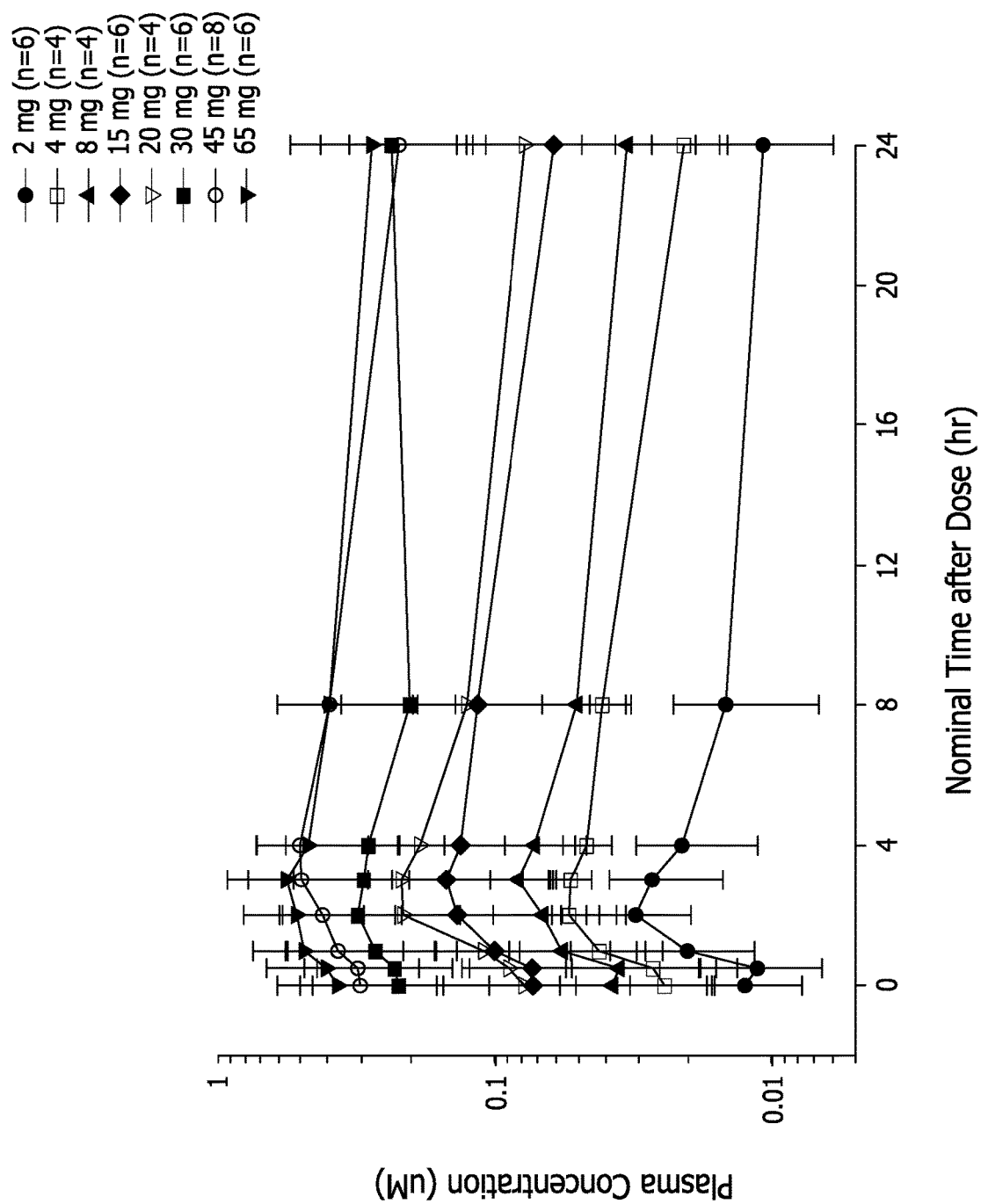
FIG. 14 is a plot of ±single day plasma concentration vs. time profiles of GDC-0084 following multiple doses.

Concentration-time profiles of GDC-0084 following single and multiple doses are presented in FIG. 13 and FIG. 14, respectively. FIG. 13 is a plot of mean±SD plasma concentration vs. time profiles of GDC-0084 following a single dose (cycle 1, day 1). FIG. 14 is a plot of ±SD plasma concentration vs. time profiles of GDC-0084 following multiple doses (cycle 1, day 15 for cohorts 1 to 6 and cycle 1, day 8 for cohorts 7 and 8). Following a single oral dose, GDC-0084 was rapidly absorbed with a median $T_{max}$ of approximately 2 hours (range 1 to 8 hours). After reaching peak plasma concentrations, concentrations decreased with an apparent terminal phase $t_{1/2}$ of approximately 18.73 hours (range 3.41 to 47.3 hours; calculated across Cohorts 1-6 (2 to 30 mg) following a single dose).

Figure 15:
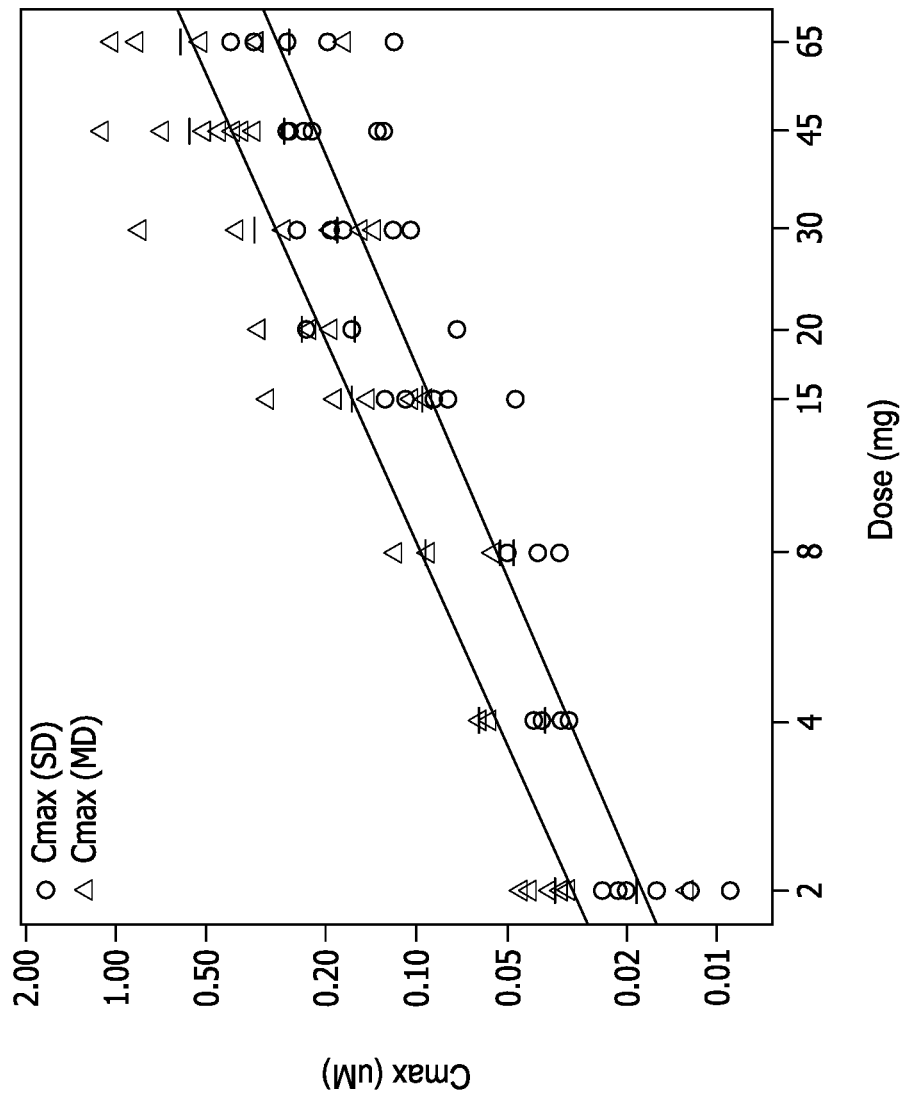
FIG. 15 is a GDC-0084 dose proportionality plot of dose (mg) versus C$_{max}$ (μM) for single dose and multiple dose regimens.
Figure 16:
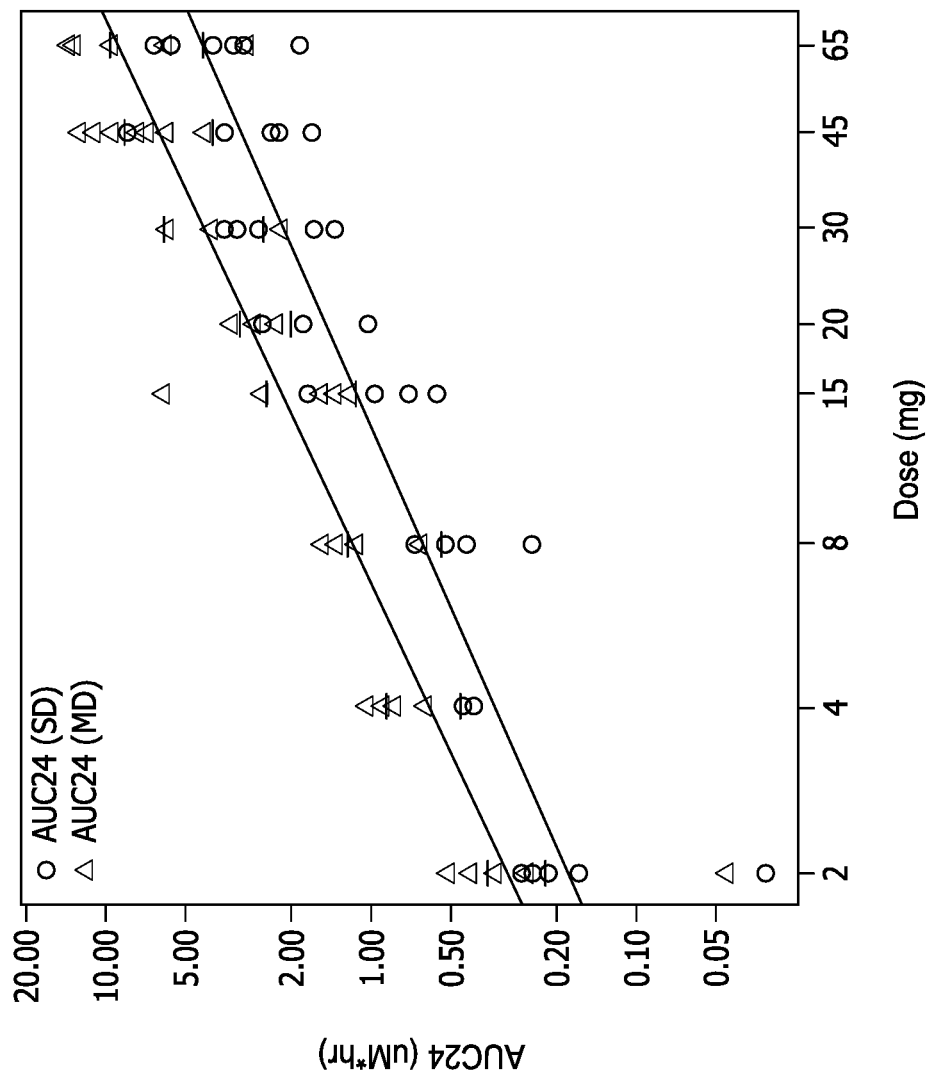
FIG. 16 is a GDC-0084 dose proportionality plot of dose (mg) versus AUC$_{24}$ (μM*hr) for single dose and multiple dose regimens.
Figure 17:
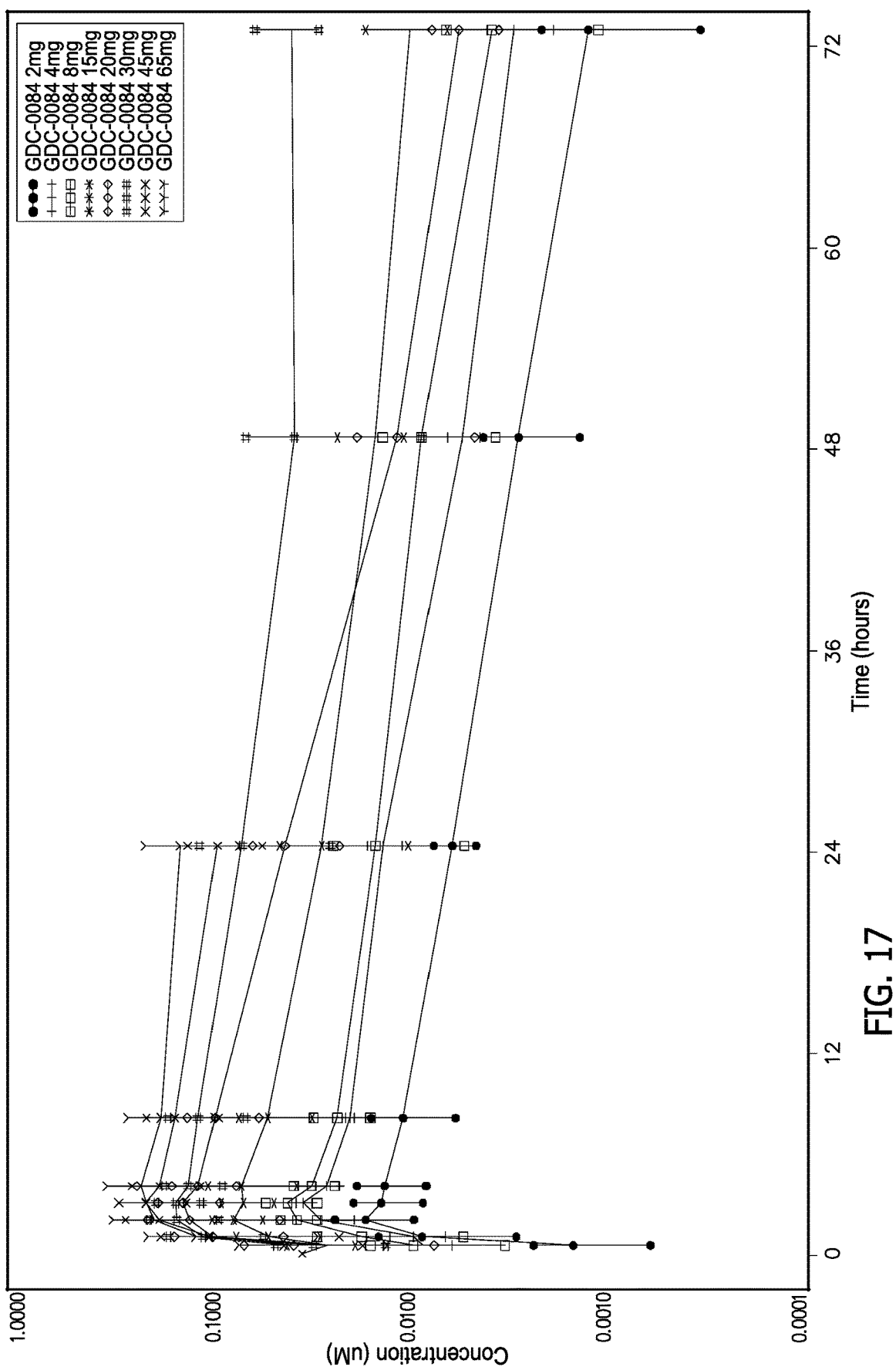
FIG. 17 is a plasma GDC-0084 mean single dose concentration versus time log scale plot.
Figure 18:
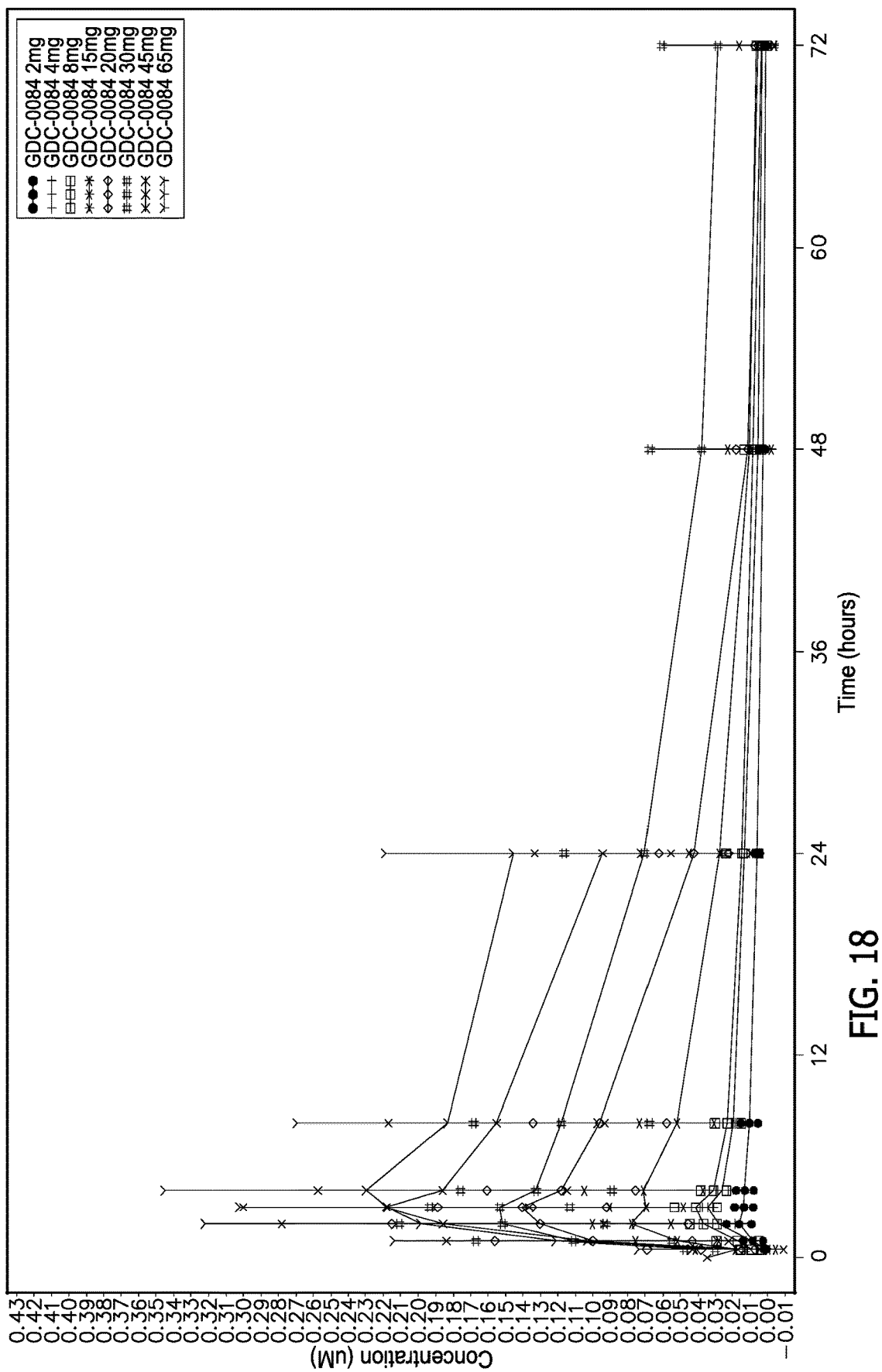
FIG. 18 is a plasma GDC-0084 mean single dose concentration versus time linear scale plot.
Figure 19:
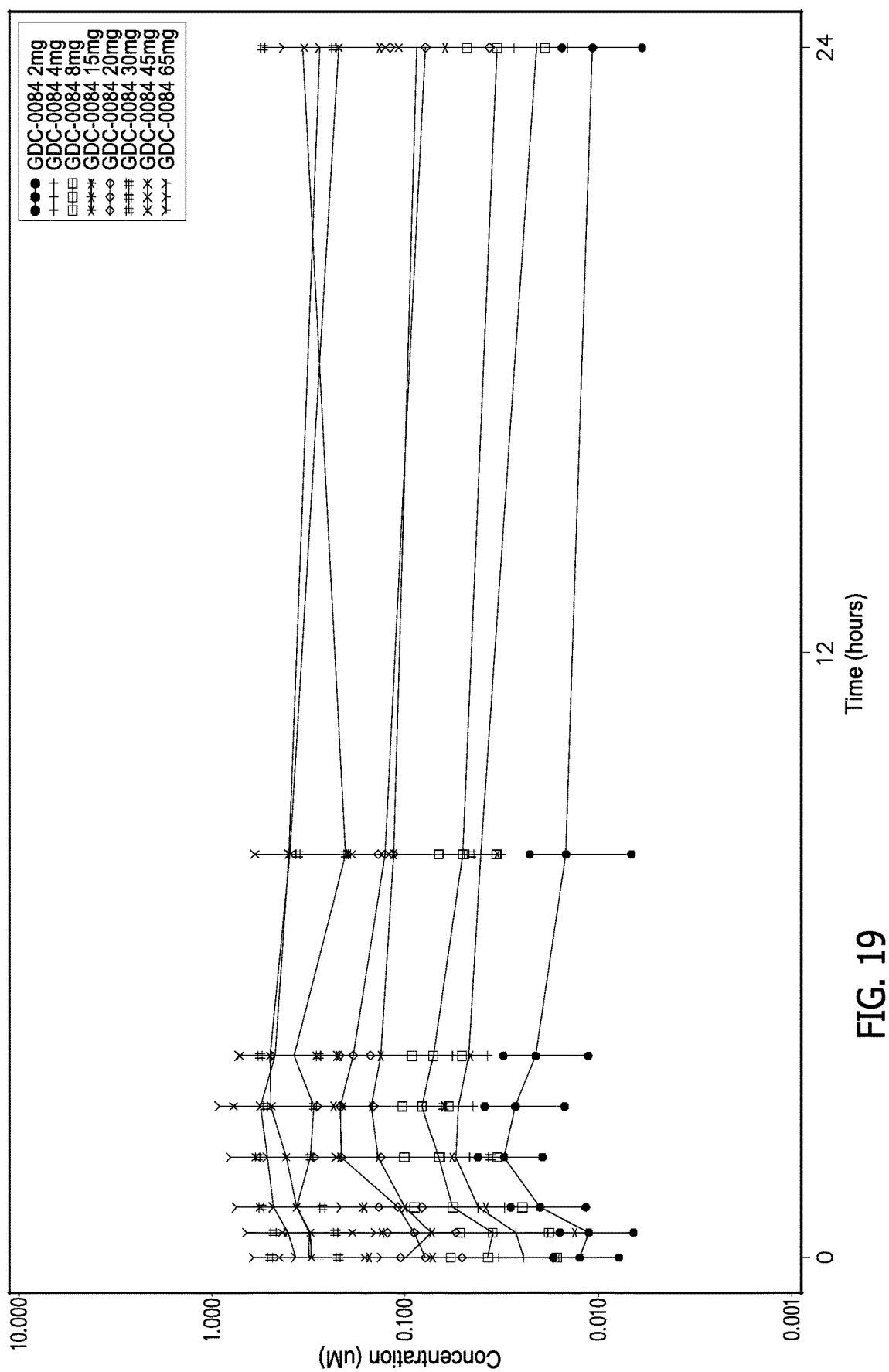
FIG. 19 is a plasma GDC-0084 mean single dose concentration versus time log scale plot.
Figure 20:
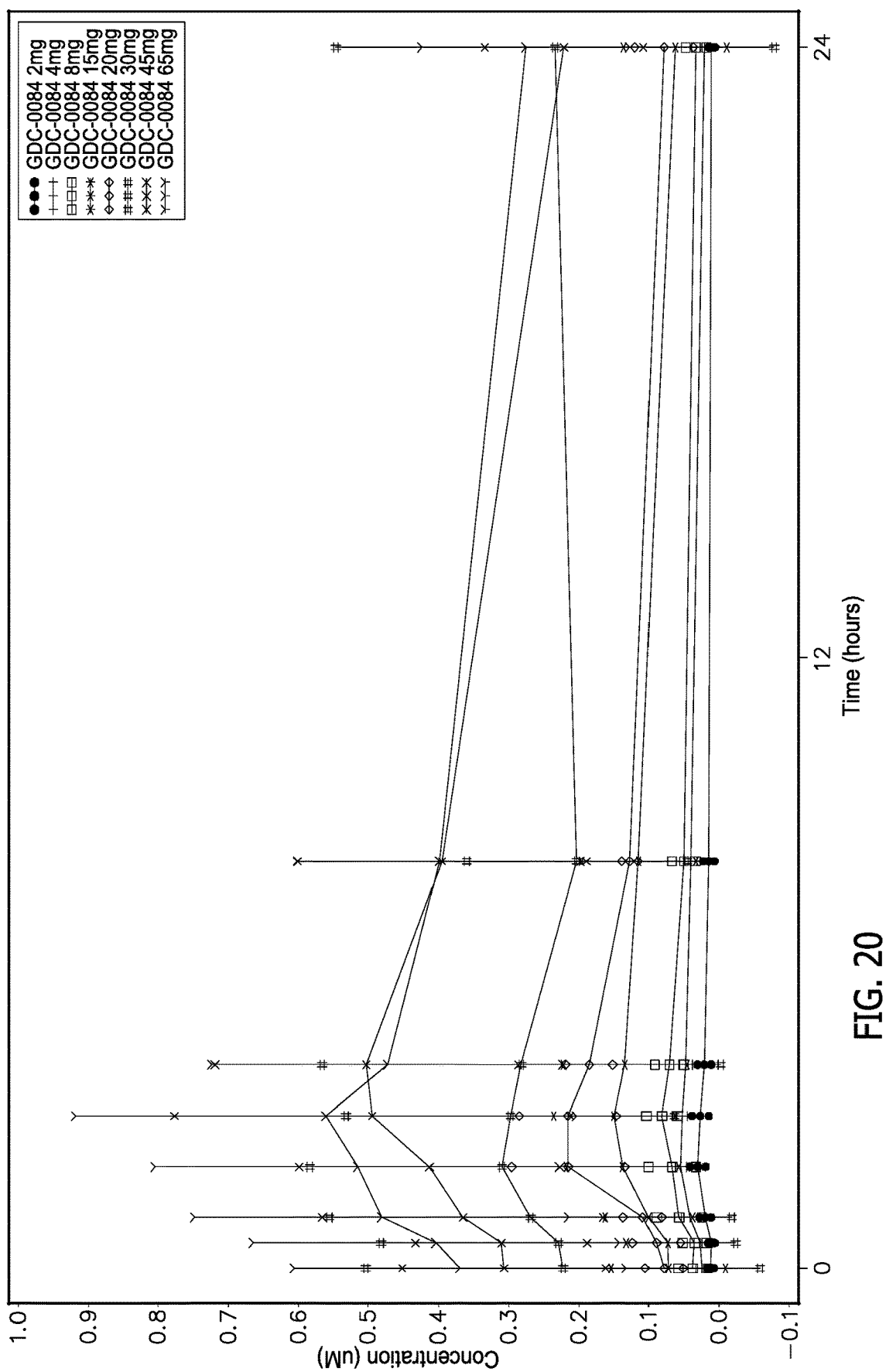
FIG. 20 is a plasma GDC-0084 mean single dose concentration versus time linear scale plot.
Figure 21:
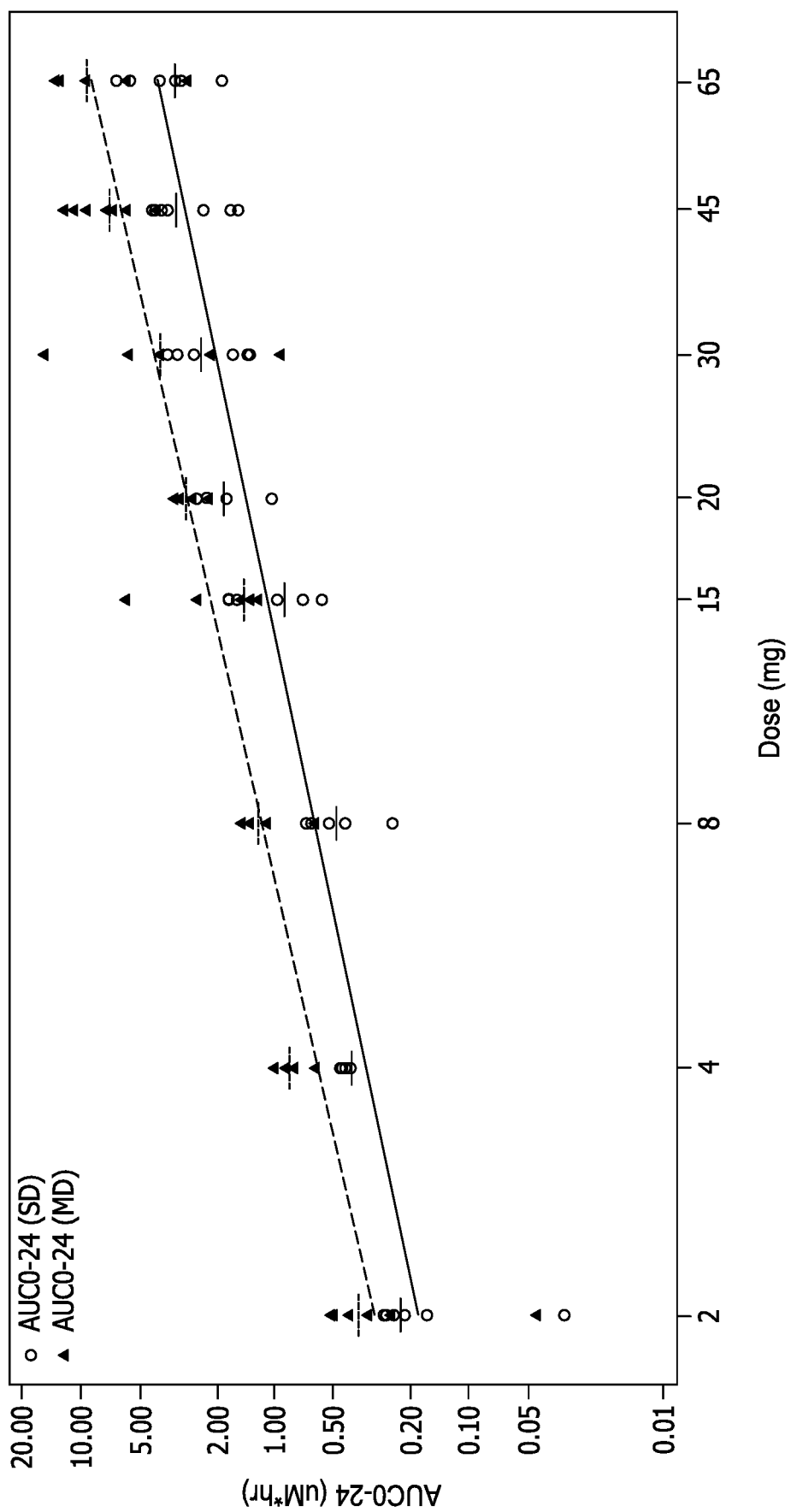
FIG. 21 is a log scale plot of AUC$_{0-24}$ (μM*hr) versus dose (mg) for GDC-0084 for single dose and multiple dose regimens.
Figure 22:
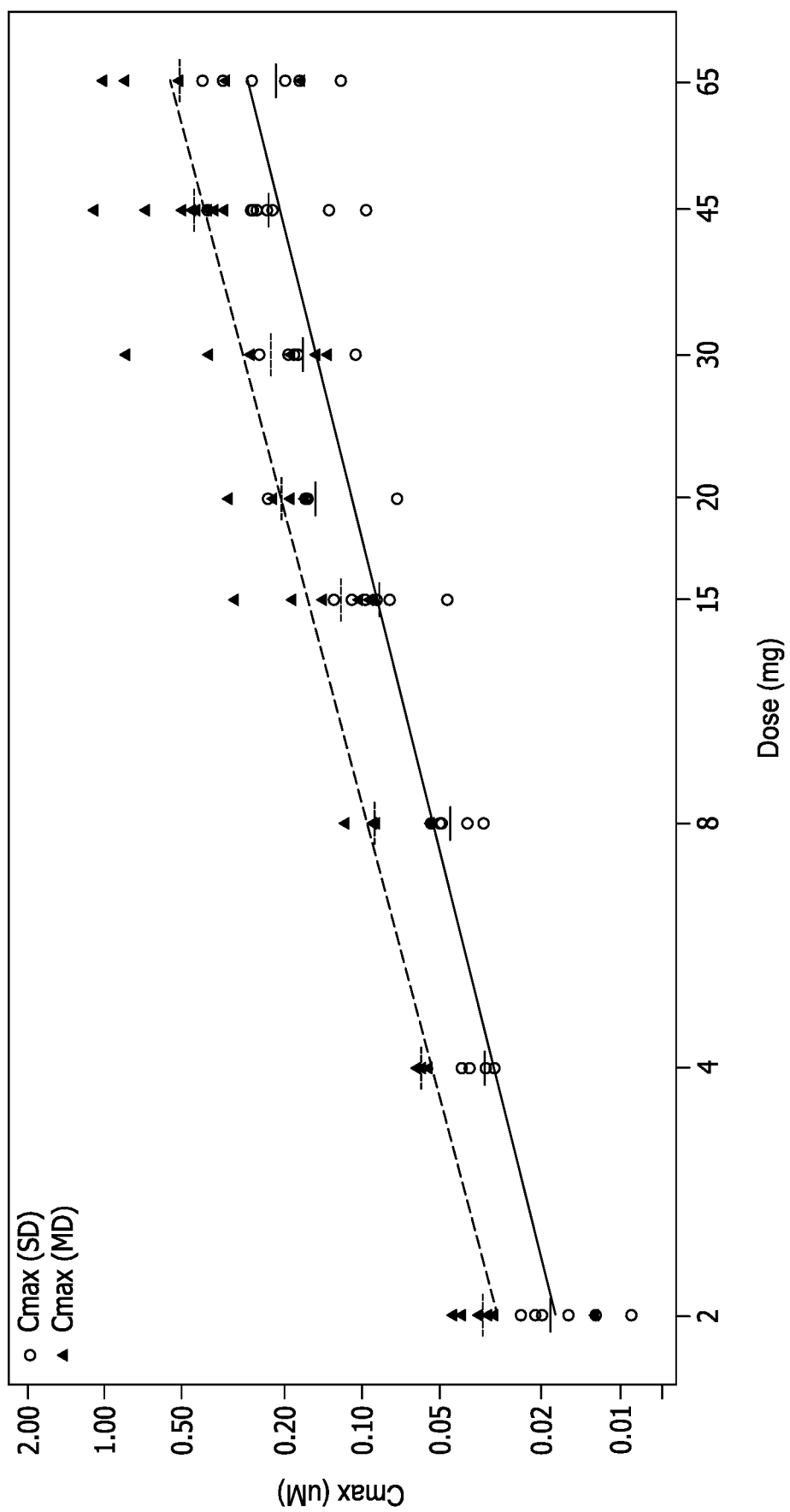
FIG. 22 is a log scale plot of Cmax (μM) versus dose (mg) for GDC-0084 for single dose and multiple dose regimens.

FIG. 15 is a GDC-0084 dose proportionality plot of dose (mg) versus $C_{max}$ (μM) for single dose ("SD") and multiple dose ("MD") regimens. FIG. 16 is a GDC-0084 dose proportionality plot of dose (mg) versus $AUC_{24}$ (μM*hr) for single dose ("SD") and multiple dose ("MD") regimens. The data indicate that the accumulation ratio ($AUC_{0-24\ hr\ multiple\ dose}/AUC_{0-24\ hr\ single\ dose}$) ranged from 0.577 to 4.84 with a mean value of 2.12±0.896. Both $C_{max}$ and $AUC_{0-24}$ for Cycle 1, Day 1 appeared to increase in a dose-proportional and dose linear fashion across all cohorts for both single and multiple doses. FIG. 17 is a plasma GDC-0084 mean single dose (SD) concentration versus time log scale plot (cycle 1, day 1). FIG. 18 is a plasma GDC-0084 mean single dose (SD) concentration versus time linear scale plot (cycle 1, day 1). FIG. 19 is a plasma GDC-0084 mean single dose (SD) concentration versus time log scale plot (cycle 1, day 8/15). FIG. 20 is a plasma GDC-0084 mean single dose (SD) concentration versus time linear scale plot (cycle 1, day 8/15). FIG. 21 is a log scale plot of $AUC_{0-24}$ (M*hr) versus dose (mg) for GDC-0084 for single dose (SD) and multiple dose (MD) regimens. FIG. 22 is a log scale plot of Cmax (μM) versus dose (mg) for GDC-0084 for single dose (SD) and multiple dose (MD) regimens.

Overall, the concentration from brain tumor tissue suggests that GDC-0084 crosses the blood brain barrier and uniformly distributes throughout the brain. The experimental results indicate that GDC-0084 inhibited human mTOR, with a mean apparent Ki of 70 nM. GDC-0084 is rapidly absorbed and demonstrates linear and dose proportional increases in exposure, with a half-life ($t_{1/2}$ of about 19 hours) supportive of once daily dosing. The MTD was determined to be 45 mg when GDC-0084 was administered orally once daily in cycles of 28 days. At a dose of 45 mg, steady-state concentrations were consistent with antitumor activity observed in xenograft models. Of the patients who underwent FDG-PET imaging, 7 of 27 patients had metabolic partial response according to pre-defined criteria. Of the 34 patients with exploratory MRI results, none of the MRI derived metrics (Ktrans, Cerebral blood volume, apparent diffusion coefficient) showed any significant trend with drug plasma exposure. GDC-0084 was rapidly absorbed with a median $T_{max}$ of approximately 2 hours following a single dose. The accumulation ratio had a mean value of 2.1±0.90, and the extent of accumulation was consistent with the theoretical accumulation based upon half-life estimates and the daily dosing interval. GDC-0084 displayed an approximately linear and dose proportional increase in $C_{max}$ and $AUC_{0-24}$ following single and multiple doses across all cohorts (2 mg to 65 mg once daily).

Tumor response was determined by either an assessment of FDG-PET or by Response Assessment in Neuro-Oncology (RANO).

FDG-PET assessments were used to evaluate the inhibition of glucose uptake and will be used as a surrogate assay to address if GDC-0084 is able to exert biological effects in tumor tissue. The outcome measure for this objective was based on the maximum standard uptake value ($SUV_{max}$) of up to five lesions. The tumor regions of interest (ROIs) were identified for each patient on pretreatment PET imaging and corresponded to a subset of the target lesions used for analysis of the patient's pretreatment tumor assessment scans. Determination of PET response was done according to the modified European Organization for Research on the Treatment of Cancer (EORTC) definitions (Young H, Baum R, Cremerius H, et al., "Measurement of clinical and subclinical tumour response using [18F]-fluorodeoxyglucose and positron emission tomograph: review and 1999 EORTC recommendations", European Organization for Research and Treatment of Cancer (EORTC) PET Study Group. Eur J Cancer 1999; 35:1773-82). Specifically, the $SUV_{max}$ of each ROI on the on-treatment scans was compared with its $SUV_{max}$ on the corresponding pretreatment scan and the percent change was determined. In the event of more than one ROI, the overall percent change in $SUV_{max}$ was the arithmetic mean of the percent changes in $SUV_{max}$ for each of the ROIs ($mSUV_{max}$). PET response is defined as follows. Progressive disease (PET-PD): percent increase of >20% in $mSUV_{max}$ or the development of a new lesion with an $SUV_{max}$ above background and not explained by another cause (e.g., infection). Stable disease (PET-SD): percent increase of ≤20% in $mSUV_{max}$ or a percent decrease of ≤20% in $mSUV_{max}$. Partial response (PET-PR): percent decrease of >20% in $mSUV_{max}$. Complete response (PET-CR): $SUV_{max}$ indistinguishable from background in all ROIs (i.e., complete disappearance of all PET lesions).

Tumor response under the RANO guidelines was done generally in accordance with the Wen method (Wen P Y, Macdonald D R, Reardon D A, et al. "Updated response assessment criteria for high-grade gliomas: Response Assessment in Neuro-Oncology Working Group", J Clin Oncol 2010; 28:1963-72) where the disease is categorized as "complete response", "partial response", "stable disease" and "progression". Among other factors, a complete response required all of the following: complete disappearance of all enhancing measurable and non-measurable disease sustained for at least 4 weeks; no new lesions; and stable or improved non-enhancing (T2/FLAIR) lesions. A partial response required, among other factors, ≥50% decrease, compared with baseline, in the sum of the products of the perpendicular diameters of all measurable enhancing lesions (such as measured by MRI) sustained for at least 4 weeks; no progression of non-measurable disease; and no new lesions. Stable disease occurred if the patient did not qualify for complete response, partial response, or progression. Progression was defined by any of the following: ≥25% increase in the sum of the products of the perpendicular diameters of all enhancing lesions (compared with the smallest tumor measurement either at baseline [pretreatment] or after initiation of therapy [i.e., compared with baseline if no decrease]) on stable or increasing doses of corticosteroids; a significant increase in T2/FLAIR nonenhancing lesions on stable or increasing doses of corticosteroids compared with baseline scan or best response after initiation of therapy, not due to co-morbid events; the appearance of any new lesions; clear progression of non-measurable lesions; or definite clinical deterioration not attributable to other causes apart from the tumor, or to a decrease in corticosteroid dose.

Some patients underwent, FDG-PET and additional exploratory MRI assessments to investigate potential pharmacodynamic effects of GDC-0084. Reduction in $^{18}$F-FDG uptake measured by PET is indicative of reduced glucose metabolism activity, a likely PD response of PI3K pathway inhibition. A total of 27 patients underwent FDG-PET imaging at baseline, cycle 2 day 1 and, for those enrolled on the 45 mg and 65 mg dose levels, also at cycle 1 day 8. On the basis of FDG-PET, five of the 27 patients (18.5%) had metabolic partial response according to pre-defined criteria. At GDC-0084 doses of at least 45 mg per day, a trend towards decreased median survival in normal brain tissue was observed suggesting central nervous system penetration of GDC-0084. GDC-0084 was detected at similar levels in brain tumor and brain tissue, with a brain tissue/tumor to plasma ratio of greater than 1 and greater than 0.5 for total drug and free drug, respectively. Of the evaluable patients, 26 patients (55.3%) had a best overall response of progressive disease, and 19 patients (40.4%) had stable disease. FDG-PET and concentration data from brain tumor tissue suggest that GDC-0084 crosses the blood-brain barrier, with a uniform distribution throughout the brain.

Thirty-four patients were evaluated by exploratory magnetic resonance imaging ("MRI"). Dynamic contrast enhanced (DCE) MRI data showed that in four patients with highest drug exposure ($AUC_{0-24\ hr}$>8 uMhr) a decrease in tumor Ktrans, a measure of tumor permeability, reflecting tumor angiogenesis, was observed. The Ktrans changes were within the likely noise range of the measurement (based on variability in low-exposure cohorts). Overall, none of the MRI derived metrics (Ktrans, Cerebral blood volume, apparent diffusion coefficient) showed any significant trend with drug plasma exposure.

Example 26: Transport Assays in Cell Monolayers

Madin-Darby canine kidney (MDCK) cells expressing human P-gp, human BCRP or mouse Bcrp1 and LLC-PK1 cells transfected with mouse P-gp (mdr1a) were used to determine whether GDC-0084 was a substrate of these transporters. MDR1-MDCKI cells were licensed from the NCI (National Cancer Institute, Bethesda, Md.) and Bcrp1-MDCKII, BCRP-MDCKII and Mdr1a-LLC-PK1 cells were obtained from the Netherlands Cancer Institute (Amsterdam, The Netherlands). For transport studies, cells were seeded on 24-well Millicell plates (Millipore, Billerca, Mass.) 4 days prior to use (polyethylene terephthalate membrane, 1 µm pore size) at a seeding density of $2.5 \times 10^5$ cells/mL (except for MDR1-MDCKI, $1.3 \times 10^5$ cells/mL). GDC-0084 was tested at 5 µM in the apical to basolateral (A-B) and basolateral to apical (B-A) directions. The compound was dissolved in transport buffer consisting of Hank's balanced salt solution (HBSS) with 10 mM HEPES (Invitrogen Corporation, Grand Island, N.Y.). Lucifer Yellow (Sigma-Aldrich, St. Louis, Mo.) was used as the paracellular and monolayer integrity marker. GDC-0084 concentrations in the donor and receiving compartments were determined by LC-MS/MS analysis. The apparent permeability ($P_{app}$), in the apical to A-B and B-A directions, was calculated after a 2-hour incubation as:

$$P_{app} = (dQ/dt) \cdot (1/AC0)$$

Where: dQ/dt=rate of compound appearance in the receiver compartment; A=Surface area of the insert; C0=Initial substrate concentration at T0. The efflux ratio (ER) was calculated as ($P_{app,\ B-A}/P_{app,\ A-B}$).

The results are presented in Table 15 below.

TABLE 15

Apparent Permeability ($P_{app}$) of GDC-0084 in Transfected Cell

| | Papp ($10^{-6}$ cm/s) | | |
|---|---|---|---|
| Cell Line | A to B | B to A | $P_{app}$ Ratio |
| MDR1-MDCKI | 13.5 ± 0.9 | 11.5 ± 1.6 | 0.85 ± 0.1 |
| Bcrp1-MDCKII | 17.6 ± 2.1 | 18.6 ± 1.1 | 1.06 ± 0.1 |
| BCRP-MDCKII | 23.2 ± 5.4 | 16.0 ± 1.1 | 0.71 ± 0.1 |
| Mdr1a-LLC-PK | 13.1 ± 1.3 | 19.4 ± 1.3 | 1.48 ± 0.1 |

The apparent permeability ($P_{app}$) was high and comparable to that of metoprolol, the high $P_{app}$ marker used in the same experiments (data not shown). The efflux ratios ($P_{app,\ B-A}/P_{app,\ A-B}$) did not markedly differ from 1 in the MDCK or LLC-PK1 transfected cells, indicating that GDC-0084 was a poor substrate of the efflux transporters P-gp and BCRP.

Example 27: Determination of Plasma Protein and Brain Binding

GDC-0084 protein binding was determined in vitro, in mouse plasma (Bioreclamation, Inc., Hicksville, N.Y.) by equilibrium dialysis using a RED device (Thermo Scientific, Rockford, Ill.), with 300 µL of plasma and 500 µL of phosphate-buffered saline in the two chambers of the device. GDC-0084 was added to pooled plasma (n≥3) at a total concentration of 5 µM. Plasma samples were equilibrated with phosphate-buffered saline (pH 7.4) at 37° C. in 90% humidity and 5% $CO_2$ for 4 hours. Following dialysis, concentration of GDC-0084 in plasma and buffer was measured by liquid chromatography-tandem mass spectrometry (LC-MS/MS). The percent GDC-0084 unbound in plasma was determined by dividing the concentration measured in the post-dialysis buffer by that measured in the post-dialysis plasma and multiplying by 100. Incubations were performed in triplicate. Parameters are presented as mean±standard deviation.

The free fraction of GDC-0084 in mouse brain was determined as described by Kalvass et al. (Kalvass J C, Maurer T S, Pollack G M, "Use of plasma and brain unbound fractions to assess the extent of brain distribution of 34 drugs: comparison of unbound concentration ratios to in vivo p-glycoprotein efflux ratios", Drug Metab. Dispos. 2007; 35(4):660-666). Briefly, brain tissue was homogenized in 3 volumes of phosphate-buffered saline and GDC-0084 was added at a final concentration of 5 µM. Aliquots of 300 µl were dialyzed in a RED device (Thermo Scientific, Rockford, Ill.) against a volume of 500 µl buffer for 4 h at 37° C. in an incubator at 90% humidity and 5% $CO_2$. Following dialysis, tissues and buffer samples were analyzed as described for the plasma protein binding studies.

The results show that GDC-0084 binding to plasma proteins was low, with a free fraction (%) of 29.5±2.7 (n=3) in mouse plasma, when tested at 5 µM. Binding to brain tissues was higher, with a free fraction of 6.7% (+1; n=3).

Example 28: Modulation of pAkt and pS6 in the Brain

Inhibition of the PI3K pathway was assessed in the brain of healthy mice through measurement of two markers, pAkt and pS6. Female CD-1 mice were dosed PO with GDC-0084 at 25 mg/kg. Brains and plasma were collected at 1 and 6 hours post-dose, from 3 animals at each time point. Individual brains were split in half for PD analysis and GDC-0084 concentration measurement. The samples were stored at −80° C. and analyzed for GDC-0084 total concentration. For PD analysis, cell extraction buffer (Invitrogen, Camarillo, Calif.) containing 10 mM Tris pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, and 0.5% deoxycholate was supplemented with phosphatase, protease inhibitors (Sigma, St. Louis, Mo.) and 1 mM PMSF and added to frozen brain biopsies. Brains were homogenized with a small pestle (Konte Glass Company, Vineland, N.J.), sonicated briefly on ice, and centrifuged at 20,000 g for 20 minutes at 4° C. Protein concentration was determined using BCA protein assay (Pierce, Rockford, Ill.). Proteins were separated by electrophoresis and transferred to NuPage nitrocellulose membranes (Invitrogen, Camarillo, Calif.). Licor Odyssey Infrared detection system (Licor, Lincoln, Nebr.) was used to assess and quantify protein expression. PI3K pathway markers were evaluated by immunoblotting using antibodies against $pAkt^{Ser473}$, total Akt, $pS6^{Ser235/236}$ and total S6 (Cell Signaling, Danvers, Mass.). The differences in marker levels between the treated and control mice were evaluated using the Student's t-test (Prism 5, GraphPad).

Figure 23:
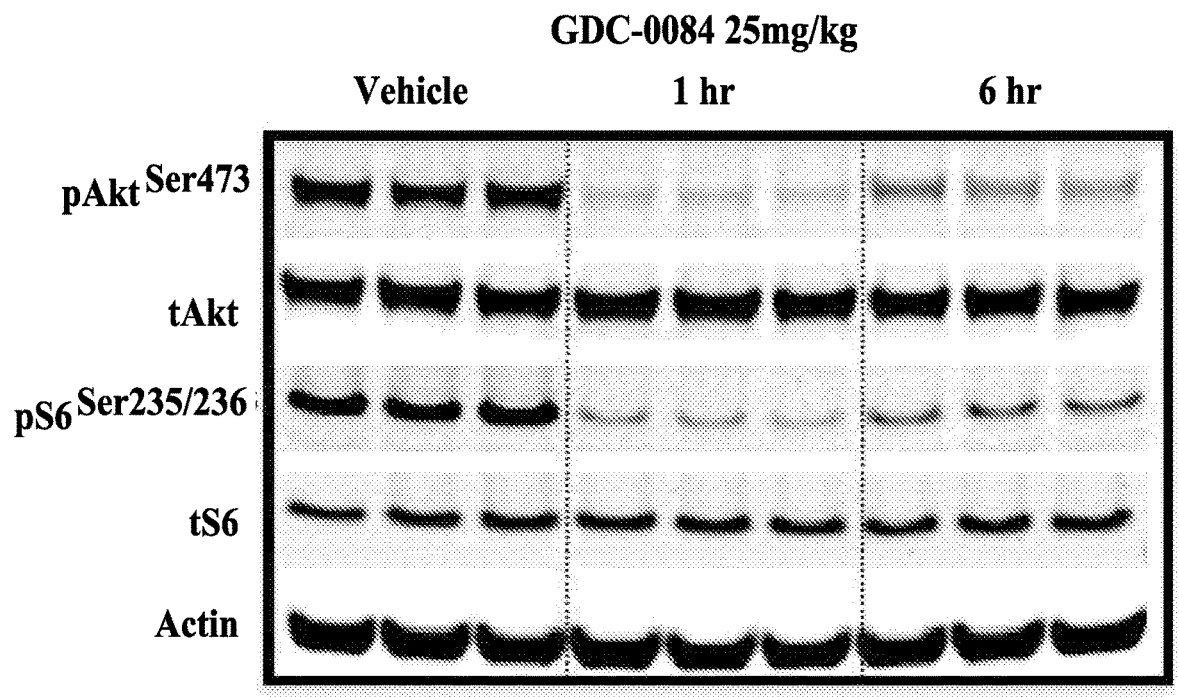
FIG. 23 is a western blot of mouse brains probed with antibodies against pAkt, total Akt, pS6, total S6 and actin.
Figure 24:
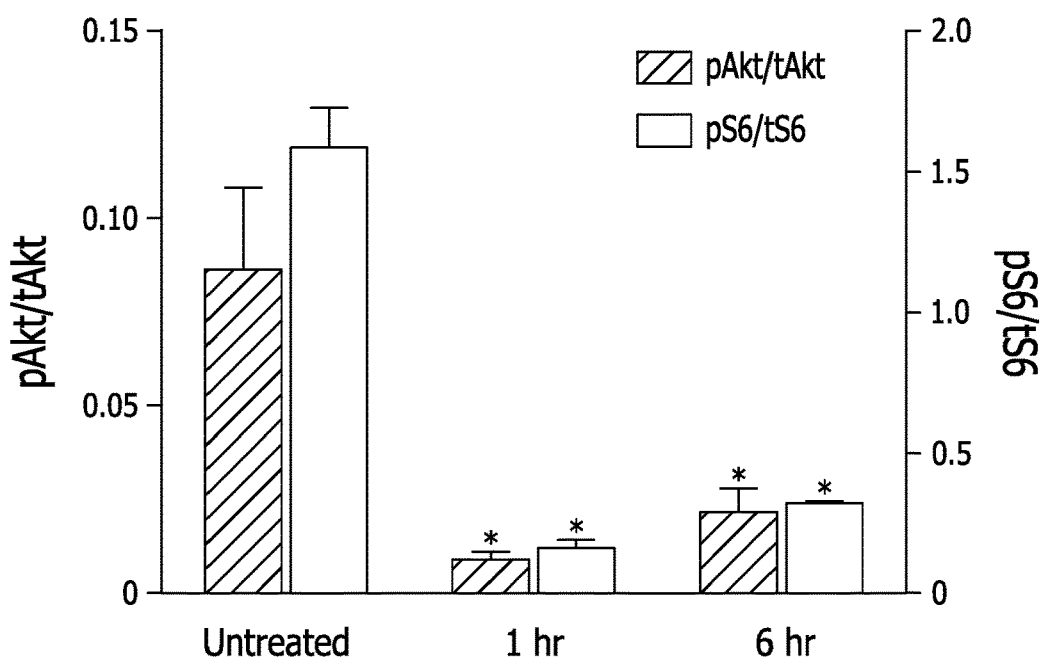
FIG. 24 is a quantitation of pAkt to total Akt and pS6 to total S6 at 1 and 6 h post-dose in CD-1 mice.

Following a single oral dose of GDC-0084 (25 mg/kg), pAkt and pS6 levels were significantly lower than those detected in the control animals (FIG. 23). Suppression of pAkt and pS6 reached 90% 1 hour post dose and stayed greater than 70% 6 hours after dosing (FIG. 24).

Example 29: U87 and GS2 First Method for Measuring Efficacy in Brain Tumor Model Six female nude mice (Charles River Laboratories) were implanted with either U87 MGM human glioblastoma cancer cells (described elsewhere herein) or GS2 tumor cells (Gunther H S, Schmidt N O, Phillips H S, et al., "Glioblastoma-derived stem cell-enriched cultures form distinct subgroups according to molecular and phenotypic criteria", Oncogene 2008; 27(20):2897-2909)), injected via stereotactic surgery into the right striatum (subcortical part of the forebrain) in a volume of 3 to 5 µL (250K U87 cells and 100K GS2 cells). A single oral dose of 15 mg/kg GDC-0084 (further comprising 0.5% methylcellulose/0.2% Tween 80 (MCT)) was administered 19 to 21 days post-implantation. Mice were euthanized at 1 and 6 hours post-dose via exsanguination by perfusion under anesthesia. Brains were excised, flash frozen in liquid $N_2$ and stored in a −80° C. freezer until analyzed. Fresh frozen tissue sections were obtained on a cryomicrotome (Leica CM3050S, Buffalo Grove, Ill.) at 12 µm thickness and thaw-mounted onto indium tin oxide coated glass slides (Bruker Daltonics, Billerica, Mass.). Tissue sections were analyzed by imaging MALDI MS, providing signal intensities (and not absolute quantitation), followed by cresyl violet staining for histological interrogation.

For MALDI MAS analysis, a 40 mg/mL solution of 2,5-dihydroxybenzoic acid (Sigma-Aldrich, St. Louis, Mo.) was prepared in methanol:water (70:30 v/v). A stable-labeled internal standard, [D6]GDC-0084, was spiked into the MALDI matrix solution at 2 µM prior to deposition onto the tissue sections. Matrix solution was homogenously spray-coated onto the tissue using a HTX™-Sprayer (HTX technologies, Chapel Hill, N.C.). Matrix-coated tissue sections were transferred to the MALDI mass spectrometer (SolariX 7T FT-ICR, Bruker Daltonics, Bremen, Germany) for imaging analysis. Imaging data were collected at 100 m pixel resolution in positive ionization mode, under continuous accumulation of selected ions (CASI) windows optimized for a 50 Da window centered on m/z 383 (m/z 358-408). Laser intensity and number of shots were optimized for sensitivity of the parent drug (1200 shots) with ion detection collected over the mass range of m/z 150-3000. Drug images were generated based on accurate mass the parent drug (GDC-0084 m/z 383.1938) using FlexImaging v4.0 64-bit (Bruker Daltonics, Billerica, Mass.) with a mass tolerance of ±2 mDa and normalized to internal standard response.

Following completion of the imaging experiments, matrix coating was removed by rinsing the glass slide in 100% methanol for 30 seconds or until the entire matrix was visibly removed. Tissue sections were stained utilizing a freshly prepared 0.5% cresyl violet staining solution (Chaurand P, Schwartz S A, Billheimer D, Xu B J, Crecelius A, Caprioli R M, "Integrating histology and imaging mass spectrometry", *Anal. Chem.* 2004; 76(4):1145-1155) by submerging the glass slide for 30 seconds, then rinsed for an additional 30 seconds in two cycles of 100% ethanol. Microscope images were obtained on an Olympus BX51 (Tokyo, Japan) at 10× magnification and stitched using MicroSuite Analytical v3.0 software (Olympus, Tokyo, Japan). Subsequently, stained images were co-registered to the optical images in FlexImaging for visualization and annotation of tumor and non-tumor regions for the drug images.

To assess drug distribution, imaging MALDI MS data from U87 and GS2 tumor models were co-registered to the cresyl violet stained microscope images in FlexImaging Regions of interest (ROIs) that were selected based on the anatomical features defined in the histological image including tumor and non-tumor regions. Drug intensity for each pixel within the defined ROI was extracted and exported. Drug intensities were binned in 0.1 increments over a range of 0.0 to 2.0. Histogram plots were created in GraphPad Prism 5 to visualize the distribution of pixel intensity frequencies.

Example 30: U87 and GS2 Second Method for Measuring Efficacy in Brain Tumor Model U87 glioblastoma cancer cells (described elsewhere herein) and GS2 glioblastoma cells were selected to test the efficacy of GDC-0084 in a mouse brain model. These U87 and GS2 models are PTEN-deficient, with the GS2 cell line presenting a copy number loss at the PTEN locus (Gunther H S, et al.) with no detectable PTEN protein by western blot (Carlson B L, Pokorny J L, Schroeder M A, Sarkaria J N., "Establishment, maintenance and in vitro and in vivo applications of primary human glioblastoma multiforme (GBM) xenograft models for translational biology studies and drug discovery", *Curr Protoc Pharmacol.* 2011; Chapter 14: Unit 14 16). The identity of the two cell lines was confirmed by STR profiling (DNA Diagnostics Center) using cells within 5 passages of those utilized for in vivo studies. The U87 (250K) and GS2 (100K) tumor cells were injected via stereotaxic surgery into the right striatum (subcortical part of the forebrain) in a volume of 3-5 µl. For each experiment, mice were randomized into groups of 10 to obtain comparable mean tumor volumes between treatment and control groups for each model. Treatments were administered GDC-0084 (15 mg/kg), or vehicle (MCT) PO daily for 2 or 4 weeks, respectively, starting 7 days (U87) or 14 days (GS2) post tumor cell inoculation. Mouse body weights were recorded twice per week during the study and animals were euthanized if body weight loss was greater than 20% from their initial body weight. Tumor volumes were monitored by ex vivo micro micro-computed tomography (micro-CT) imaging and T2 MRI for the GBM models U87 and GS2, respectively. The differences between treatment groups were evaluated using Student's t test in Prism (Prism 5, Graph-Pad). MRI was performed on a Varian 9.4T MRI system with a 30 mm quadrature volume coil. During the imaging, animals were kept under anesthesia with 2% isoflurane in air. Body temperature was continuously monitored using a rectal probe and was maintained at 37° C. by a heated-air flow system regulated by in-house LabVIEW controller software. A T2-weighted fast spin echo, multi-slice (FSEMS) sequence was used to detect lesions by MRI. 12-20 axial 0.5-0.8 mm-thick slices were acquired with a 20×20 mm field of view (FOV), and 128×128 matrix, zero-filled to 256×256 images. TR=3500-4000 ms, TE=9-10 ms, ETL=8, k-zero=4, NEX=8. Tumor volumes were calculated from the T2-weighted FSEMS images using an intensity threshold based region growing tool in MRVision software. Brain sample preparation, micro-CT scanning, and image analysis for ex-vivo micro-CT imaging were performed as described previously (de Crespigny A, Bou-Reslan H, Nishimura M C, Phillips H, Carano R A, D'Arceuil H E, "3D micro-CT imaging of the postmortem brain", *J. Neurosci. Methods.* 2008; 171(2):207-213).

In the studies conducted with the GS2 tumor-bearing mice, plasma and brains were also collected at the end of treatment to measure GDC-0084 and assess PI3K pathway modulation in the tumor. Each brain was dissected to separate the tumor from the healthy tissues. Plasma and normal brains were processed and analyzed by LC-MS/MS. The GS2 tumors isolated from the brains were processed and the PI3K pathway markers pAkt, pS6 and p4EBP1 were measured as described previously.

Example 31: MALDI Imaging Results

Figures 25A, 25B:
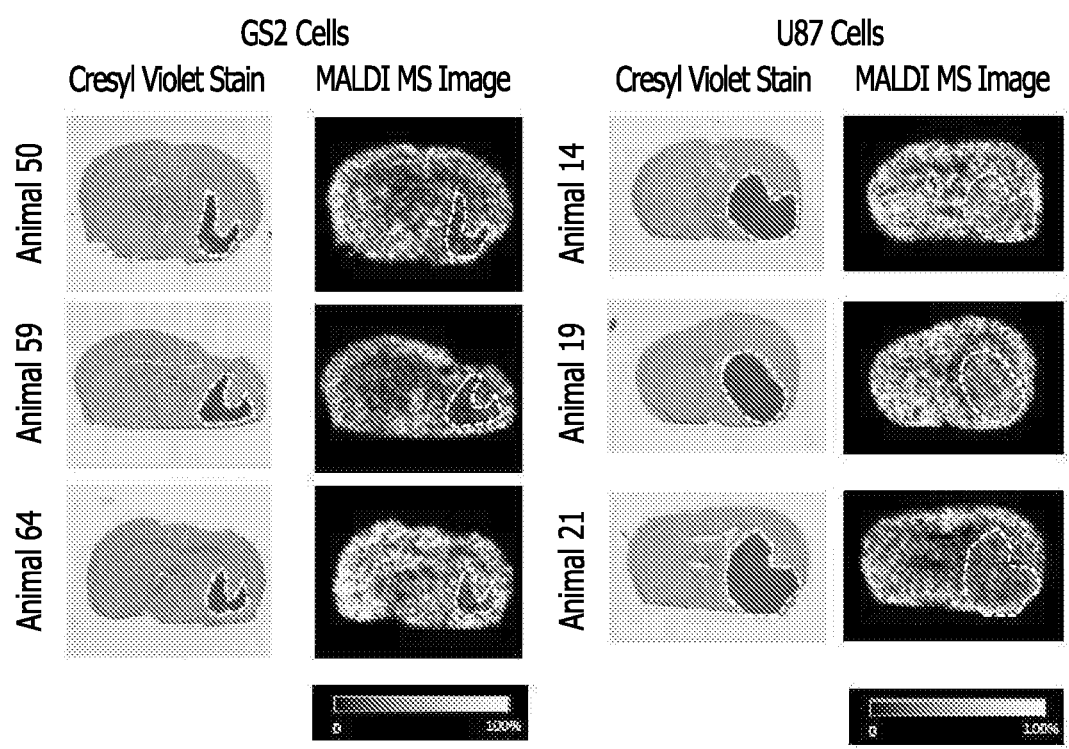
FIG. 25A depicts images of GDC-0084 mouse brain distribution one hour following oral administration of 15 mg/kg of GDC-0084 in an orthotopic model of GS2 glioblastoma intracranial tumors. Localization of the tumors by cresyl violet staining and drug distribution in MALDI MS images are presented.
FIG. 25B depicts images of GDC-0084 mouse brain distribution one hour following oral administration of 15 mg/kg of GDC-0084 in an orthotopic model of U87 glioblastoma intracranial tumors. Localization of the tumors by cresyl violet staining and drug distribution in MALDI MS images are presented.
Figure 26A:
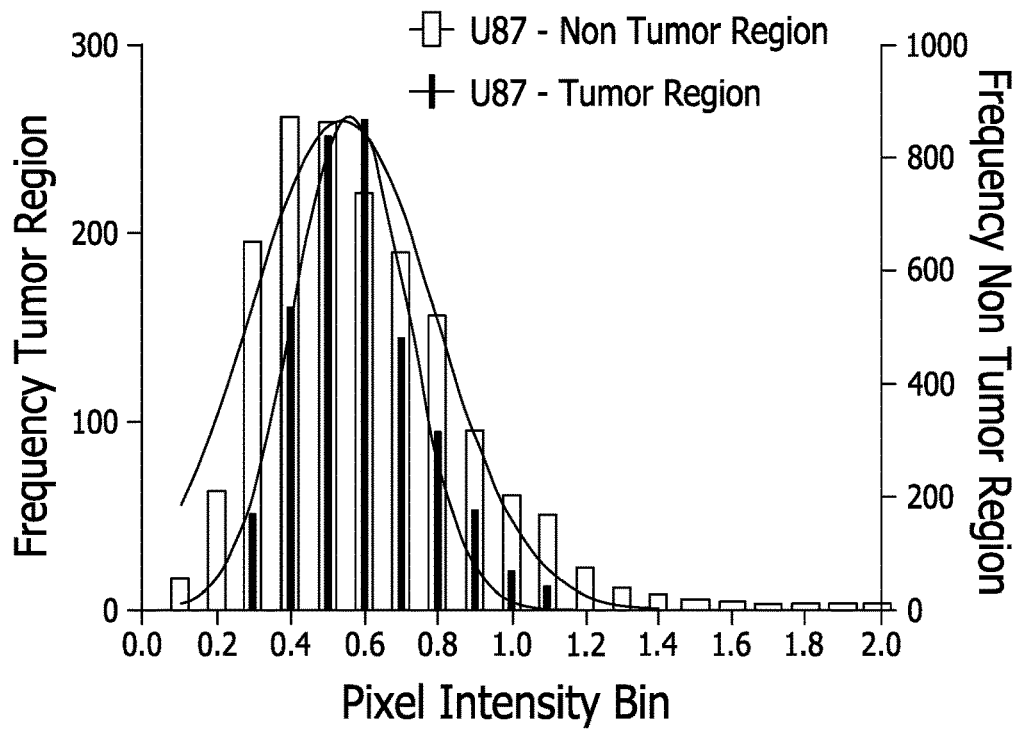
FIG. 26A depicts the actual and Gaussian distribution of MALDI imaging signal intensity of GDC-0084 in orthotopic mouse model U87 intracranial tumors and non-tumor brain regions.
Figure 26B:
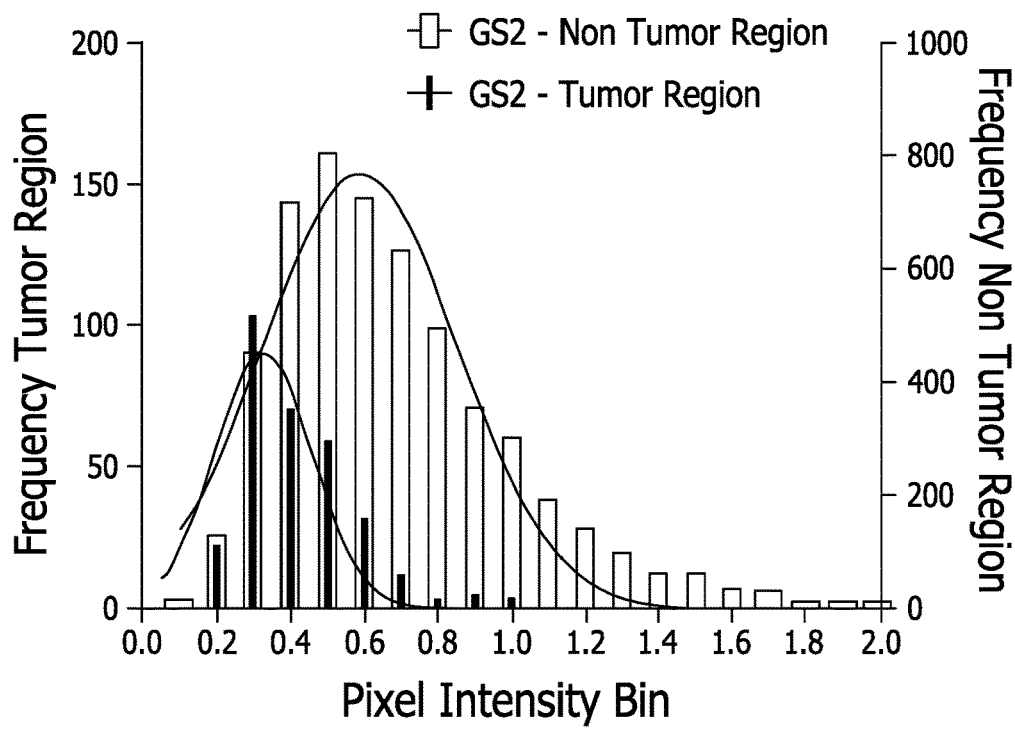
FIG. 26B depicts the actual and Gaussian distribution of MALDI imaging signal intensity of GDC-0084 in orthotopic mouse model GS2 intracranial tumors and non-tumor brain regions.
Figure 26C:
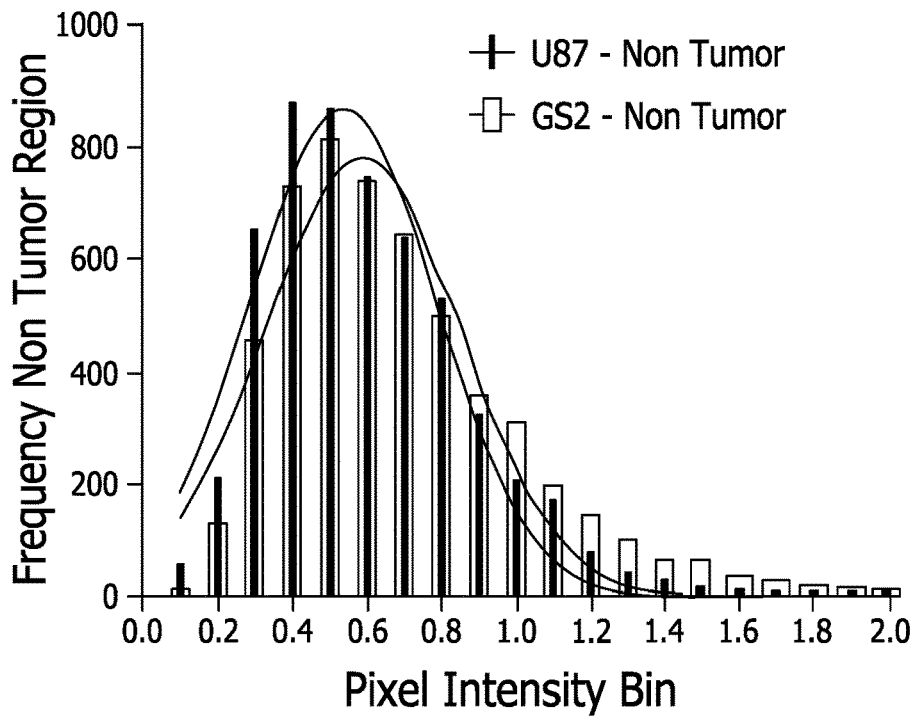
FIG. 26C depicts the actual and Gaussian distribution of MALDI imaging signal intensity of GDC-0084 in the non-tumor regions of the U87 and GS2 orthotopic mouse models.
Figure 26D:
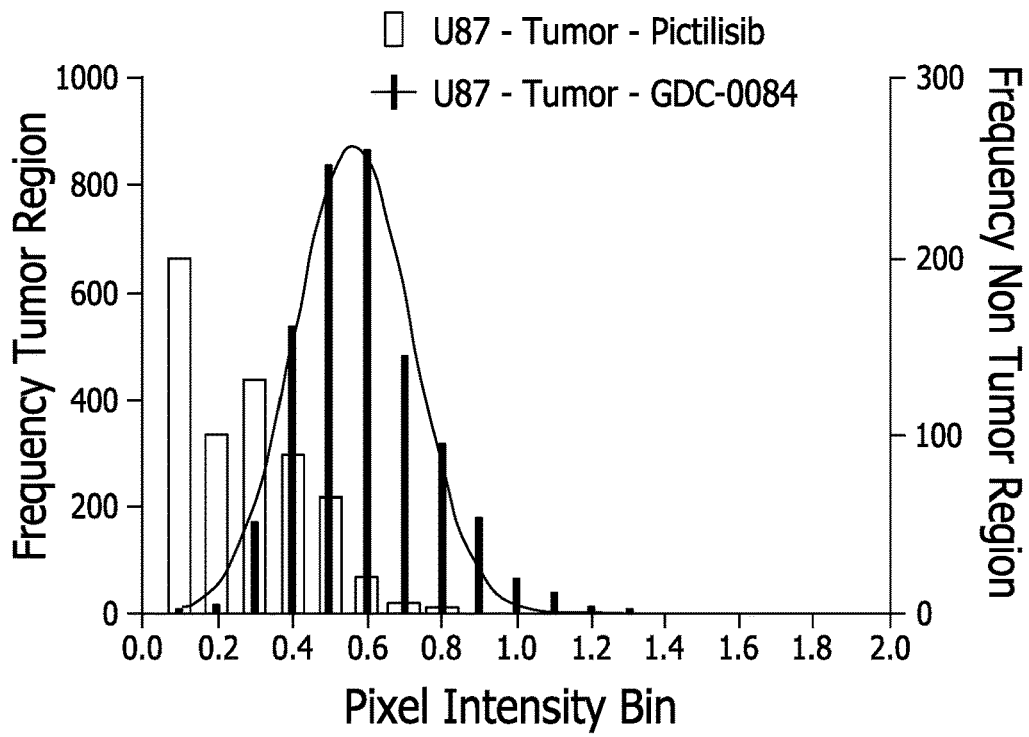
FIG. 26D depicts the actual and Gaussian distribution of signal intensity of GDC-0084 and the actual distribution of pictilisib in the U87 orthotopic GBM model.

Distribution of GDC-0084 in the brain and intracranial U87 and GS2 tumors following administration of a single PO dose (15 mg/kg) was investigated by MALDI imaging. Brains were collected 1 hour post dose and images presented in FIGS. 25A and 25B show that GDC-0084 distributed readily and quite evenly throughout the brain, including in the GS2 (FIG. 25A) and U87 (FIG. 25B) tumors. In addition, the homogeneity and pattern of distributions of GDC-0084 in the tumors and non-tumored regions of the brains were further analyzed. The frequency of signal intensities (frequency of pixel intensities) appeared to follow a normal distribution in healthy brain, superimposed (mean pixel intensity 0.54) to that observed in U87 tumors (FIG. 26A); mean pixel intensity 0.54). A Gaussian distribution of signals was also observed in GS2 tumors (FIG. 26B), with however a slightly lower mean in pixel intensity (0.34 vs. 0.55), suggesting an overall lower GDC-0084 concentration in GS2 tumors than in normal brain. Comparisons of the GDC-0084 signal homogeneity in non-tumored brain regions between the U87 and GS2 tumor-bearing mice showed identical distribution (FIG. 26C), confirming the reproducible and consistent brain penetration properties of GDC-0084. Similar results were obtained in brains collected at 6 hours post dose. Furthermore, to contrast the distribution of GDC-0084 to that of a non-brain penetrant compound, MALDI images previously obtained with pictilisib in the U87 tumor model (Salphati L, Shahidi-Latham S, Quiason C, et al., "Distribution of the phosphatidylinositol 3-kinase inhibitors Pictilisib (GDC-0941) and GNE-317 in U87 and GS2 intracranial glioblastoma models-assessment by matrix-assisted laser desorption ionization imaging", *Drug Metab Dispos.* 2014; 42(7):1110-1116) were re-analyzed using the approach utilized here. In comparative analysis, reanalysis of data previously obtained with the non-brain penetrant compound pictilisb (Salphati, et al.) showed heterogeneous (non Gaussian) intra-tumor distribution of pixel intensities (FIG. 26D). While signal intensities in the U87 tumor for GDC-0084 could be fit to a Gaussian curve, signals from pictilisib were concentrated in the low intensity bins, with a distribution that appeared more heterogeneous (FIG. 26D). As compared to pictilisib, GDC-0084 provided for improved homogeneous and undifferentiated compound distribution throughout healthy brain tissue and tumor tissue. Based on the brain tumor model results, it is believed that GDC-0084 provides for improved treatment, not only the core of the tumor, but also invasive glioma cells protected by an intact BBB or blood-tumor barrier.

Example 32: Brain Tumor Model Results

Figure 27A:
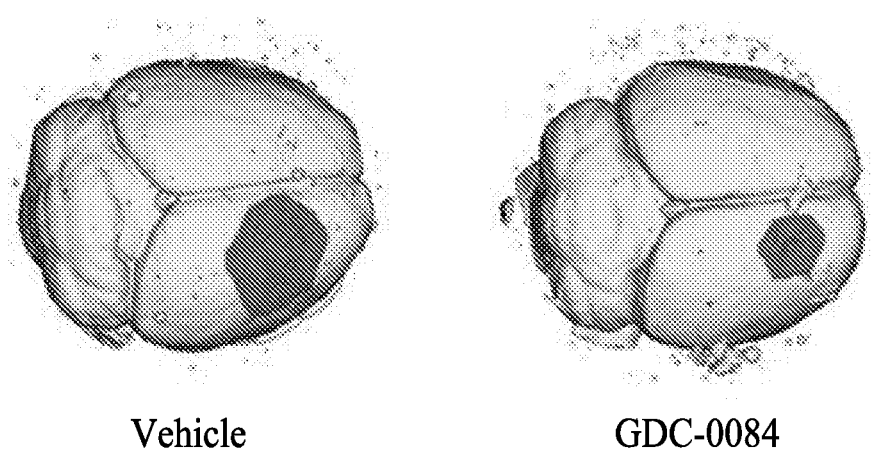
FIG. 27A depicts micro-CT images reflecting the tumor size (efficacy) of GDC-0084 in an U87 orthotopic mouse model following oral administration of 15 mg/kg GDC-0084 daily for two weeks as compared to treatment with a control (GDC-0084 vehicle).
Figure 27B:
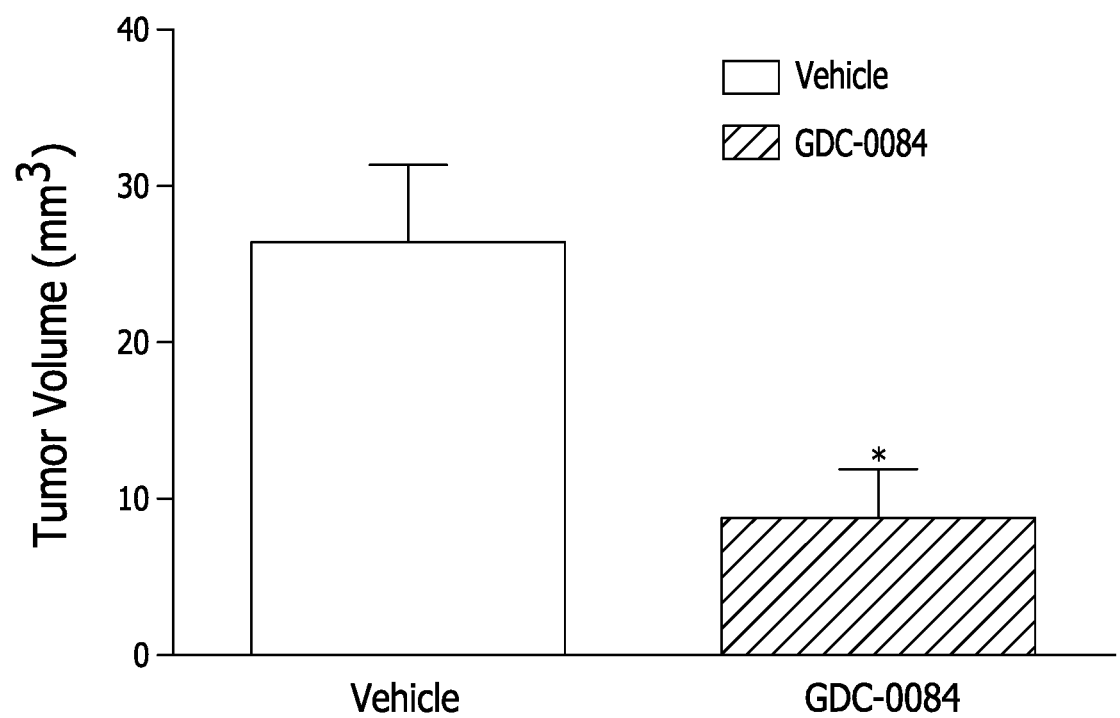
FIG. 27B depicts the tumor volume (in mm$^3$) for mice treated with oral administration of 15 mg/kg GDC-0084 daily in an U87 orthotopic model as compared to control mice where the results are presented as the mean±S.E. often animals.
Figure 27C:
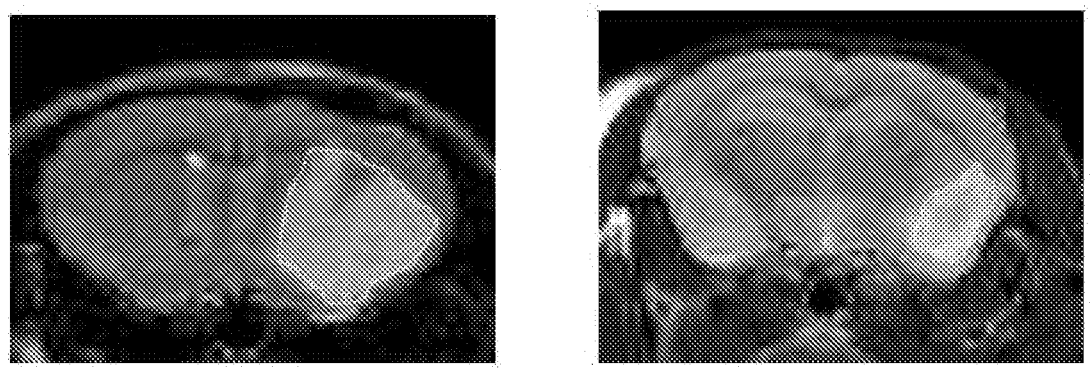
FIG. 27C depicts representative T-2 weighted MRI images showing the efficacy of GDC-0084 in a GS2 neurosphere tumor mouse model following oral administration of 15 mg/kg GDC-0084 daily for four weeks as compared to control animals.
Figure 27D:
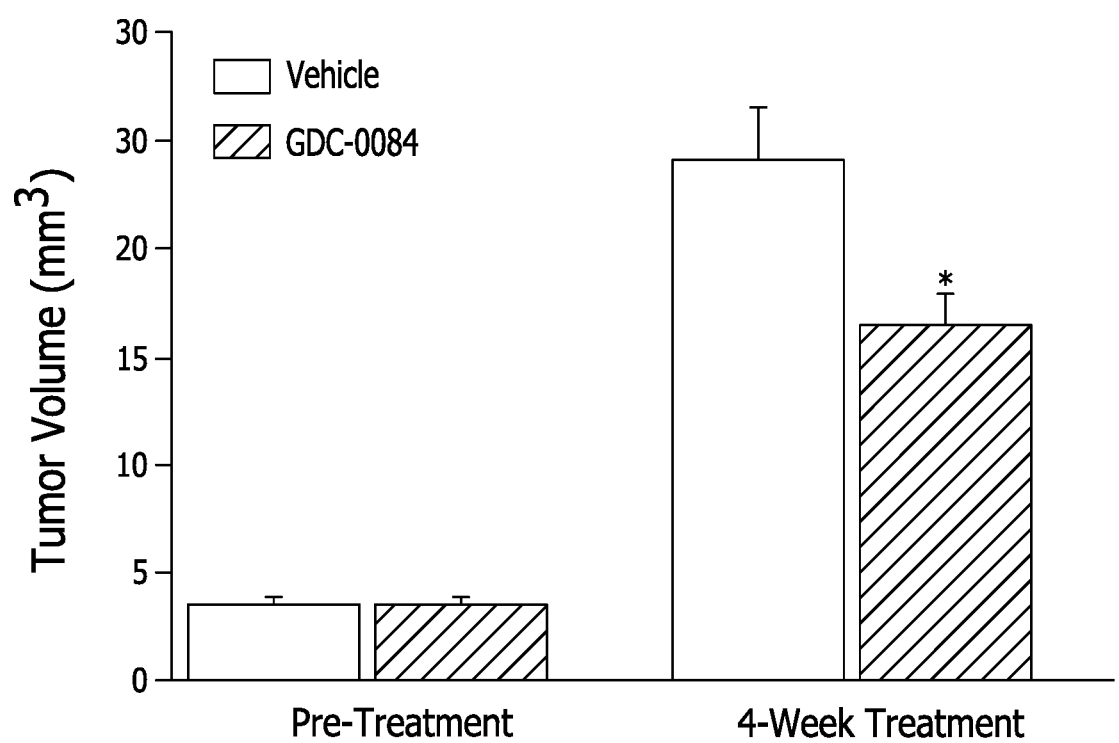
FIG. 27D depicts the tumor volume (in $mm^3$) for mice treated with oral administration of 15 mg/kg GDC-0084 daily in an U87 orthotopic model as compared to control mice where the results are presented as the mean±S.E. often animals.
Figure 28A:
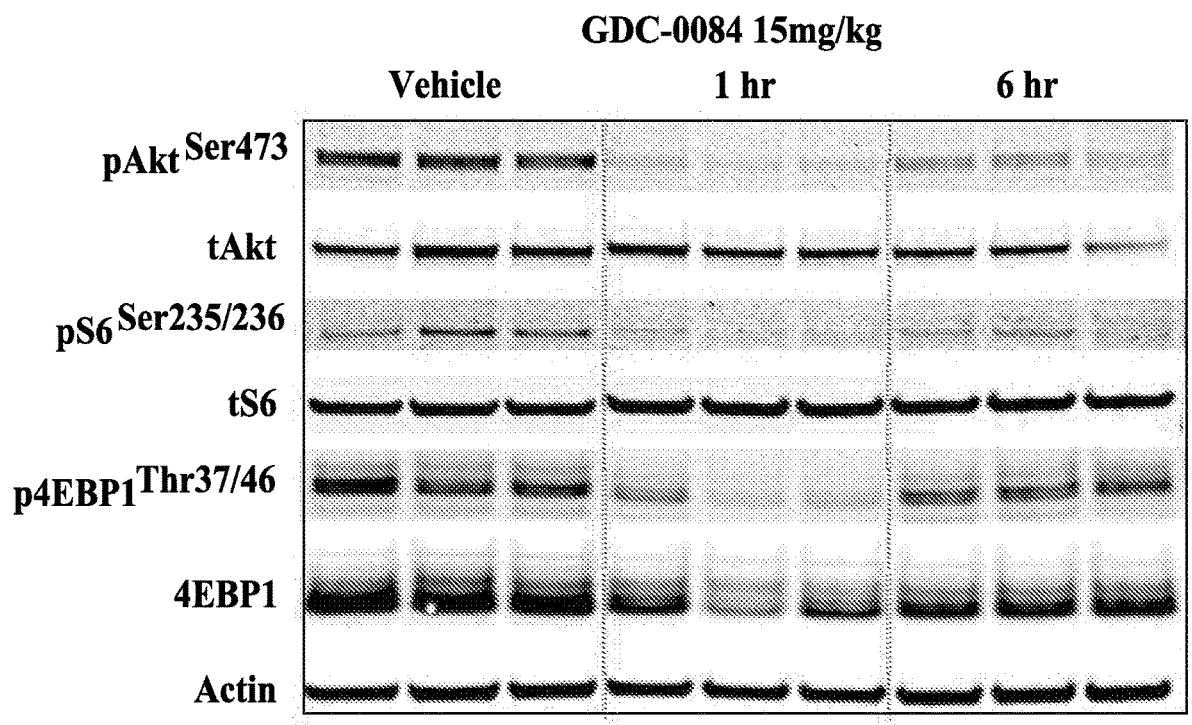
FIG. 28A depicts a western blot of the PI3K pathway markers pAkt, pS6 and p4EBP1 in intracranial GS2 xenografts following oral administration of 15 mg/kg GDC-0084 daily for four weeks, wherein modulation of the PI3K pathway in the GS2 tumors was assessed by western blot at the end of the 4-week dosing period and at 2 and 8 hours after the final administration of 15 mg/kg GDC-0084.
Figure 28B:
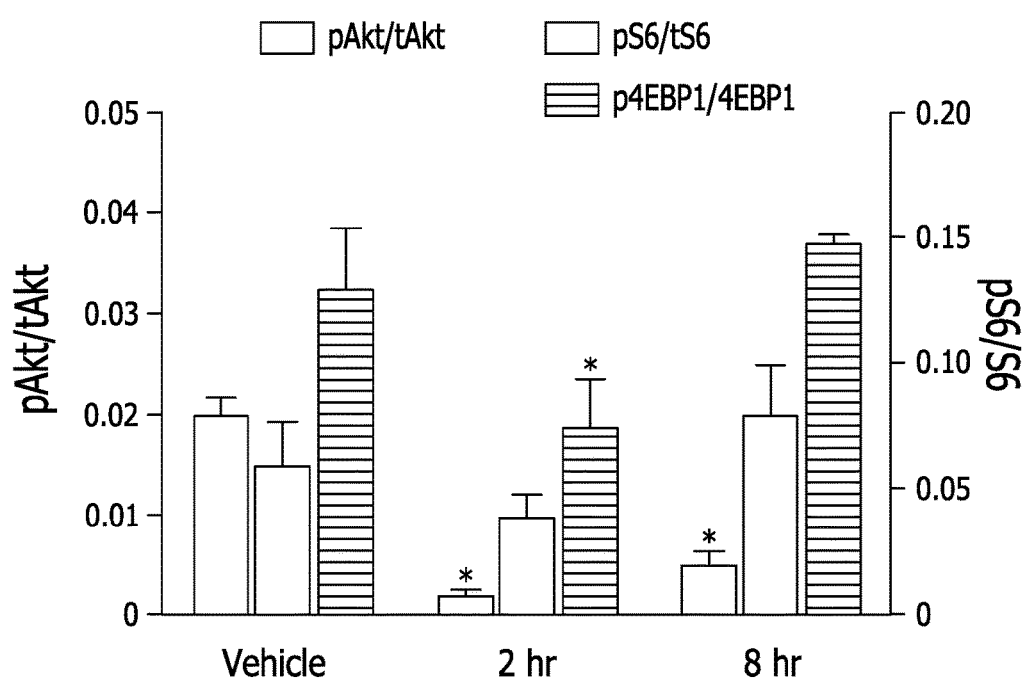
FIG. 28B depicts the quantitation of pAkt/total Akt, p4EBP1/total 4EBP1 and pS6/total S6 at 2 and 6 h following the last 15 mg/kg dose of GDC-0084.

The efficacy of GDC-0084 was tested in the U87 and GS2 intracranial models. GDC-0084 was administered PO at 15 mg/kg daily for 2 and 4 weeks to U87 and GS2 tumor-bearing mice, respectively. The effect of the treatment on the U87 and GS2 tumor volumes was assessed at the end of the dosing period. Images of U87 tumor obtained by micro-CT are presented in FIG. 27A. The U87 tumor volumes were reduced by approximately 70%, when compared to the vehicle control, (FIG. 27B) following treatment with GDC-0084. Similarly, the GS2 tumors measured by MRI (FIG. 27C) in the treated mice were significantly (p<0.01) smaller (≈40%) than those in the control group (FIG. 27D). Plasma and healthy brain concentrations of GDC-0084 were measured at the end of the study in the GS2 tumor-bearing mice and are presented along with brain-to-plasma ratios in Table 16 below. Brain concentrations in the normal part of the brain and brain-to-plasma ratios were comparable to those obtained previously (Table 9). Modulation of the PI3K pathway in the GS2 tumors was assessed by western blot at the end of the dosing period, 2 and 8 hours after the final administration of GDC-0084 (FIG. 28A). Levels of pAkt were significantly reduced at 2 and 8 hours, by 90 and 70%, respectively. Suppression of pS6 and p4EBP1 was less pronounced at 2 hours, reaching 35 and 43%, respectively. These two markers were back to baseline levels 8 hours post-dose (FIG. 28B)

TABLE 16

Plasma Concentrations, Brain Concentrations and Brain-to-Plasma Ratio Measured 2 and 8 hours Following PO Administration of GDC-0084 (15 mg/kg) to GS2 Tumor-Bearing Mice (non-tumored half of the brain)

| Time post-dose (h) | Brain (μM) | Plasma (μM) | Brain-to-Plasma Ratio |
| --- | --- | --- | --- |
| 2 | 5.51 ± 1.58 | 3.64 ± 2.05 | 1.67 ± 0.51 |
| 8 | 2.48 ± 1.25 | 2.01 ± 1.19 | 1.29 ± 0.16 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EMBODIMENTS

A. A process for preparing a compound of Formula III from a compound of Formula II in a reaction mixture according to the following reaction scheme:

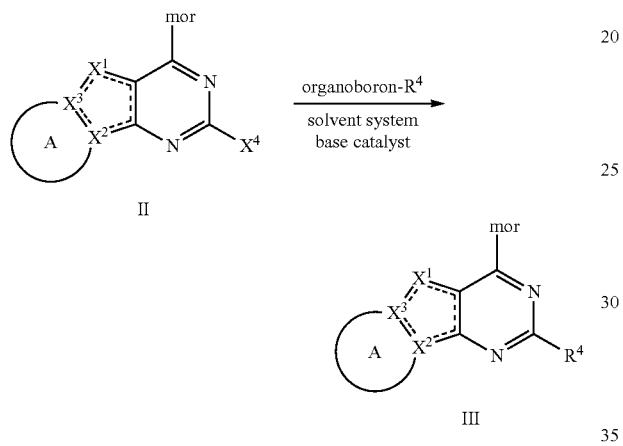

the process comprising:
(i) forming a reaction mixture comprising the compound Formula II, organoboron-$R^4$, the solvent system comprising at least 5 v/v % water, the base and the catalyst;
(ii) reacting the reaction mixture at a temperature of less than 100° C. to form a reaction product mixture comprising compound Formula III; and
(iii) isolating the compound Formula III, a stereoisomer, geometric isomer, tautomer, or a pharmaceutically acceptable salt thereof, from the reaction product mixture,
wherein
the catalyst comprises palladium and the reaction mixture comprises less than 0.05 equivalents of catalyst per equivalent of compound Formula II;
$X^1$ is S, O, N, $NR^6$, $CR^1$, $C(R^1)_2$, or —$C(R^1)_{20}$—;
$X^2$ is C, $CR^2$ or N;
$X^3$ is C, $CR^3$ or N;
$X^4$ is halogen;
A is a 5, 6, or 7-membered carbocyclyl or heterocyclyl ring fused to $X^2$ and $X^3$, optionally substituted with one or more $R^5$, $R^{10}$ or $R^{15}$ groups;
$R^6$ is H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)(—$C_2$-$C_{20}$ heterocyclyl), —($C_1$-$C_{12}$ alkylene)-C(=O)—($C_2$-$C_{20}$ heterocyclyl), ($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$(CH_3)_2OH$, —$CH_2OCH_3$, —CN, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^1$, $R^2$, and $R^3$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2$, —$CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^4$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —CN, —$CF_3$, —$CH_2OH$, —$CO_2H$, —$CONH_2$, $CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —$NHC(O)NHCH_3$, —$NHC(O)NHCH_2CH_3$, —$NHS(O)_2CH_3$, —$N(CH_3)C(O)OC(CH_3)_3$, —$S(O)_2CH_3$, benzyl, benzyloxy, morpholinyl, morpholinomethyl, and 4-methylpiperazin-1-yl;

Each $R^5$, $R^{10}$ and $R^{15}$ is independently selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl); or two geminal $R^5$, $R^{10}$ and/or $R^{15}$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —NH—$COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl; and
mor is selected from:

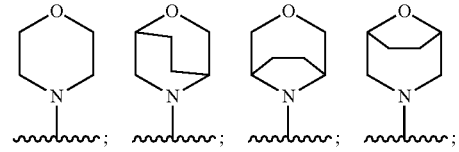

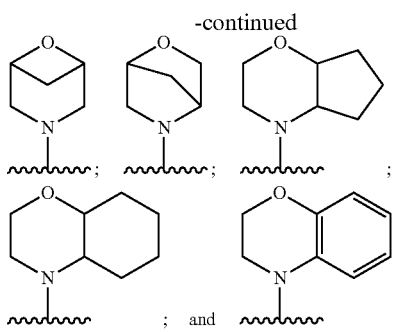

wherein mor is optionally substituted with one or more $R^7$ groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2OH$, —$CH(CH_3)OH$, —$CH(CH_2CH_3)OH$, —$CH_2CH(OH)CH_3$, —$C(CH_3)_2OH$, —$C(CH_3)_2OCH_3$, —$CH(CH_3)F$, —$C(CH_3)F_2$, —$CH(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —$NHCH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, =O, —OH, —$OCH_3$, —$OCH_2CH_3$, —$OCH(CH_3)_2$, —SH, —$NHC(O)NHCH_3$, —$NHC(O)NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, and —$CH_2S(O)_2CH_3$.

A1. The process of embodiment A wherein the solvent system further comprises at least one polar aprotic solvent selected from N-methylpyrrolidone, methyl isobutyl ketone, methyl ethyl ketone, tetrahydrofuran, dichloromethane, ethyl acetate, acetone, N,N-dimethylformamide, acetonitrile and dimethyl sulfoxide.

A2. The process of embodiment A1 wherein the ratio of water to the at least one polar aprotic solvent is from about 1:10 v/v to about 5:1 v/v, from about 1:1 v/v to about 1:10 v/v, or from about 1:3 v/v to about 1:7 v/v.

A3. The process of embodiment A1 or A2 wherein the solvent system comprises water and tetrahydrofuran.

A4. The process of any one of embodiments A1 to A3 wherein the solvent system consists essentially of water and the at least one polar aprotic solvent.

A5. The process of any one of embodiments A to A4 wherein the organoboron-$R^4$ is 5-(4,4,5,5-tetramethyl-1,3,2-dioxaborolan-2 yl)-$R^4$.

A6. The process of any one of embodiments A to A5 wherein the base is selected from $K_3PO_4$, $Cs_2CO_3$, and KOH.

A7. The process of any one of embodiments A to A6 wherein the base is $K_3PO_4$.

A8. The process of any one of embodiments A to A7 wherein the equivalent ratio of base to compound Formula II is at least 1:1, from about 1:1 to about 3:1, or about 2:1.

A9. The process of any one of embodiments A to A8 wherein the catalyst comprising palladium is selected from chloro(2-dicyclohexylphosphino-2',4',6'-triisopropyl-1,1'-biphenyl)[2-(2-aminoethyl) phenyl)]palladium(II) ("Pd Xphos"); 1,1'-bis(diphenylphosphino)ferrocene]dichloropalladium(II) complex with dichloromethane ("PdCl$_2$ dppf CH$_2$Cl$_2$"); Bis(di-tert-butyl(4-dimethylaminophenyl)phosphine)dichloropalladium(II) ("Pd(amphos)Cl$_2$"); dichlorobis(di-tert-butylphenylphosphine)palladium(II) ("Pd 122"); PdCl$_2$(PPh$_3$)$_2$; Pd(t-Bu)$_3$; Pd(PPh$_3$)$_4$; Pd(Oac)/PPh$_3$; Cl$_2$Pd[(Pet$_3$)]$_2$; Pd(DIPHOS)$_2$; Cl$_2$Pd(Bipy); [PdCl(Ph$_2$PCH$_2$PPh$_2$)]$_2$; Cl$_2$Pd[P(o-tol)$_3$]$_2$; Pd$_2$(dba)$_3$/P(o-tol)$_3$; Pd$_2$(dba)/P(furyl)$_3$; Cl$_2$Pd[P(furyl)$_3$]$_2$; Cl$_2$Pd(PmePh$_2$)$_2$; Cl$_2$Pd[P(4-F-Ph)$_3$]$_2$; Cl$_2$Pd[P(C$_6$F$_6$)$_3$]$_2$; Cl$_2$Pd[P(2-COOH-Ph)(Ph)$_2$]$_2$; Cl$_2$Pd[P(4-COOH-Ph)(Ph)$_2$]$_2$; palladium acetate, microencapsulated in a polyuria matrix, comprising 0.4 mmol/g Pd; palladium acetate and triphenylphosphine, microencapsulated in a polyuria matrix, comprising 0.4 mmol/g Pd and 0.3 mmol/g phosphorous; and palladium acetate and BINAP, microencapsulated in a polyuria matrix, comprising 0.4 mmol/g Pd.

A10. The process of embodiment A9 wherein the catalyst comprising palladium is selected from chloro(2-dicyclohexylphosphino-2',4',6'-triisopropyl-1,1'-biphenyl)[2-(2-aminoethyl) phenyl)]palladium(II) and 1,1'-bis(diphenylphosphino)ferrocene]dichloropalladium(II) complex with dichloromethane, or is chloro(2-dicyclohexylphosphino-2',4',6'-triisopropyl-1,1'-biphenyl) [2-(2-aminoethyl) phenyl)]palladium(II).

A11. The process of any one of embodiments A to A10 wherein the equivalent ratio of the catalyst comprising palladium to compound Formula II is between about 0.003:1 and 0.05:1, from about 0.003:1 to about 0.03:1 or from about 0.004:1 to about 0.02:1.

A12. The process of any one of embodiments A to A11 wherein the catalyst is chloro(2-dicyclohexylphosphino-2',4',6'-triisopropyl-1,1'-biphenyl) [2-(2-aminoethyl) phenyl)]palladium(II) and the equivalent ratio of the catalyst comprising palladium to compound Formula II is from about 0.004:1 to about 0.015:1, from about 0.004:1 to about 0.01:1, from about 0.004:1 to about 0.007:1, or about 0.005:1.

A13. The process of any one of embodiments A to A11 wherein the catalyst is chloro(2-dicyclohexylphosphino-2',4',6'-triisopropyl-1,1'-biphenyl) [2-(2-aminoethyl) phenyl)]palladium(II) or 1,1'-bis(diphenylphosphino)ferrocene]dichloropalladium(II) complex with dichloromethane and the equivalent ratio of the catalyst comprising palladium to compound Formula II is from about 0.005:1 to about 0.04:1, from about 0.005:1 to about 0.03:1, from about 0.01:1 to about 0.03:1, or about 0.02:1.

A14. The process of any one of embodiments A to A13 wherein the reaction temperature is between about 40° C. and 100° C., from about 40° C. to about 90° C., from about 40° C. to about 80° C., from about 50° C. to about 80° C. or from about 55° C. to about 75° C.

A15. The process of any one of embodiments A to A14 further comprising adding a polar protic solvent to the reaction product mixture to form an admixture comprising greater than 25 v/v % water and separating compound Formula III from the reaction product mixture by solid liquid separation.

A16. The process of embodiment A15 wherein the polar protic solvent is selected from water, methanol, ethanol, isopropanol, n-propanol, and acetic acid.

A17. The process of embodiment A16 wherein the polar protic solvent is water.

A18. The process of embodiment A17 wherein the volume ratio of the solvent system to water added to the reaction product mixture is from about 1:5 v/v to about 5:1 v/v, from about 1:3 v/v to about 3:1 v/v, from about 1:2 v/v to about 2:1 v/v, from about 1:1.5 v/v to about 1.5:1 v/v, or about 1:1 v/v.

A19. The process of embodiment A17 or embodiment A18 further comprising adding compound Formula III seed crystals to admixture of the reaction product mixture and water.

A20. The process of any one of embodiments A to A19 further comprising a purification step comprising:
(i) admixing compound Formula III with a metal scavenger in a solvent system comprising at least one polar protic solvent;
(ii) heating the admixture to dissolve compound Formula III;
(iii) filtering the heated admixture;
(iv) reducing the temperature of the filtrate and admixing compound Formula III seed crystals with the cooled filtrate;
(v) reducing the temperature of the admixture of filtrate and seed crystals to induce crystallization of purified compound Formula III; and
(vi) collecting purified compound Formula III crystals.

A21. The process of embodiment A20 wherein:
(i) the solvent system comprises water and acetic acid or consists essentially of water and acetic acid wherein the volume ratio of acetic acid to water is from about 1:1 to about 10:1, from about 1:1 to about 5:1 or from about 1:1 to about 3:1, or about 3:1;
(ii) the metal scavenger is silica-thiol; and
(iii) the dissolution temperature is from about 80° C. to about 100° C., the seed crystals are combined with the filtrate at a temperature of from about 70° C. to about 80° C., and the crystallization temperature is from about 0° C. to about 10° C.

A22. The process of any one of embodiments A to A21 wherein the yield of compound Formula III is at least 75%, at least 80% at least 85% or at least 90%.

A23. The process of any one of embodiments A to A22 wherein the purity of compound Formula III is at least 97%, at least 97.5%, or at least 98% (area % as determined by HPLC).

A24. The process of any one of embodiments A to A23 wherein $X^1$ is N, $NR^6$, $CR^1$, $C(R^1)_2$ or $C(R^1)_2O$ and $X^3$ is C or $CR^3$.

A25. The process of embodiment A24 wherein $X^1$ and $X^2$ are N, and $X^3$ is C.

A26. The process of any one of embodiments A to A25 wherein A is an optionally substituted 6-membered heterocycle comprising at least one heteroatom selected from N and O.

A27. The process of embodiment A26 wherein $X^2$ is N and A is optionally substituted morpholine.

A28. The process of any one of embodiments A to A27 wherein mor is optionally substituted morpholine.

A29. The process of any one of embodiments A to A28 wherein $R^4$ is selected from optionally substituted $C_6$ aryl, optionally substituted $C_6$ heterocycle and optionally substituted $C_6$ heteroaryl.

A30. The process of embodiment A29 wherein $R^4$ is optionally substituted $C_6$ heteroaryl comprising one or two N heteroatoms.

A31. The process of embodiment A30 wherein $R^4$ is optionally substituted pyrimidine.

A32. The process of any one of embodiments A to A31 wherein compound Formula III is

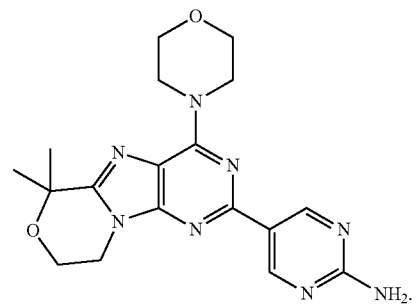 [SMILES: CC1(C)OCCn2c1nc1c(N3CCOCC3)nc(-c3cnc(N)nc3)nc12]

B. A process for preparing a compound of Formula IIa from a compound of Formula I in a reaction mixture according to the following reaction scheme:

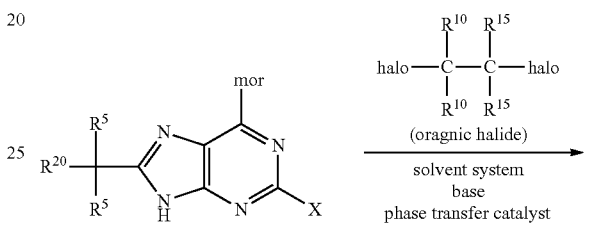

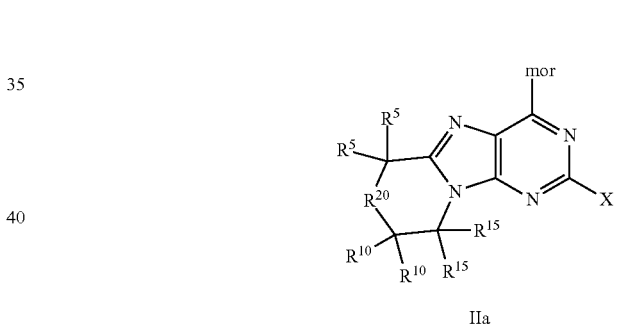

the process comprising:
(i) forming a reaction mixture comprising compound Formula I, organic halide, a solvent system, a phase transfer catalyst, and a base, (ii) reacting the reaction mixture to form a reaction product mixture comprising compound Formula IIa, a stereoisomer, geometric isomer, tautomer, or a pharmaceutically acceptable salt thereof, and (iii) isolating compound Formula IIa from the reaction product mixture,
wherein
the solvent system comprises at least 5 v/v % water;
X is a halide;
Each $R^5$, $R^{10}$ and $R^{15}$ are independently selected from H, $C_1$-$C_{10}$ hydrocarbyl or from $C_1$-$C_5$ hydrocarbyl, wherein each hydrocarbyl is optionally substituted, two geminal $R^5$, $R^{10}$ and/or $R^{15}$ groups are oxo, or two geminal $R^5$, $R^{10}$ and/or $R^{15}$ groups form a 3, 4, 5, 6, or 7-membered carbocyclyl or heterocyclyl, wherein the carbocyclyl or heterocyclyl is optionally substituted;

mor is selected from:

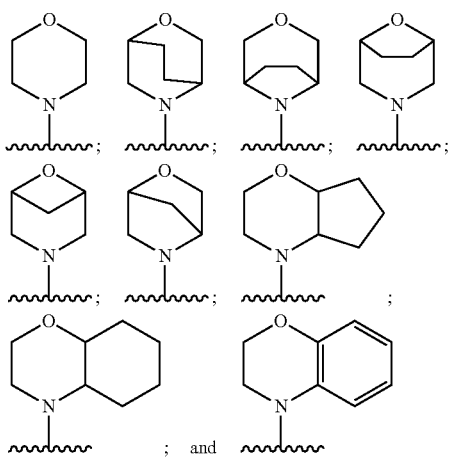
; and wherein mor is optionally substituted with one or more R[7] groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(O)NHCH$_3$, —NHC(O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, and —CH$_2$S(O)$_2$CH$_3$; and wherein in formula I R[20] is —OH or —NHR[21] wherein R[21] is as defined for R[5], and wherein in formula IIa R[20] is —O— or —NR[21]—.

B1. The process of embodiment B wherein the solvent system comprises at least 50 v/v % water, at least 75 v/v % water, at least 90 v/v % water, or consists essentially of water.

B2. The process of embodiment B or embodiment B1 wherein the base is selected from K$_3$PO$_4$, Cs$_2$CO$_3$, K$_2$CO$_3$, KOAc, NaOAc, Na$_2$CO$_3$ and KOH.

B3. The process of embodiment B2 wherein the base is KOH.

B4. The process of any one of embodiments B to B3 wherein the phase transfer catalyst is selected from a quaternary ammonium salt and a phosphonium salt.

B5. The process of embodiment B4 wherein the phase transfer catalyst is selected from tetra-n-butylammonium bromide, benzyltrimethylammonium chloride, benzyltriethylammonium chloride, methyltricaprylammonium chloride, methyltributylammonium chloride, and methyltrioctylammonium chloride.

B6. The process of embodiment B5 wherein the phase transfer catalyst is tetra-n-butylammonium bromide.

B7. The process of any one of embodiments B to B6 wherein the molar ratio of the organic halide dibromoethane to compound Formula I is from greater than 2:1 to about 4:1, between 2:1 and about 4:1, or about 3:1.

B8. The process of any one of embodiments B to B7 wherein the organic halide and the base are present in about equimolar amounts.

B9. The process of any one of embodiments B to B8 wherein the reaction temperature is from about 40° C. to about 90° C., from about 40° C. to about 70° C., from about 40° C. to about 60° C., or about 50° C.

B10. The process of any one of embodiments B to B9 further comprising admixing a polar protic solvent with the reaction product mixture followed by reducing the temperature of the admixture to induce crystallization of compound Formula IIa in the reaction product mixture, wherein the crystallized compound Formula IIa is isolated from the reaction product mixture.

B11. The process of embodiment B10 wherein the polar protic solvent is selected from water, methanol, ethanol, isopropanol, n-propanol, and acetic acid.

B12. The process of embodiment B11 wherein the polar protic solvent is ethanol.

B13. The process of embodiment B12 wherein volume ratio of the solvent system to ethanol is from about 1:5 v/v to about 5:1 v/v, from about 1:3 v/v to about 3:1 v/v, from about 1:2 v/v to about 2:1 v/v, from about 1:1 v/v to about 1:2 v/v, or about 1:1.3 v/v.

B14. The process of embodiment B12 or B13 further comprising adding compound Formula IIa seed crystals to the admixture of the reaction product mixture and ethanol.

B15. The process of any one of embodiments B to B14 wherein the yield of compound Formula II is at least 60%, at least 65% at least 70% or at least 75%.

B16. The process of any one of embodiments B to B15 wherein the purity of compound Formula II is at least 97%, at least 97.5%, at least 98%, at least 98.5% or at least 99% (area % as determined by HPLC.

B17. The process of any one of embodiments B to B16 wherein each R[5], R[10] and R[15] is independently selected from H and optionally substituted C$_{1-5}$ alkyl, or two geminal R[5], R[10] and/or R[15] groups together are oxo or form a 3 to 6-membered cycloalkyl or heterocycloalkyl having one or two hetero atoms selected from N and O.

B18. The process of embodiment B17 wherein each R[5], R[10] and R[15] is independently selected from H, C$_{1-5}$ alkyl and C$_{1-5}$ alkyl substituted with at least one of deuterium, halogen and hydroxyl.

B19. The process of any one of embodiments B to B 18 wherein in formula I R[20] is —OH, —NH$_2$ or —NH—C$_{1-5}$ alkyl.

B20. The process of embodiment B 19 wherein in formula I R[20] is —OH.

B21. The process of any one of embodiments B to B20 wherein the organic halide is 1,2-dibromoethane.

B22. The process of any one of embodiments B to B21 wherein compound Formula IIa is

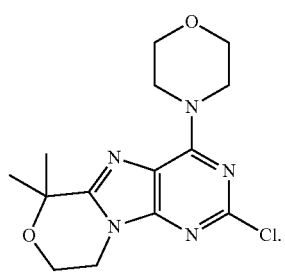 [SMILES: CC1(C)OCCn2c1nc1c(N3CCOCC3)nc(Cl)nc12]

C. The process of any one of embodiments B to B22 further comprising preparing a compound of Formula IIIa from a compound of Formula IIa in a reaction mixture according to the following reaction scheme:

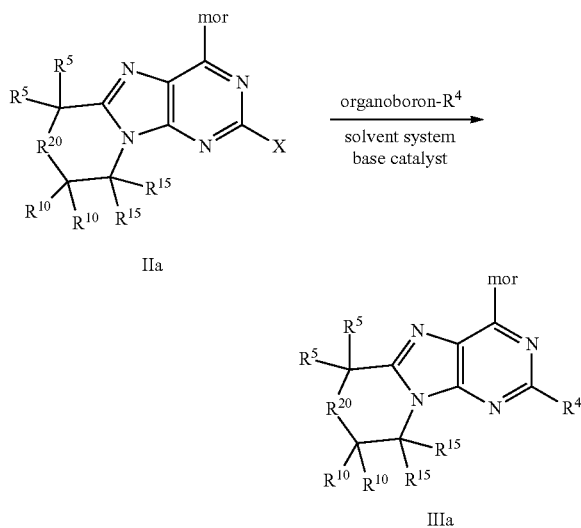

the process comprising:
(i) forming a reaction mixture comprising compound Formula IIa, organoboron-$R^4$, the solvent system comprising at least 5 v/v % water, the base and the catalyst;
(ii) reacting the reaction mixture to form a reaction product mixture comprising compound Formula IIIa; and
(iii) isolating compound Formula IIIa, a stereoisomer, geometric isomer, tautomer, or a pharmaceutically acceptable salt thereof, from the reaction product mixture by solid liquid separation wherein the yield of compound Formula IIIa is at least 75%,
wherein
the catalyst comprises palladium and the reaction mixture comprises less than 0.05 equivalents of catalyst per equivalent of compound Formula IIa; and
$R^4$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —$CN$, —$CF_3$, —$CH_2OH$, —$CO_2H$, —$CONH_2$, $CONH(CH_3)$, —$CON(CH_3)_2$, —$NO_2$, —$NH_2$, —$NHCH_3$, —$NHCOCH_3$, —$OH$, —$OCH_3$, —$OCH_2CH_3$, —$OCH(CH_3)_2$, —$SH$, —$NHC(O)NHCH_3$, —$NHC(O)NHCH_2CH_3$, —$NHS(O)_2CH_3$, —$N(CH_3)C(O)OC(CH_3)_3$, —$S(O)_2CH_3$, benzyl, benzyloxy, morpholinyl, morpholinomethyl, and 4-methylpiperazin-yl.

C1. The process of embodiment C wherein the solvent system further comprises at least one polar aprotic solvent selected from tetrahydrofuran, dichloromethane, ethyl acetate, acetone, N,N-dimethylformamide, acetonitrile and dimethyl sulfoxide.

C2. The process of embodiment C1 wherein the ratio of water to the at least one polar aprotic solvent is from about 1:10 v/v to about 5:1 v/v, from about 1:1 v/v to about 1:10 v/v, or from about 1:3 v/v to about 1:7 v/v.

C3. The process of embodiment C1 or C2 wherein the solvent system comprises water and tetrahydrofuran.

C4. The process of any one of embodiments C1 to C3 wherein the solvent system consists essentially of water and the at least one polar aprotic solvent.

C5. The process of any one of embodiments C to C4 wherein the organoboron-$R^4$ is 5-(4,4,5,5-tetramethyl-1,3,2-dioxaborolan-2 yl)-$R^4$.

C6. The process of any one of embodiments C to C5 wherein the base is selected from $K_3PO_4$, $Cs_2CO_3$, and KOH.

C7. The process of any one of embodiments C to C6 wherein the base is $K_3PO_4$.

C8. The process of any one of embodiments C to C7 wherein the equivalent ratio of base to compound Formula IIa is at least 1:1, from about 1:1 to about 3:1, or about 2:1.

C9. The process of any one of embodiments C to C8 wherein the catalyst comprising palladium is selected from chloro(2-dicyclohexylphosphino-2',4',6'-triisopropyl-1,1'-biphenyl)[2-(2-aminoethyl) phenyl)]palladium(II) ("Pd Xphos"); 1,1'-bis(diphenylphosphino)ferrocene]dichloropalladium(II) complex with dichloromethane ("PdCl$_2$ dppf CH$_2$Cl$_2$"); Bis(di-tert-butyl(4-dimethylaminophenyl)phosphine)dichloropalladium(II) ("Pd(amphos)Cl$_2$"); dichlorobis(di-tert-butylphenylphosphine)palladium(II) ("Pd 122"); PdCl$_2$(PPh$_3$)$_2$; Pd(t-Bu)$_3$; Pd(PPh$_3$)$_4$; Pd(Oac)/PPh$_3$; Cl$_2$Pd[(Pet$_3$)]$_2$, Pd(DIPHOS)$_2$; Cl$_2$Pd (Bipy); [PdCl(Ph$_2$PCH$_2$PPh$_2$)]$_2$; Cl$_2$Pd[P(o-tol)$_3$]$_2$; Pd$_2$(dba)$_3$/P(o-tol)$_3$; Pd$_2$(dba)/P(furyl)$_3$; Cl$_2$Pd[P(furyl)$_3$]$_2$; Cl$_2$Pd(PmePh$_2$)$_2$; Cl$_2$Pd[P(4-F-Ph)$_3$]$_2$; Cl$_2$Pd[P(C$_6$F$_6$)$_3$]$_2$; Cl$_2$Pd[P(2-COOH-Ph)(Ph)$_2$]$_2$; Cl$_2$Pd[P(4-COOH-Ph)(Ph)$_2$]$_2$; palladium acetate, microencapsulated in a polyuria matrix, comprising 0.4 mmol/g Pd; palladium acetate and triphenylphosphine, microencapsulated in a polyuria matrix, comprising 0.4 mmol/g Pd and 0.3 mmol/g phosphorous; and palladium acetate and BINAP, microencapsulated in a polyuria matrix, comprising 0.4 mmol/g Pd.

C10. The process of embodiment C9 wherein the catalyst comprising palladium is selected from chloro(2-dicyclohexylphosphino-2',4',6'-triisopropyl-1,1'-biphenyl)[2-(2-aminoethyl) phenyl)]palladium(II) and 1,1'-bis(diphenylphosphino)ferrocene]dichloropalladium(II) complex with dichloromethane.

C11. The process of any one of embodiments C to C10 wherein the equivalent ratio of the catalyst comprising palladium to compound Formula IIa is between about 0.003:1 and 0.05:1, from about 0.003:1 to about 0.03:1 or from about 0.004:1 to about 0.02:1.

C12. The process of any one of embodiments C to C11 wherein the catalyst is chloro(2-dicyclohexylphosphino-2',4',6'-triisopropyl-1,1'-biphenyl) [2-(2-aminoethyl) phenyl)]palladium(II) and the equivalent ratio of the catalyst comprising palladium to compound Formula IIa is from about 0.004:1 to about 0.015:1, from about 0.004:1 to about 0.01:1, from about 0.004:1 to about 0.007:1, or about 0.005:1.

C13. The process of any one of embodiments C to C11 wherein the catalyst is chloro(2-dicyclohexylphosphino-2',4',6'-triisopropyl-1,1'-biphenyl) [2-(2-aminoethyl) phenyl)]palladium(II) and 1,1'-bis(diphenylphosphino)ferrocene]dichloropalladium(II) complex with dichloromethane and the equivalent ratio of the catalyst comprising palladium to compound Formula IIa is from about 0.005:1 to about 0.04:1, from about 0.005:1 to about 0.03:1, from about 0.01:1 to about 0.03:1, or about 0.02:1.

C14. The process of any one of embodiments C to C13 further comprising adding a polar protic solvent to the reaction product mixture to form an admixture comprising at least 25 v/v % water and separating compound Formula IIIa from the reaction product mixture.

C15. The process of embodiment C14 wherein the polar protic solvent is selected from water, methanol, ethanol, isopropanol, n-propanol, and acetic acid.

C16. The process of embodiment C15 wherein the polar protic solvent is water.

C17. The process of embodiment C16 wherein the volume ratio of the solvent system to water added to the reaction product mixture is from about 1:5 v/v to about 5:1 v/v, from about 1:3 v/v to about 3:1 v/v, from about 1:2 v/v to about 2:1 v/v, from about 1:1.5 v/v to about 1.5:1 v/v, or about 1:1 v/v.

C18. The process of embodiment C16 or C17 further comprising adding compound Formula IIIa seed crystals to admixture of the reaction product mixture and water.

C19. The process of any one of embodiments C to C18 further comprising a purification step comprising:
  (i) admixing compound Formula IIIa with a metal scavenger in a solvent system comprising at least one polar protic solvent;
  (ii) heating the admixture to dissolve compound Formula IIIa;
  (iii) filtering the heated admixture;
  (iv) reducing the temperature of the filtrate and admixing compound Formula IIIa seed crystals with the cooled filtrate;
  (v) reducing the temperature of the admixture of filtrate and seed crystals to induce crystallization of purified compound Formula IIIa; and
  (vi) collecting purified compound Formula IIIa crystals.

C20. The process of embodiment C19 wherein:
  (i) the solvent system comprises water and acetic acid or consists essentially of water and acetic acid wherein the volume ratio of acetic acid to water is from about 1:1 to about 10:1, from about 1:1 to about 5:1 or from about 1:1 to about 3:1, or about 3:1;
  (ii) the metal scavenger is silica-thiol; and
  (iii) the dissolution temperature is from about 80° C. to about 100° C., the seed crystals are combined with the filtrate at a temperature of from about 70° C. to about 80° C., and the crystallization temperature is from about 0° C. to about 20° C.

C21. The process of any one of embodiments C to C20 wherein the yield of compound Formula IIIa based on compound Formula IIa is at least 75%, at least 80% at least 85% or at least 90%.

C22. The process of any one of embodiments C to C21 wherein the purity of compound Formula IIIa is at least 97%, at least 97.5%, or at least 98% (area % as determined by HPLC).

C23. The process of any one of embodiments C to C22 wherein compound Formula IIIa is

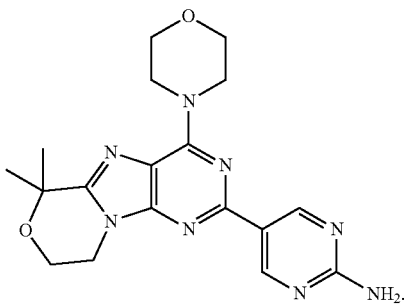 [SMILES: CC1(C)OCCn2c1nc1c(N3CCOCC3)nc(-c3cnc(N)nc3)nc12]

D. A method for treating cancer in a patient wherein the cancer is characterized by the overexpression of PI3 kinase, the method comprising administering a therapeutically effective amount of a PI3 kinase inhibitor compound of Formula III according to embodiment A to a person in need of such treatment.

D1. The method of embodiment D wherein the PI3 kinase inhibitor compound is compound IIIat of the formula:

D2. The method of embodiment D or embodiment D1 wherein the dose of the PI3 kinase inhibitor compound is from about 0.2 mg/kg/day to about 1.5 mg/kg/day, from about 0.3 mg/kg/day to about 1 mg/kg/day, or from about 0.4 mg/kg/day to about 0.75 mg/kg/day.

D3. The method of any one of embodiments D to D2 wherein the terminal half-life of the PI3 kinase inhibitor compound in a plurality of cancer cells is from about 10 hours to about 24 hours, from about 12 hours to about 22 hours, or from about 15 hours to about 20 hours after a single dose administered on the first day of a dosage cycle.

D4. The method of any one of embodiments D to D3 wherein the time to maximum plasma concentration for the PI3 kinase inhibitor is from about 1 hours to about 8 hours, from about 2 hours to about 6 hours, from about 2 hours to about 4 hours, or from about 2 hours to about 3 hours after a single dose administered on the first day of a dosage cycle.

D5. The method of any one of embodiments D to D4 wherein the maximum plasma concentration for the PI3 kinase inhibitor is from about 0.01 µM to about 0.5 µM, from about 0.05 µM to about 0.4 µM, or from about 0.1 µM to about 0.3 µM after a single dose administered on the first day of a dosage cycle.

D6. The method of any one of embodiments D to D5 wherein area under the concentration-time curve in a plurality of cancer cells from time 0 to infinity for the PI3 kinase inhibitor is from about 0.2 µM*hr to about 10 µM*hr, from about 0.5 µM*hr to about 10 µM*hr, from about 1 µM*hr to about 8 µM*hr, or from about 2 µM*hr to about 6 µM*hr after a single dose administered on the first day of a dosage cycle.

D7. The method of any one of embodiments D to D6 wherein the area under the concentration curve in a plurality of cancer cells for the PI3 kinase inhibitor from time 0 to 24 hours is from about 0.1 µM*hr to about 10 µM*hr, from about 0.5 µM*hr to about 5 µM*hr, from about 1 µM*hr to about 5 µM*hr, or from about 2 µM*hr to about 4 µM*hr after a single dose administered on the first day of a dosage cycle.

D8. The method of any one of embodiments D to D7 wherein the PI3 kinase inhibitor is administered orally.

D9. The method of any one of embodiments D to D8 wherein the PI3 kinase inhibitor is administered orally without food or under fasting conditions.

D10. The method of any one of embodiments D to D9 wherein the cancer is a brain cancer.

D11. The method of any one of embodiments D to D10 wherein the cancer is glioma.

D12. The method of any one of embodiments D to D10 wherein the cancer is glioblastoma.

D13. The method of any one of embodiments D to D12 wherein the method further comprises administering to the patient an additional therapeutic agent selected from a chemotherapeutic agent, an anti-angiogenesis therapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

D14. The method of D13 wherein the additional therapeutic agent is bevacizumab.

D15. The method of D13 wherein the additional therapeutic agent is temozolomide.

The claims defining the invention are as follows:

1. A process for preparing a compound of Formula III,

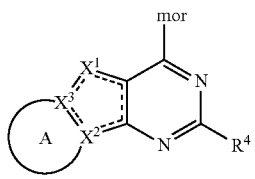

III from a compound of Formula II,

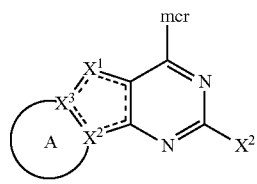

II in a reaction mixture, the process comprising:
(i) forming a reaction mixture comprising the compound Formula II, organoboron-$R^4$, the solvent system comprising at least 5 v/v % water, the base and the catalyst;
(ii) reacting the reaction mixture at a temperature of less than 100° C. to form a reaction product mixture comprising compound Formula III;
(iii) further comprising adding a polar protic solvent to the reaction product mixture to form an admixture comprising greater than 25 v/v % of the polar protic solvent and separating compound Formula III from the reaction product mixture by solid-liquid separation; and
(iv) isolating the compound Formula III, a stereoisomer, geometric isomer, tautomer, or a pharmaceutically acceptable salt thereof, from the reaction product mixture, the process further comprising a purification step comprising:
(i) admixing the compound of Formula III with a metal scavenger in a solvent system comprising at least one polar protic solvent;
(ii) heating the admixture to dissolve the compound of Formula III;
(iii) filtering the heated admixture;
(iv) reducing the temperature of the filtrate and admixing seed crystals of the compound of Formula III with the cooled filtrate;
(v) reducing the temperature of the admixture of filtrate and seed crystals to induce crystallization of the purified compound of Formula III; and
(vi) collecting crystals of the purified compound of Formula III, wherein
the catalyst comprises palladium and the reaction mixture comprises less than 0.05 equivalents of catalyst per equivalent of compound Formula II;
$X^1$ is S, O, N, $NR^6$, $CR^1$, $C(R^1)_2$, or —$C(R^1)_2O$—;
$X^2$ is C, $CR^2$ or N;
$X^3$ is C, $CR^3$ or N;
$X^4$ is halogen;
A is a 5, 6, or 7-membered carbocyclyl or heterocyclyl ring fused to $X^2$ and $X^3$, optionally substituted with one or more $R^5$, $R^{10}$ or $R^{15}$ groups;
$R^6$ is H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)(-$C_2$-$C_{20}$ heterocyclyl), —($C_1$-$C_{12}$ alkylene)-C(=O)—($C_2$-$C_{20}$ heterocyclyl), ($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$(CH_3)_2OH$, —$CH_2OCH_3$, —CN, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, or 1,1-dioxo-thiopyran-4-yl;
$R^1$, $R^2$, and $R^3$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CH_2H$, —$COCH_3$, —$COC(CH_3)_3$, —$CO_2CH_3$, —$CONH_2$, —$CONHCH_3$, —$CON(CH_3)_2$, —$C(CH_3)_2$, —$CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, or 1,1-dioxo-thiopyran-4-yl;
$R^4$ is selected from $C_6$-$C_{20}$ aryl, $C_2$-$C_{20}$ heterocyclyl, or $C_1$-$C_{20}$ heteroaryl, each of which are optionally substituted with one or more groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —CN, —$CF_3$, —$CH_2OH$, —$CO_2H$, —$CONH_2$, $CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —NHC(O)

NHCH$_3$, —NHC(O)NHCH$_2$CH$_3$, —NHS(O)$_2$CH$_3$, —N(CH$_3$)C(O)OC(CH$_3$)$_3$, —S(O)$_2$CH$_3$, benzyl, benzyloxy, morpholinyl, morpholinomethyl, or 4-methylpiperazin-1-yl;

each R$^5$, R$^{10}$ and R$^{15}$ is independently selected from C$_1$-C$_{12}$ alkyl, C$_2$-C$_8$ alkenyl, C$_2$-C$_8$ alkynyl, —(C$_1$-C$_{12}$ alkylene)-(C$_3$-C$_{12}$ carbocyclyl), —(C$_1$-C$_{12}$ alkylene)-(C$_2$-C$_{20}$ heterocyclyl), —(C$_1$-C$_{12}$ alkylene)-C(O)—(C$_2$-C$_{20}$ heterocyclyl), —(C$_1$-C$_{12}$ alkylene)-(C$_6$-C$_{20}$ aryl), or —(C$_1$-C$_{12}$ alkylene)-(C$_1$-C$_{20}$ heteroaryl); or two geminal R$^5$, R$^{10}$, or R$^{15}$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —C(CH$_3$)$_3$, —CH$_2$OH, —CH$_2$CH$_2$OH, —C(CH$_3$)$_2$OH, —CH$_2$OCH$_3$, —CN, —CH$_2$F, —CHF$_2$, —CF$_3$, —CO$_2$H, —COCH$_3$, —COC(CH$_3$)$_3$, —CO$_2$CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NH—COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —S(O)$_2$CH$_3$, cyclopropyl, cyclobutyl, oxetanyl, morpholino, or 1,1-dioxo-thiopyran-4-yl; and mor is selected from:

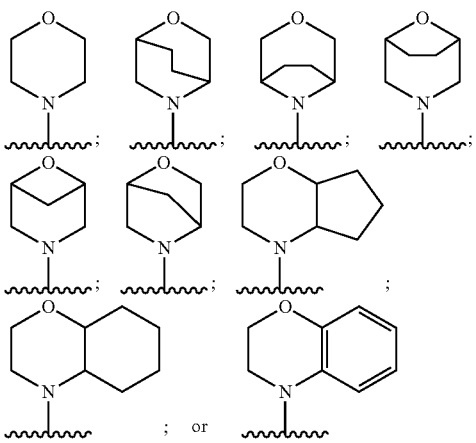

wherein mor is optionally substituted with one or more R$^7$ groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(O)NHCH$_3$, —NHC(O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, or —CH$_2$S(O)$_2$CH$_3$.

2. The process of claim 1 wherein the solvent system further comprises at least one polar aprotic solvent selected from N-methylpyrrolidone, methyl isobutyl ketone, methyl ethyl ketone, tetrahydrofuran, dichloromethane, ethyl acetate, acetone, N,N-dimethylformamide, acetonitrile, or dimethyl sulfoxide.

3. The process of claim 2 wherein the ratio of water to the at least one polar aprotic solvent is about 1:10 v/v to about 5:1 v/v.

4. The process of claim 2 wherein the solvent system comprises water and tetrahydrofuran.

5. The process of claim 2 wherein the solvent system consists essentially of water and the at least one polar aprotic solvent.

6. The process of claim 1 wherein the organoboron-R$^4$ is 5-(4,4,5,5-tetramethyl-1,3,2-dioxaborolan-2-yl)-R$^4$.

7. The process of claim 1 wherein the base is selected from K$_3$PO$_4$, Cs$_2$CO$_3$, or KOH.

8. The process of claim 1 wherein the catalyst comprising palladium is selected from chloro(2-dicyclohexylphosphino-2',4',6'-triisopropyl-1,1'-biphenyl)[2-(2-aminoethyl) phenyl)]palladium(II) [1,1'-bis(diphenylphosphino)ferrocene]dichloropalladium(II) complex with dichloromethane; Bis(di-tert-butyl(4-dimethylaminophenyl)phosphine)dichloropalladium(II); dichlorobis(di-tert-butylphenylphosphine)palladium(II); PdCl$_2$(PPh$_3$)$_2$; Pd(t-Bu)$_3$; Pd(PPh$_3$)$_4$; Pd(Oac)/PPh$_3$; Cl$_2$Pd[(Pet$_3$)]$_2$; Pd(DIPHOS)$_2$; Cl$_2$Pd(Bipy); [PdCl(Ph$_2$PCH$_2$PPh$_2$)]$_2$; Cl$_2$Pd[P(o-tol)$_3$]$_2$; Pd$_2$(dba)$_3$/P(o-tol)$_3$; Pd$_2$(dba)/P(furyl)$_3$; Cl$_2$Pd[P(furyl)$_3$]$_2$; Cl$_2$Pd(PmePh$_2$)$_2$; Cl$_2$Pd[P(4-F-Ph)$_3$]$_2$; Cl$_2$Pd[P(C$_6$F$_6$)$_3$]$_2$; Cl$_2$Pd[P(2-COOH-Ph)(Ph)$_2$]$_2$; Cl$_2$Pd[P(4-COOH-Ph)(Ph)$_2$]$_2$; palladium acetate, microencapsulated in a polyuria matrix, comprising 0.4 mmol/g Pd; palladium acetate and triphenylphosphine, microencapsulated in a polyuria matrix, comprising 0.4 mmol/g Pd and 0.3 mmol/g phosphorous; or palladium acetate and BINAP, microencapsulated in a polyuria matrix, comprising 0.4 mmol/g Pd.

9. The process of claim 8 wherein the catalyst comprising palladium is chloro(2-dicyclohexylphosphino-2',4',6'-triisopropyl-1,1'-biphenyl)[2-(2-aminoethyl) phenyl)]palladium (II) or [1,1'-bis(diphenylphosphino)ferrocene]dichloropalladium(II) complex with dichloromethane.

10. The process of claim 1 wherein the equivalent ratio of the catalyst comprising palladium to the compound of Formula II is about 0.003:1 to about 0.05:1.

11. The process of claim 1 wherein the catalyst is chloro (2-dicyclohexylphosphino-2',4',6'-triisopropyl-1,1'-biphenyl)[2-(2-aminoethyl) phenyl)]palladium(II) and the equivalent ratio of the catalyst comprising palladium to the compound of Formula II is about 0.004:1 to about 0.015:1.

12. The process of claim 1 wherein the catalyst is chloro (2-dicyclohexylphosphino-2',4',6'-triisopropyl-1,1'-biphenyl)[2-(2-aminoethyl) phenyl)]palladium(II) or 1,1'-bis(diphenylphosphino)ferrocene] dichloropalladium(II) complex with dichloromethane and the equivalent ratio of the catalyst comprising palladium to the compound of Formula II is about 0.005:1 to about 0.04:1.

13. The process of claim 1 wherein the reaction temperature is about 40° C. to about 100° C.

14. The process of claim 1 wherein the polar protic solvent is selected from water, methanol, ethanol, isopropanol, n-propanol, or acetic acid.

15. The process of claim 14 wherein the polar protic solvent is water.

16. The process of claim 15 wherein the volume ratio of the solvent system to water added to the reaction product mixture is about 1:5 v/v to about 5:1 v/v.

17. The process of claim 15 further comprising adding seed crystals of the compound of Formula III to the admixture of the reaction product mixture and water.

18. The process of claim 1 wherein:
(i) the solvent system comprises water and acetic acid or consists essentially of water and acetic acid wherein the volume ratio of acetic acid to water is about 1:1 to about 10:1;
(ii) the metal scavenger is silica-thiol; and
(iii) the dissolution temperature is about 80° C. to about 100° C., the seed crystals are combined with the filtrate at a temperature of about 70° C. to about 80° C., and the crystallization temperature is about 0° C. to about 10° C.

19. The process of claim 1 wherein the purity of the compound of formula III is at least 97% area % as determined by HPLC.

20. The process of claim 1 wherein the compound of Formula III is:

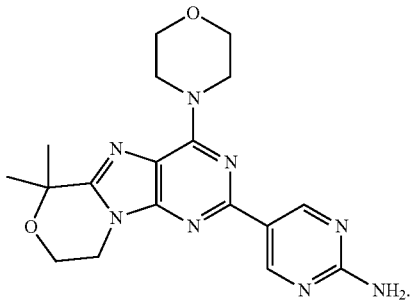 [SMILES: CC1(C)OCCn2c1nc1c(N3CCOCC3)nc(-c3cnc(N)nc3)nc12]

21. The process of claim 18 wherein the volume ratio of acetic acid to water is about 1:1 to about 5:1.

22. The process of claim 18 wherein the volume ratio of acetic acid to water is about 1:1 to about 3:1.

23. The process of claim 18 wherein the volume ratio of acetic acid to water is about 3:1.

24. The process of claim 1 wherein the catalyst comprising palladium is chloro(2-dicyclohexylphosphino-2',4',6'-triisopropyl-1,1'-biphenyl)[2-(2'-amino-1,1'-biphenyl)]palladium(II).

25. The process of claim 10 wherein the catalyst comprising palladium is chloro(2-dicyclohexylphosphino-2',4',6'-triisopropyl-1,1'-biphenyl)[2-(2'-amino-1,1'-biphenyl)]palladium(II).

* * * * *

UNITED STATES PATENT AND TRADEMARK OFFICE
CERTIFICATE OF CORRECTION

PATENT NO. : 10,906,918 B2
APPLICATION NO. : 15/780328
DATED : February 2, 2021
INVENTOR(S) : Andreas Stumpf et al.

It is certified that error appears in the above-identified patent and that said Letters Patent is hereby corrected as shown below:

In the Claims

In Claim 1 (Column 127, Line 45), please replace " 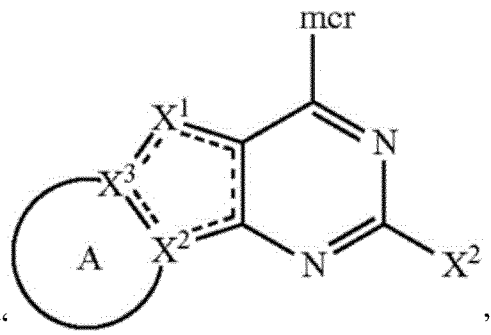 " with 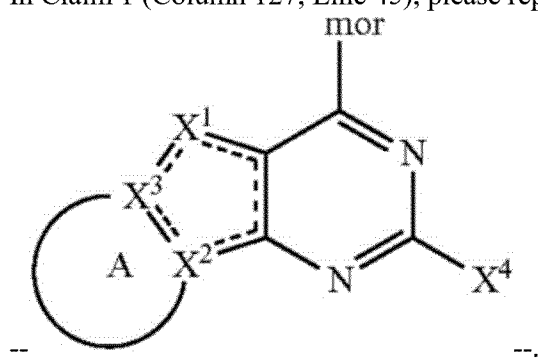.

In Claim 1 (Column 128, Line 50), please replace "—CH₂H" with -- —CO₂H--.

Signed and Sealed this
Third Day of May, 2022

Katherine Kelly Vidal
*Director of the United States Patent and Trademark Office*